United States Patent
Ashwell et al.

(10) Patent No.: US 8,114,873 B2
(45) Date of Patent: Feb. 14, 2012

(54) 1,4-DISUBSTITUTED NAPHTHALENES AS INHIBITORS OF P38 MAP KINASE

(75) Inventors: Mark A. Ashwell, Carlisle, MA (US); Yanbin Liu, Acton, MA (US); Syed M. Ali, North Andover, MA (US); Jason Hill, Auburndale, MA (US); Woj Wrona, Waltham, MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 12/854,687

(22) Filed: Aug. 11, 2010

(65) Prior Publication Data

US 2010/0311754 A1 Dec. 9, 2010

Related U.S. Application Data

(62) Division of application No. 11/631,617, filed as application No. PCT/US2005/024441 on Jul. 8, 2005, now Pat. No. 7,829,560.

(60) Provisional application No. 60/585,862, filed on Jul. 8, 2004.

(51) Int. Cl.
A61K 31/5355 (2006.01)
A61K 31/5375 (2006.01)
C07D 265/30 (2006.01)
A61P 29/00 (2006.01)

(52) U.S. Cl. .................... 514/238.2; 544/106
(58) Field of Classification Search .............. 544/106; 514/238.2
See application file for complete search history.

(56) References Cited

U.S. PATENT DOCUMENTS

| | | | |
|---|---|---|---|
| 3,455,924 A | 7/1969 | Lednicer | 260/256.4 |
| 4,794,114 A | 12/1988 | Bender et al. | 514/333 |
| 4,892,578 A | 1/1990 | Chang et al. | 71/94 |
| 5,317,019 A | 5/1994 | Bender et al. | 514/224.2 |
| 5,777,097 A | 7/1998 | Lee et al. | 536/24.31 |
| 5,783,664 A | 7/1998 | Lee et al. | 530/350 |
| 5,869,043 A | 2/1999 | McDonnell et al. | 424/94.1 |
| 5,871,934 A | 2/1999 | Lee et al. | 435/7.1 |
| 5,955,366 A | 9/1999 | Lee et al. | 435/471 |
| 5,994,412 A | 11/1999 | Lee et al. | 514/721 |
| 6,033,873 A | 3/2000 | McDonnell et al. | 435/69.1 |
| 6,090,626 A | 7/2000 | Monia et al. | 435/375 |
| 6,162,613 A | 12/2000 | Su et al. | 435/15 |
| 6,187,799 B1 | 2/2001 | Wood et al. | 514/363 |
| 6,302,838 B1 | 10/2001 | O'Reilly et al. | 574/365 |
| 6,344,476 B1 | 2/2002 | Ranges et al. | 514/447 |
| 6,376,214 B1 | 4/2002 | Kumar | 435/69.1 |
| 6,387,641 B1 | 5/2002 | Bellon et al. | 435/15 |
| 6,410,518 B1 | 6/2002 | Monia | 514/44 |
| 6,437,147 B1 | 8/2002 | Andersen et al. | 548/304.1 |
| 6,683,100 B2 | 1/2004 | van Hoogevest | 514/365 |
| 6,689,883 B1 | 2/2004 | Dumas et al. | 544/235 |
| 6,806,258 B2 | 10/2004 | Monia | 514/44 |
| 2001/0006975 A1 | 7/2001 | Wood et al. | 514/363 |
| 2002/0042517 A1 | 4/2002 | Uday et al. | 546/285 |
| 2002/0058659 A1 | 5/2002 | Andersen et al. | 514/234.5 |
| 2002/0137774 A1 | 9/2002 | Riedl et al. | 514/353 |
| 2002/0165394 A1 | 11/2002 | Dumas et al. | 546/143 |
| 2003/0078432 A1 | 4/2003 | Letavic et al. | 548/181 |
| 2003/0125359 A1 | 7/2003 | Lyons et al. | 514/350 |
| 2003/0144278 A1 | 7/2003 | Riedl et al. | 514/227.8 |
| 2003/0181442 A1 | 9/2003 | Riedl et al. | 514/227.5 |
| 2003/0207872 A1 | 11/2003 | Riedl et al. | 514/227.8 |
| 2003/0207914 A1 | 11/2003 | Dumas et al. | 514/307 |
| 2003/0216396 A1 | 11/2003 | Dumas et al. | 514/247 |

(Continued)

FOREIGN PATENT DOCUMENTS

DE 1927595 * 12/1969

(Continued)

OTHER PUBLICATIONS

Adams, et al., "Pyrimidinylimidazole Inhibitors of CSBP/p38 Kinase Demonstrating Decreased Inhibition of Hepatic Cytochrome P450 Enzymes" *Bioorg. Med. Chem. Lett.*, 8:3111-3116 (1998). Adams, et al., "Pyrimidinylimidazole Inhibitors of p38: Cyclic N-1 Imidazole Substituents Enhance p38 Kinase Inhibition and Oral Activity," *Bioorg. Med. Chem. Lett.*, 11:2867-2870 (2001).
Badger, et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," *J. Pharmacol. Exp. Ther.*, 279:1453-1461 (1996).

(Continued)

*Primary Examiner* — James O Wilson
*Assistant Examiner* — Cecilia M Jaisle
(74) *Attorney, Agent, or Firm* — Sunstein Kann Murphy & Timbers LLP

(57) ABSTRACT

Naphthalene-based compounds having linked heterocyclic and aromatic rings capable of inhibiting P38, methods for inhibiting P38 in vivo or in vitro, diagnostics for determining activity in the treatment of P38 and/or cytokine-associated conditions and methods for treating conditions associated with P38 activity or cytokine activity; more particularly naphthalene-based compounds of Formula (I) having a morpholine heterocyclic ring, and methods of use thereof

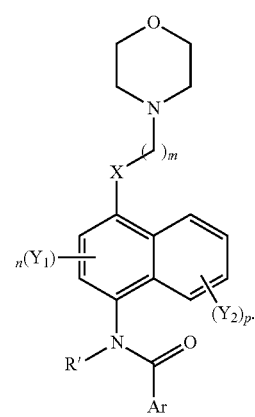

(I)

9 Claims, No Drawings

U.S. PATENT DOCUMENTS

| | | | |
|---|---|---|---|
| 2003/0216446 A1 | 11/2003 | Dumas et al. | 514/350 |
| 2004/0023961 A1 | 2/2004 | Dumas et al. | 514/238.8 |
| 2004/0087626 A1 | 5/2004 | Renhowe et al. | 514/338 |
| 2004/0122237 A1 | 6/2004 | Amiri et al. | 548/161 |

FOREIGN PATENT DOCUMENTS

| | | |
|---|---|---|
| EP | 0 951 467 B1 | 4/2003 |
| EP | 1 114 051 B1 | 4/2003 |
| EP | 1 449 834 A3 | 8/2004 |
| EP | 1 449 834 A2 | 12/2004 |
| JP | 61214793 | 8/1986 |
| WO | WO 91/00092 A1 | 1/1991 |
| WO | WO 95/03297 A1 | 2/1995 |
| WO | WO 97/32604 A1 | 9/1997 |
| WO | WO 97/36587 A1 | 10/1997 |
| WO | WO 98/27098 A1 | 6/1998 |
| WO | WO 98/52559 A1 | 11/1998 |
| WO | WO 99/20624 A1 | 4/1999 |
| WO | WO 99/32106 A1 | 7/1999 |
| WO | WO 99/32436 A1 | 7/1999 |
| WO | WO 99/32455 A1 | 7/1999 |
| WO | WO 00/12074 A2 | 3/2000 |
| WO | WO 00/12074 A3 | 3/2000 |
| WO | WO 00/17204 A1 | 3/2000 |
| WO | WO 00/42012 A1 | 7/2000 |
| WO | WO 00/71535 A1 | 11/2000 |
| WO | WO 02/04447 A1 | 1/2002 |
| WO | WO 02/062763 A2 | 8/2002 |
| WO | WO 02/062763 A3 | 8/2002 |
| WO | WO 02/083628 A1 | 10/2002 |
| WO | WO 02/085857 A2 | 10/2002 |
| WO | WO 02/085857 A3 | 10/2002 |
| WO | WO 03/000682 A1 | 1/2003 |
| WO | WO 03/033502 A1 | 4/2003 |
| WO | WO 03/047523 A2 | 6/2003 |
| WO | WO 03/047523 A3 | 6/2003 |
| WO | WO 03/047579 A1 | 6/2003 |
| WO | WO 03/068223 A1 | 8/2003 |
| WO | WO 03/068229 A1 | 8/2003 |
| WO | WO 03/068746 A1 | 8/2003 |
| WO | WO 03/087087 A2 | 10/2003 |
| WO | WO 03/087087 A3 | 10/2003 |
| WO | WO 03/102139 A2 | 12/2003 |
| WO | WO 03/102139 A3 | 12/2003 |
| WO | WO 2004/014870 A1 | 2/2004 |
| WO | WO 2004/019941 A1 | 3/2004 |
| WO | WO 2004/037789 A2 | 5/2004 |
| WO | WO 2004/037789 A3 | 5/2004 |
| WO | WO 2004/072025 A2 | 8/2004 |
| WO | WO 2004/072025 A3 | 8/2004 |
| WO | WO 2004/080464 A1 | 9/2004 |
| WO | WO 2004/085399 A1 | 10/2004 |
| WO | WO 2004/087905 A2 | 10/2004 |
| WO | WO 2004/087905 A3 | 10/2004 |
| WO | WO 2004/089929 A1 | 10/2004 |
| WO | WO 2005/023761 A2 | 3/2005 |
| WO | WO 2005/023761 A3 | 3/2005 |
| WO | WO 2005023761 * | 3/2005 |

OTHER PUBLICATIONS

Bingham, III, "The Pathogenesis of Rheumatoid Arthritis: Pivotal Cytokines Involved in Bone Degradation and Inflammation," *J Rheumatol. Suppl.*, 65:3-9 (2002).

Boehm, et al., "New Inhibitors of p38 Kinase," *Expert Opinion on Therapeutic Patents*, 1 0(1):25-37 (2000).

Bondeson, et al., "Tumour Necrosis Factor as a Therapeutic Target in Rheumatoid Arthritis and Other Chronic Inflammatory Diseases: The Clinical Experience with Infliximab (REMICADE)," *Int. J. Clin. Pract.*, 55:211-216 (2001).

Bradley and Robinson, Kationoid Reactivity of Aromatic Compounds. Part I, (Database Beilstein, Beilstein Institute zur Foerderung der Wissenschaften), Accession No. 316203, *J.Chem. Soc.* 1254-1263 (1932).

Brinkman, et al., "Engagement of Tumor Necrosis Factor (TNF) Receptor 1 Leads to ATF-2- and p38 Mitogen-Activated Protein Kinase-Dependent TNF-alpha Gene Expression," *J. Biol. Chem.*, 274:30882-30886 (1999).

Dodeller, "The p38 mitogen-activated protein kinase signaling cascade in CD4 T cells" Arthritis Res Ther. 2006;8(2):205.

Dong, et al., "MAP Kinases in the Immune Response," *Annu. Rev. Immunol.*, 20:55-72 (2002).

English, et al., "Pharmacological Inhibitors of MAPK Pathways," *Trends in Pharmacological Sciences*, 23:40-45 (2002).

Enslen, et al., "Selective Activation of p38 Mitogen-Activated Protein (MAP) Kinase Isoforms by the MAP Kinase Kinases MKK3 and MKK6," *J. Biol. Chem.*, 273:1741-1748 (1998).

Feldmann, "Rheumatoid Arthritis Affects Millions of Individuals Worldwide. Luckily, It Is the Autoimmune Disease With the Most Promising Clinical Results." *Nature Immunology*, vol. 2, No. 9, Sep. 2001, pp. 771-773.

Feldmann, et al., "Role of Cytokines in Rheumatoid Arthritis," *Annu. Rev. Immunol.*, 14:397-440 (1996).

Fresneda, et al., "Synthetic Studies Towards the 2-Aminopyrimidine Alkaloids Variolins and Meridianins from Marine Origin," *Tetrahedron Letters*, 41 :4777-4780 (2000).

Fuchs, et al., "Stability of the ATF2 Transcription Factor is Regulated by Phosphorylation and Dephosphorylation," *J. Biol. Chem.*, 275:12560-12564 (2000).

Griswold, et al., "Differentiation in vivo of Classical Non-Steroidal Antiinflammatory Drugs from Cytokine Suppressive Antiinflammatory Drugs and Other Pharmacological Classes Using Mouse Tumour Necrosis Factor Alpha Production," *Drugs Exp. Clin. Res.*, 19:243-248 (1993).

Hashimoto, et al., "Selective Inhibitor of p38 Mitogen-Activated Protein Kinase Inhibits Lipopolysaccharide-Induced Interleukin-8 Expression in Human Pulmonary Vascular Endothelial Cells" *J. of Pharmacol. & Exper. Therap.*, vol. 293, No. 2, pp. 370-375, 2000.

Joe, et al., "Animal Models of Rheumatoid Arthritis and Related Inflammation," *Curr. Rheumatol. Rep.*, 1:139-148 (1999).

Johnson, et al., "Mitogen-Activated Protein Kinase Pathways Mediated by ERK, JNK, and p38 Protein Kinases" *Science*, vol. 298, Dec. 6, 2002, 1911-1912.

Keffer, et al., "Transgenic Mice Expressing Human Tumour Necrosis Factor: A Predictive Genetic Model of Arthritis," *EMBO J.*, 10:4025-4031 (1991).

Keesler, et al., "Purification and Activation of Recombinant p38 Isoforms Alpha, Beta, Gamma, and Delta," *Protein Expr. Purif.*, 14:221-228 (1998).

Laufer, et al., "An in vitro Screening Assay for the Detection of Inhibitors of Proinflammatory Cytokine Synthesis: a Useful Tool for the Development of New Antiarthritic and Disease Modifying Drugs," *Osteoarthritis Cartilage*, 10:961-967 (2002).

Laufer, et al., "From Imidazoles to Pyrimidines: New Inhibitors of Cytokine Release," *J. Med. Chem.*, 45:2733-2740 (2002).

Lee, et al., "A Protein Kinase Involved in the Regulation of Inflammatory Cytokine Biosynthesis," *Nature*, 372:739-746 (1994).

Lee, et al., "Bicyclic Imidazoles as a Novel Class of Cytokine Biosynthesis Inhibitors," *Ann. N.Y. Acad. Sci.*, 696:149-170 (1993).

Lee, et al., "Inhibition of p38 MAP Kinase as a Therapeutic Strategy," *Immunopharmacology*, 47:185-201 (2000).

Liverton, et al., "Design and Synthesis of Potent, Selective, and Orally Bioavailable Tetrasubstituted Imidazole Inhibitors of p38 Mitogen-Activated Proteins Kinase," *J. Med. Chem.*, 42:2180-2190 (1999).

McLay, et al., "The Discovery of RPR 200765A, a p38 MAP Kinase Inhibitor Displaying a Good Oral Anti-Arthritic Efficacy," *Bioorg. Med. Chem.*, 9:537-554 (2001).

Mekonnen, et al., "A New and Facile Synthesis of Imidazo[2,1-b]Oxazoles," *J. Heterocyclic Chem.*, 34:589-599 (1997).

Newton, et al., "New aspects of p38 mitogen activated protein kinase (MAPK) biology in lung inflammation" *Drug Discovery Today: Disease Mechanisms*, 2006, pp. 53-61.

Ono, et al., "The p38 Signal Transduction Pathway: Activation and Function," *Cell. Signal.*, 12:1-13 (2000).

Pargellis, et al., "Inhibition of p38 MAP Kinase by Utilizing a Novel Allosteric Binding Site," *Nat. Struct. Biol.*, 9:268-272 (2002).

Pugsley, "Etanercept. Immunex," *Curr. Opin. Investig. Drugs*, 2:1725-1731 (2001).

Raingeaud, et al., "Pro-Inflammatory Cytokines and Environmental Stress Cause p38 Mitogen-Activated Protein Kinase Activation by Dual Phosphorylation on Tyrosine and Threonine," *J. Biol. Chem.*, 270:7420-7426 (1995).

Raingeaud, et al., "MKK3- and MKK6-Regulated Gene Expression is Mediated by the p38 Mitogen-Activated Protein Kinase Signal Transduction Pathway," *Mol. Cell. Biol.*, 16:1247-1255 (1996).

Regan, et al., "Pyrazole Urea-Based Inhibitors of p38 MAP Kinase: From Lead Compound to Clinical Candidate," *J. Med. Chem.*, 45:2994-3008 (2002).

Revesz, et al., "SAR of 4-Hydroxypiperidine and Hydroxyalkyl Substituted Heterocycles as Novel p38 Map Kinase Inhibitors," *Bioorg. Med. Chem. Lett.*, 10:1261-1264 (2000).

Schreiber, et al., "Oral p38 mitogen-activated protein kinase inhibition with BIRB 796 for active Crohn's disease: a randomized, double-blind, placebo-controlled trial." *Clin. Gastroenterol. Hepatol.*, Mar. 2006, 4(3): pp. 325-334.

See, et al., "p38 MAP kinase as a therapeutic target in cardiovascular disease" *Drug Discovery Today: Therapeutic Strategies*, 2004, pp. 149-154.

Sun, et al., "p38 MAP kinase is activated at early stages in Alzheimer's disease brain" *Exp. Neurol.* Oct. 2003; 183(2): pp. 394-405.

Turconi, et al., "Synthesis of a New Class of 2,3-Dihydro-2-0xo-1H-Benzimidazole-1-Carboxylic Acid Derivatives as Highly Potent 5-HT$_3$ Receptor Antagonists," *J. Med. Chem.*, 33:2101-2108 (1990).

Yang, et al., "The cytokine activity of HMGB1" *J. Leukocyte Biol.*, 2005;78:1-8.

International Searching Authority, International Search Report, International Application No. PCT/US2004/015368, 2 pages, Feb. 2, 2005.

International Searching Authority, International Search Report, International Application No. PCT/US2004/024441, 1 page, Mar. 15, 2005.

\* cited by examiner

1,4-DISUBSTITUTED NAPHTHALENES AS INHIBITORS OF P38 MAP KINASE

CROSS-REFERENCE TO RELATED APPLICATIONS

This application is a divisional application of U.S. patent application Ser. No. 11/631,617, filed Jul. 20, 2007, which is a national phase application under 35 U.S.C. §371 of International Application PCT/US2005/024441, filed Jul. 8, 2005, which claims the benefit of U.S. Provisional Application No. 60/585,862, filed Jul. 8, 2004, all of which are incorporated herein by reference in their entirety.

BACKGROUND OF THE INVENTION

Many chronic and acute conditions are associated with perturbation of the inflammatory response. A large number of cytokines participate in this response, including, but not limited to, IL-1, IL-6, IL-8 and TNFα. Although these cytokines are expressed in a normal response to many physiological stimuli, excess, unregulated, or otherwise aberrant production of these cytokines can lead to inflammation and tissue damage. Diseases, for example, inflammatory and autoimmune diseases such as rheumatoid arthritis, can mediate morbidity though such aberrant production of cytokines (Keffer, J., et al, EMBO J., 13: 4025-4031, 1991, Feldmann, M., et al, Annu. Rev. Immunol., 14: 397-440, 1996 and Bingham, C. O., J. Rheumatol. Suppl., 65: 3-9, 2002). Currently there are several therapeutic agents that aim to reduce systemic levels of proinflammatory cytokines such as TNFα (Pugsley, M. K. Curr. Opin. Invest. Drugs, 2: 1725-1731, 2001 and Bondeson, J., and Maini, R. N., J. Clin. Pract., 55: 211-216, 2001; which are hereby incorporated by reference), and can thereby ameliorate disease. The current therapeutic agents act to reduce circulating levels of cytokines or neutralize activity of cytokines. The current therapeutic agents do not, however, directly block the intracellular proteins that regulate expression and secretion of proinflammatory cytokines. Moreover, the current therapeutic agents do not regulate the expression of other mediators of inflammation and tissue destruction.

The p38 MAP Kinase (also known as CSBP or SAPK, and hereinafter referred to as "p38") signaling pathway has been reported to be responsible for the expression of pro-inflammatory cytokines that are elevated in many inflammatory and autoimmune diseases (see, e.g., Dong, C., et al., Annu. Rev. Immunol., 20: 55-72, 2002; which is hereby incorporated by reference). Inhibitors of any part of the p38 pathway or inhibitors of pathways that regulate the p38 pathway may be useful as therapeutics for diseases or conditions in which inflammation or autoimmune responses are involved. (Lee, J. C., et al, Immunopharm, 47: 185-201, 2000; which is hereby incorporated by reference). The p38 pathway has been shown to be activated by cellular stressors, such as osmotic shock, UV light, free radicals, bacterial toxins, viruses, cytokines, and chemokines, to name a few, and in response, mediates the expression of several cytokines including, but not limited to, IL-1, IL-6, IL-8 and TNFα (Ono, K. and Han, J., Cellular Signalling, 12: 1-13, 2000; which is hereby incorporated by reference).

The p38 pathway can be directly or indirectly activated by cell surface receptors, such as receptor tyrosine kinases, chemokine or G protein-coupled receptors, which have been activated by a specific ligand, e.g., cytokines, chemokines or lipopolysaccharide (LPS) binding to a cognate receptor. The p38 is activated by phosphorylation on residues threonine 180 and tyrosine 182. After activation, p38 can phosphorylate other intracellular proteins, including protein kinases, and can be translocated to the cell nucleus, where it can phosphorylate and activate transcription factors leading to the expression of pro-inflammatory cytokines and other proteins that contribute to the inflammatory response, cell adhesion, and proteolytic degradation. For example, in cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of a physiological response to cellular stress, acute or chronic cellular stress can lead to excess, unregulated, prolonged, or otherwise aberrant expression of pro-inflammatory cytokines. This aberrant expression can lead to tissue damage, which often results in pain and debilitation. There are four known isoforms of p38 (p38α, p38β, p38δ and p38γ), each of which shows different expression levels, different tissue distribution, and different regulation patterns. This evidence supports the conclusion that p38 has a role in the etiology or sequelae of many diseases and physiological disturbances.

Many autoimmune diseases and diseases associated with chronic inflammation, as well as acute responses, have been linked to activation of p38, and activation of p38 in association with overexpression or dysregulation of other inflammatory cytokines. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptured, or prolapsed intervertebral disk syndrome; osteopetrosis; thrombosis; cancer; restenosis; silicosis; pulmonary sarcosis; bone resorption diseases, such as osteoporosis; graft-versus-host reaction; and autoimmune diseases, such as Multiple Sclerosis, lupus and fibromyalgia; AIDS and other viral diseases such as Herpes Zoster, Herpes Simplex I or II, influenza virus and cytomegalovirus; and diabetes mellitus.

Studies have shown that reducing the activity of p38 blunts the inflammatory response and prevents or minimizes tissue damage (see, e.g., English, J. M. and Cobb, M. H., Trends in Pharmacol. Sci., 23: 40-45, 2002; and Dong, C., et al, Annu. Rev. Immunol., 20: 55-72, 2002; which are hereby incorporated by reference). Therefore, inhibitors of p38 activity that also inhibit excess or unregulated cytokine production and inhibitors that can inhibit more than a single pro-inflammatory cytokine may be useful as anti-inflammatory agents and therapeutics. The large number of diseases accompanied by p38-associated inflammatory responses indicates that there is a need for effective methods for treating p38- and cytokine-associated conditions. However, no approved drugs are available that are known to directly inhibit the p38 family of enzymes. Moreover, the approved drugs that act by reducing or neutralizing cytokine levels through binding to the cytokine are not orally bioavailable and must, therefore, be administered by techniques such as injection.

Accordingly, new compounds and methods for treating p38- and cytokine-associated conditions are needed.

SUMMARY OF THE INVENTION

In general, the present invention relates to compounds capable of inhibiting p38, methods for inhibiting p38 in vivo or in vitro, methods for treating conditions associated with p38 activity or cytokine activity, and to compounds useful for preparing the compounds of the invention.

In one aspect, the present invention provides compounds represented by Formula I:

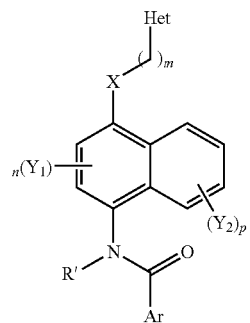

wherein
X is O, NR, $CH_2$, or a bond;
R is H or alkyl;
R' is H or alkyl;
m is 0, 1, or 2;
n is 0, 1, or 2;
p is 0, 1, 2, 3, or 4;
Ar is an aryl group;
Het is a heterocyclic group;
$Y_1$ is independently selected from the group consisting of halogen, alkyl, nitro, hydroxyl, and alkyloxy; and
$Y_2$ is independently selected from the group consisting of halogen, alkyl, nitro, hydroxyl, and alkyloxy.

In a preferred embodiment of Formula I, the compound is represented by Formula Ia:

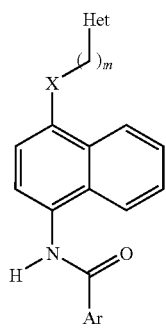

wherein
Ar, Het, X, R, and m have the meanings described for Formula I.

In another preferred embodiment, the compound is represented by the structure Formula Ib:

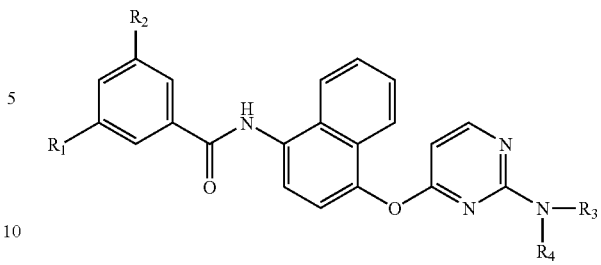

wherein
$R_1$ is H or F;
$R_2$ is selected from the group consisting of:

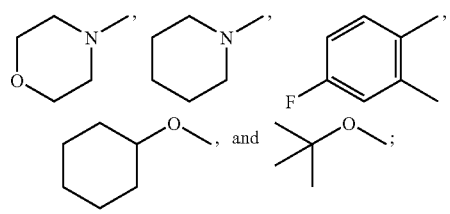

$R_3$ and $R_4$ are independently selected from hydrogen, aliphatic or aromatic secondary or tertiary amine and secondary or tertiary amine with additional functional groups such as alcohols, sulfone, heterocyclic aromatic rings with tertiary amines, and aliphatic tertiary amines; and wherein $R_3$ and $R_4$ together may form a ring having from 3-8 heteroatoms in the ring.

In another aspect, the present invention provides pharmaceutical compositions comprising one or more compounds of Formula I, together with a pharmaceutically acceptable carrier.

In another aspect, the present invention provides methods for treating p38-associated conditions. Methods of the present invention can include administering to the mammal an effective amount of compound of Formula I, such that the p38-associated condition is treated. In a preferred embodiment of the present invention, the p38-associated condition is rheumatoid arthritis, osteoarthritis or gouty arthritis (more preferably rheumatoid arthritis); Crohn's disease, ulcerative colitis, inflammatory bowel disease or psoriasis; or a proliferative disease, an autoimmune disease or an inflammatory disease.

In still another aspect, the present invention provides methods for treating conditions associated with cytokine activity. These methods can include administering to a mammal an effective amount of compound of Formula I, such that a condition associated with altered cytokine activity is treated. In a preferred embodiment, the cytokine-associated condition is rheumatoid arthritis, osteoarthritis or gouty arthritis; Crohn's disease, ulcerative colitis, inflammatory bowel disease or psoriasis; or a proliferative disease, an autoimmune disease or an inflammatory disease.

In still another aspect, the invention provides methods for treating conditions associated with specific isoforms of p38, for example, p38α, p38β, p38δ, p38γ, or combinations of these. In a most preferred embodiment of the present invention p38α is the specific isoform of p38. In a preferred embodiment, the p38α-associated condition is rheumatoid arthritis, osteoarthritis or gouty arthritis; Crohn's disease, ulcerative colitis, inflammatory bowel disease or psoriasis; or a proliferative disease, an autoimmune disease or an inflammatory disease.

In still another aspect, the invention provides methods for treating conditions associated with or mediated by p38, other kinases, or p38 and other kinases.

In still another aspect, the invention provides methods for treating disease conditions associated with one or more cytokines, where a cytokine is preferably selected from the group consisting of IL-1, IL-6, IL-8, and TNFα. In general, these methods include administering to a mammal or patient (e.g., a mammal in need of such treatment) an effective amount of a compound of Formula I, such that the mammal is treated. A preferred mammal is a human.

In yet another aspect, the present invention provides methods for inhibiting the activity of p38 in a cell, in vitro or in vivo. In general, these methods can include contacting a cell containing p38 with an effective p38-inhibiting amount of a compound of Formula I, under conditions such that p38 activity in the cell is inhibited.

In another aspect, the invention provides methods for characterizing p38 in a cell or tissue sample by determining, for example, the presence, location, or quantity of p38. These methods can include the steps of a) contacting the cell or tissue sample with a compound of Formula I under conditions such that the compound of Formula I can bind to p38 protein; and b) determining the presence, location and/or quantity of the compound of Formula I in the cell or tissue sample, thereby determining the presence, location and/or quantity of p38 protein in the cell or tissue sample.

In certain embodiments of the therapeutic methods of the present invention, one or more compound of Formula I may be combined with another agent, e.g., another pharmaceutically-active agent, for use in the inventive methods.

In still another aspect, the present invention provides a method for preparing a compound of Formula I or a salt thereof. The method can include reacting a compound of Formula II:

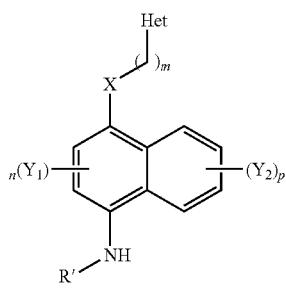

wherein
X, R, R', m, n, p, Het, $Y_1$ and $Y_2$ are as described for Formula I;
with a compound of Formula III:

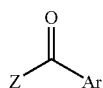

wherein
Ar is as described in Formula I; and
Z is OH or a leaving group;

under conditions such that a compound of Formula I is prepared.

These and other aspects and advantages of the invention will be apparent from the description herein.

DETAILED DESCRIPTION

The present invention provides compounds, pharmaceutical compositions, and methods useful for treatment of human and veterinary conditions related to p38 or cytokine activity or to p38 and cytokine activity or compounds, pharmaceutical compositions, and methods useful for treatment of human and veterinary conditions associated with p38 or cytokines or p38 and cytokines.

Definitions

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. A $C_1$-$C_6$ alkyl group is an alkyl group having from one to six carbon atoms in the straight or branched alkyl backbone. Alkyl groups optionally can be substituted with one or more moieties such as hydroxyl group, carboxylate, oxo, halogen, thiol, cyano, nitro, amino, —$NR_{12}R_{13}$, $C_1$-$C_6$ alkylthio, arylthio, $C_1$-$C_6$ alkyl, $C_1$-$C_6$ alkoxy, aryloxy, alkylcarbonyloxy, arylcarbonyloxy, $C_3$-$C_6$ cycloalkyl, $C_3$-$C_6$ cycloalkyloxy, $C_2$-$C_6$ alkenyl, $C_2$-$C_6$ alkynyl, aryl, aminocarbonyl, $C_1$-$C_6$ alkylcarbonyl, $C_3$-$C_6$ cycloalkylcarbonyl, heterocyclylcarbonyl, arylcarbonyl, aryloxycarbonyl, $C_1$-$C_6$ alkoxycarbonyl, $C_3$-$C_6$ cycloalkyloxycarbonyl, heterocyclyloxycarbonyl, $C_1$-$C_6$ alkylsulfonyl, arylsulfonyl, a heterocyclyl group, and the like.

A "cycloalkyl" group refers to a cyclic alkyl group which has a ring having from three to seven carbon atoms in the ring portion. A cycloalkyl group may be substituted with one or moieties as described for alkyl groups.

The term "alkenyl" refers to a hydrocarbon radical having at least one carbon-carbon double bond. A $C_2$-$C_6$ alkenyl group is an alkenyl group having from two to six carbon atoms in straight or branched alkenyl backbone. Exemplary alkenyl radicals include, without limitation, vinyl, propenyl, 2-butenyl, and the like. An alkenyl group may be substituted with one or moieties as described for alkyl groups.

The term "alkynyl," as used herein, refers to a hydrocarbon radical having at least one carbon-carbon triple bond. A $C_2$-$C_6$ alkynyl group is an alkynyl group having from two to six carbon atoms in straight or branched alkynyl backbone. Exemplary alkynyl moieties include propynyl, 3-hexynyl, and the like. An alkynyl group may be substituted with one or moieties as described for alkyl groups.

The term "aryl" refers to an aromatic carbocyclic or heteroaromatic moiety, having one, two, or three rings. An aryl group may be carbocyclic or may optionally contain from 1-4 heteroatoms (such as nitrogen, sulfur, or oxygen) in the aromatic ring. Exemplary aryl radicals include, without limitation, phenyl, naphthyl, pyridyl, pyrimidyl, triazyl, quinazolinyl, thiazolyl, benzothiophenyl, furanyl, imidazolyl, and the like. An aryl group optionally can be substituted with one or more substituents such as hydroxyl group, halogen, thiol, cyano, nitro, amino, —$NR_{12}R_{13}$, $C_1$-$C_6$ alkylthio, arylthio, $C_1$-$C_6$ alkyl, $C_1$-$C_6$ alkoxy, aryloxy, alkylcarbonyloxy, arylcarbonyloxy, $C_3$-$C_6$ cycloalkyl, $C_3$-$C_6$ cycloalkyloxy, $C_2$-$C_6$ alkenyl, $C_2$-$C_6$ alkynyl, aryl, carboxylate, aminocarbonyl, $C_1$-$C_6$ alkylcarbonyl, $C_3$-$C_6$ cycloalkylcarbonyl, heterocyclylcarbonyl, arylcarbonyl, aryloxycarbonyl, $C_1$-$C_6$ alkoxycarbonyl, $C_3$-$C_6$ cycloalkyloxycarbonyl, heterocyclyloxycarbonyl, aryloxycarbonyl, $C_1$-$C_6$ alkoxycarbonyl, $C_1$-$C_6$ alkylsulfonyl, arylsulfonyl, a heterocyclyl group, and the like.

The term "heterocyclyl" or "heterocycle" refers to a stable 3-8 membered monocyclic heterocyclic ring or 7-11 membered bicyclic heterocyclic ring which is either saturated or unsaturated (including aromatic), and may be fused, spiro or bridged to form additional rings. Each heterocycle consists of one or more carbon atoms and from one to four heteroatoms selected from the group consisting of nitrogen, oxygen and sulfur. A heterocyclyl radical may be attached at any endocyclic atom which results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, pyranyl, pyridinyl, pyridonyl, tetrazolyl, triazolyl, piperazinyl, morpholinyl, thiamorpholinyl, thiamorphinyl sulfone, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl. A heterocycle may optionally be substituted with one or more substituents as described above for alkyl groups, although an endocyclic oxygen may not be substituted, and an endocyclic nitrogen atom may be substituted with hydrogen, $C_1$-$C_6$ alkyl, $C_3$-$C_6$ cycloalkyl, $C_2$-$C_6$ alkenyl, $C_2$-$C_6$ alkynyl, aryl, aminocarbonyl, $C_1$-$C_6$ alkylcarbonyl, arylcarbonyl, aryloxycarbonyl, $C_1$-$C_6$ alkoxycarbonyl, $C_1$-$C_6$ alkylsulfonyl, arylsulfonyl, or a heterocyclyl group. An "azacycle," as used herein, refers to an endocyclic-nitrogen-containing heterocycle as described above. Preferred azacycles include (without limitation) substituted or unsubstituted pyrrolidinyl, piperidinyl, piperazinyl, morpholino, azepinyl, pyridinyl, triazolyl, tetrazolyl, quinuclidinyl(1-azabicyclo[2.2.2]octanyl), and tropanyl(8-methyl-8-azabicyclo[3.2.1]octanyl).

The term "halogen" refers to an atom selected from fluorine, chlorine, bromine, and iodine.

The term "amino," as used herein, refers to a moiety represented by the formula —$NR_{10}R_{11}$, in which $R_{10}$ and $R_{11}$ are each independently selected from the group consisting of hydrogen, $C_1$-$C_6$ alkyl, $C_3$-$C_6$ cycloalkyl, aryl, and a heterocyclyl moiety; or $R_{10}$ and $R_{11}$, together with the nitrogen atom to which they are both attached, form a 3-8 membered heterocyclic ring (which may be fused or bridged as described above for heterocyclyl moieties). Preferred amino groups include —$NH_2$, monoalkylamino (—$NHC_1$-$C_6$ alkyl), dialkylamino (—$N(C_1$-$C_6$ alkyl)$_2$), monoarylamino (—NH-aryl), arylalkylamino (—N(aryl)($C_1$-$C_6$ alkyl)), and the like.

$R_{12}$ is selected from the group consisting of hydrogen, $C_1$-$C_6$ alkyl, and aryl. $R_{13}$ is selected from the group consisting of —C(O)—$C_1$-$C_6$ alkyl, —C(O)—$C_3$-$C_6$ cycloalkyl, —C(O)-aryl, —C(O)-heterocyclyl, —C(O)O—$C_1$-$C_6$ alkyl, —C(O)O—$C_3$-$C_6$ cycloalkyl, —C(O)O-aryl, —C(O)O-heterocyclyl, —C(O)-amino, —$SO_2$—$C_1$-$C_6$ alkyl, —$SO_2$—$C_3$-$C_6$ cycloalkyl —$SO_2$-aryl, and —$SO_2$-heterocyclyl.

Unless specifically indicated otherwise, the N-oxide form of any nitrogen atom is included in the compounds and methods of the invention.

I. Compounds of the Invention

In one aspect, the invention provides compounds represented by Formula I:

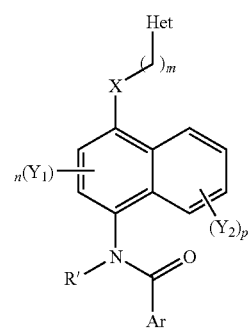

wherein
X is O, NR, $CH_2$, or a bond;
R is H or alkyl;
R' is H or alkyl;
m is 0, 1, or 2;
n is 0, 1, or 2;
p is 0, 1, 2, 3, or 4;
Ar is an aryl group;
Het is a heterocyclic group;
$Y_1$ is independently selected from the group consisting of halogen, alkyl, nitro, hydroxyl, and alkyloxy; and
$Y_2$ is independently selected from the group consisting of halogen, alkyl, nitro, hydroxyl, and alkyloxy.

In an embodiment of Formula I, m is 1 or 2.
In an embodiment of Formula I, n is 0.
In an embodiment of Formula I, p is 0.
In a preferred embodiment of Formula I, the compound is represented by the structure Formula Ia:

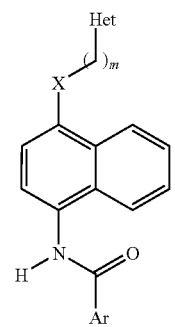

wherein Ar, Het, X, R, and m have the meanings described for Formula I.

In a preferred embodiment of Formula I, X is selected from the group consisting of $CH_2$ and oxygen.

In a preferred embodiment of Formula I, Ar is a phenyl group. In a preferred embodiment, the phenyl group is substituted with a group selected from the group consisting of:

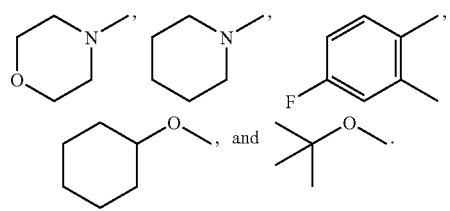

In a preferred embodiment, Ar is disubstituted. In a highly preferred embodiment, Ar is a phenyl group substituted with a fluorine group and a group selected from the group consisting of

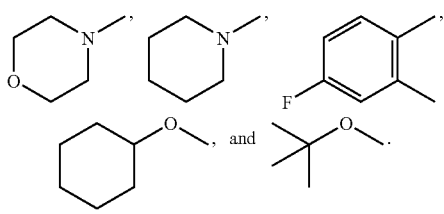

In a highly preferred embodiment of Formula I, Het is selected from the group consisting of:

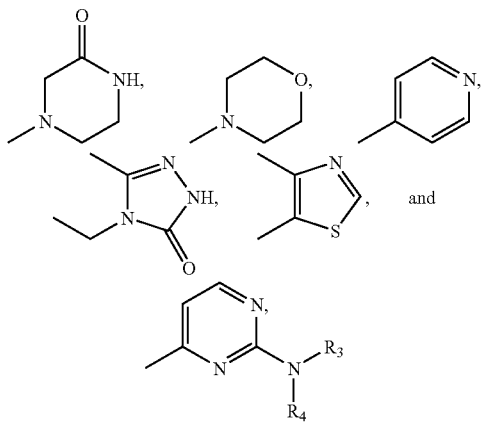

wherein:

$R_3$ and $R_4$ are independently selected from hydrogen, aliphatic or aromatic secondary or tertiary amine, secondary or tertiary amine with additional functional groups such as alcohols, sulfone, heterocyclic aromatic rings with tertiary amines, and aliphatic tertiary amines; and wherein $R_3$ and $R_4$ together may form a ring having from 3-8 heteroatoms in the ring.

In another highly preferred embodiment, Het is selected from the group consisting of:

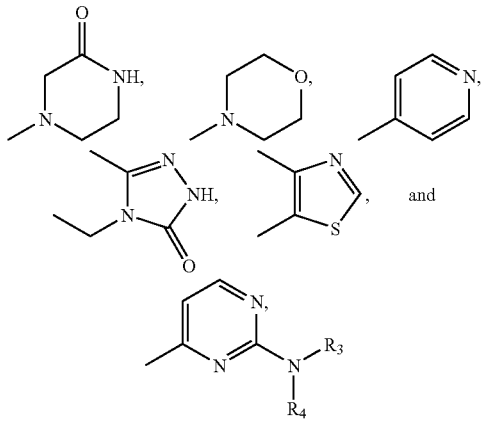

wherein $R_3$ and $R_4$ are independently selected from hydrogen, aliphatic or aromatic secondary or tertiary amine, secondary or tertiary amine with additional functional groups such as alcohols, sulfone, heterocyclic aromatic rings with tertiary amines, and aliphatic tertiary amines;

wherein $R_3$ and $R_4$ together may form a ring having from 3-8 heteroatoms in the ring;

and Ar is substituted with a fluorine group and a phenyl group, wherein the phenyl group is substituted with a group selected from the group consisting of

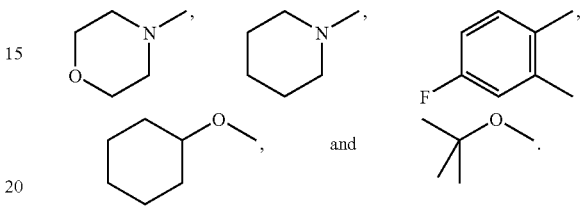

In a very highly preferred embodiment of Formula I, the compound is represented by Formula Ib:

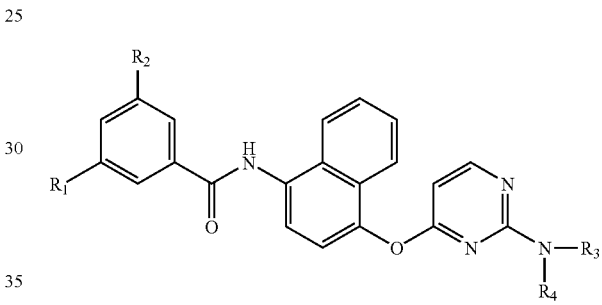

wherein
$R_1$ is H or F;
$R_2$ is selected from the group consisting of:

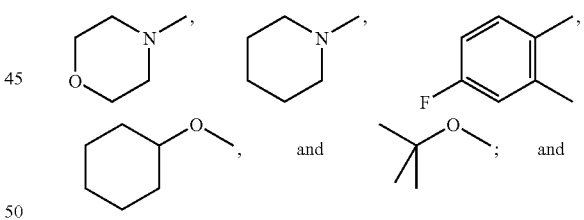

wherein
$R_3$ and $R_4$ are independently selected from hydrogen, aliphatic or aromatic secondary or tertiary amine and secondary or tertiary amine with additional functional groups such as alcohols, sulfone, heterocyclic aromatic rings with tertiary amines, and aliphatic tertiary amines; and wherein $R_3$ and $R_4$ together may form a ring having from 3-8 heteroatoms in the ring.

Compounds of Formula I can also include tracers, tags or labeling moieties, e.g., radioisotopes (such as tritium, carbon-14, or sulfur-35), fluorescent labels, and the like, which are known to one of ordinary skill in the art. Such labeled compounds can be used in methods for detecting or determining the presence of p38 in a cell or a tissue type.

In preferred embodiments, compounds of Formula I are selected to preserve the desired activity of the compounds (e.g., inhibition of cytokine activity, including inhibition of TNFα activity and IL-1 activity, or inhibition of p38 activity). Thus, substituents of a compound of Formula I should be selected to preserve such activity. For example, in a preferred embodiment, the substituent R' (attached to the amide nitrogen of a compound of Formula I) is hydrogen. Preservation of activity can be determined using in vivo and in vitro assays such as the assays described elsewhere in this specification.

Preferred embodiments of the invention include, for example, compounds depicted as Formula Ia and Formula Ib.

A compound of the invention can inhibit phosphorylation of a substrate by p38 MAP Kinase in vitro or in vivo. In a preferred embodiment, a compound of the invention inhibits phosphorylation of a substrate by p38 MAP Kinase in vitro. In a preferred embodiment, the substrate is ATF2. Inhibition of phosphorylation of a substrate by p38 MAP Kinase can be measured by any method known to the skilled artisan. Inhibition of phosphorylation can be measured as the concentration of compound at which 50% inhibition of phosphorylation results ($IC_{50}$). Inhibition of phosphorylation occurs at any concentration of compound where the phosphorylation of a substrate by p38 MAP Kinase is decreased in comparison to the phosphorylation of the substrate by p38 MAP Kinase in the absence of the compound. In an embodiment, a compound exhibits an $IC_{50}$ value between about 0.0001 and about 100 µM ($IC_{50}$). In a preferred embodiment, a compound of the invention has an $IC_{50}$ value of between about 0.0001 and about 10 µM; more preferably the $IC_{50}$ value is less than about 5 µM; more preferably less than about 2 µM; more preferably less than about 1 µM; and even more preferably less than about 0.1 µM.

In a preferred embodiment, a compound of the invention inhibits cytokine release in vitro or in vivo. In a preferred embodiment, a compound of the invention inhibits cytokine release in vitro Inhibition of the release of any cytokine can be measured by any method known to the skilled artisan. Inhibition of cytokine release can be measured as the concentration of compound at which 50% inhibition of cytokine release results ($IC_{50}$). In a preferred embodiment, TNFα or IL-1β is inhibited or both TNFα and IL-1β are inhibited. Inhibition of cytokine release occurs at any concentration of compound where the cytokine release is decreased in comparison to the cytokine release in the absence of the compound. In an embodiment, a compound exhibits an $IC_{50}$ value between about 0.0001 and about 100 µM ($IC_{50}$). In a preferred embodiment, a compound of the invention has an $IC_{50}$ value of between about 0.0001 and about 10 µM; more preferably the $IC_{50}$ value is less than about 5 µM; more preferably less than about 2 µM; more preferably less than about 1 µM; and even more preferably less than about 0.1 µM.

In general, structures depicted herein are meant to include all stereochemical forms of the structure; i.e., the R and S configurations for each asymmetric center, unless a particular stereochemistry is specifically indicated. Therefore, single stereochemical isomers (i.e., substantially pure enantiomers and diasteromers) as well as enantiomeric and diastereomeric mixtures, such as racemic mixtures, of the present compounds are within the scope of the invention. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated.

The present invention includes salts of the compounds of the invention. In a preferred embodiment, a salt of a compound of the present is a "pharmaceutically acceptable salt." A "pharmaceutically acceptable salt" means a salt which is, within the scope of sound medical judgment, suitable for pharmaceutical use in a patient without undue toxicity, irritation, allergic response, and the like, and effective for the intended use.

The present invention also includes compounds that are prodrugs of an active compound. In general, a prodrug is a compound that is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the compounds of the invention. Examples of pharmaceutically-acceptable prodrug types contemplated by the present invention are described in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The compounds and compositions of the invention can also include metabolites. As used herein, the term "metabolite" means a product of metabolism of a compound of the invention or a pharmaceutically acceptable salt, analog, or derivative thereof, that exhibits a similar activity in vitro or in vivo to a compound of the invention.

The compounds and compositions of the invention can also include hydrates and solvates. As used herein, the term "solvate" refers to a complex formed by a solute (in this invention, a compound of Formula I and a solvent, for example). Such solvents for the purpose of the invention preferably should not interfere with the biological activity of the solute. Solvents may be, by way of example, water, ethanol, or acetic acid.

II. Methods and Intermediates for Preparing Compounds of the Invention

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic to Chemistry: Reactions, Mechanisms, and Structure, 5$^{th}$ ed.; John Wiley & Sons: New York, 2001; and Greene, T.W.; Wuts, P.G. M. Protective Groups in Organic Synthesis, 3$^{rd}$; John Wiley & Sons: New York, 1999 are useful and recognized reference textbooks of organic synthesis known to those in the art. The following descriptions of synthetic methods are designed to illustrate, but not limit, general procedures for the preparation of compounds of the invention.

For example, a method for synthesis can include reacting a compound of Formula II:

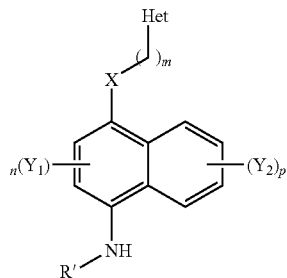

wherein
X, R, R', m, n, p, Het, $Y_1$ and $Y_2$ are as described for Formula I;
with a compound of Formula III:

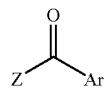

wherein
Ar is as described in Formula I; and
Z is OH or a leaving group;
under conditions such that a compound of Formula I is prepared.

This amide-forming reaction can be performed under a range of conditions, some of which are known in the art, and may involve the use of coupling reagents, bases, or other reagents. A wide variety of compounds of Formula III can be purchased from commercial vendors, or can be prepared according to methods known to one of ordinary skill in the art.

Preparation of compounds of the invention is further described, for example, in the Examples and Schemes below.

III. Therapeutic and Diagnostic Methods of the Invention

In another aspect, the invention provides methods for treating disease conditions associated with (e.g., mediated directly or indirectly by) p38 or one or more cytokines. For example, in a preferred embodiment, the methods include administering to a subject in need of treatment (e.g., a mammal in need of such treatment) a therapeutically or prophylactically effective amount of a compound of the invention. The compound of the invention can be a compound of Formula I. Preferably, the compound may be a compound of Formula Ia, Formula Ib, or any combination thereof. A subject may include one or more cells or tissues, or organisms. A preferred subject is a mammal A mammal may include any mammal As a non-limiting example, preferred mammals include cattle, pigs, sheep, goats, horses, camels, buffalo, cats, dogs, rats, mice, and humans. A highly preferred subject mammal is a human.

According to the methods of the invention, the compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

In one embodiment, the invention provides methods for treating disease conditions in which p38 activity contributes to the disease phenotype. The method includes administering a therapeutically or prophylactically effective amount of a compound of the invention to a subject in need thereof. Again, the compound of the invention can be a compound of Formula I or any combination of compounds of Formula I. In a preferred embodiment, the compound may be a compound of Formula Ia or Formula Ib, or any combination thereof.

The term "p38-associated condition" means a disease or other deleterious condition in which the p38 MAP kinase signaling pathway is implicated, whether directly or indirectly. This includes, but is not limited to, conditions caused by IL-1, TNFα, IL-6 or IL-8 dysregulation or overexpression resulting from sustained, prolonged, enhanced or elevated levels of p38 activity. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the prostaglandin or cyclooxygenase and lipoxygenase signalling pathways, e.g., conditions involving prostaglandin endoperoxide synthase-2. A p38-associated condition can include any condition associated with or mediated by an isoform of p38. In a preferred embodiment, the p38-associated condition is a condition associated with p38α.

The term "modulating p38 activity" means increasing or decreasing p38 activity, whether in vitro or in vivo. Modulating p38 activity preferably means decreasing (inhibiting) p38 activity. In certain preferred embodiments, p38 activity in a cell is inhibited by at least 20%, more preferably at least 30%, 40%, 50%, 80%, 90%, 95%, or 99% compared to the p38 activity of an untreated control cell, tissue or organism. In preferred embodiments, p38 activity in a cell (or tissue or organism) is restored to a normal range for the cell (or tissue or organism) type upon treatment according to the methods of the invention.

In another embodiment, the invention provides methods for treating disease conditions associated with a cytokine or cytokines. The method includes administering a therapeutically or prophylactically effective amount of a compound of the invention to a subject in need thereof. Again, the compound of the invention can be a compound of Formula I. Preferably, the compound may be a compound of Formula Ia, Formula Ib, or any combination thereof. In a preferred embodiment, at least one of the cytokine or cytokines is preferably selected from the group consisting of IL-1, IL-6, IL-8, and TNFα. In a more preferred embodiment, all of the cytokine or cytokines are selected from the group consisting of IL-1, IL-6, IL-8, and TNFα. By way of non-limiting example, the methods include administering to a subject in need of treatment (e.g., a mammal in need of such treatment) an effective amount of a compound of the invention.

A condition associated with altered cytokine activity, as used herein, refers to a condition in which cytokine activity is altered compared to a non-diseased state. This includes, but is not limited to, conditions caused by IL-1, TNFα, IL-6 or IL-8 overproduction or dysregulation resulting in sustained, prolonged, enhanced or elevated levels of cytokine activity, which may be associated with p38 activity. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the prostaglandin or cyclooxygenase and lipoxygenase signaling pathways, such as prostaglandin endoperoxide synthase-2. A cytokine-associated condition can include any condition associated with or mediated by IL-1 (particularly IL-1β), TNFα, IL-6 or IL-8, or any other cytokine which can be regulated by p38. In preferred embodiments, the cytokine-associated condition is a condition associated with TNFα.

The term "therapeutically effective amount", as used herein, refers to any amount of a compound of the invention sufficient to treat a disease or condition, including preventing a disease or condition, ameliorating symptoms, slowing progression, reversing damage, ameliorating the disease or condition, or a combination thereof, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, pigs, or primates. The animal model may also be used to determine the appropriate concentration range and route of administration. Such information can then be used to determine useful doses and routes for administration in humans. Therapeutic/prophylactic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosages for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the initial target plasma concentration may range from approximately 10 ng/mL to approximately 100 μg/mL, preferably from approximately 10 ng/mL to approximately 10 μg/mL, more preferably from approximately 10 ng/mL to approximately 1 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage can be determined by the practitioner, in light of factors related to the subject that requires treatment. Dosage and administration are adjusted to provide sufficient levels of the active agent or agents or to maintain the desired effect. Factors which may be taken into account include the severity of the disease state, general health of the subject, age, weight, and gender of the subject, diet, time and frequency of administration, drug combination or combinations, reaction sensitivities, and tolerance/response to therapy. Long-acting pharmaceutical compositions may be administered every 3 to 4 days, every week, or once every two weeks depending on half-life and clearance rate of the particular formulation.

The inventive methods can also be used to treat autoimmune diseases and diseases associated with acute and chronic inflammation. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; chronic obstructive pulmonary disease; chronic pulmonary inflammation; inflammatory bowel disease; Crohn's disease; psoriasis; eczema; ulcerative colitis; glomerular nephritis; scleroderma; chronic thyroiditis; Grave's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and autoimmune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the invention can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation. In addition, compounds of the invention may be useful for treatment of protozoal diseases in animals, including mammals.

It will be appreciated that treatment according to the invention includes preventing a disease or condition, ameliorating symptoms, slowing progression, reversing damage, ameliorating a disease or condition, or a combination thereof.

In one aspect, treating a disease condition associated with p38 or one or more cytokines results in an increase in average survival time of a population of treated subjects in comparison to a population of untreated subjects. Preferably, the average survival time is increased by more than 30 days; more preferably, by more than 60 days; more preferably, by more than 90 days; and even more preferably by more than 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating a disease condition associated with p38 or one or more cytokines results in a decrease in the mortality rate of a population of treated subjects in comparison to a population of subjects receiving carrier alone. In another aspect, treating a disease condition associated with p38 or one or more cytokines results in a decrease in the mortality rate of a population of treated subjects in comparison to an untreated population. In a further aspect, treating a disease condition associated with p38 or one or more cytokines results a decrease in the mortality rate of a population of treated subjects in comparison to a population receiving monotherapy with a drug that is not a compound of the present invention, or a pharmaceutically acceptable salt, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating a disease condition associated with p38 or one or more cytokines results in a decrease in growth rate of a tumor. Preferably, after treatment, tumor growth rate is reduced by at least 5% relative to the tumor growth rate prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. Tumor growth rate may be measured by any reproducible means of measurement. In a preferred aspect, tumor growth rate is measured according to a change in tumor diameter per unit time.

In another aspect, treating a disease condition associated with p38 or one or more cytokines results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 60%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating a disease condition associated with p38 or one or more cytokines results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 60%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating a disease condition associated with p38 or one or more cytokines results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 60%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating a disease condition associated with p38 or one or more cytokines results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating a disease condition associated with p38 or one or more cytokines results in a decrease in inflammation. Preferably, after treatment, the size of an area of inflammation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. Size of an area of inflammation may be measured by any reproducible means of measurement. In a preferred aspect, size of an area of inflammation may be measured as a diameter or width of the area of inflammation.

The methods of the present invention may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds of the invention may be formulated in pharmaceutical compositions, if desired, and can be administered by any route that permits treatment of the disease or condition. A preferred route of administration is oral administration. Administration may take the form of single dose administration, or the compound of the invention can be administered over a period of time, either in divided doses or in a continuous-release formulation or administration method (e.g., a pump). However the compounds of the invention are administered to the subject, the amounts of compound administered and the route of administration chosen should be selected to permit efficacious treatment of the disease condition.

The methods of the invention also include the use of a compound or compounds of the invention together with one or more additional therapeutic agents for the treatment of disease conditions. Thus, for example, in certain embodiments, the invention provides the use of a compound of the invention, or a pharmaceutically acceptable salt or solvate thereof, in combination with other pharmaceutically active agents in the treatment of disease. Pharmaceutically active agents include any pharmaceutical agents that are useful for the treatment of any disease condition. In one non-limiting example, the compounds of the invention are pharmaceutically active agents that can be combined with other pharmaceutically active agents for the treatment of rheumatoid arthritis. Such other pharmaceutically active agents include, but are not limited to: matrix metalloprotease inhibitors and other DMARDs (disease-modifying anti-rheumatic drugs) such as methotrexate, sulfasalazine, hydroxychloroquine, penicillamine, cyclosporin A, gold sodium thiomalate, auroanofin and aurothioglucose; CD8 antagonists; anti-TNFα agents; immunosuppressants and NSAIDs (non-steroidal anti-inflammatories). For treatment of other disease conditions, any additional active agents may be used, as will be apparent to the skilled artisan.

According to the methods of the invention, the combination of active ingredients may be: (1) co-formulated and administered or delivered simultaneously in a combined formulation; (2) delivered by alternation or in parallel as separate formulations; or (3) delivered by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In an embodiment of the present invention, methods are provided for inhibiting the activity of p38 in a cell, in vitro or in vivo. The methods include contacting a cell or tissue containing p38 with an effective p38-inhibiting amount of a compound of the invention, under conditions such that p38 activity in the cell or tissue is inhibited. Contacting a cell refers to a condition in which a compound or other composition of matter is in direct contact with a cell or tissue, or is close enough to induce a desired biological effect in a cell or tissue. For example, contacting a cell or tissue containing p38 with a compound of the invention may be conducted by any means that permits an interaction between p38 and the compound of the invention, resulting in the desired biological effect in a cell. Contacting a cell or tissue may be accomplished, for example, by introduction of a compound of the invention such as a Formula I compound, prodrug or intermediate. Contacting a cell or tissue may be accomplished by introduction of a pharmaceutical composition. Contacting a cell or tissue may be accomplished by direct introduction of the active compound to the cell or tissue containing p38. Alternatively, for example, contacting a cell or tissue may be accomplished by introducing a compound in a manner that the compound will be targeted, directly or indirectly, to a cell or tissue containing p38. Contacting a cell or tissue may be accomplished under conditions such that a compound of the invention, preferably Formula I, can bind to p38 protein. Such conditions may include proximity of the compound and p38-containing cell or tissue, pH, temperature, or any condition that affects the binding of a compound of the invention to p38 protein.

In another aspect, the invention provides a method for modulating p38 activity in a cell or secreted by a cell. The method includes contacting a cell containing p38 with an effective p38-inhibiting amount of a compound of the invention, under conditions such that p38 activity in the cell is modulated (more preferably, inhibited). In certain embodiments, the cell is contacted with the compound of the invention in vitro; in other embodiments, the cell is contacted with the compound of the invention in vivo. In certain embodiments, the compound of the invention is provided in the form of a pharmaceutical composition, together with a pharmaceutically acceptable carrier.

In another aspect, the invention provides a method for modulating cytokine activity or levels in a cell. The method includes contacting a cell containing cytokines with an effective cytokine-inhibiting amount of a compound of the invention, under conditions such that cytokine activity or levels in the cell are modulated (more preferably, inhibited). In certain embodiments, the cell is contacted with the compound of the invention in vitro; in other embodiments, the cell is contacted with the compound of the invention in vivo. In certain embodiments, the compound of the invention is provided in the form of a pharmaceutical composition, together with a pharmaceutically acceptable carrier.

In another aspect, the invention provides methods for determining whether a compound of Formula I is potentially useful as a therapeutic agent for the treatment of p38- or cytokine-associated conditions. In some embodiments, the methods comprise contacting p38 with a compound of the invention, and determining whether the compound of the invention modulates (preferably, inhibits) the activity of p38. In some embodiments, the methods comprise contacting p38 with a compound of the invention, and determining whether the compound of the invention modulates (preferably, inhibits) the activity of cytokines. In preferred embodiments, the contacting step takes place in vitro; in certain preferred embodiments, the contacting step comprises contacting a cell comprising p38 with a compound of Formula I.

The methods of the invention have many uses. For example, methods of inhibiting p38 activity in vitro may be useful, e.g., in developing screening assays (e.g., as a positive control), or as a research or diagnostic tool for studying the role of p38 in cellular function (e.g., inhibiting p38 to determine the effect of such inhibition on other functions in the cell). Especially useful for this purpose are compounds of the invention in which the compounds contain a label or tag such as a radioisotope or a fluorescent label. Such labeled compounds can be used in methods for detecting or determining the presence, activity or distribution of p38 in a cell or a tissue type, e.g., by contacting a cell or tissue with a labeled compound of the invention, and then detecting the presence or absence of the label in the cell or tissue.

Accordingly, diagnostic tests are contemplated as part of the present invention. For example, a tissue biopsy sample can be taken from a subject suffering from a p38-associated or cytokine-associated condition. The biopsy sample can be tested to determine the level of p38 activity (or cytokine levels) present in the sample; the sample can then be contacted with a compound of the invention, and the p38 activity (or cytokine levels) measured to determine whether the compound of Formula I has a desired effect (e.g., inhibition of p38 or cytokine activity). Such a test could be used to determine whether treatment with a compound of the invention is likely to be effective in that subject. Alternatively, the sample could be contacted with a labeled compound of the invention (e.g., a fluorescently-labeled compound) and the sample then examined (e.g., under a confocal microscope) to determine the distribution of p38 in the tissue sample. Repeated biopsy samples taken during a course of treatment could also be used to study the efficacy of the treatment. Other diagnostic tests using the compounds of the invention will be apparent to one of ordinary skill in the art in light of the teachings of this specification.

Thus, for example, the invention provides methods for determining the presence, location, or quantity, or any combination thereof of p38 protein in a cell or tissue sample. The methods include a) contacting the cell or tissue sample with a compound of the invention under conditions such that the compound can bind to p38 protein; and b) determining the presence, location, or quantity, or any combination thereof of the compound of the invention in the cell or tissue sample, thereby determining the presence, location, or quantity, or any combination thereof of p38 protein in the cell or tissue sample. Determining the presence, location, or quantity, or any combination thereof of the compound of the invention in the cell or tissue sample may be conducted by any means that reveals the presence, location, or quantity, or any combination thereof of the compound in the cell or tissue. For example, as described previously, radioactive or fluorescent labeling methods may be used. Additional methods of determining the presence, location, or quantity, or any combination thereof of a compound of the invention will be apparent to a skilled artisan.

In another embodiment, the invention provides methods for determining (1) whether a compound of the invention will be a useful therapeutic agent for treatment of a subject suffering from a p38-associated condition, or (2) the severity of disease or (3) the course of disease during treatment with a disease-modifying agent. The methods include: a) obtaining a cell or tissue sample from the subject before, during and after termination of treatment with a compound of the invention or another disease-modifying agent; b) contacting the sample with a compound of the invention; and c) determining the amount of the compound of the invention that binds to the sample, wherein binding to p38 protein by the compound is related to the amount of p38 protein in the sample.

In another embodiment, the invention provides methods for determining (1) whether a compound of the invention will be a useful therapeutic agent for treatment of a subject suffering from a cytokine-associated condition, or (2) the severity of disease or (3) the course of disease during treatment with a disease-modifying agent. The methods include: a) obtaining a cell or tissue sample from the subject before, during and after termination of treatment with a compound of the invention or another disease-modifying agent; b) contacting the sample with a compound of the invention and c) determining the amount of the compound of the invention that binds to the sample, wherein binding to p38 protein by the compound is related to the amount of p38 protein in the sample, and the amount of p38 in the sample is related to the quantity of cytokines released. In an exemplary embodiment, such a method may be conducted by obtaining cells from a cancer cell line, contacting cells from the cancer cell line, such as, for example, cells from a metastatic breast carcinoma, colorectal carcinoma, malignant melanoma, gastric cancer, or non-small cell lung cancer line with a compound of the present invention and determining the binding.

IV. Pharmaceutical Compositions

While it is possible for the compounds of the present invention to be administered neat, it may be preferable to formulate the compounds as pharmaceutical compositions. As such, in yet another aspect of the invention, pharmaceutical compositions useful in the methods of the invention are provided. More particularly, the pharmaceutical compositions of the invention may be useful, inter alia, for treating conditions associated with p38 activity or cytokine activity or any combination thereof. A pharmaceutical composition contains an amount of a compound of the invention sufficient to achieve an intended therapeutic effect.

A pharmaceutical composition is any composition that may be administered in vitro or in vivo or both to a subject in order to treat a disease or condition by preventing a disease or condition, ameliorating symptoms, slowing progression, reversing damage, ameliorating a disease or condition, or a combination thereof. In a preferred embodiment, a pharmaceutical composition may be administered in vivo. As described previously herein, a subject may include one or more cells or tissues, or organisms. A preferred subject is a mammal A mammal includes any mammal, such as by way of non-limiting example, cattle, pigs, sheep, goats, horses, camels, buffalo, cats, dogs, rats, mice, and humans. A highly preferred subject mammal is a human.

The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositons of the invention may optionally include one or more ingredients such as preservatives, absorption promoters to enhance bioavailability, fluorocarbons, other solubilizing or dispersing agents or any combination of such ingredients. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment or prevention of bacterial infection (e.g., anti-bacterial or anti-microbial agents).

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use, tablets, troches, lozenges, dragees, aqueous or oil suspensions, non-aqueous solutions, dispersible powders or granules (including micronized particles or nanoparticles), emulsions, hard or soft capsules, syrups or elixirs, for example, may be prepared. Compositions intended for oral use may be prepared according to any method known in the art for the manufacture of pharmaceutical compositions, and such compositions may contain one or more agents including preserving agents or sweetening agents, flavoring agents, and coloring agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occuring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using any suitable dispersing or wetting agents and suspending agents such as those mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition of the invention, a pharmaceutically acceptable salt of a compound of the invention may be dissolved in an aqueous solution of an organic or inorganic acid, such as for example, a 0.3 M solution of succinic acid, or more preferably, citric acid. If a soluble salt form is not available, the compound of formula (I) may be dissolved in a suitable co-solvent or combination of co-solvents. Examples of suitable co-solvents include alcohol, propylene glycol, polyethylene glycol 300, polysorbate 80, glycerin and the like in concentrations ranging from 0 to 60% of the total volume. In one embodiment, the active compound of Formula I is dissolved in DMSO and diluted with water. The pharmaceutical composition may also be in the form of a solution of a salt form of the active ingredient in an appropriate aqueous vehicle, such as for example, water or isotonic saline or dextrose solution. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

In another embodiment, pharmaceutical compositions of the invention may be formulated for administration by inhalation. For administration by inhalation, a pharmaceutical composition of the present invention may be formulated as a powdered mix containing a compound of the invention and a suitable powder base such as lactose or starch for example. Such pharmaceutical compositions can be delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas.

In an embodiment, pharmaceutical compositions are prepared for topical application. Pharmaceutical compositions for topical administration can be formulated in a suitable ointment containing the active component suspended or dissolved in one or more excipients. Excipients for topical administration of the compounds of this invention can include, but are not limited to, mineral oil, liquid petrolatum, white petrolatum, propylene glycol, polyoxyethylene, polyoxypropylene compound, emulsifying wax and water. Alternatively, pharmaceutical compositions of the present invention can be formulated in a suitable lotion or cream containing active components of the present invention suspended or dissolved in one or more pharmaceutically acceptable excipients. Suitable excipients can include, but are not limited to, mineral oil, sorbitan monostearate, polysorbate 60, cetyl esters wax, cetearyl alcohol, 2-octyldodecanol, benzyl alcohol and water.

The compounds of the invention can also be formulated in pharmaceutical compositions suitable for rectal administration such as suppositories or retention enemas, e.g., containing conventional suppository bases such as cocoa butter or other glycerides.

A pharmaceutical composition contains a total amount of the active ingredient or ingredients sufficient to achieve an intended therapeutic effect. More specifically, in some embodiments, the pharmaceutical composition contains a therapeutically effective amount of a p38-inhibiting compound of the invention (i.e., an amount of a p38-inhibiting compound of the invention that is effective in the prevention or treatment of the existing symptoms of a disease or condition associated with or mediated directly or indirectly by p38). In certain embodiments, to the pharmaceutical composition contains a therapeutically effective amount of a cytokine-inhibiting compound of the invention (i.e., an amount effective to prevent development of or to alleviate the existing symptoms of a disease or condition associated with a cytokine or cytokines, such as, but not limited to, IL-1, IL-6, IL-8 and TNF$\alpha$). The total amounts of the compound of the invention that may be combined with the carrier materials to produce a unitary dosing form will vary depending upon the host treated and the particular mode of administration. Preferably, the compositions are formulated so that a dose of between about 0.0001 to 100 mg/kg body weight/day of a p38-inhibiting agent or cytokine-inhibiting agent or both 38- and cytokine-inhibiting agent is administered to a patient receiving the compositions.

Pharmaceutical compositions of the present invention may also be prepared for sustained release. Various sustained-release materials have been established and are known by those skilled in the art. Sustained-release pharmaceutical compositions can, depending on their chemical nature, release a compound of the invention for a period of a few hours, a few days or weeks up to over 100 days.

To assist in understanding the present invention, the following Examples are included. The experiments relating to this invention should not, of course, be construed as specifically limiting the invention. Such variations of the invention, now known or later developed, which would be within the purview of one skilled in the art, are considered to fall within the scope of the invention as described herein and hereinafter claimed.

EXAMPLES

Synthesis of Compounds

Examples of compounds of the invention represented by Formula I can be prepared according to the following representative methods.

Commercially available compounds are used as received unless otherwise stated. A representative synthetic scheme is shown in Scheme 1, below.

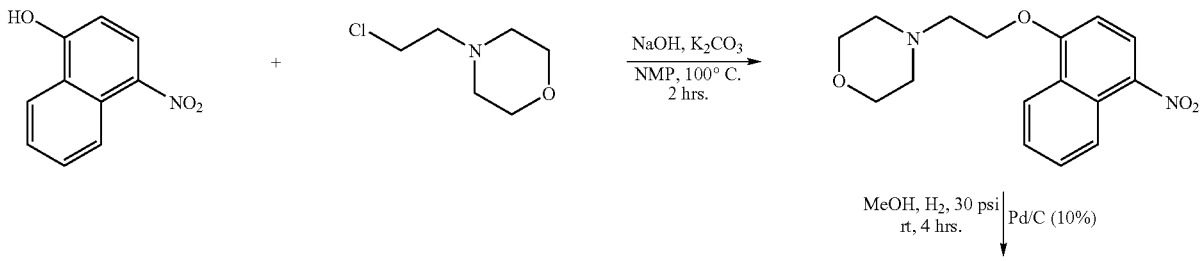

-continued

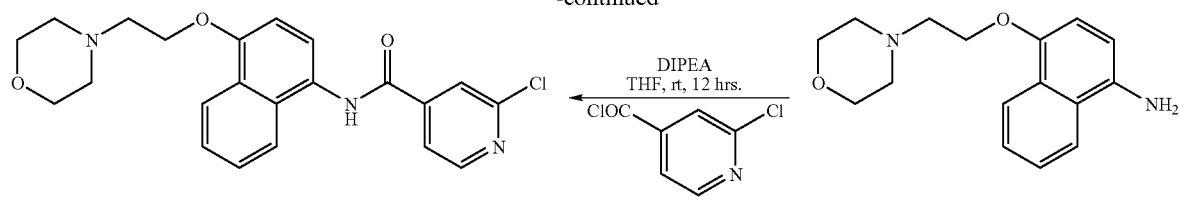

Example 1

Step 1

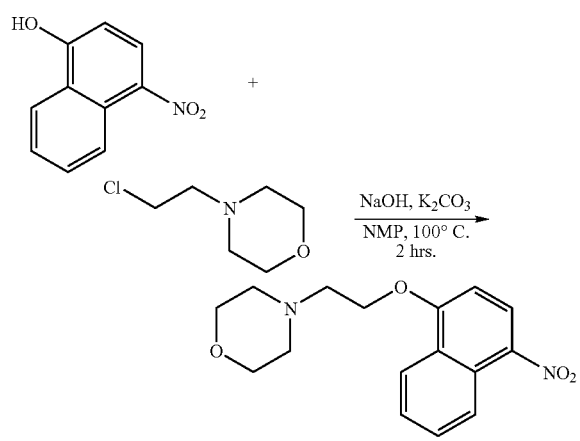

4-[2-(4-Nitro-naphthalen-1-yloxy)-ethyl]-morpholine. A mixture of 4-nitro-1-hydroxynaphthalene (10.0 g, 52.8 mmol), 4-(2-chloroethyl)-morpholine hydrochloride (13.77 g, 74.0 mmol), NaOH (3.0 g, 74.0 mmol), K$_2$CO$_3$ (17.53 g, 126.8 mmol) and 1-methyl-2-pyrrolidinone (400 ml) is heated to 90-100° C. and held for 2-3 hours. The mixture is cooled to 40° C. and water (300 ml) is added. The mixture is cooled to 0° C. and held for 4 hours. The product is collected by filtration, washed with water, cyclohexane and dried under vacuum to constant weight to yield 4-[2-(4-nitro-naphthalen-1-yloxy)-ethyl]-morpholine 14.73 g, 92.6%.

$^1$H NMR (300 MHz, CDCl$_3$) δ 8.80 (d, 1H), 8.38 (t, 2H), 7.75 (t, 1H), 7.63 (t, 1H), 6.84 (d, 1H), 4.40 (t, 2H), 3.75 (t, 4H), 3.01 (t, 2H), 2.66 (t, 4H). MS: 303 (M+1).

Step 2

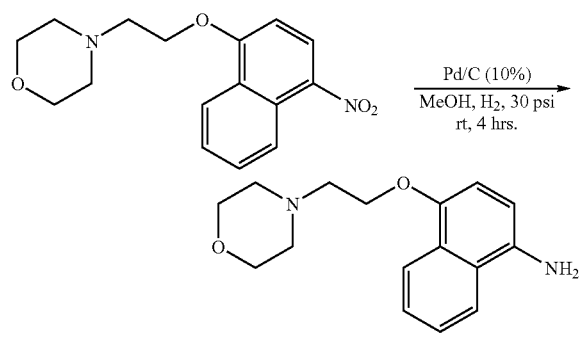

4-(2-Morpholin-4-yl-ethoxy)-naphthalen-1-ylamine. A mixture of 4-[2-(4-nitro-naphthalen-1-yloxy)-ethyl]-morpholine (10 g, 33.0 mmol), MeOH (80 ml) and Pd/C (10%, 1.0 g) is shaken under a hydrogen atmosphere at 30 psi for 4 hours. The mixture is then filtered through a bed of Celite under a stream of nitrogen. The filtrate is reduced under vacuum to give 4-(2-morpholin-4-yl-ethoxy)-naphthalen-1-ylamine (7.32 g, 81.3%). $^1$H NMR (300 MHz, CDCl$_3$) δ 8.21 (m, 1H), 7.81 (m, 1H), 7.49 (m, 2H), 6.69 (s, 2H), 4.23 (t, 2H), 3.76 (t, 4H), 2.92 (t, 2H), 2.65 (t, 4H). MS: 273 (M+1).

Step 3

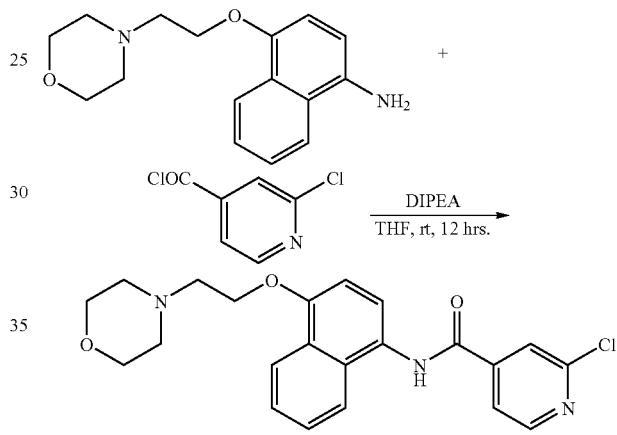

2-Chloro-N-[4-(2-morpholin-4-yl-ethoxy)-naphthalen-1-yl]-isonicotinamide. A mixture of 4-(2-morpholin-4-yl-ethoxy)-naphthalen-1-ylamine (1.38 g, 5.07 mmol), 2-chloroisonicotinoyl chloride (1.34 g, 7.6 mmol), DIPEA (1.81 ml, 10.1 mmol) and THF (30 ml) is stirred at room temperature for 12 hours. The mixture is quenched with water (100 ml). The crude product is extracted with EtOAc (2×50 ml), the combined organic layers are dried over sodium sulfate, filtered and concentrated under reduced pressure. The residue is purified by flash column chromatography (3% MeOH in EtOAc) to afford 2-chloro-N-[4-(2-morpholin-4-yl-ethoxy)-naphthalen-1-yl]-isonicotinamide (1.07 g, 51%). $^1$H NMR (DMSO-d$_6$) δ 10.61 (s, 1H), 8.62 (d, 1H), 8.21 (d, 1H), 8.10 (s, 1H), 7.95 (m, 2H), 7.59 (d, 2H), 7.49 (d, 1H), 7.09 (d, 1H), 4.33 (m, 2H), 3.61 (m, 4H), 2.92 (m, 2H), 2.61 (m, 4H). MS: 412 (M+1).

General Procedure A

Step 4

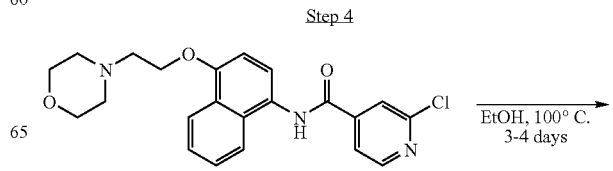

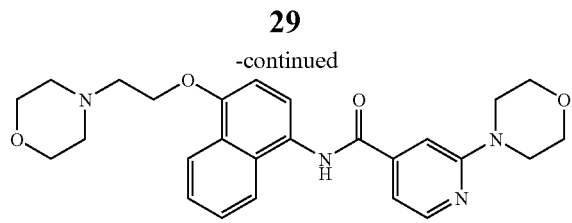

2-Morpholin-4-yl-N-[4-(2-morpholin-4-yl-ethoxy)-naphthalen-1-yl]-isonicotinamide (Compound B122). A mixture of 2-chloro-N-[4-(2-morpholin-4-yl-ethoxy)-naphthalen-1-yl]-isonicotinamide (200 umol, 1 eq), morpholine (2 mmol, 10 eq.) and ethanol (2 ml) is heated at 100° C. for 3-4 days in a 2-dram vial with agitation. The mixture is cooled to room temperature and concentrated. The crude mixture is purified by flash column chromatography and re-crystallized from methanol to afford 2-morpholin-4-yl-N-[4-(2-morpholin-4-yl-ethoxy)-naphthalen-1-yl]-isonicotinamide. $^1$H NMR (300 MHz, DMSO-$d_6$) δ 10.41 (s, 1H), 8.31 (d, 1H), 8.21 (m, 1H), 7.85 (m, 1H), 7.58 (m, 2H), 2.42 (m, 2H), 7.23 (d, 1H), 7.08 (d, 1H), 4.38 (t, 2H), 3.78 (m, 4H), 3.60 (m, 8H), 2.88 (t, 2H) 2.58 (m, 4H). MS: 463.3 (M+1).

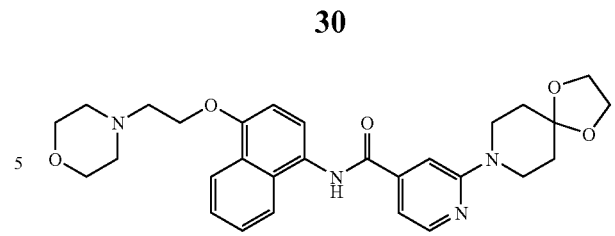

2-(1,4-Dioxa-8-aza-spiro[4.5]dec-8-yl)-N-[4-(2-morpholin-4-yl-ethoxy)-naphthalen-1-yl]-isonicotinamide (Compound B44). Compound is formed by reacting 2-chloro-N-[4-(2-morpholin-4-yl-ethoxy)-naphthalen-1-yl]-isonicotinamide and 1,4-dioxa-8-aza-spiro[4.5]decane under conditions described in general procedure A. $^1$H NMR (300 MHz, DMSO-$d_6$) δ 10.29 (s, 1H), 8.29 (d, 1H), 8.20 (m, 1H), 7.88 (m, 1H), 7.59 (m, 2H), 7.42 (d, 2H), 7.19 (d, 1H), 7.01 (d, 1H), 4.31 (t, 2H), 3.95 (s, 4H), 3.75 (m, 4H), 3.61 (m, 4H), 2.88 (t, 2H), 2.60 (m, 4H), 2.66 (m, 4H). MS: 519.3 (M+1).

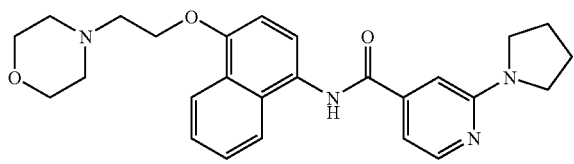

N-[4-(2-Morpholin-4-yl-ethoxy)-naphthalen-1-yl]-2-pyrrolidin-1-yl-isonicotinamide (Compound B45). Compound is formed by reacting 2-chloro-N-[4-(2-morpholin-4-yl-ethoxy)-naphthalen-1-yl]-isonicotinamide and pyrrolidine under conditions described in general procedure A. $^1$H NMR (300 MHz, DMSO-$d_6$) δ 10.38 (s, 1H), 8.21 (m, 2H), 7.83 (m, 1H), 7.59 (m, 2H), 7.42 (d, 1H), 7.10 (d, 1H), 7.02 (m, 2H), 4.31 (t, 2H), 3.61 (m, 4H), 3.49 (m, 4H), 2.87 (t, 2H), 2.58 (m, 4H), 1.99 (m, 4H). MS: 447.2 (M+1).

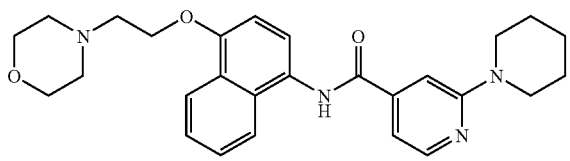

3,4,5,6-Tetrahydro-2H-[1,2']bipyridinyl-4'-carboxylic acid [4-(2-morpholin-4-yl-ethoxy)-naphthalen-1-yl]-amide (Compound B127). Compound is formed by reacting 2-chloro-N-[4-(2-morpholin-4-yl-ethoxy)-naphthalen-1-yl]-isonicotinamide and piperidine under conditions described in general procedure A. $^1$H NMR (300 MHz, DMSO-$d_6$) δ 10.34 (s, 1H), 8.28 (d, 1H), 8.22 (m, 1H), 7.88 (m, 1H), 7.59 (m, 2H), 7.42 (d, 1H), 7.40 (s, 1H), 7.15 (m, 1H), 7.05 (d, 1H), 4.35 (broad t, 2H), 3.61 (m, 4H), 3.38 (s, 4H), 2.90 (broad t, 2H), 2.60 (m, 4H), 1.60 (m, 6H). MS: 461.4 (M+1).

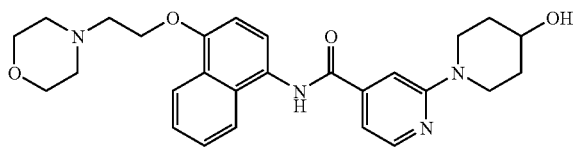

4-Hydroxy-3,4,5,6-tetrahydro-2H-[1,2']bipyridinyl-4'-carboxylic acid [4-(2-morpholin-4-yl-ethoxy)-naphthalen-1-yl]-amide (Compound B43). Compound is formed by reacting 2-chloro-N-[4-(2-morpholin-4-yl-ethoxy)-naphthalen-1-yl]-isonicotinamide and piperidin-4-ol under conditions described in general procedure A. $^1$H NMR (300 MHz, DMSO-$d_6$) δ 10.39 (s,1H), 8.29 (d, 1H), 8.21 (m, 1H), 7.85 (m, 1H), 7.59 (m, 2H), 7.41 (m, 2H), 7.15 (d, 1H), 7.05 (d, 1H), 4.31 (t, 2H), 4.10 (m, 2H), 3.75 (m, 1H), 3.60 (t, 4H), 3.20 (m, 2H), 2.89 (t, 2H), 2.59 (m, 4H), 1.81 (m, 2H), 1.40 (m, 2H). MS: 477.3 (M+1).

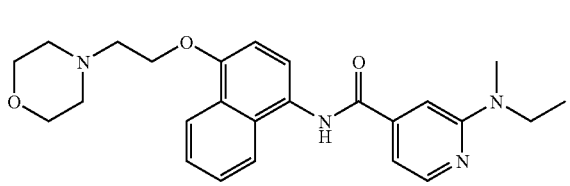

2-(Ethyl-methyl-amino)-N-[4-(2-morpholin-4-yl-ethoxy)-naphthalen-1-yl]-isonicotinamide (Compound B133). Compound is formed by reacting 2-chloro-N-[4-(2-morpholin-4-yl-ethoxy)-naphthalen-1-yl]-isonicotinamide and N-methylethylamine under conditions described in general procedure A. $^1$H NMR (300 MHz, DMSO-$d_6$) δ 10.33 (s, 1H), 8.25 (m, 2H), 7.84 (m, 1H), 7.56 (m, 2H), 7.45 (d, 1H), 7.17 (s, 1H), 7.10 (d, 1H), 7.05 (d, 1H), 4.31 (t, 2H), 3.62 (m, 4H), 3.06 (s, 3H), 2.88 (t, 2H), 2.57 (t, 4H), 1.10 (t, 3H). MS: 435.2 (M+1)

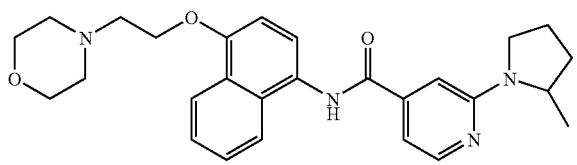

2-(2-Methyl-pyrrolidin-1-yl)-N-[4-(2-morpholin-4-yl-ethoxy)-naphthalen-1-yl]-isonicotinamide (Compound B130). Compound is formed by reacting 2-chloro-N-[4-(2-morpholin-4-yl-ethoxy)-naphthalen-1-yl]-isonicotinamide and 2-methylpyrrolidine under conditions described in general procedure A. $^1$H NMR (300 MHz, DMSO-$d_6$) δ 10.32 (s, 1H), 8.24 (m, 2H), 7.86 (m, 1H), 7.57 (m, 2H), 7.49 (d, 1H), 7.09 (d, 1H), 7.05 (s, 1H), 7.01 (s, 1H), 4.31 (t, 2H), 3.60 (m, 6H), 2.88 (t, 2H), 2.57 (m, 4H), 2.07 (m, 4H), 1.70 (m, 1H), 1.21 (d, 3H). MS: 461.2 (M+1).

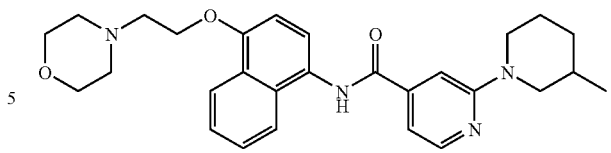

3-Methyl-3,4,5,6-tetrahydro-2H-[1,2']bipyridinyl-4'-carboxylic acid [4-(2-morpholin-4-yl-ethoxy)-naphthalen-1-yl]-amide (Compound B126). Compound is formed by reacting 2-chloro-N-[4-(2-morpholin-4-yl-ethoxy)-naphthalen-1-yl]-isonicotinamide and 4-methyl piperidine under conditions described in general procedure A. $^1$H NMR (300 MHz, DMSO-$d_6$) δ 10.34 (s, 1H), 8.24 (m, 2H), 7.84 (m, 1H), 7.57 (m, 2H), 7.45 (d, 1H), 7.38 (s, 1H), 7.12 (d, 1H), 7.05 (d, 1H), 4.31 (m, 4H), 3.60 (m, 4H), 2.88 (m, 4H), 2.56 (m, 4H), 1.82-1.40 (m, 4H), 1.20 (m, 1H), 0.94 (d, 3H). MS: 475.2 (M+1).

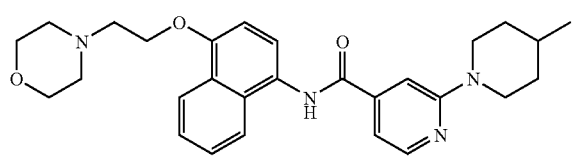

4-Methyl-3,4,5,6-tetrahydro-2H-[1,2']bipyridinyl-4'-carboxylic acid [4-(2-morpholin-4-yl-ethoxy)-naphthalen-1-yl]-amide (Compound B128). Compound is formed by reacting 2-chloro-N-[4-(2-morpholin-4-yl-ethoxy)-naphthalen-1-yl]-isonicotinamide and 4-methylpiperidine under conditions described in general procedure A. $^1$H NMR (300 MHz, DMSO-$d_6$) δ 10.34 (s, 1H), 8.26 (d, 1H), 8.22 (m, 1H), 7.84 (m, 1H), 7.57 (m, 2H), 7.45 (d, 1H), 7.39 (s, 1H), 7.13 (d, 1H), 7.05 (d, 1H), 4.41 (d, 2H), 4.31 (t, 2H), 3.60 (t, 4H), 2.88 (m, 4H), 2.57 (m, 4H), 1.68 (m, 4H), 1.11 (m, 1H), 0.95 (d, 3H). MS: 475.2 (M+1).

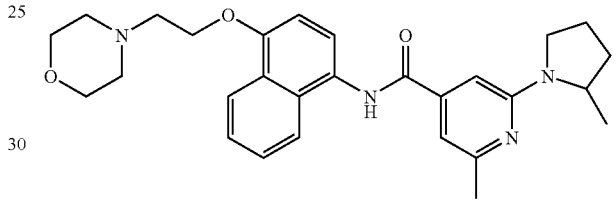

2-Methyl-6-(2-methyl-pyrrolidin-1-yl)-N-[4-(2-morpholin-4-yl-ethoxy)-naphthalen-1-yl]-isonicotinamide (Compound B155). Compound is formed by reacting 2-chloro-6-methyl-N-[4-(2-morpholin-4-yl-ethoxy)-naphthalen-1-yl]-isonicotinamide with 2-methylpyrrolidine under conditions described in general procedure A. $^1$H NMR (300 MHz, DMSO-$d_6$) δ 10.34 (s, 1H), 8.26 (d, 1H), 8.22 (m, 1H), 7.84 (m, 1H), 7.57 (m, 2H), 7.45 (d, 1H), 7.39 (s, 1H), 7.13 (d, 1H), 7.05 (d, 1H), 4.41 (d, 2H), 4.31 (t, 2H), 3.60 (m, 4H), 2.88 (m, 4H), 2.58 (m, 4H), 1.7 (m, 4H), 1.11 (m 1H), 0.95 (d, 3H). MS: 475.2 (M+1).

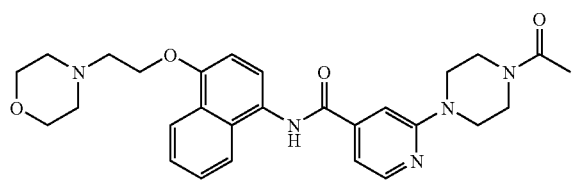

2-(4-Acetyl-piperazin-1-yl)-N-[4-(2-morpholin-4-yl-ethoxy)-naphthalen-1-yl]-isonicotinamide (Compound B123). Compound is formed by reacting 2-chloro-N-[4-(2-morpholin-4-yl-ethoxy)-naphthalen-1-yl]-isonicotinamide and 4-acetylpiperazine under conditions described in general procedure A. $^1$H NMR (300 MHz, DMSO-$d_6$) δ 10.38 (s, 1H), 8.32 (d, 1H, J=5.4), 8.20 (m, 1H), 7.84 (m, 1H), 7.58 (m, 2H), 7.46 (d, 2H), 7.23 (d, 1H, J=5.4), 7.05 (d, 1H, J=8.1), 4.31 (t, 2H), 3.58 (m, 12H), 2.88 (t, 2H), 2.57 (t, 4H), 2.06 (s, 3H). MS: 504.2 (M+1).

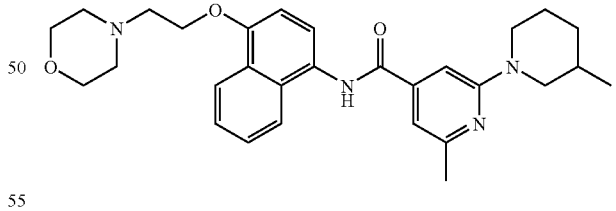

3,6'-Dimethyl-3,4,5,6-tetrahydro-2H-[1,2']bipyridinyl-4'-carboxylic acid [4-(2-morpholin-4-yl-ethoxy)-naphthalen-1-yl]-amide (Compound B153). Compound is formed by reacting 2-chloro-6-methyl-N-[4-(2-morpholin-4-yl-ethoxy)-naphthalen-1-yl]-isonicotinamide with 3-methylpiperidine under conditions described in general procedure A. $^1$H NMR (300 MHz, DMSO-$d_6$) δ 10.27 (s, 1H), 8.22 (d, 1H), 7.85 (m, 1H), 7.57 (m, 2H), 7.43 (d, 1H), 7.17 (s, 1H), 7.04 (d, 1H), 6.99 (s, 1H), 4.31 (m, 2H), 3.60 (t, 4H), 2.88 (t, 2H), 2.79 (t, 2H), 2.56 (t, 4H), 2.39 (s, 3H), 1.85-1.20 (m, 6H), 1.15 (m, 1H), 0.94 (d, 3H). MS: 489.2 (M+1).

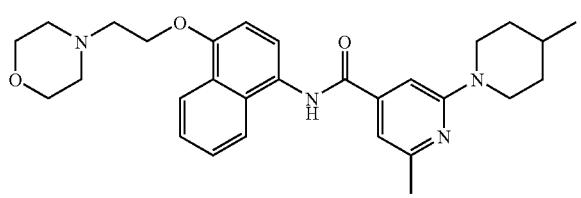

4,6'-Dimethyl-3,4,5,6-tetrahydro-2H-[1,2']bipyridinyl-4'-carboxylic acid [4-(2-morpholin-4-yl-ethoxy)-naphthalen-1-yl]-amide (Compound B154). Compound is formed by reacting 2-chloro-6-methyl-N-[4-(2-morpholin-4-yl-ethoxy)-naphthalen-1-yl]-isonicotinamide with 4-methylpiperidine under conditions described in general procedure A. $^1$H NMR (300 MHz, DMSO-$d_6$) δ 10.28 (s, 1H), 8.22 (m, 1H), 7.85 (m, 1H), 7.57 (m, 2H), 7.34 (d, 1H), 7.18 (s, 1H), 7.04 (m, 2H), 4.41 (d, 2H), 4.31 (t, 2H), 3.60 (t, 4H), 2.90-2.78 (m, 7H), 2.56 (t, 4H), 1.67 (m, 4H), 1.13 (m, 1H), 0.95-0.86 (m, 3H). MS: 489.2 (M+1).

Additional compounds of the invention can be prepared as described in Example 2.

A representative synthetic scheme is shown in Scheme 2, below.

Scheme 2

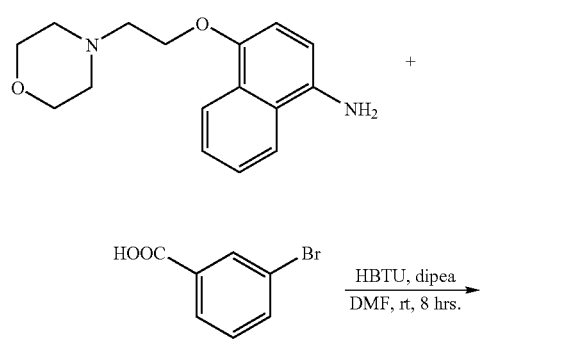

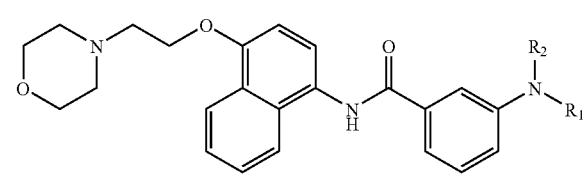

Example 2

Step 1

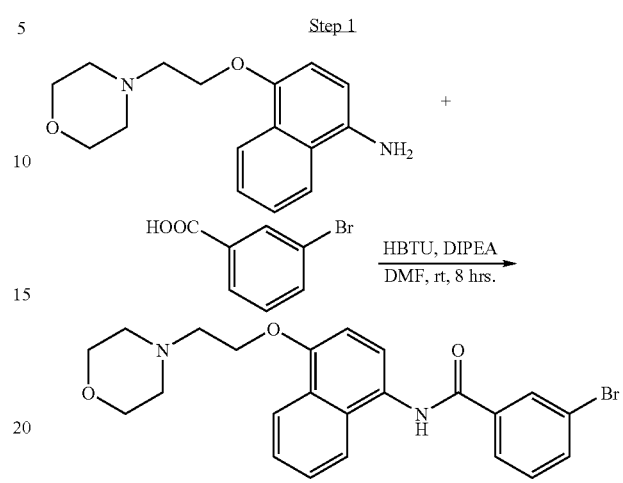

3-Bromo-N-[4-(2-morpholin-4-yl-ethoxy)-naphthalen-1-yl]-benzamide. To a 40 ml vial is added 4-(2-morpholin-4-yl-ethoxy)-naphthalen-1-amine (1.5 g, 5.50 mmol), 3-bromobenzoic acid (1.66 g, 8.2 mmol), HBTU (3.13 g, 8.2 mmol) and Hunig's base (2.0 ml, 11.0 mmol). The mixture is dissolved in DMF (10 ml), flushed with argon, sealed and agitated at room temperature for 8 hrs. The crude mixture is diluted with water (100 ml) and partitioned with EtOAc (100 ml). The organic layer is washed with water (100 ml). The combined aqueous layers are extracted with EtOAc (2×50 ml). The combined organic layers are dried over sodium sulfate, filtered and concentrated under reduced pressure. The residue is purified by flash column chromatography (5% MeOH in ethyl acetate) to afford 3-bromo-N-[4-(2-morpholin-4-yl-ethoxy)-naphthalen-1-yl]-benzamide (1.27 g, 48%). MS: 455 (M+1).

General Procedure B

Step 2

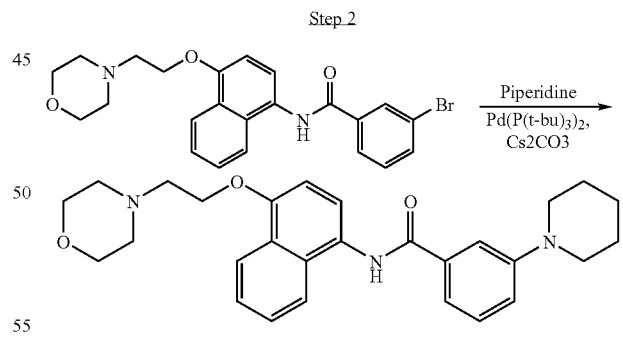

N-[4-(2-Morpholin-4-yl-ethoxy)-naphthalen-1-yl]-3-piperidin-1-yl-benzamide (Compound B48). A mixture of 3-bromo-N-[4-(2-morpholin-4-yl-ethoxy)-naphthalen-1-yl]-benzamide (200 μmol, 1 eq.), cesium carbonate (300 μmol, 1.5 eq), and piperidine (300 μmol, 1.5 eq.) is suspended in anhydrous dioxane (2 ml) in a 2-dram vial. To the heterogeneous mixture is added bis(tri-t-butylphosphine)palladium (0) (5 mg, 5 mol %). The mixture is heated and agitated for 12 hours. The mixture is cooled to room temperature, filtered and concentrated. The residue is purified using reverse phase conditions (5:95; AcCN:H$_2$O) to give N-[4-(2-morpholin-4-ylethoxy)-naphthalen-1-yl]-3-piperidin-1-yl-benzamide. Mp: 147-148° C. $^1$H NMR (300 MHz, DMSO-d$_6$): δ 10.16 (s, 1H), 8.22 (m, 1H), 7.87 (m, 1H), 7.60 (s, 1H), 7.55 (m, 2H), 7.47 (m, 3H), 7.17 (d, 1H), 7.04 (d, 1H, J=8.7), 4.33 (t, 2H, J=5.7), 3.62 (t, 4H, J=4.5), 3.32 (m, 4H), 2.90 (t, 2H, J=5.7), 2.58 (m, 4H), 1.65 (m, 4H), 1.57 (m, 2H). MS: 460.2 (M+1).

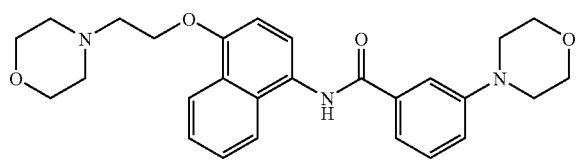

3-Morpholin-4-yl-N-[4-(2-morpholin-4-yl-ethoxy)-naphthalen-1-yl]-benzamide (Compound B169). Compound is formed by reacting 3-bromo-N-[4-(2-morpholin-4-yl-ethoxy)-naphthalen-1-yl]-benzamide with morpholine under conditions described in general procedure B. Mp: 90-92° C. $^1$H NMR (300MHz, DMSO-d$_6$): δ 10.16 (s, 1H), 8.19 (m, 1H), 7.81 (m, 1H), 7.58 (s, 1H), 7.53 (m, 3H), 7.40 (m, 2H), 7.17 (d, 1H, J=8.4), 7.01 (d, 1H, J=8.7), 4.30 (t, 2H, J=4.8), 3.74 (m, 4H), 3.57(m, 4H), 3.18 (m, 4H), 2.85 (t, 2H, J=5.7), 2.54 (m, 4H). MS: 462.2 (M+1).

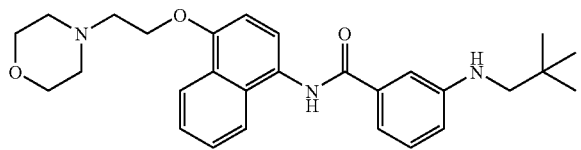

3-(2,2-Dimethyl-propylamino)-N-[4-(2-morpholin-4-yl-ethoxy)-naphthalen-1-yl]-benzamide (Compound B173). Compound is formed by reacting 3-bromo-N-[4-(2-morpholin-4-yl-ethoxy)-naphthalen-1-yl]-benzamide with 2,2-dimethylpropylamine under conditions described in general procedure B. $^1$H NMR (300 MHz, DMSO-d$_6$) δ 10.05 (s, 1H), 8.22 (m, 1H), 7.86 (m, 1H), 7.56 (m, 2H), 7.41 (d, 1H, J=8.4), 7.28 (s, 1H), 7.21 (d, 2H, J=5.7), 6.87 (m, 1H), 5.70 (m, 1H), 4.32 (t, 2H, J=5.7), 3.62 (t, 4H, J=4.8), 2.89 (t, 4H, J=5.4), 2.58 (t, 4H, J=4.8), 1.48(t, 1H, J=14.1), 0.97 (s, 9H). MS: 462.2 (M+1).

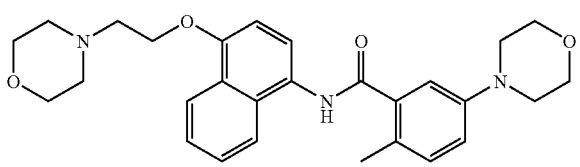

2-Methyl-5-morpholin-4-yl-N-[4-(2-morpholin-4-yl-ethoxy)-naphthalen-1-yl]-benzamide (Compound B39). Compound is formed by reacting 5-bromo-2-methyl-N-[4-(2-morpholin-4-yl-ethoxy)-naphthalen-1-yl]-benzamide with morpholine under conditions described in general procedure B. $^1$H NMR (300 MHz, CDCl$_3$) δ 8.33 (d, 1H, J=6.9), 7.85 (t, 2H, J=7.8), 7.61 (s, 1H), 7.54 (m, 2H), 7.34 (m, 2H), 7.19 (d, 1H, J=7.5), 6.88 (d, 1H, J=8.4), 4.33 (t, 2H, J=5.7), 3.88 (t, 4H, J=3.9), 3.75 (t, 4H, J=4.5), 2.95 (m, 6H), 2.66 (t, 4H, J=4.5), 2.63 (s, 3H). MS: 476.2 (M+1).

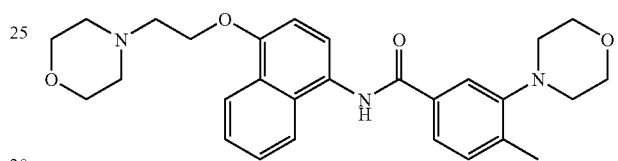

4-Methyl-3-morpholin-4-yl-N-[4-(2-morpholin-4-yl-ethoxy)-naphthalen-1-yl]-benzamide (Compound B40). Compound is formed by reacting 3-bromo-4-methyl-N-[4-(2-morpholin-4-yl-ethoxy)-naphthalen-1-yl]-benzamide with morpholine under conditions described in general procedure B. $^1$H NMR (300 MHz, CDCl$_3$) δ 8.32 (m, 1H), 7.98 (broad s, 1H), 7.86 (m, 1H), 7.74 (m, 2H), 7.53 (m, 3H), 7.32 (m, 1H), 6.87 (t, 1H, J=7.5), 4.34 (m, 2H), 3.88 (m, 4H), 3.77 (m, 4H), 2.97 (m, 6H), 2.68 (m, 4H), 2.42 (d, 3H, J=5.7). MS: 476.2 (M+1).

Additional compounds of the invention can be prepared as described in Example 3.

A representative synthetic scheme is shown in Scheme 3, below.

Scheme 3

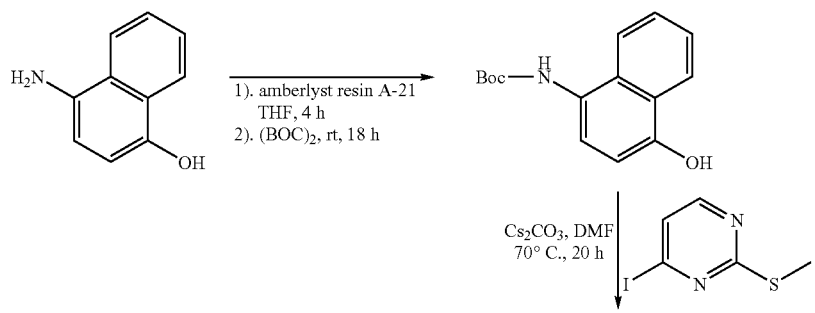

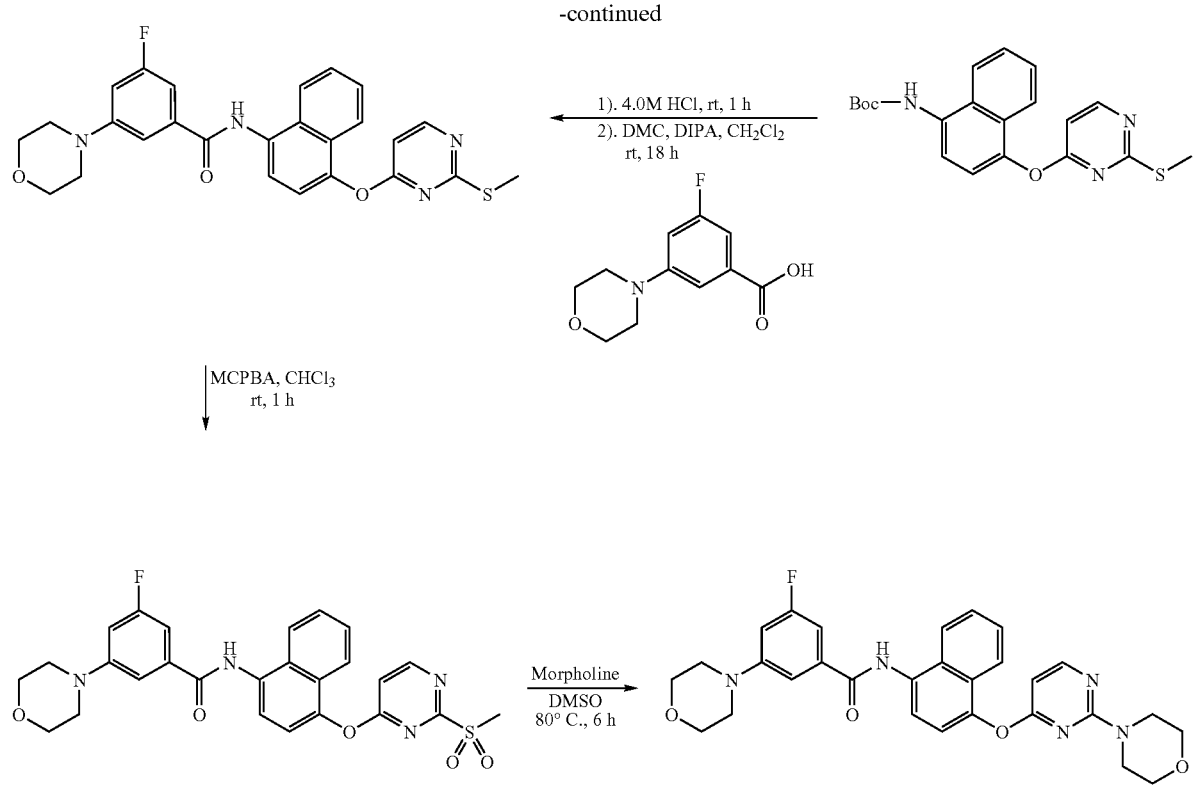

Example 3

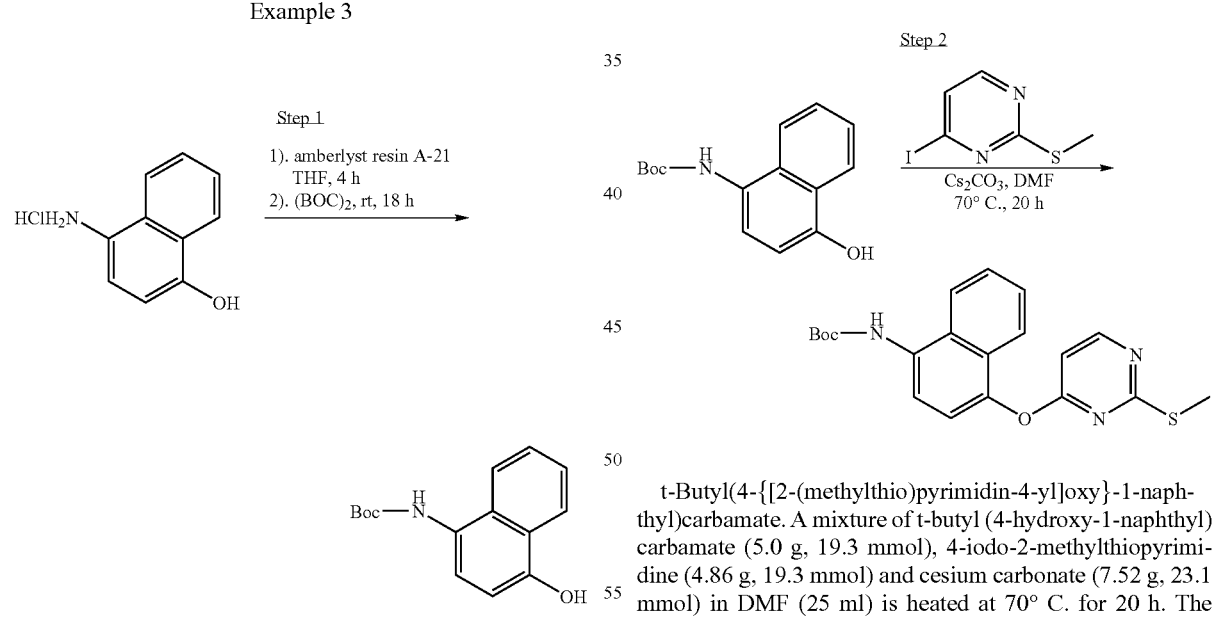

t-Butyl(4-hydroxy-1-naphthyl)carbamate. A mixture of 4-amino-1-naphthol hydrochloride (25.0 g, 128 mmol) and Amberlyst A-21 ion-exchange resin (37.0 g) in THF (600 ml) is stirred at room temperature for 4 h. Di-t-butyldicarbonate (27.9 g, 128 mmol) is then added. The mixture is stirred at room temperature for 18 h and filtered. The filtrate is concentrated and purified by silica gel column chromatography (30% EtOAc in hexane) to give t-butyl(4-hydroxy-1-naphthyl)carbamate (17.0 g) as a deep red solid. Mp: 172-174° C. MS: 260 (M+1).

t-Butyl(4-{[2-(methylthio)pyrimidin-4-yl]oxy}-1-naphthyl)carbamate. A mixture of t-butyl (4-hydroxy-1-naphthyl) carbamate (5.0 g, 19.3 mmol), 4-iodo-2-methylthiopyrimidine (4.86 g, 19.3 mmol) and cesium carbonate (7.52 g, 23.1 mmol) in DMF (25 ml) is heated at 70° C. for 20 h. The resulting mixture is diluted with $CH_2Cl_2$ (50 ml), washed with water (25 ml×3), dried over $Na_2SO_4$ and concentrated. This residue is dissolved in minimum volume of EtOAc at 70° C. and then hexane (20 ml) is added. The resulting solution is left at room temperature overnight, filtered and washed with hexane to obtain t-butyl(4-{[2-(methylthio)pyrimidin-4-yl] oxy}-1-naphthyl)carbamate as a pink solid (4.2 g); Mp: 173-174° C.; $^1$H NMR (300 MHz, $CDCl_3$) δ 1.56(s, 9H), 2.30(s, 3H), 6.45(d, J=5.7 Hz, 1H), 6.86(s, 1H), 7.27(d, J=8.1 Hz, 1H), 7.47-7.60(m, 2H), 7.87-7.94(m, 3H), 8.32(d, J=5.7 Hz, 1H); MS: 384 (M+1).

Step 3

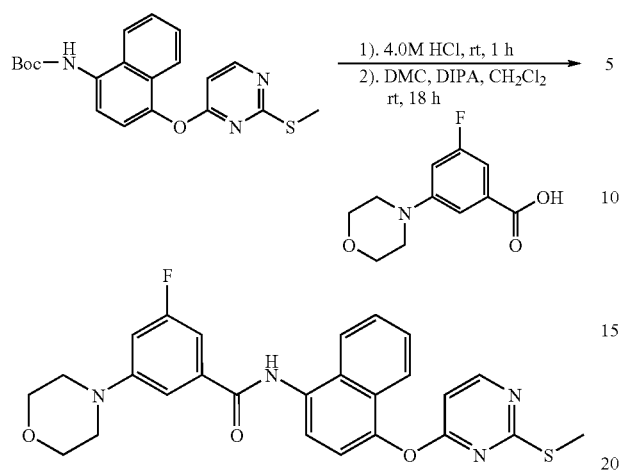

3-Fluoro-N-(4-{[2-(methylthio)pyrimidin-4-yl]oxy}-1-naphthyl)-5-morpholin-4-ylbenzamide (Compound B246). A solution of t-butyl(4-{[2-(methylthio)pyrimidin-4-yl]oxy}-1-naphthyl)carbamate (1.0 g, 2.61 mmol) in 4.0 M HCl in dioxane (10 ml) is stirred at room temperature for 1 h. The mixture is then evaporated to dryness. The residue is then dissolved in CH$_2$Cl$_2$ (5 ml) containing diisopropylamine (1.0 ml). To this mixture is added a solution of 3-fluoro-5-morpholinebenzoic acid (0.70 g, 3.13 mmol), 2-chloro-1,3-dimethylimidazolinium chloride (0.525 g, 3.13 mmol) and diisopropylamine (1.27 ml) in CH$_2$Cl$_2$ (10 ml) at room temperature. The mixture is stirred at room temperature overnight and then washed with saturated NaHCO$_3$ solution, brine, dried over Na$_2$SO$_4$ and concentrated. The residue is purified by column chromatography on silica gel (10-60% EtOAc in hexane) to give 3-fluoro-N-(4-{[2-(methylthio)pyrimidin-4-yl]oxy}-1-naphthyl)-5-morpholin-4-ylbenzamide as an off-white solid (0.75 g). Mp: 189-190° C.; $^1$H NMR (300 MHz, CDCl$_3$) δ 2.29(s, 3H), 3.25(t, J=4.8 Hz, 4H), 3.87(t, J=5.1 Hz, 4H), 6.53(d, J=6.0 Hz, 1H), 6.75-6.80(m, 1H), 7.07(d, J=8.4 Hz, 1H), 7.30-7.33(m, 2H), 7.49-7.56(m, 2H), 7.89-7.97(m, 3H), 8.16(s, 1H), 8.36(d, J=5.7 Hz, 1H); MS: 491 (M+1).

Step 4

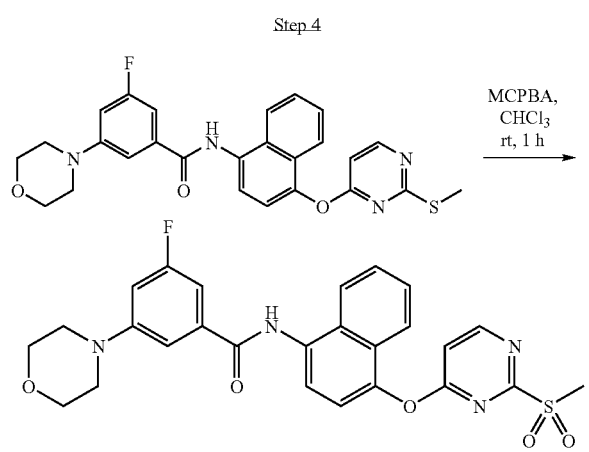

3-Fluoro-N-(4-{[2-(methylsulfonyl)pyrimidin-4-yl]oxy}-1-naphthyl)-5-morpholin-4-ylbenzamide (Compound B268). A mixture of 3-fluoro-N-(4-{[2-(methylthio)pyrimidin-4-yl]oxy}-1-naphthyl)-5-morpholin-4-ylbenzamide (0.49 g, 1.0 mmol) and MCPBA (0.491 g, 2.2 mmol) in CHCl$_3$ (5 ml) is stirred at room temperature for 1 h. The reaction mixture is diluted with CHCl$_3$ (5 ml) and washed with saturated NaHCO$_3$ solution (5 ml), water (5 ml), and dried with sodium sulfate. The organic layer is then evaporated to dryness. The residue is purified by column chromatography on silica gel (1-2% methanol in CH$_2$Cl$_2$) to give 3-fluoro-N-(4-{[2-(methylsulfonyl)pyrimidin-4-yl]oxy}-1-naphthyl)-5-morpholin-4-ylbenzamide as a white solid. Mp: 173-175° C.; $^1$H NMR (300 MHz, CDCl$_3$) δ 2.70 (s, 3H), 2.99 (d, J=11.4 Hz, 1H), 3.13 (d, J=11.1 Hz, 1H), 3.73-3.90 (m, 4H), 4.47-4.55 (m, 2H), 7.11 (d, J=5.7 Hz, 1H), 7.23-7.31 (m, 2H), 7.44-7.46 (m, 2H), 7.65 (d, J=9.3 Hz, 1H), 7.73-7.83 (m, 2H), 7.92 (d, J=8.4 Hz, 1H), 8.69 (d, J=5.7 Hz, 1H), 9.23(s, 1H); MS: 523 (M+1).

General Procedure C

Step 5

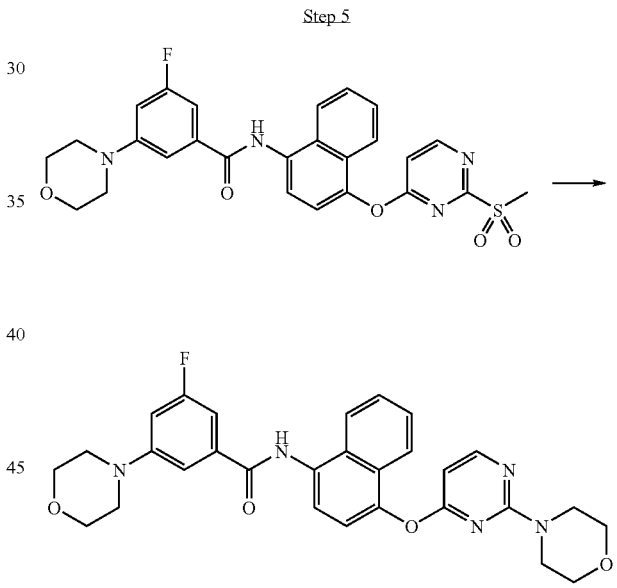

3-Fluoro-5-morpholin-4-yl-N-{4-[(2-morpholin-4-ylpyrimidin-4-yl)oxy]-1-naphthyl}benzamide (Compound B248). A mixture of 3-fluoro-N-(4-{[2-(methylsulfonyl)pyrimidin-4-yl]oxy}-1-naphthyl)-5-morpholin-4-ylbenzamide (0.1 mmol) and morpholine (0.087 ml, 1.0 mmol) in DMSO (0.5 ml) is heated at 80° C. for 6 h. The resulting mixture is diluted with CH$_2$Cl$_2$ (2 ml), washed with 0.01 N NaOH, and dried over sodium sulfate. After evaporation to dryness, the residue is purified by column chromatography on silica gel (50% EtOAc in hexane) to give 3-fluoro-5-morpholin-4-yl-N-{4-[(2-morpholin-4-ylpyrimidin-4-yl)oxy]-1-naphthyl}benzamide as a white solid (25 mg). Mp: 104-106° C.; $^1$H NMR (300 MHz, CDCl$_3$) δ 3.26 (bs, 4H), 3.64 (bs, 8H), 3.87 (bs, 4H), 6.07 (d, J=4.5 Hz, 1H), 6.77 (d, J=11.7 Hz, 1H), 7.07 (d, J=7.5 Hz, 1H), 7.32 (bs, 2H), 7.52-7.59 (m, 2H), 7.89-8.00 (m, 3H), 8.12-8.19(m, 2H); MS: 530 (M+1).

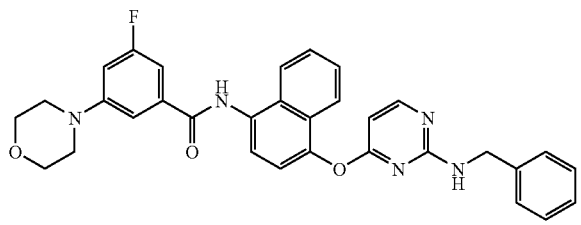

N-(4-{[2-(Benzylamino)pyrimidin-4-yl]oxy}-1-naphthyl)-3-fluoro-5-morpholin-4-ylbenzamide (Compound B249). Compound is formed from 3-fluoro-N-(4-{[2-(methylsulfonyl)pyrimidin-4-yl]oxy}-1-naphthyl)-5-morpholin-4-ylbenzamide (0.1 mmol) and benzylamine (10 mmol) according to conditions described in general procedure C. A light yellow solid (20 mg) is produced. Mp: 121-123° C.; $^1$H NMR (300 MHz, CDCl$_3$) δ 3.23(bs, 4H), 3.85(bs, 4H), 4.41 (bs, 2H), 5.48(bs, 1H). 6.16(d, J=5.7 Hz, 1H), 6.75(d, J=12.3 Hz, 1H), 7.05-7.30(m, 7H), 7.48-7.59(m, 3H), 7.88-7.97(m, 3H), 8.15(s, 2H); MS: 550 (M+1H).

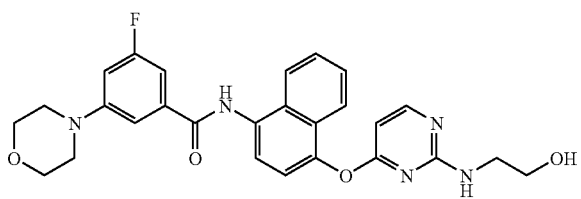

3-Fluoro-N-[4-({2-[(2-hydroxyethyl)amino]pyrimidin-4-yl}oxy)-1-naphthyl]-5-morpholin-4-ylbenzamide (Compound B252). Compound is formed from 3-fluoro-N-(4-{[2-(methylsulfonyl)pyrimidin-4-yl]oxy}-1-naphthyl)-5-morpholin-4-ylbenzamide (0.2 mmol) and ethanolamine (20 mmol) according to conditions described in general procedure C. A yellow solid (35 mg) is produced. Mp: 127-129° C.; $^1$H NMR (300 MHz, CDCl$_3$) δ 3.21(bs, 4H), 3.30(bs, 2H), 3.52(bs, 2H), 3.83(bs, 4H), 5.56(s, 1H), 6.21(d, J=4.8 Hz, 1H), 6.75(d, J=11.1 Hz, 1H), 7.06(d, J=7.5 Hz, 1H), 7.16(d, J=7.5 Hz, 1H), 7.29(s, 1H), 7.48-7.50(m, 2H), 7.61(bs, 1H), 7.83-7.90(m, 2H), 8.10(d, J=4.8 Hz, 1H), 8.44(s, 1H); MS: 504 (M+1).

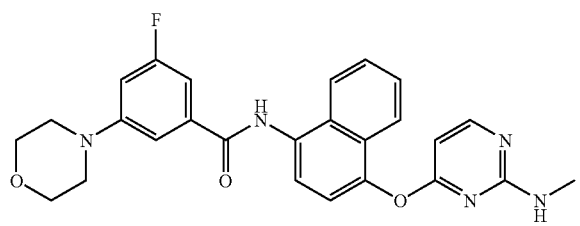

3-Fluoro-N-(4-{[2-(methylamino)pyrimidin-4-yl]oxy}-1-naphthyl)-5-morpholin-4-ylbenzamide (Compound B251). Compound is formed from 3-fluoro-N-(4-{[2-(methylsulfonyl)pyrimidin-4-yl]oxy}-1-naphthyl)-5-morpholin-4-ylbenzamide (0.1 mmol) and methylamine in methanol (2.0 M, 10 mmol) according to conditions described in general procedure C. A white solid (10 mg) is produced. Mp: 110-113° C.; $^1$H NMR (300 MHz, CDCl$_3$) δ 2.87(bs, 2H), 3.24(bs, 4H), 3.86(bs, 5H), 5.14(s, 1H), 6.07(s, 1H), 6.77 (d, J=11.4 Hz, 1H), 7.07(d, J=7.8 Hz, 1H), 7.29-7.31(m, 2H), 7.51-7.57(m, 2H), 7.87-7.98(m, 3H), 8.15(s, 1H), 8.21(s, 1H); MS: 474 (M+1).

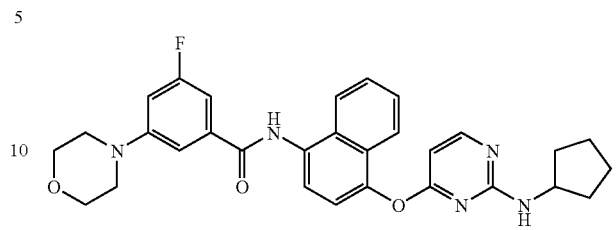

N-(4-{[2-(Cyclopentylamino)pyrimidin-4-yl]oxy}-1-naphthyl)-3-fluoro-5-morpholin-4-ylbenzamide (Compound B250). Compound is prepared from 3-fluoro-N-(4-{[2-(methylsulfonyl)pyrimidin-4-yl]oxy}-1-naphthyl)-5-morpholin-4-ylbenzamide (0.1 mmol) and cyclopentylamine (10 mmol) according to conditions described in general procedure C. Compound is produced (25 mg) as a light yellow solid; Mp: 119-120° C.; $^1$H NMR (300 MHz, CDCl$_3$) δ 1.23-1.38(m, 4H), 1.53-1.88(m, 4H), 3.22-3.25(m, 4H), 3.84-3.86(m, 4H), 4.08-4.15(m, 1H), 5.06(bs, 1H), 6.07(bs, 1H), 6.76(d, J=11.7 Hz, 1H), 7.07(d, J=8.4 Hz, 1H), 7.25-7.31(m, 2H), 7.48-7.58 (m, 2H), 7.85-7.98(m, 3H), 8.14(s, 1H), 8.25(s, 1H); MS: 528 (M+1).

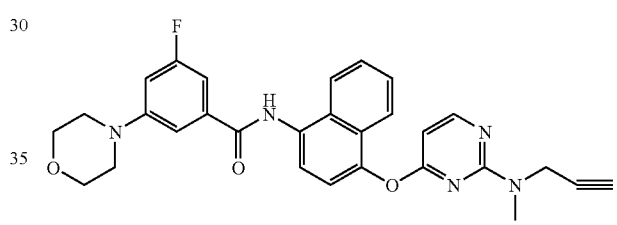

3-Fluoro-N-[4-({2-[methyl(prop-2-yn-1-yl)amino]pyrimidin-4-yl}oxy)-1-naphthyl]-5-morpholin-4-ylbenzamide (Compound B352). Compound is prepared from 3-fluoro-N-(4-{[2-(methylsulfonyl)pyrimidin-4-yl]oxy}-1-naphthyl)-5-morpholin-4-ylbenzamide and N-methylprop-2-ynylamine according to conditions described in general procedure C. Mp: 97-98° C.; $^1$H NMR (400 MHz, DMSO-d$_6$) δ 2.88 (s, 3H), 3.26-3.33 (m, 5H), 3.77 (t, J=4.8 Hz, 4H), 4.24 (s, 2H), 6.32 (d, J=5.5 Hz, 1H), 7.06 (d, J=14.3 Hz, 1H), 7.26 (d, J=8.8 Hz, 1H), 7.45-7.64 (m, 5H), 7.85-7.87 (m, 1H), 8.01 (d, J=8.0 Hz, 1H), 8.32 (d, J=5.5 Hz, 1H), 10.49 (s, 1H).

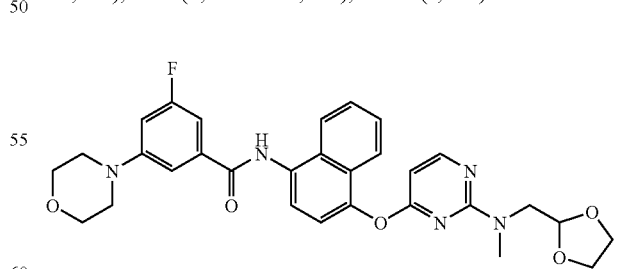

N-[4-({2-[(1,3-Dioxolan-2-ylmethyl)(methyl)amino]pyrimidin-4-yl}oxy)-1-naphthyl]-3-fluoro-5-morpholin-4-ylbenzamide (Compound B349). Compound is prepared from 3-fluoro-N-(4-{[2-(methylsulfonyl)pyrimidin-4-yl]oxy}-1-naphthyl)-5-morpholin-4-ylbenzamide and [1,3]dioxolan-2-ylmethyl-methylamine according to conditions described in general procedure C. Mp: 111-112° C.; ¹H NMR (400 MHz, DMSO-d₆) δ 2.75-3.96 (m, 8H), 3.27 (m, 4H), 3.80 (m, 4H), 4.75-5.0 (m, 2H), 6.27 (d, J=5.1 Hz, 1H), 7.05 (d, J=12.5 Hz, 1H), 7.28 (d, J=8.8 Hz, 1H), 7.42-7.62 (m, 5H), 7.84 (d, J=7.7 Hz, 1H), 7.99-8.01 (m, 1H), 8.28 (d, J=5.5 Hz, 1H), 10.47 (s, 1H).

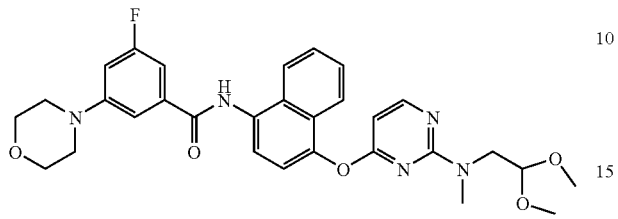

N-[4-({2-[(2,2-Dimethoxyethyl)(methyl)amino]pyrimidin-4-yl}oxy)-1-naphthyl]-3-fluoro-5-morpholin-4-ylbenzamide (Compound B351). Compound is prepared from 3-fluoro-N-(4-{[2-(methylsulfonyl)pyrimidin-4-yl]oxy}-1-naphthyl)-5-morpholin-4-ylbenzamide and (2,2-dimethoxyethyl)-methylamine according to conditions described in general procedure C. Mp: 92-94° C.; ¹H NMR (400 MHz, DMSO-d₆) δ 2.84-3.6 (m, 11H), 3.28 (m, 4H), 3.77 (m, 4H), 4.5 (s, 1H), 6.26-6.24 (m, 1H), 7.04 (d, J=12.0 Hz, 1H), 7.26 (d, J=9.1 Hz, 1H), 7.47-7.65 (m, 5H), 7.82 (m, 1H), 7.99-8.01 (m, 1H), 8.29 (m, 1H), 10.45 (s, 1H).

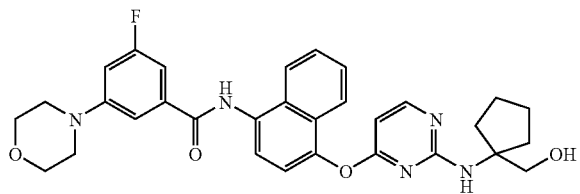

3-Fluoro-N-{4-[(2-{[1-(hydroxymethyl)cyclopentyl]amino}pyrimidin-4-yl)oxy]-1-naphthyl}-5-morpholin-4-ylbenzamide (Compound B350). Compound is prepared from 3-fluoro-N-(4-{[2-(methylsulfonyl)pyrimidin-4-yl]oxy}-1-naphthyl)-5-morpholin-4-ylbenzamide and (1-amino-cyclopentyl)-methanol according to conditions described in general procedure C. Mp: 115-117° C.; ¹H NMR (400 MHz, DMSO-d₆) δ 1.16-1.50 (m, 8H), 3.00-3.34 (m, 2H), 3.27 (m, 4H), 3.77 (m, 4H), 6.30 (d, J=5.5 Hz, 1H), 6.65 (s, 1H), 7.05 (d, J=12.1 Hz, 1H), 7.27 (d, J=8.8 Hz, 1H), 7.39 (d, J=8.0 Hz, 1H), 7.49 (s, 1H), 7.56-7.61 (m, 3H), 7.82 (d, J=6.6 Hz, 1H), 8.00 (d, J=8.4 Hz, 1H), 8.20 (d, J=5.5 Hz, 1H), 10.46 (s, 1H).

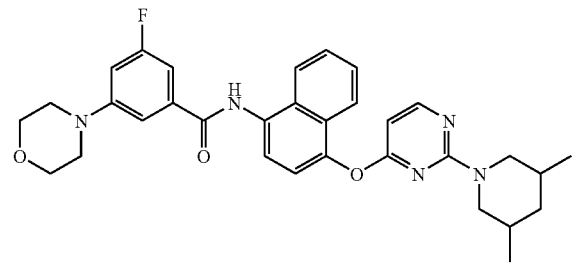

N-(4-{[2-(3,5-Dimethylpiperidin-1-yl)pyrimidin-4-yl]oxy}-1-naphthyl)-3-fluoro-5-morpholin-4-ylbenzamide (Compound B348). Compound is prepared from 3-fluoro-N-(4-{[2-(methylsulfonyl)pyrimidin-4-yl]oxy}-1-naphthyl)-5-morpholin-4-ylbenzamide and 3,5-dimethylpiperidine according to conditions described in general procedure C. Mp: 102-104° C.; ¹H NMR (400 MHz, DMSO-d₆) δ 0.76-0.88 (m, 6H), 1.33-3.22 (m, 8H), 3.27 (m, 4H), 3.77 (m, 4H), 6.17 (d, J=5.5 Hz, 1H), 7.02-7.06 (m, 1H), 7.27 (d, J=8.8 Hz, 1H), 7.41 (d, J=8.0 Hz, 1H), 7.25-7.62 (m, 4H), 7.62-7.83 (m, 1H), 7.99-8.01 (m, 1H), 8.24 (d, J=5.5 Hz, 1H), 10.47 (s, 1H).

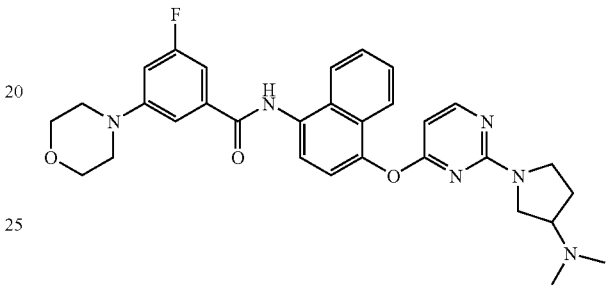

N-[4-({2-[3-(Dimethylamino)pyrrolidin-1-yl]pyrimidin-4-yl}oxy)-1-naphthyl]-3-fluoro-5-morpholin-4-ylbenzamide (Compound B365). Compound is prepared from 3-fluoro-N-(4-{[2-(methylsulfonyl)pyrimidin-4-yl]oxy}-1-naphthyl)-5-morpholin-4-ylbenzamide and dimethyl-pyrrolidin-3-yl-amine according to conditions described in general procedure C. Mp: 106-108° C.; ¹H NMR (400 MHz, DMSO-d₆) δ 2.07-2.17 (m, 10H), 2.45-3.15 (m, 3H), 3.27 (t, J=4.4 Hz, 4H), 3.77 (t, J=5.1 Hz, 4H), 6.15 (m, 1H), 7.05 (d, J=12.1 Hz, 1H), 7.27 (d, J=9.5 Hz, 1H), 7.42-7.62 (m, 5H), 7.85-7.87 (m, 1H), 8.00 (d, J=7.7 Hz, 1H), 8.23 (d, J=5.5 Hz, 1H), 10.47 (s, 1H).

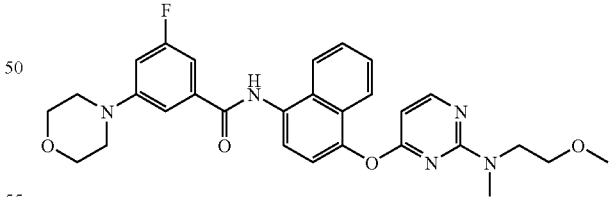

3-Fluoro-N-[4-({2-[(2-methoxyethyl)(methyl)amino]pyrimidin-4-yl}oxy)-1-naphthyl]-5-morpholin-4-ylbenzamide (Compound B370). Compound is prepared from 3-fluoro-N-(4-{[2-(methylsulfonyl)pyrimidin-4-yl]oxy}-1-naphthyl)-5-morpholin-4-ylbenzamide and (2-methoxy-ethyl)-methylamine according to conditions described in general procedure C. Mp: 96-98° C.; ¹H NMR (400 MHz, DMSO-d₆) δ 2.90-3.15 (m, 4 H), 3.27 (t, J=4.8 Hz, 4 H), 3.20-3.40 (m, 6 H), 3.77 (t, J=4.8 Hz, 4H), 6.28 (s, 1 H), 7.05 (d, J=12.4 Hz, 1 H), 7.27 (d, J=8.7 Hz, 1 H), 7.43-7.62 (m, 5 H), 7.82 (s, 1 H), 8.00 (d, J=7.7 Hz, 1 H), 8.26 (d, J=5.1 Hz, 1 H), 10.47 (s, 1 H).

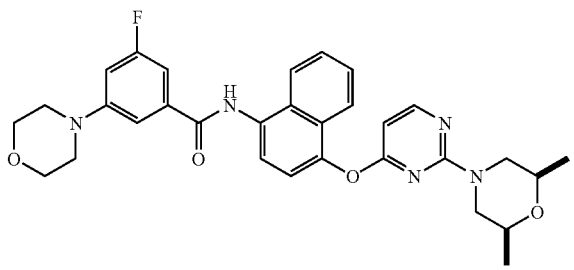

N-[4-({2-[(2R,6S)-2,6-Dimethylmorpholin-4-yl]pyrimidin-4-yl}oxy)-1-naphthyl]-3-fluoro-5-morpholin-4-ylbenzamide (Compound B364). Compound is prepared from 3-fluoro-N-(4-{[2-(methylsulfonyl)pyrimidin-4-yl]oxy}-1-naphthyl)-5-morpholin-4-ylbenzamide and 2,6-dimethylmorpholine according to conditions described in general procedure C. Mp: 118-120° C.; $^1$H NMR (400 MHz, DMSO-$d_6$) δ 1.01-1.02 (m, 6 H), 2.39 (t, J=11.7 Hz, 2 H), 3.25-3.30 (m, 4 H), 3.75-3.77 (m, 4H), 4.20 (bs, 2 H), 6.18-6.20 (m, 1 H), 7.02-7.06 (m, 1 H), 7.25-7.27 (m, 1 H), 7.42-7.44 (m, 1 H), 7.49 (s, 1 H), 7.57-7.62 (m, 3 H), 7.82-7.84 (m, 1 H), 8.00 (d, J=8.0 Hz, 1 H), 8.26-8.28 (m, 1 H), 10.47 (s, 1 H).

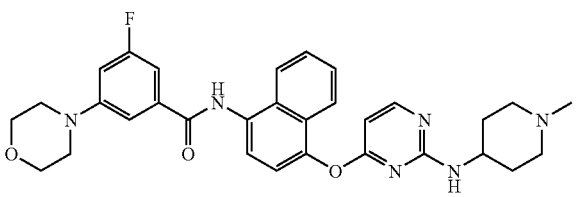

3-Fluoro-N-[4-({2-[(1-methylpiperidin-4-yl)amino]pyrimidin-4-yl}oxy)-1-naphthyl]-5-morpholin-4-ylbenzamide (Compound B362). Compound is prepared from 3-fluoro-N-(4-{[2-(methylsulfonyl)pyrimidin-4-yl]oxy}-1-naphthyl)-5-morpholin-4-ylbenzamide and 1-methyl-piperidin-4-ylamine according to conditions described in general procedure C. Mp: 128-129° C.; $^1$H NMR (400 MHz, DMSO-$d_6$) δ 1.41-1.84 (m, 4 H), 2.09 (s, 3 H), 2.66 (bs, 2 H), 3.26-3.80 (m, 3 H), 3.27 (t, J=4.7 Hz, 4 H), 3.76 (t, J=4.7 Hz, 4H), 6.32 (s, 1 H), 7.05 (d, J=12.4 Hz, 2 H), 7.27 (d, J=8.4 Hz, 1 H), 7.40 (d, J=8.0 Hz, 1 H), 7.47 (s, 1 H), 7.55-7.60 (m, 3H), 7.82 (d, J=8.0 Hz, 1 H), 8.00 (d, J=7.7 Hz, 1 H), 8.23 (bs, 1 H), 10.45 (s, 1 H).

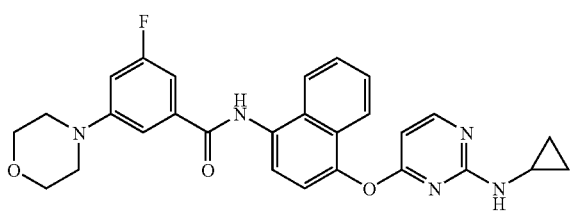

N-(4-{[2-(Cyclopropylamino)pyrimidin-4-yl]oxy}-1-naphthyl)-3-fluoro-5-morpholin-4-ylbenzamide (Compound B321). Compound is prepared from 3-fluoro-N-(4-{[2-(methylsulfonyl)pyrimidin-4-yl]oxy}-1-naphthyl)-5-morpholin-4-ylbenzamide and cyclopropylamine according to conditions described in general procedure C. Mp: 118-120° C.; $^1$H NMR (400 MHz, CDCl$_3$) δ 0.42-0.49(m, 2 H), 0.70(d, J=5.6 Hz, 2 H), 2.65(s, 1 H), 3.25(t, J=4.0 Hz, 4 H), 3.86(t, J=4.8 Hz, 4H), 5.25(s, 1 H), 6.15(d, J=4.8 Hz, 1 H), 6.78(d, J=11.6 Hz, 1 H), 7.06(d, J=8.4 Hz, 2 H), 7.26-7.31(m, 2 H), 7.49-7.57(m, 2 H), 7.89(d, J=8.0 Hz, 1H), 7.96(d, J=8.0 Hz, 1 H), 8.15(s, 1 H), 8.20(d, J=4.4 Hz, 1 H).

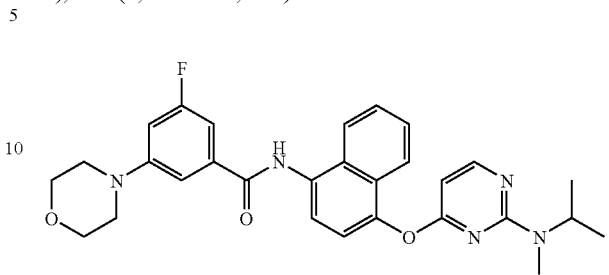

3-Fluoro-N-[4-({2-[isopropyl(methyl)amino]pyrimidin-4-yl}oxy)-1-naphthyl]-5-morpholin-4-ylbenzamide (Compound B322). Compound is prepared from 3-fluoro-N-(4-{[2-(methylsulfonyl)pyrimidin-4-yl]oxy}-1-naphthyl)-5-morpholin-4-ylbenzamide and N-isopropylmethylamine according to conditions described in general procedure C. Mp: 94-96° C.; $^1$H NMR (400 MHz, CDCl$_3$) δ 1.06-1.14(m, 6 H), 2.84(s, 3 H), 3.25(t, J=4.0 Hz, 4 H), 3.87(t, J=4.8 Hz, 4H), 5.95(d, J=5.2 Hz, 1 H), 6.78(d, J=11.2 Hz, 1 H), 7.07(d, J=8.0 Hz, 1H), 7.31(d, J=8.0 Hz, 1 H), 7.49-7.59(m, 3 H), 7.89(d, J=8.8 Hz, 1 H), 7.96(d, J=7.6 Hz, 1H), 8.01(d, J=8.0 Hz, 1 H), 8.14-8.17(m, 2 H).

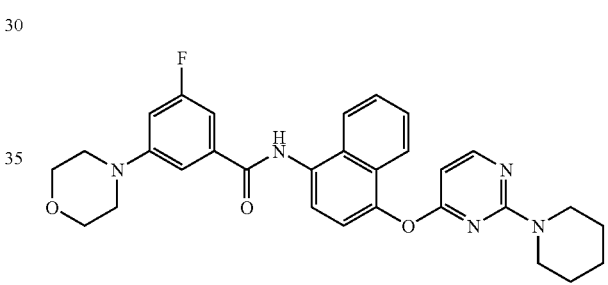

3-Fluoro-5-morpholin-4-yl-N-{4-[(2-piperidin-1-ylpyrimidin-4-yl)oxy]-1-naphthyl}benzamide (Compound B324). Compound is prepared from 3-fluoro-N-(4-{[2-(methylsulfonyl)pyrimidin-4-yl]oxy}-1-naphthyl)-5-morpholin-4-ylbenzamide and piperidine according to conditions described in general procedure C. Mp: 190-191° C.; $^1$H NMR (400 MHz, CDCl$_3$) δ 1.52-1.63(m, 6 H), 3.27-3.63(m, 4 H), 3.72 (m, 4H), 3.87(m, 4 H), 5.81-5.83(m, 1 H), 5.92-5.94(m, 1 H), 6.78(d, J=10.0 Hz, 1 H), 7.08(d, J=6.4 Hz, 1 H), 7.33-7.35(m, 2 H), 7.50-7.61(m, 2 H), 7.89-7.91(m, 1 H), 7.96-8.14(m, 1 H), 8.12-8.17(m, 2 H).

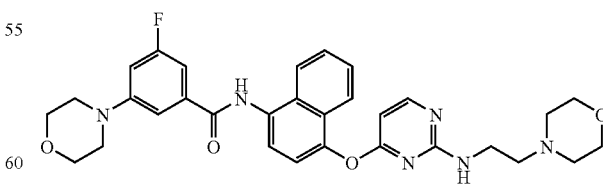

3-Fluoro-5-morpholin-4-yl-N-[4-({2-[(2-morpholin-4-ylethyl)amino]pyrimidin-4-yl}oxy)-1-naphthyl]benzamide (Compound B326). Compound is prepared from 3-fluoro-N-(4-{[2-(methylsulfonyl)pyrimidin-4-yl]oxy}-1-naphthyl)-5-morpholin-4-ylbenzamide and 2-morpholin-4-yl-ethylamine according to conditions described in general procedure C. Mp: 112-114° C.; ¹H NMR (400 MHz, CDCl₃) δ 2.33-2.43 (m, 6 H), 3.25-3.31(m, 6 H), 3.65-3.71(m, 4H), 3.84-3.89(m, 4 H), 5.54(s, 1 H), 6.08-6.10(m, 1 H), 6.77-6.80(m, 1 H), 7.09(d, J=8.0 Hz, 1 H), 7.27-7.33(m, 2 H), 7.50-7.57(m, 2 H), 7.92-7.97(m, 2 H), 8.13-8.17(m, 2 H).

benzamide and azetidine according to conditions described in general procedure C. Mp: 196-197° C.; ¹H NMR (400 MHz, DMSO-d₆) δ 2.17-2.25(m, 2 H), 3.23-3.30(m, 6 H), 3.75-3.78 (m, 4 H), 3.87(s, 1 H), 6.14(d, J=5.5 Hz, 1 H), 7.03-7.06(m, 1 H), 7.25(d, J=8.8 Hz, 1 H), 7.40-7.63(m, 5 H), 7.84-7.86 (m, 1 H), 7.99-8.01(m, 1 H), 8.22(d, J=5.5 Hz, 1 H), 10.47(s, 1 H).

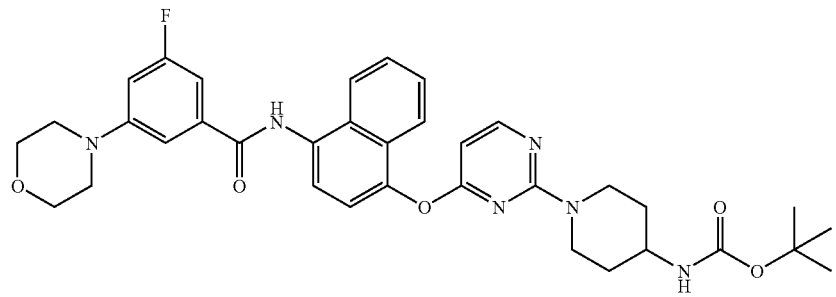

t-Butyl-{1-[4-({4-[(3-fluoro-5-morpholin-4-ylbenzoyl) amino]-1-naphthyl}oxy)pyrimidin-2-yl]piperidin-4-yl}-carbamate (Compound B366). Compound is prepared from 3-fluoro-N-(4-{[2-(methylsulfonyl)pyrimidin-4-yl]oxy}-1-naphthyl)-5-morpholin-4-ylbenzamide and piperidin-4-yl-carbamic acid t-butyl ester according to conditions described in general procedure C. Mp: 214-216° C.; ¹H NMR (400 MHz, DMSO-d₆) δ 1.33-1.41(m, 14 H), 2.47-3.41(m, 4H), 3.25-3.28(m, 4H), 3.75-3.78(m, 4 H), 4.20(s, 1 H), 6.20(d, J=5.5 Hz, 1H), 6.77-6.79(m, 1 H), 7.00-7.05(m, 1H), 7.18-7.26(m, 1H), 7.38-7.63(m, 5H), 7.85(d, J=9.2 Hz, 1 H), 8.00 (d, J=8.4 Hz, 1H), 8.26(d, J=5.5 Hz, 1H), 10.47(s, 1H).

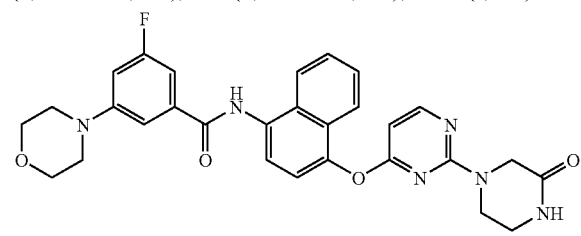

3-Fluoro-5-morpholin-4-yl-N-(4-{[2-(3-oxopiperazin-1-yl)pyrimidin-4-yl]oxy}-1-naphthyl)benzamide (Compound B368). Compound is prepared from 3-fluoro-N-(4-{[2-(methylsulfonyl)pyrimidin-4-yl]oxy}-1-naphthyl)-5-morpholin-4-ylbenzamide and piperazin-2-one according to conditions described in general procedure C. Mp: 108-110° C.; ¹H NMR (400 MHz, DMSO-d₆) δ 3.14-3.35(m, 8 H), 3.73-3.78(m, 6 H), 6.37(d, J=5.5 Hz, 1 H), 7.03-7.06(m, 2 H), 7.26(d, J=8.5 Hz, 1 H), 7.44-7.63(m, 4 H), 7.84-7.86(m, 1 H), 8.00-8.04(m, 2H), 8.35(d, J=5.1 Hz, 1 H), 10.51(s, 1 H).

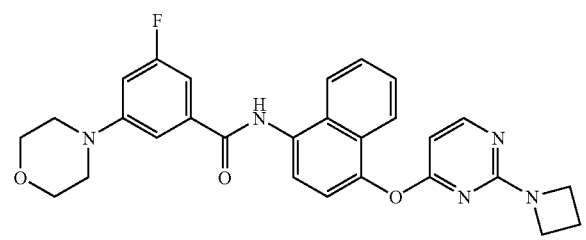

N-{4-[(2-azetidin-1-ylpyrimidin-4-yl)oxy]-1-naphthyl}-3-fluoro-5-morpholin-4-ylbenzamide (Compound B363). Compound is prepared from 3-fluoro-N-(4-{[2-(methylsulfonyl)pyrimidin-4-yl]oxy}-1-naphthyl)-5-morpholin-4-yl-

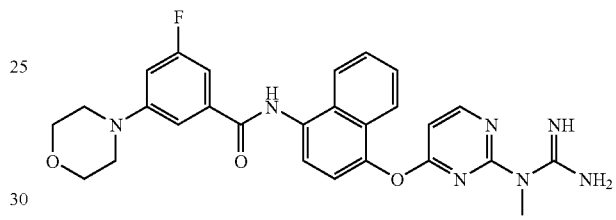

N-[4-({2-[[amino(imino)methyl](methyl)amino]pyrimidin-4-yl}oxy)-1-naphthyl]-3-fluoro-5-morpholin-4-ylbenzamide (Compound B367). Compound is prepared from 3-fluoro-N-(4-{[2-(methylsulfonyl)pyrimidin-4-yl]oxy}-1-naphthyl)-5-morpholin-4-ylbenzamide and N-methylguanidine according to conditions described in general procedure C. Mp: 155-157° C.; ¹H NMR (400 MHz, DMSO-d₆) δ 3.19-3.33(m, 7 H), 3.75-3.78(m, 4 H), 6.50(d, J=5.5 Hz, 1H), 7.04(d, J=12.0 Hz, 1 H), 7.27(d, J=9.1 Hz, 1 H), 7.34-7.68(m, 7 H), 7.80(d, J=8.8 Hz, 1H), 7.99(d, J=8.2 Hz, 1 H), 8.29(d, J=5.5 Hz, 1 H), 10.47(s, 1 H).

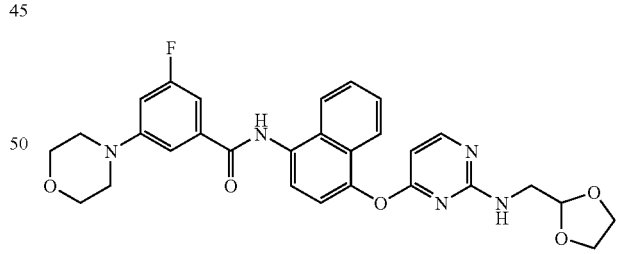

N-[4-({2-[(1,3-dioxolan-2-ylmethyl)amino]pyrimindin-4-yl}oxy)-1-naphthyl]-3-fluoro-5-morpholin-4-ylbenzamide (Compound B369). Compound is prepared from 3-fluoro-N-(4-{[2-(methylsulfonyl)pyrimidin-4-yl]oxy}-1-naphthyl)-5-morpholin-4-ylbenzamide and C-[1,3]dioxolan-2-yl-methylamine according to conditions described in general procedure C. Mp: 122-124° C.; ¹H NMR (400 MHz, DMSO-d₆) δ 3.25-3.30 (m, 6 H), 3.73-3.83 (m, 8 H), 4.19 (bs, 1 H), 6.36 (bs, 1 H), 7.04 (d, J=12.0 Hz, 1 H), 7.26-7.31 (m, 2 H), 7.38-7.61 (m, 5 H), 7.83 (d, J=8.8 Hz, 1 H), 7.99 (d, J=9.2 Hz, 1 H), 8.20 (s, 1 H), 10.46 (s, 1 H).

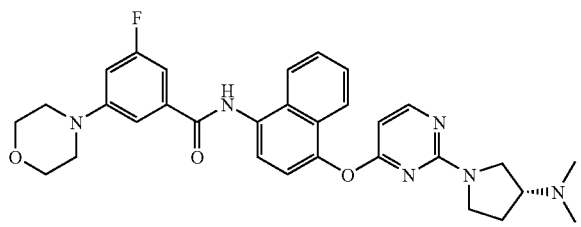

N-[4-({2-[(3R)-3-(dimethylamino)pyrrolidin-1-yl]pyrimidin-4-yl}oxy)-1-naphthyl]-3-fluoro-5-morpholin-4-ylbenzamide (Compound B342). Compound is prepared from 3-fluoro-N-(4-{[2-(methylsulfonyl)pyrimidin-4-yl]oxy}-1-naphthyl)-5-morpholin-4-ylbenzamide and (R)—N,N-dimethylpyrrolidin-3-amine according to conditions described in general procedure C. Mp: 115-117° C.; $^1$H NMR (400 MHz, DMSO-$d_6$) δ 1.70-2.10(m, 2 H), 2.13(s, 6H), 2.68-3.10 (m, 5 H), 3.25(t, J=4.4 Hz, 4 H), 3.74(t, J=4.8 Hz, 4 H), 6.15(bd, 1 H), 7.04(d, J=12.0 Hz, 1 H), 7.24(d, J=8.4 Hz, 1 H), 7.40-7.61(m, 5 H), 7.84(d, J=8.0 Hz, 1 H), 7.98(d, J=8.4 Hz, 1 H), 8.22(d, J=5.5 Hz, 1 H), 10.45(s, 1 H).

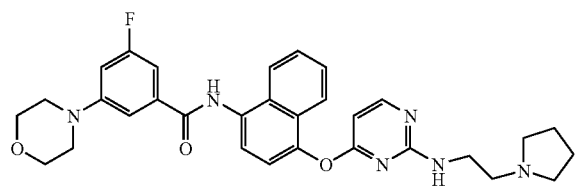

3-Fluoro-5-morpholin-4-yl-N-[4-({2-[(2-pyrrolidin-1-ylethyl)amino]pyrimidin-4-yl}oxy)-1-naphthyl]benzamide (Compound B338). Compound is prepared from 3-fluoro-N-(4-{[2-(methylsulfonyl)pyrimidin-4-yl]oxy}-1-naphthyl)-5-morpholin-4-ylbenzamide and 2-pyrrolidin-1-yl-ethylamine according to conditions described in general procedure C. Mp: 95-97° C.; $^1$H NMR (400 MHz, DMSO-$d_6$) δ 1.59 (bs, 4 H), 2.08-2.2 (m, 2 H), 2.37-2.47 (m, 4 H), 2.92 (bs, 1 H), 3.23-3.25 (m, 5 H), 3.74 (t, J=4.4 Hz, 4 H), 6.32 (bd, 1 H), 6.59 (bs, 1 H), 7.04 (d, J=11.4 Hz, 1 H), 7.24 (d, J=8.8 Hz, 1 H), 7.38 (d, J=8.0 Hz, 1 H), 7.46 (s, 1 H), 7.53-7.58 (m, 3 H), 7.80 (d, J=6.6 Hz, 1 H), 7.98 (d, J=7.7 Hz, 1 H), 8.22 (s, 1 H), 10.43 (s, 1 H).

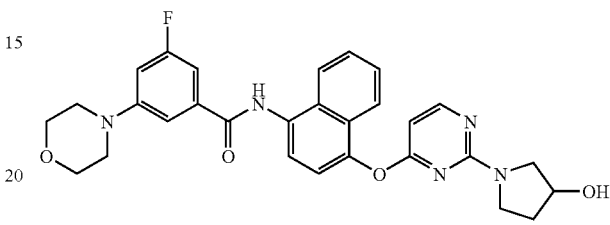

3-Fluoro-N-(4-{[2-(3-hydroxypyrrolidin-1-yl)pyrimidin-4-yl]oxy}-1-naphthyl)-5-morpholin-4-ylbenzamide (Compound B339). Compound is prepared from 3-fluoro-N-(4-{[2-(methylsulfonyl)pyrimidin-4-yl]oxy}-1-naphthyl)-5-morpholin-4-ylbenzamide and pyrrolidin-3-ol according to conditions described in general procedure C. Mp: 137-139° C.; $^1$H NMR (400 MHz, DMSO-$d_6$) δ 1.59 (bs, 4 H), 1.74-1.90 (m, 2 H), 2.99-3.16 (m, 2 H), 3.27 (t, J=4.4 Hz, 4 H), 3.40-3.46 (m, 2 H), 3.77 (t, J=5.1 Hz, 4H), 4.29 (bs, 1 H), 6.20 (bs, 1 H), 7.04 (d, J=12.0 Hz, 1 H), 7.27 (d, J=8.8 Hz, 1 H), 7.44-7.63 (m, 5 H), 7.86 (d, J=8.0 Hz, 1 H), 8.00 (d, J=8.4 Hz, 1 H), 8.25 (d, J=5.5 Hz, 1 H), 10.48 (s, 1 H).

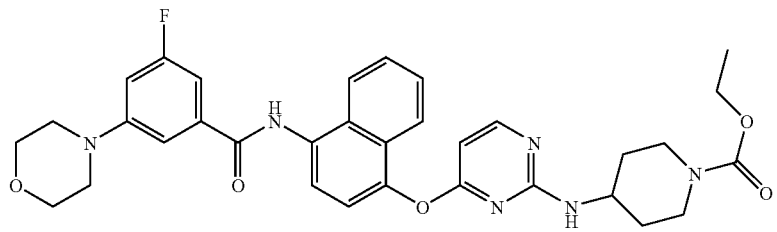

Ethyl-4-{[4-({4-[(3-fluoro-5-morpholin-4-ylbenzoyl)amino]-1-naphthyl}oxy)pyrimidin-2-yl]amino}piperidine-1-carboxylate (Compound B341) Compound is prepared from 3-fluoro-N-(4-{[2-(methylsulfonyl)pyrimidin-4-yl]oxy}-1-naphthyl)-5-morpholin-4-ylbenzamide and 4-aminopiperidine-1-carboxylic acid ethyl ester according to conditions described in general procedure C. Mp: 122-124° C.; $^1$H NMR (400 MHz, DMSO-$d_6$) δ 1.14 (t, J=6.9 Hz, 3 H), 1.17-1.26 (m, 2 H), 1.73 (bs, 2 H), 2.82 (bs, 2 H), 3.26 (t, J=4.4 Hz, 4 H), 3.34 (bs, 1 H), 3.77 (t, J=4.8 Hz, 4 H), 3.89 (bs, 1 H), 3.96-4.01 (m, 2 H), 6.36 (bd, 1 H), 7.04 (d, J=12.4 Hz, 1H), 7.12 (s, 1 H), 7.27 (d, J=8.8 Hz, 1 H), 7.40 (d, J=8.0 Hz, 1 H), 7.47 (s, 1 H), 7.56-7.62 (m, 3 H), 7.82 (d, J=7.6 Hz, 1 H), 8.00 (d, J=8.0 Hz, 1 H), 8.23 (s, 1 H), 10.45 (s, 1 H).

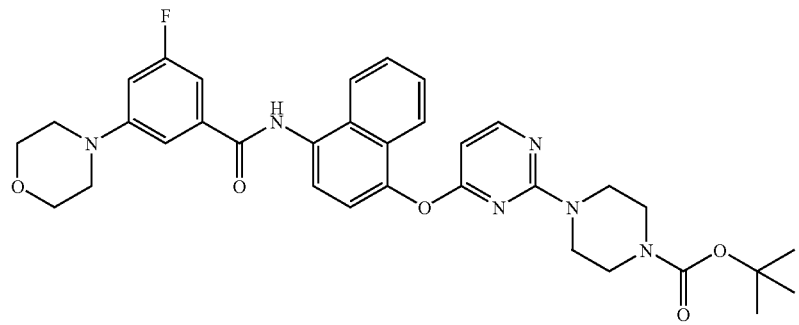

t-Butyl-4-[4-({4-[(3-fluoro-5-morpholin-4-ylbenzoyl)amino]-1-naphthyl}oxy)pyrimidin-2-yl]piperazine-1-carboxylate (Compound B340). Compound is prepared from 3-fluoro-N-(4-{[2-(methylsulfonyl)pyrimidin-4-yl]oxy}-1-naphthyl)-5-morpholin-4-ylbenzamide and piperazine-1-carboxylic acid t-butyl ester according to conditions described in general procedure C. Mp: 131-133° C.; $^1$HNMR (400 MHz, DMSO-$d_6$) δ 1.38 (s, 9 H), 3.27-3.34 (m, 8H), 3.50 (bs, 4 H), 3.77 (t, J=4.38 Hz, 4 H), 6.24-25 (m, 1 H), 7.04 (d, J=11.3 Hz, 1 H), 7.26 (d, J=8.4 Hz, 1 H), 7.44 (d, J=8.0 Hz, 1 H), 7.50 (s, 1 H), 7.56-7.63 (m, 3 H), 7.85 (d, J=8.4 Hz, 1 H), 8.01 (d, J=8.8 Hz, 1 H), 8.29-8.30 (m, 1 H), 10.48 (s, 1 H).

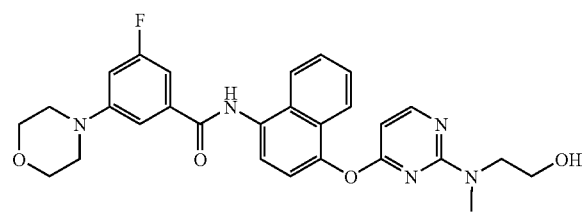

3-Fluoro-N-[4-({2-[(2-hydroxyethyl)(methyl)amino]pyrimindin-4-yl}oxy)-1-naphthyl]-5-morpholin-4-ylbenzamide (Compound B333). Compound is prepared from 3-fluoro-N-(4-{[2-(methylsulfonyl)pyrimidin-4-yl]oxy}-1-naphthyl)-5-morpholin-4-ylbenzamide and 2-methylaminoethanol according to conditions described in general procedure C. Mp: 100-102° C.; $^1$H NMR (400 MHz, DMSO-$d_6$) δ 2.77-3.52 (m, 4 H), 3.26 (s, 4 H), 3.76 (m, 4 H), 4.62 (m, 1 H), 6.19-6.22 (m, 1 H), 7.02-7.05 (m, 1 H), 7.26 (d, J=8.4 Hz, 1 H), 7.41 (d, J=8.0 Hz, 1H), 7.50 (s, 1 H), 7.56-7.63 (m, 3 H), 7.85 (d, J=7.6 Hz, 1 H), 8.00 (d, J=7.6 Hz, 1 H), 8.25 (d, J=5.4 Hz, 1 H), 10.47 (s, 1 H).

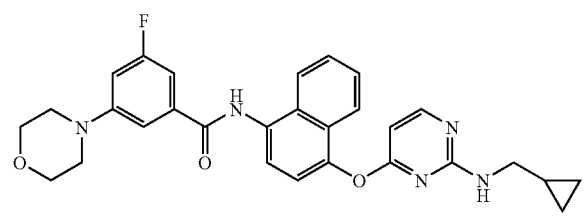

N-[4-({2-[(Cyclopropylmethyl)amino]pyrimidin-4-yl}oxy)-1-naphthyl]-3-fluoro-5-morpholin-4-ylbenzamide (Compound B336). Compound is prepared from 3-fluoro-N-(4-{[2-(methylsulfonyl)pyrimidin-4-yl]oxy}-1-naphthyl)-5-morpholin-4-ylbenzamide and cyclopropylmethylamine according to conditions described in general procedure C. Mp: 116-117° C.; $^1$H NMR (400 MHz, DMSO-$d_6$) δ 0.1-0.3 (m, 4 H), 0.97 (bs, 1 H), 2.75-3.02 (m, 2 H) 3.26 (s, 4 H), 3.76 (s, 4 H), 6.25 (bd, 1 H), 7.03 (d, J=12.4 Hz, 1 H), 7.24-7.27 (m, 2 H), 7.38-7.41 (m, 1 H), 7.48 (s, 1 H), 7.56-7.59 (m, 3 H), 7.80-7.83 (m, 1 H), 7.98 (d, J=7.3 Hz, 1 H), 8.20 (s, 1 H), 10.45 (s, 1 H).

3-Fluoro-5-morpholin-4-yl-N-{4-[(2-pyrrolidin-1-ylpyrimidin-4-yl)oxy]-1-naphthyl}benzamide (Compound B334). Compound is prepared from 3-fluoro-N-(4-{[2-(methylsulfonyl)pyrimidin-4-yl]oxy}-1-naphthyl)-5-morpholin-4-ylbenzamide and pyrrolidine according to conditions described in general procedure C. Mp: 205-207° C.; $^1$H NMR (400 MHz, DMSO-$d_6$) δ 1.81 (s, 4 H), 3.06 s, 2 H), 3.27 (s, 4 H), 3.41 (s, 2 H), 3.77 (s, 4 H), 6.27-6.19 (m, 1 H), 7.03-7.06 (m, 1 H), 7.27 (d, J=9.1 Hz, 1H), 7.42-7.46 (m, 1H), 7.51 (s, 1 H), 7.57-7.639 (m, 3 H), 7.86 (d, J=8.4 Hz, 1 H), 8.00 (d, J=8.3 Hz, 1 H), 8.23-8.25 (m, 1 H), 10.47 (s, 1 H).

3-Fluoro-N-[4-({2-[(4-methylcyclohexyl)amino]pyrimidin-4-yl}oxy)-1-naphthyl]-5-morpholin-4-ylbenzamide (Compound B337). Compound is prepared from 3-fluoro-N-(4-{[2-(methylsulfonyl)pyrimidin-4-yl]oxy}-1-naphthyl)-5-morpholin-4-ylbenzamide and 4-methylcyclohexylamine according to conditions described in general procedure C. Mp: 116-117° C.; $^1$H NMR (400 MHz, DMSO-$d_6$) δ 1.83-0.85 (m, 3 H), 1.17-1.75 (m, 9 H), 3.27 (s, 4 H), 3.34 (s, 1 H), 3.77 (s, 4 H), 6.29 (bs, 1 H), 6.98-7.06 (m, 2 H), 7.27 (d, J=8.4 Hz, 1 H), 7.39-7.42 (m, 1 H), 7.48 (s, 1 H), 7.58-7.60 (m, 3 H), 7.84 (m, 1 H), 7.98-8.00 (m, 1 H), 8.21 (m, 1H), 10.45 (s, 1 H).

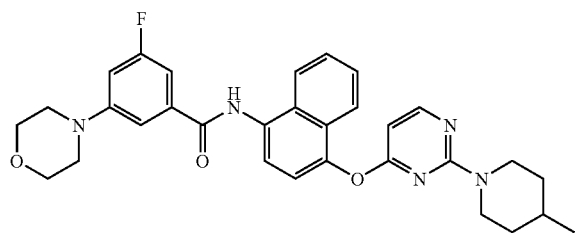
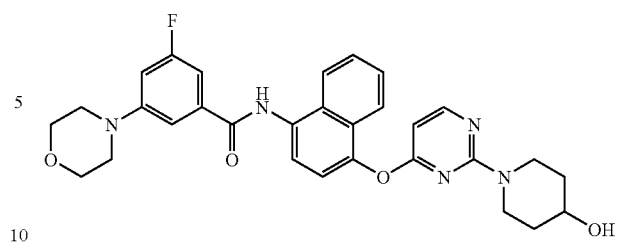

3-Fluoro-N-(4-{[2-(4-methylpiperidin-1-yl)pyrimidin-4-yl]oxy}-1-naphthyl)-5-morpholin-4-ylbenzamide (Compound B335). Prepared from 3-fluoro-N-(4-{[2-(methylsulfonyl)pyrimidin-4-yl]oxy}-1-naphthyl)-5-morpholin-4-ylbenzamide and 4-methylpiperidine according to conditions described in general procedure C. Mp: 117-118° C.; $^1$H NMR (400 MHz, DMSO-d$_6$) δ 0.84-0.94 (m, 5 H), 1.49-1.52 (m, 3 H), 2.67 (t, J=12.0 Hz, 2 H), 3.25 (m, 4 H), 3.73 (m, 4 H), 4.30 (s, 2 H), 6.19-6.20 (m, 1 H), 7.03-7.06 (m, 1 H), 7.27 (d, J=8.4 Hz, 1 H), 7.41-7.63 (m, 5 H), 7.83-7.85 (m, 1 H), 7.98-8.01 (m, 1 H), 8.25-8.27 (m, 1H), 10.47 (s, 1 H).

3-Fluoro-N-(4-{[2-(4-hydroxypiperidin-1-yl)pyrimidin-4-yl]oxy}-1-naphthyl)-5-morpholin-4-ylbenzamide (Compound B332). Compound is prepared from 3-fluoro-N-(4-{[2-(methylsulfonyl)pyrimidin-4-yl]oxy}-1-naphthyl)-5-morpholin-4-ylbenzamide and piperidin-4-ol according to conditions described in general procedure C. Mp: 106-108° C.; $^1$H NMR (400 MHz, CDCl$_3$) δ 1.37-1.46 (m, 2 H), 1.81-1.85 (m, 2 H), 3.13-3.20 (m, 2H), 3.24 (t, J=4.4 Hz, 4 H), 3.83-3.92 (m, 5 H), 4.20 (d, J=12.4 Hz, 1 H), 5.98 (d, J=5.6 Hz, 1 H), 6.76 (d, J=11.6 Hz, 1 H), 7.07 (d, J=8.0 Hz, 1 H), 7.30 (d, J=8.0 Hz, 1 H), 7.49-7.58 (m, 3 H), 7.88-7.93 (m, 2 H), 7.99 (d, J=8.4 Hz, 1 H), 8.16 (d, J=5.2 Hz, 1 H), 8.21 (s, 1 H).

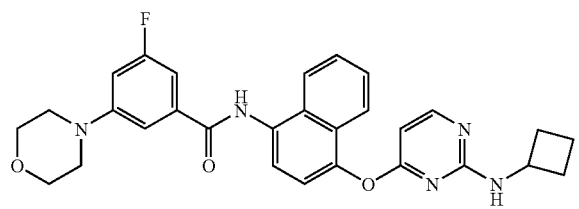

N-(4-{[2-(Cyclobutylamino)pyrimidin-4-yl]oxy}-1-naphthyl)-3-fluoro-5-morpholin-4-ylbenzamide (Compound B331). Compound is prepared from 3-fluoro-N-(4-{[2-(methylsulfonyl)pyrimidin-4-yl]oxy}-1-naphthyl)-5-morpholin-4-ylbenzamide and cyclobutylamine according to conditions described in general procedure C. Mp: 110-112° C.; $^1$H NMR (400 MHz, CDCl$_3$) δ 1.63 (s, 2 H), 1.73-1.80 (m, 2 H), 2.42 (s, 2 H), 3.19-3.29 (m, 4H), 3.79-3.92 (m, 4 H), 4.30 (s, 1 H), 5.27 (s, 1 H), 6.08 (s, 1H), 6.75-6.78 (m, 1 H), 7.05 (d, J =7.6 Hz, 1 H), 7.24-7.26 m, 1 H), 7.32 (s, 1 H), 7.47-7.57 (m, 2 H), 7.88-8.02 (m, 3 H), 8.16 (m, 1 H), 8.25 (s, 1 H).

N-(4-{[2-(Cyanoamino)pyrimidin-4-yl]oxy}-1-naphthyl)-3-fluoro-5-morpholin-4-ylbenzamide (Compound B330). Compound is prepared from 3-fluoro-N-(4-{[2-(methylsulfonyl)pyrimidin-4-yl]oxy}-1-naphthyl)-5-morpholin-4-ylbenzamide and cyanamide according to conditions described in general procedure C. $^1$H NMR (400 MHz, CDCl$_3$) δ 3.21 (t, J=4.8 Hz, 4 H), 3.81 (t, J=5.2 Hz, 4 H), 6.34 (d, J=6.0 Hz, 1 H), 6.70 (d, J=12.0 Hz, 1H), 7.16-7.20 (m, 2 H), 7.32-7.46 (m, 4 H), 7.76-7.78 (s, 1 H), 7.86-7.89 (m 1 H), 8.05 (d, J=6.4 Hz, 1 H), 9.61 (s, 1 H).

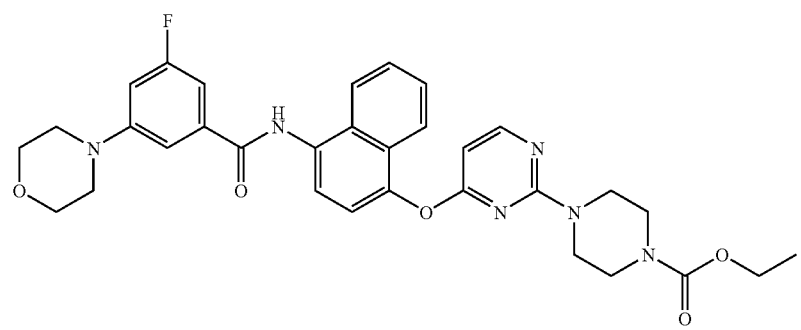

Ethyl-4-[4-({4-[(3-fluoro-5-morpholin-4-ylbenzoyl)amino]-1-naphthyl}oxy)pyrimidin-2-yl]piperazine-1-carboxylate (Compound B329). Compound is prepared from 3-fluoro-N-(4-{[2-(methylsulfonyl)pyrimidin-4-yl]oxy}-1-naphthyl)-5-morpholin-4-ylbenzamide and piperazine-1-carboxylic acid ethyl ester according to conditions described in general procedure C. ¹H NMR (400 MHz, CDCl₃) δ 1.27 (t, J=7.6 Hz, 3 H), 3.27 (s, 4 H), 3.44 (m, 4 H), 3.64 (s, 4 H), 3.89 (m, 4 H), 4.12-4.17 (m, 2 H), 6.07-6.09 (m, 1 H), 6.78-6.81 (m, 1 H), 7.10 (d, J=8.0 Hz, 1 H), 7.31-7.35 (m, 2 H), 7.51-7.61 (m, 2 H), 7.92-8.01 (m, 2 H), 8.19-8.24 (m, 2 H).

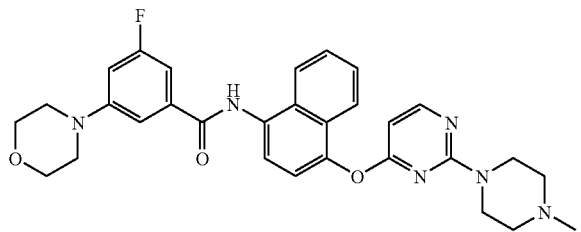

3-Fluoro-N-(4-{[2-(4-methylpiperazin-1-yl)pyrimidin-4-yl]oxy}-1-naphthyl)-5-morpholin-4-ylbenzamide (Compound B328). Compound is prepared from 3-fluoro-N-(4-{[2-(methylsulfonyl)pyrimidin-4-yl]oxy}-1-naphthyl)-5-morpholin-4-ylbenzamide and N-methylpiperazine according to conditions described in general procedure C. Mp: 195-197° C.; ¹H NMR (400 MHz, CDCl₃) δ 2.35 (s, 3 H), 2.39 (t, J=4.4 Hz, 4 H), 3.25 (t, J=4.8 Hz, 4 H), 3.69 (s, 4 H), 3.87 (t, J=4.4 Hz, 4 H), 6.01 (d, J=5.6 Hz, 1 H), 6.78 (d, J=11.6 Hz, 1 H), 7.07 (d, J=8.0 Hz, 1 H), 7.30-7.32 (m, 2 H), 7.49-7.59 (m, 2 H), 7.89-8.00 (m, 3 H), 8.15-8.18 (m, 2 H).

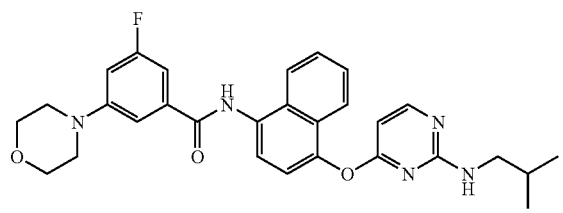

3-Fluoro-N-(4-{[2-(isobutylamino)pyrimidin-4-yl]oxy}-1-naphthyl)-5-morpholin-4-ylbenzamide (Compound B318). Compound is prepared from 3-fluoro-N-(4-{[2-(methylsulfonyl)pyrimidin-4-yl]oxy}-1-naphthyl)-5-morpholin-4-ylbenzamide and isobutylamine according to conditions described in general procedure C. Mp: 96-97° C.; ¹H NMR (400 MHz, DMSO-d₆) δ 0.60-0.80 (m, 6 H), 1.80 (m, 1 H), 2.89 (s, 2 H), 3.26 (t, J=4.8 Hz, 4 H), 3.77 (t, J=5.2 Hz, 4 H), 6.20-6.40 (bd, 1 H), 7.03-7.07 (m, 1 H), 7.22 (s, 1 H), 7.27 (d, J=8.4 Hz, 1 H), 7.40 (d, J=8.0 Hz, 1 H), 7.47 (s, 1 H), 7.55-7.62 (m, 3 H), 7.81-7.83 (m, 1H), 8.00 (d, J=8.4 Hz, 1 H), 8.21 (s, 1 H), 10.45 (s, 1 H).

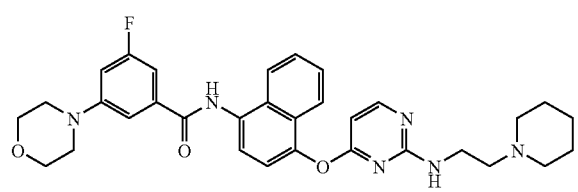

3-Fluoro-5-morpholin-4-yl-N-[4-({2-[(2-piperidin-1-yl-ethyl)amino]pyrimidin-4-yl}oxy)-1-naphthyl]benzamide (Compound B343). Compound is prepared from 3-fluoro-N-(4-{[2-(methylsulfonyl)pyrimidin-4-yl]oxy}-1-naphthyl)-5-morpholin-4-ylbenzamide and 2-piperidin-1-yl-ethylamine according to conditions described in general procedure C. Mp: 98-100° C.; ¹H NMR (400 MHz, DMSO-d₆) δ 1.42 (bs, 6 H), 2.06 (s, 2 H), 2.33 (s, 4 H), 2.55-2.94 (m, 2 H), 3.26 (t, J=4.4 Hz, 4 H), 3.77 (t, J=4.8 Hz, 4 H), 6.20-6.35 (bd, 1 H), 6.95 (s, 1 H), 7.04 (d, J=12.0 Hz, 1 H), 7.26 (d, J=8.4 Hz, 1 H), 7.40 (d, J=8.0 Hz, 1 H), 7.48 (s, 1 H), 7.55-7.61 (m, 3H), 7.81-7.83 (m, 1 H), 8.00 (d, J=8.4 Hz, 1 H), 8.23 (s, 1 H), 10.45 (s, 1 H).

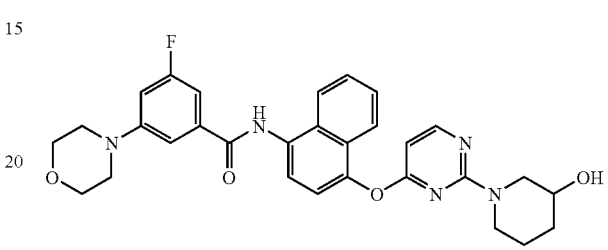

3-Fluoro-N-(4-{[2-(3-hydroxypiperidin-1-yl)pyrimidin-4-yl]oxy}-1-naphthyl)-5-morpholin-4-ylbenzamide (Compound B346). Compound is prepared from 3-fluoro-N-(4-{[2-(methylsulfonyl)pyrimidin-4-yl]oxy}-1-naphthyl)-5-morpholin-4-ylbenzamide and piperidin-3-ol according to conditions described in general procedure C. Mp: 180-181° C.; ¹H NMR (400 MHz, DMSO-d₆) δ 1.26-1.31 (m, 2 H), 1.54 (s, 2 H), 1.81-1.83 (m, 2 H), 2.70-2.82 (m, 2 H), 3.27 (t, J=4.4 Hz, 4 H), 3.36 (s, 2 H), 3.77 (t, J=4.8 Hz, 4 H), 4.22 (bs, 1 H), 4.82 (s, 1 H), 6.16 (d, J=5.1 Hz, 1 H), 7.03-7.06 (m, 1 H), 7.26 (d, J=8.4 Hz, 1 H), 7.43 (d, J=8.0 Hz, 1H), 7.50 (s, 1 H), 7.55-7.63 (m, 3 H), 7.84-7.87 (m, 1 H), 7.99-8.01 (m, 1 H), 8.25 (d, J=5.8 Hz, 1 H), 10.49 (s, 1 H).

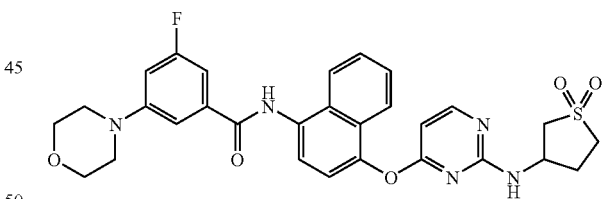

N-[4-({2-[(1,1-Dioxidotetrahydro-3-thienyl)amino]pyrimidin-4-yl}oxy)-1-naphthyl]-3-fluoro-5-morpholin-4-ylbenzamide (Compound B347). Compound is prepared from 3-fluoro-N-(4-{[2-(methylsulfonyl)pyrimidin-4-yl]oxy}-1-naphthyl)-5-morpholin-4-ylbenzamide and 1,1-Dioxo-tetrahydro-1λ6-thiophen-3-ylamine according to conditions described in general procedure C. Mp: 150-151° C.; ¹H NMR (400 MHz, DMSO-d₆) δ 2.04 (s, 2 H), 2.30 (s, 1 H), 2.88 (s, 2 H), 3.07 (s, 2 H), 3.26 (t, J=4.4 Hz, 4 H), 3.77 (t, J=4.8 Hz, 4 H), 4.56 (s, 1 H), 6.49 (s, 1 H), 7.04 (d, J=12.4 Hz, 1 H), 7.26 (d, J=8.8 Hz, 1 H), 7.43 (d, J=8.0 Hz, 1 H), 7.47 (s, 1 H), 7.56-7.61 (m, 3 H), 7.81-7.84 (m, 1 H), 7.99 (d, J=7.6 Hz, H), 8.30 (d, J=4.0 Hz, 1H), 10.46 (s, 1 H).

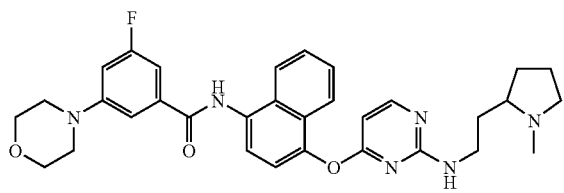

3-Fluoro-N-{4-[(2-{[2-(1-methylpyrrolidin-2-yl)ethyl]amino}pyrimidin-4-yl)oxy]-1-naphthyl}-5-morpholin-4-yl-benzamide (Compound B344). Compound is prepared from 3-fluoro-N-(4-{[2-(methylsulfonyl)pyrimidin-4-yl]oxy}-1-naphthyl)-5-morpholin-4-ylbenzamide and 2-(1-methyl-pyrrolidin-2-yl)-ethylamine according to conditions described in general procedure C. Mp: 100-101° C.; $^1$H NMR (400 MHz, DMSO-$d_6$) δ 1.33-2.17 (m, 12 H), 2.88 (s, 2 H), 3.26 (t, J=4.4 Hz, 4 H), 3.77 (t, J=4.8 Hz, 4 H), 6.17-6.32 (bd, 1 H), 7.02-7.06 (m, 1 H), 7.12 (s, 1 H), 7.27 (d, J=8.7 Hz, 1 H), 7.40 (d, J=8.0 Hz, 1 H), 7.48 (s, 1 H), 7.55-7.61 (m, 3H), 7.82 (d, J=8.4 Hz, 1 H), 7.99 (d, J=7.7 Hz, 1 H), 8.23 (s, 1 H), 10.46 (s, 1 H).

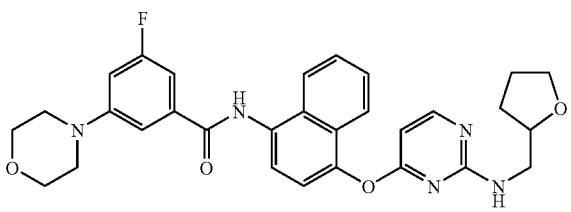

3-Fluoro-5-morpholin-4-yl-N-[4-({2-[(tetrahydrofuran-2-ylmethyl)amino]pyrimidin-4-yl}oxy)-1-naphthyl]benzamide (Compound B327). Compound is prepared from 3-fluoro-N-(4-{[2-(methylsulfonyl)pyrimidin-4-yl]oxy}-1-naphthyl)-5-morpholin-4-ylbenzamide and C-(tetrahydrofuran-2-yl)-methylamine according to conditions described in general procedure C. Mp: 103-105° C.; $^1$H NMR (400 MHz, CDCl$_3$) δ 1.55-1.80 (m, 4 H), 3.21 (t, J=4.4 Hz, 4 H), 3.45-3.89 (m, 5 H), 3.83 (t, J=4.8 Hz, 4 H), 5.42 (s, 1 H), 6.06 (s, 1 H), 6.75 (d, J=11.7 Hz, 1H), 7.07 (d, J=8.0 Hz, 1 H), 7.22 (d, J=8.4 Hz, 1H), 7.30 (s, 1 H), 7.42-7.52 (m, 2 H), 7.77-7.94 (m, 3 H), 8.11 (s, 1 H), 8.40 (s, 1 H).

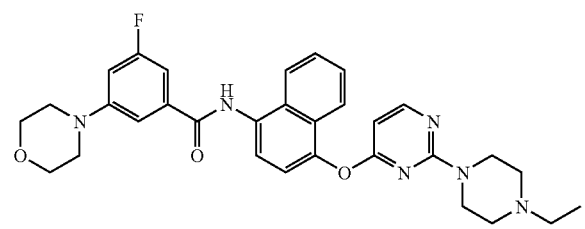

N-(4-{[2-(4-Ethylpiperazin-1-yl)pyrimidin-4-yl]oxy}-1-naphthyl)-3-fluoro-5-morpholin-4-ylbenzamide (Compound B345). Compound is prepared from 3-fluoro-N-(4-{[2-(methylsulfonyl)pyrimidin-4-yl]oxy}-1-naphthyl)-5-morpholin-4-ylbenzamide and N-ethylpiperazine according to conditions described in general procedure C. Mp: 185-186° C.; $^1$H NMR (400 MHz, DMSO-$d_6$) δ 0.98 (t, J=6.9 Hz, 3 H), 2.31 (bs, 6 H), 3.27 (t, J=4.0 Hz, 6 H), 3.50 (bs, 2 H), 3.77 (t, J=4.4 Hz, 4 H), 6.22-6.24 (m, 1 H), 7.04 (d, J=12.0 Hz, 1 H), 7.27 (d, J=8.0 Hz, 1 H), 7.43 (d, J=8.0 Hz, 1 H), 7.50 (s, 1 H), 7.56-7.63 (m, 3 H), 7.84-7.86 (m, 1 H), 8.00 (d, J=8.0 Hz, 1 H), 8.27-8.29 (m, 1 H), 10.48 (s, 1 H).

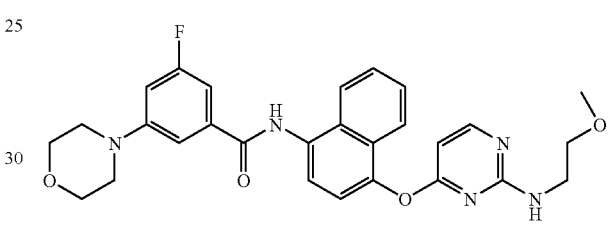

3-Fluoro-N-[4-({2-[(2-methoxyethyl)amino]pyrimidin-4-yl}oxy)-1-naphthyl]-5-morpholin-4-ylbenzamide (Compound B319). Compound is prepared from 3-fluoro-N-(4-{[2-(methylsulfonyl)pyrimidin-4-yl]oxy}-1-naphthyl)-5-morpholin-4-ylbenzamide and 2-methoxyethylamine according to conditions described in general procedure C. Mp: 95-97° C.; $^1$H NMR (400 MHz, CDCl$_3$) δ 3.25 (t, J=4.7 Hz, 4H), 3.29 (s, 3 H), 3.43 (bs, 4 H), 3.87 (t, J=4.7 Hz, 4 H), 5.32 (s, 1 H), 6.10 (s, 1 H), 6.77 (d, J=12.3 Hz, 1 H), 7.07 (d, J=7.8 Hz, 1 H), 7.28-7.32 (m, 2 H), 7.50-7.59 (m, 2 H), 7.89-7.98 (m, 3 H), 8.13 (s, 2 H).

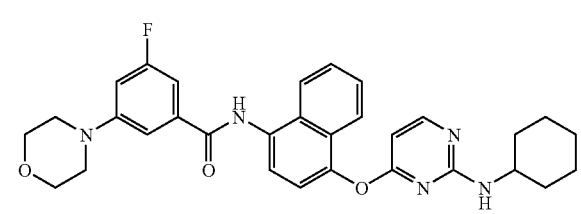

N-(4-{[2-(Cyclohexylamino)pyrimidin-4-yl]oxy}-1-naphthyl)-3-fluoro-5-morpholin-4-ylbenzamide (Compound B323). Compound is prepared from 3-fluoro-N-(4-{[2-(methylsulfonyl)pyrimidin-4-yl]oxy}-1-naphthyl)-5-morpholin-4-ylbenzamide and cyclohexylamine according to conditions described in general procedure C. Mp: 135-136° C.; $^1$H NMR (400 MHz, CDCl$_3$) δ 1.10-1.25 (m, 6 H), 1.58-1.64 (m, 4 H), 1.19 (bs, 1 H), 3.27 (s, 4H), 3.87-3.89 (m, 4 H), 4.90 (s, 1 H), 6.05 (s, 1 H), 6.78 (d, J=11.3 Hz, 1 H), 7.07 (d, J=7.8 Hz, 1 H), 7.26 (s, 1 H), 7.31-7.33 (m, 2 H), 7.51-7.61 (m, 2 H), 7.90 (d, J=8.6 Hz, 1 H), 7.97-8.00 (m, 2 H), 8.07 (s, 1 H), 8.12 (s, 1 H).

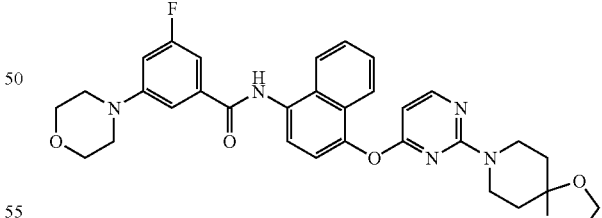

N-(4-{[2-(1,4-Dioxa-8-azaspiro[4.5]dec-8-yl)pyrimidin-4-yl]oxy}-1-naphthyl)-3-fluoro-5-morpholin-4-ylbenzamide (Compound B320). Compound is prepared from 3-fluoro-N-(4-{[2-(methylsulfonyl)pyrimidin-4-yl]oxy}-1-naphthyl)-5-morpholin-4-ylbenzamide and 1,4-dioxa-8-azaspiro[4.5]decane according to conditions described in general procedure C. Mp: 115-117° C.; $^1$H NMR (400 MHz, CDCl$_3$) δ 1.64 (t, J=5.0 Hz, 4 H), 3.26 (t, J=4.3 Hz, 4 H), 3.77 (s, 4 H), 3.88 (t, J=4.7 Hz, 4 H), 3.96 (s, 4 H), 5.98-5.99 (m, 1 H), 6.77 (d, J=11.7 Hz, 1H), 7.07 (d, J=7.8 Hz, 1 H), 7.32-7.34 (m, 2 H), 7.50-7.60 (m, 3 H), 7.90 (d, J=8.2 Hz, 1 H), 8.00 (d, J=8.6 Hz, 1 H), 8.10 (s, 2 H), 8.15-8.17 (m, 1 H).

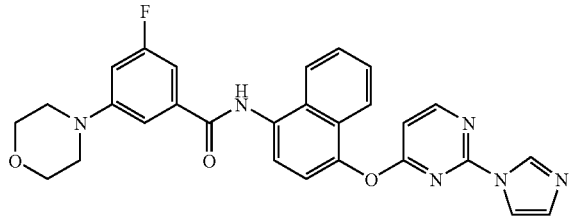

3-Fluoro-N-(4-{[2-(1H-imidazol-1-yl)pyrimidin-4-yl]oxy}-1-naphthyl)-5-morpholin-4-ylbenzamide (Compound B325). Compound is prepared from 3-fluoro-N-(4-{[2-(methylsulfonyl)pyrimidin-4-yl]oxy}-1-naphthyl)-5-morpholin-4-ylbenzamide and imidazole according to conditions described in general procedure C. Mp: 153-154° C.; $^1$H NMR (400 MHz, CDCl$_3$) δ 3.29 (s, 4 H), 3.89 (s, 4 H), 6.79-6.85 (m, 2 H), 7.01 (d, J=1.5 Hz, 1 H), 7.12 (d, J=8.2 Hz, 1 H), 7.35 (d, J=2.7 Hz, 1 H), 7.38 (d, J=2.3 Hz, 1 H), 7.53-7.64 (m, 3 H), 7.91-7.93 (m, 1 H), 7.97 (d, J=7.4 Hz, 1 H), 8.05 (d, J=8.2 Hz, 1 H), 8.25-8.27 (m, 2 H), 8.53-8.56 (m, 1 H).

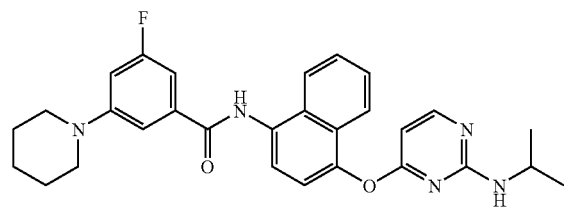

3-Fluoro-N-(4-{[2-(isopropylamino)pyrimidin-4-yl]oxy}-1-naphthyl)-5-piperidin-1-ylbenzamide (Compound B396). Compound is prepared from 3-fluoro-N-[4-(2-methanesulfonyl-pyrimidin-4-yloxy)-naphthalen-1-yl]-5-piperidin-1-yl-benzamide (obtained from t-butyl(4-{[2-(methylthio)pyrimidin-4-yl]oxy}-1-naphthyl)carbamate and 3-fluoro-5-piperidinylbenzoic acid according to conditions described in Example 3, Steps 3 and 4 and isopropylamine according to conditions described in general procedure C. Mp: 86-87° C.; $^1$H NMR (400 MHz, DMSO-d$_6$) δ 0.99 (bs, 6 H), 1.60 (m, 6 H), 3.23-3.31 (m, 4 H), 3.98 (s, 1 H), 6.28 (s, 1 H), 6.95 (d, J=12.5 Hz, 1 H), 7.14 (d, J=8.7 Hz, 1 H), 7.37 (d, J=8.0 Hz, 1 H), 7.43 (s, 1 H), 7.50-7.60 (m, 3 H), 7.80-7.82 (m, 1 H), 7.95 (d, J=7.3 Hz, 1 H), 8.18 (s, 1 H), 10.40 (s, 1 H).

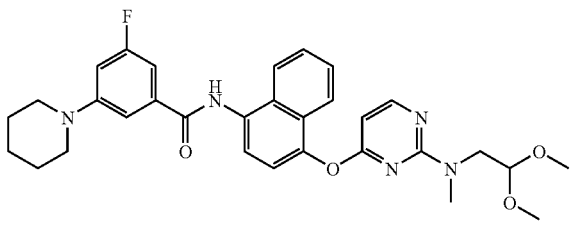

N-[4-({2-[(2,2-Dimethoxyethyl)(methyl)amino]pyrimidin-4-yl}oxy)-1-naphthyl]-3-fluoro-5-piperidin-1-ylbenzamide (Compound B403). Compound is prepared from 3-fluoro-N-[4-(2-methanesulfonyl-pyrimidin-4-yloxy)-naphthalen-1-yl]-5-piperidin-1-yl-benzamide and (2,2-dimethoxy-ethyl)-methylamine according to conditions described in general procedure C. Mp: 135-136° C.; $^1$H NMR (400 MHz, DMSO-d$_6$) δ 1.59-1.61 (m, 6 H), 2.82 (s, 3 H), 3.01-3.08 (m, 2 H), 3.27-3.30 (m, 10 H), 3.60 (s, 1 H), 6.25-6.40 (bd, 1 H), 6.93-6.98 (m, 1 H), 7.16 (d, J=8.5 Hz, 1 H), 7.40 (d, J=9.0 Hz, 1 H), 7.45 (s, 1 H), 7.54-7.59 (m, 3 H), 7.80 (s, 1 H), 7.96-7.99 (m, 1 H), 8.27 (d, J=4.4 Hz, 1 H), 10.41 (s, 1 H).

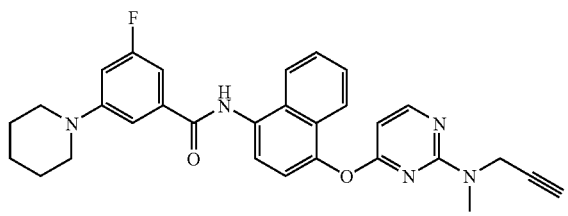

3-Fluoro-N-[4-({2-[methyl(prop-2-yn-1-yl)amino]pyrimidin-4-yl}oxy)-1-naphthyl]-5-piperidin-1-ylbenzamide (Compound B407). Compound is prepared from 3-fluoro-N-[4-(2-methanesulfonyl-pyrimidin-4-yloxy)-naphthalen-1-yl]-5-piperidin-1-yl-benzamide and methyl-prop-2-ynylamine according to conditions described in general procedure C. Mp: 116-117° C.; $^1$H NMR (400 MHz, DMSO-d$_6$) δ 1.58-1.61 (m, 6 H), 2.85 (m, 3 H), 3.27-3.30 (m, 5 H), 4.22 (s, 2 H), 6.30 (d, J=5.5 Hz, 1 H), 6.94-6.98 (m, 1 H), 7.15 (d, J=8.8 Hz, 1 H), 7.43 (d, J=8.0 Hz, 1 H), 7.46 (s, 1 H), 7.55-7.60 (m, 3 H), 7.82-7.84 (m, 1 H), 7.98 (d, J=7.4 Hz, 1 H), 8.30 (d, J=5.5 Hz, 1 H), 10.44 (s, 1 H).

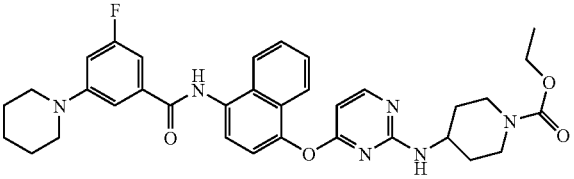

Ethyl-4-{[4-({4-[(3-fluoro-5-piperidin-1-ylbenzoyl)amino]-1-naphthyl}oxy)pyrimidin-2-yl]amino}piperidine-1-carboxylate (Compound B401). Compound is prepared from 3-fluoro-N-[4-(2-methanesulfonyl-pyrimidin-4-yloxy)-naphthalen-1-yl]-5-piperidin-1-yl-benzamide and 4-amino-piperidine-1-carboxylic acid ethyl ester according to conditions described in general procedure C. $^1$H NMR (400 MHz, DMSO-d$_6$) δ 1.05-1.19 (m, 5 H), 1.43-1.70 (m, 8 H), 2.79 (s, 2 H), 3.23-3.28 (m, 4 H), 3.70-3.98 (m, 5 H), 6.16-6.34 (bd, 1 H), 6.95 (d, J=12.4 Hz, 1 H), 7.10-7.20 (m, 2 H), 7.38 (d, J=8.0 Hz, 1 H), 7.42 (s, 1 H), 7.53-7.60 (m, 3 H), 7.79 (d, J=7.7 Hz, 1 H), 7.96 (d, J=8.0 Hz, 1 H), 8.21 (s, 1 H), 10.40 (s, 1 H).

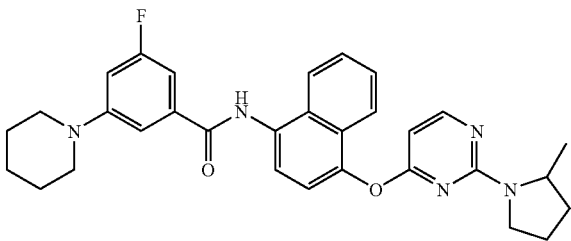

3-Fluoro-N-(4-{[2-(2-methylpyrrolidin-1-yl)pyrimidin-4-yl]oxy}-1-naphthyl)-5-piperidin-1-ylbenzamide (Compound B404). Compound is prepared from 3-fluoro-N-[4-(2-methanesulfonyl-pyrimidin-4-yloxy)-naphthalen-1-yl]-5-piperidin-1-yl-benzamide and 2-methylpyrrolidine according to conditions described in general procedure C. Mp: 93-94° C.; $^1$H NMR (400 MHz, DMSO-d$_6$) δ 0.64 (bs, 2 H), 1.11 (bs, 1 H), 1.58-1.61 (m, 6 H), 1.73-1.84 (m, 4 H), 3.27-3.36 (m, 7 H), 6.24 (s, 1 H), 6.95 (d, J=12.8 Hz, 1 H), 7.14 (d, J=8.4 Hz, 1 H), 7.39 (d, J=8.0 Hz, 1 H), 7.46 (s, 1 H), 7.53-7.63 (m, 3 H), 7.81 (d, J=6.5 Hz, 1 H), 7.96 (d, J=7.7 Hz, 1 H), 8.22 (d, J=5.5 Hz, 1 H), 10.42 (s, 1 H).

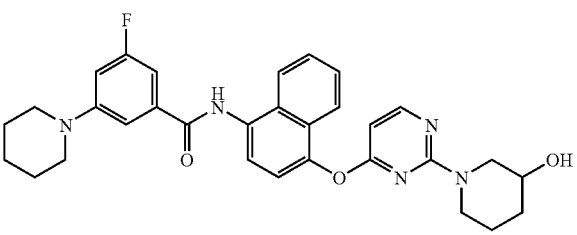

3-Fluoro-N-(4-{[2-(3-hydroxypiperidin-1-yl)pyrimidin-4-yl]oxy}-1-naphthyl)-5-piperidin-1-ylbenzamide (Compound B402). Compound is prepared from 3-fluoro-N-[4-(2-methanesulfonyl-pyrimidin-4-yloxy)-naphthalen-1-yl]-5-piperidin-1-yl-benzamide and piperidin-3-ol according to conditions described in general procedure C. Mp: 93-95° C.; $^1$H NMR (400 MHz, DMSO-d$_6$) δ 1.24-1.26 (m, 2 H), 1.58-1.60 (m, 7 H), 1.75-1.85 (m, 1 H), 2.68-2.80 (m, 2 H), 3.27-3.36 (m, 6 H), 4.80 (d, J=4.0 Hz, 1 H), 6.14 (d, J=5.5 Hz, 1 H), 6.95 (d, J=12.8 Hz, 1 H), 7.14 (d, J=9.1 Hz, 1 H), 7.40 (d, J=8.0 Hz, 1 H), 7.46 (s, 1 H), 7.55-7.61 (m, 3 H), 7.82-7.84 (m, 1 H), 7.97 (d, J=7.3 Hz, 1 H), 8.22 (d, J=5.4 Hz, 1 H), 10.44 (s, 1 H).

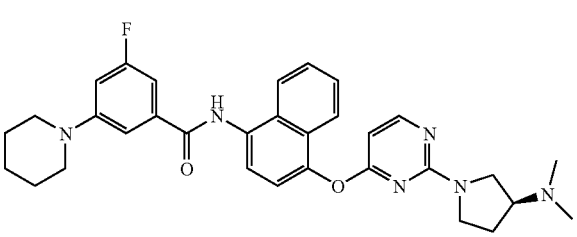

N-[4-({2-[(3R)-3-(Dimethylamino)pyrrolidin-1-yl]pyrimidin-4-yl}oxy)-1-naphthyl]-3-fluoro-5-piperidin-1-ylbenzamide (Compound B405). Compound is prepared from 3-fluoro-N-[4-(2-methanesulfonyl-pyrimidin-4-yloxy)-naphthalen-1-yl]-5-piperidin-1-yl-benzamide and (R)—N,N-dimethylpyrrolidin-3-amine according to conditions described in general procedure C. Mp: 93-94° C.; $^1$H NMR (400 MHz, DMSO-d$_6$) δ 1.58 (s, 6 H), 1.60-2.00 (m, 2 H), 2.16 (s, 6H), 2.64 (m, 1 H), 2.90-3.70 (m, 4 H), 3.27-3.28 (m, 4 H), 6.06-6.17 (bd, 1 H), 6.94-6.98 (m, 1H), 7.14 (d, J=8.8 Hz, 1 H), 7.43 (d, J=8.0 Hz, 1 H), 7.46 (s, 1 H), 7.50-7.64 (m, 3 H), 7.82-7.84 (m, 1 H), 7.96-7.98 (m, 1 H), 8.22 (d, J=5.5 Hz, 1 H), 10.43 (s, 1 H).

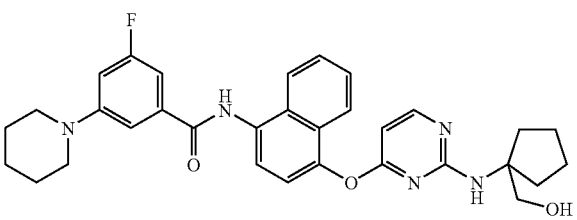

3-Fluoro-N-{4-[(2-{[1-(hydroxymethyl)cyclopentyl]amino}pyrimidin-4-yl)oxy]-1-naphthyl}-5-piperidin-1-yl-benzamide (Compound B399). Compound is prepared from 3-fluoro-N-[4-(2-methanesulfonyl-pyrimidin-4-yloxy)-naphthalen-1-yl]-5-piperidin-1-yl-benzamide and 1-aminocyclopentylmethanol according to conditions described in general procedure C. $^1$H NMR (400 MHz, DMSO-d$_6$) δ 1.14 (s, 4 H), 1.58-1.61 (m, 10 H), 3.26-3.31 (m, 6 H), 6.27 (d, J=5.5 Hz, 1 H), 6.53 (s, 1 H), 6.95 (d, J=12.4 Hz, 1 H), 7.15 (d, J=8.8 Hz, 1 H), 7.35 (d, J=7.7 Hz, 1 H), 7.44 (s, 1 H), 7.52-7.59 (m, 3 H), 7.78 (s, 1 H), 7.95-7.97 (m, 1H), 8.16 (d, J=5.5 Hz, 1 H), 10.41 (s, 1 H).

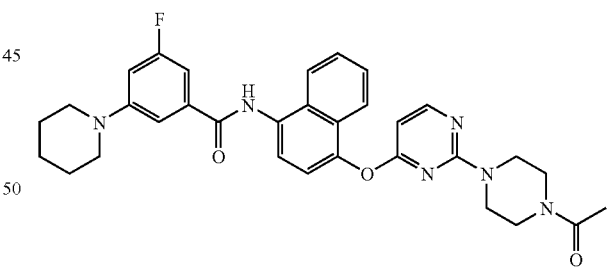

N-(4-{[2-(4-Acetylpiperazin-1-yl)pyrimidin-4-yl]oxy}-1-naphthyl)-3-fluoro-5-piperidin-1-ylbenzamide (Compound B400). Compound is prepared from 3-fluoro-N-[4-(2-methanesulfonyl-pyrimidin-4-yloxy)-naphthalen-1-yl]-5-piperidin-1-yl-benzamide and N-acetylpiperazine according to conditions described in general procedure C. Mp: 102-104° C.; $^1$H NMR (400 MHz, DMSO-d$_6$) δ 1.58-1.61 (m, 6 H), 1.96 (s, 3 H), 3.28-3.30 (m, 4 H), 3.36 (s, 4H), 3.47-3.51 (m, 4 H), 6.25 (d, J=5.5 Hz, 1 H), 6.94-6.98 (m, 1 H), 7.15 (d, J=8.8 Hz, 1 H), 7.42 (d, J=8.0 Hz, 1 H), 7.46 (s, 1 H), 7.54-7.62 (m, 3 H), 7.82-7.84 (m, 1 H), 7.98-8.00 (m, 1H), 8.28 (d, J=5.5 Hz, 1 H), 10.44 (s, 1 H).

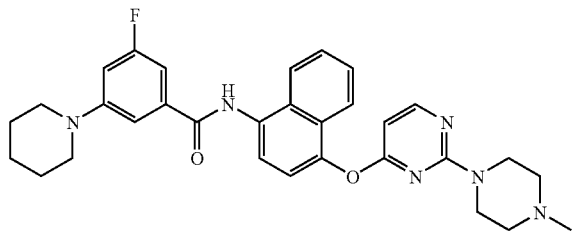

3-Fluoro-N-(4-{[2-(4-methylpiperazin-1-yl)pyrimidin-4-yl]oxy}-1-naphthyl)-5-piperidin-1-ylbenzamide (Compound B372). Compound is prepared from 3-fluoro-N-[4-(2-methanesulfonyl-pyrimidin-4-yloxy)-naphthalen-1-yl]-5-piperidin-1-yl-benzamide and N-methylpiperazine according to conditions described in general procedure C. Mp: 182-184° C.;

$^1$H NMR (400 MHz, DMSO-d$_6$) δ 1.60 (s, 6 H), 2.13 (s, 2 H), 2.20 (s, 3 H), 2.49-2.54 (m, 2 H), 3.22 (s, 2 H), 3.30 (s, 4 H), 3.48 (s, 2 H), 6.22-6.24 (m, 1 H), 6.97 (d, J=12.8 Hz, 1 H), 7.15 (d, J=8.8 Hz, 1 H), 7.42 (d, J=8.0 Hz, 1 H), 7.48 (s, 1 H), 7.55-7.63 (m, 3 H), 7.84 (d, J=7.3 Hz, 1 H), 7.99 (d, J=8.4 Hz, 1 H), 8.26-8.28 (m, 1 H), 10.45 (s, 1 H).

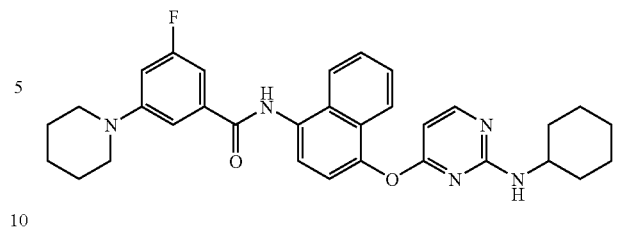

N-(4-{[2-(cyclohexylamino)pyrimidin-4-yl]oxy}-1-naphthyl)-3-fluoro-5-piperidin-1-ylbenzamide (Compound B371). Compound is prepared from 3-fluoro-N-[4-(2-methanesulfonyl-pyrimidin-4-yloxy)-naphthalen-1-yl]-5-piperidin-1-yl-benzamide and cyclohexylamine according to conditions described in general procedure C. Mp: 118-120° C.;

$^1$H NMR (400 MHz, DMSO-d$_6$) δ 1.00-1.23 (m, 6 H), 1.60-1.74 (m, 10 H), 3.10-3.29 (m, 5 H), 6.10-6.30 (m, 1 H), 6.97-7.00 (m, 2 H), 7.17 (d, J=8.8 Hz, 1 H), 7.40 (d, J=8.0 Hz, 1 H), 7.46 (s, 1 H), 7.55-7.62 (m, 3 H), 7.83 (d, J=8.0 Hz, 1 H), 7.99 (d, J=8.0 Hz, 1 H), 8.21 (s, 1 H), 10.47 (s, 1 H).

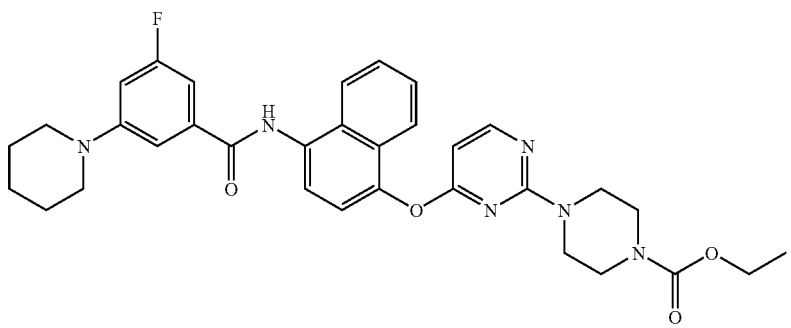

Ethyl 4-[4-({4-[(3-fluoro-5-piperidin-1-ylbenzoyl)amino]-1-naphthyl}oxy)pyrimidin-2-yl]piperazine-1-carboxylate (Compound B376). Compound is prepared from 3-fluoro-N-[4-(2-methanesulfonyl-pyrimidin-4-yloxy)-naphthalen-1-yl]-5-piperidin-1-yl-benzamide and piperazine-1-carboxylic acid ethyl ester according to conditions described in general procedure C. Mp: 105-106° C.; $^1$H NMR (400 MHz, DMSO-d$_6$) δ 1.14-1.18 (m, 3 H), 1.60-1.62 (m, 6 H), 3.11-3.33 (m, 8 H), 3.52 (s, 4 H), 4.00-4.05 (m, 2 H), 6.22-6.24 (m, 1 H), 6.97 (d, J=11.3 Hz, 2H), 7.17 (d, J=9.1 Hz, 1 H), 7.42-7.45 (m, 1 H), 7.48 (s, 1 H), 7.57-7.62 (m, 3 H), 7.85 (d, J=8.0 Hz, 1 H), 7.99 (d, J=8.0 Hz, 1 H), 8.29-8.30 (m, 1 H), 10.46 (s, 1 H).

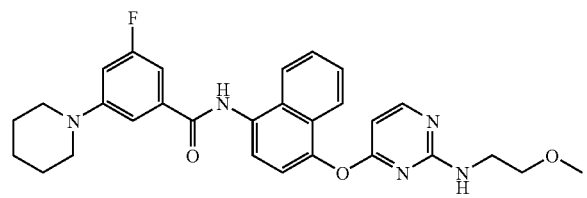

3-Fluoro-N-[4-({2-[(2-methoxyethyl)amino]pyrimidin-4-yl}oxy)-1-naphthyl]-5-piperidin-1-ylbenzamide (Compound B374). Compound is prepared from 3-fluoro-N-[4-(2-methanesulfonyl-pyrimidin-4-yloxy)-naphthalen-1-yl]-5-piperidin-1-yl-benzamide and 2-methoxyethylamine according to conditions described in general procedure C. Mp: 87-88° C.;

$^1$H NMR (400 MHz, DMSO-d$_6$) δ 1.60-1.63 (m, 6 H), 3.00-3.38 (m, 11 H), 6.20-6.40 (m, 1 H), 6.99 (d, J=12.4 Hz, 1 H), 7.09-7.18 (m, 2 H), 7.40 (d, J=7.7 Hz, 1 H), 7.46 (s, 1 H), 7.55-7.62 (m, 3 H), 7.82 (d, J=8.0 Hz, 1 H), 7.99 (d, J=8.0 Hz, 1 H), 8.23 (s, 1 H), 10.43 (s, 1 H).

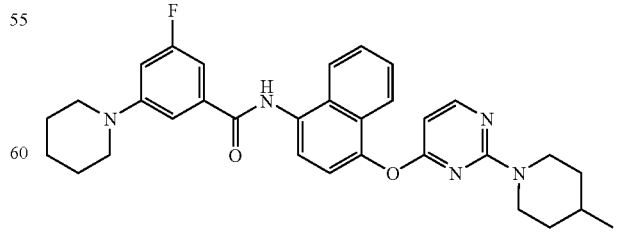

3-Fluoro-N-(4-{[2-(4-methylpiperidin-1-yl)pyrimidin-4-yl]oxy}-1-naphthyl)-5-piperidin-1-ylbenzamide (Compound B381). Compound is prepared from 3-fluoro-N-[4-(2- methanesulfonyl-pyrimidin-4-yloxy)-naphthalen-1-yl]-5-piperidin-1-yl-benzamide and 4-methylpiperidine according to conditions described in general procedure C. Mp: 145-146° C.; $^1$H NMR (400 MHz, DMSO-d$_6$) δ 0.86 (d, J=6.0 Hz, 3 H), 1.50-1.62 (m, 11 H), 3.30 (m, 8H), 6.19-6.21 (m, 1 H), 6.99 (d, J=11.0 Hz, 1 H), 7.19 (d, J=9.0 Hz, 1 H), 7.41-7.43 (m, 1 H), 7.49 (s, 1 H), 7.57-7.62 (m, 3 H), 7.85 (d, J=8.2 Hz, 1H), 7.99 (d, J=8.5 Hz, 1 H), 8.25-8.27 (m, 1 H), 10.46 (s, 1 H).

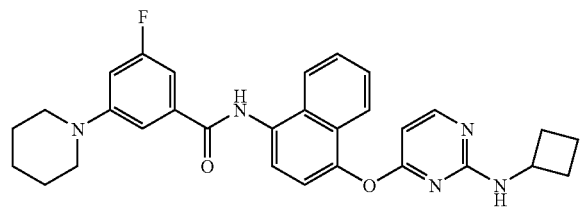

N-(4-{[2-(Cyclobutylamino)pyrimidin-4-yl]oxy}-1-naphthyl)-3-fluoro-5-piperidin-1-ylbenzamide (Compound B383). Compound is prepared from 3-fluoro-N-[4-(2-methanesulfonyl-pyrimidin-4-yloxy)-naphthalen-1-yl]-5-piperidin-1-yl-benzamide and cyclobutylamine according to conditions described in general procedure C. Mp: 112-114° C.; $^1$H NMR (400 MHz, DMSO-d$_6$) δ 1.58-1.61 (m, 7 H), 1.80 (bs, 2 H), 2.10 (s, 1 H), 3.27-3.28 (m, 5 H), 6.32 (s, 1 H), 6.98 (d, 1 H), 7.15 (d, 1 H), 7.36-7.54 (m, 3 H), 7.57-7.62 (m, 3 H), 7.80 (d, 1 H), 7.95 (d, 1 H), 8.20 (s, 1 H), 10.41 (s, 1 H).

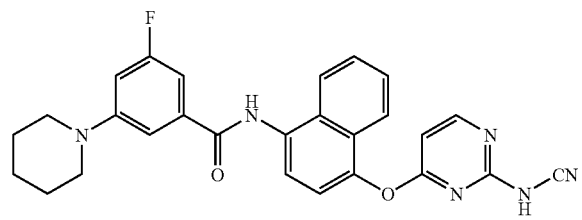

N-(4-{[2-(Cyanoamino)pyrimidin-4-yl]oxy}-1-naphthyl)-3-fluoro-5-piperidin-1-ylbenzamide (Compound B380). Compound is prepared from 3-fluoro-N-[4-(2-methanesulfonyl-pyrimidin-4-yloxy)-naphthalen-1-yl]-5-piperidin-1-yl-benzamide and cyanamide according to conditions described in general procedure C. Mp: 160-162° C.; $^1$H NMR (400 MHz, DMSO-d$_6$) δ 1.58 (s, 6 H), 3.27-3.29 (m, 4 H), 6.32 (d, J=5.1 Hz, 1 H), 6.95 (d, J=12.4, 1 H), 7.15 (d, J=9.1 Hz, 1 H), 7.42-7.45 (m, 2 H), 7.55-7.62 (m, 3 H), 7.83 (d, J=8.8 Hz, 1 H), 7.97 (d, J=8.0 Hz, 1 H), 8.13 (d, J=5.8 Hz, 1 H), 10.44 (s, 1 H).

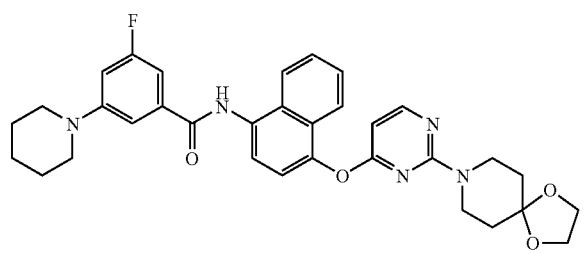

N-(4-{[2-(1,4-Dioxa-8-azaspiro[4.5]dec-8-yl)pyrimidin-4-yl]oxy}-1-naphthyl)-3-fluoro-5-piperidin-1-ylbenzamide (Compound B378). Compound is prepared from 3-fluoro-N-[4-(2-methanesulfonyl-pyrimidin-4-yloxy)-naphthalen-1-yl]-5-piperidin-1-yl-benzamide and 1,4-dioxa-8-aza-spiro[4.5]decane according to conditions described in general procedure C. Mp: 195-196° C.; $^1$H NMR (400 MHz, DMSO-d$_6$) δ 1.46-1.59 (s, 10 H), 3.27-3.31 (m, 4 H), 3.56 (s, 4 H), 3.84 (s, 4 H), 6.20-6.22 (m, 1 H), 6.95 (d, J=12.8, 1 H), 7.15 (d, J=9.1 Hz, 1 H), 7.40-7.42 (m, 1 H), 7.45 (s, 1 H), 7.55-7.60 (m, 3 H), 7.83 (d, J=7.7 Hz, 1 H), 7.97 (d, J=8.0 Hz, 1H), 8.25-8.27 (m, 1 H), 10.43 (s, 1 H).

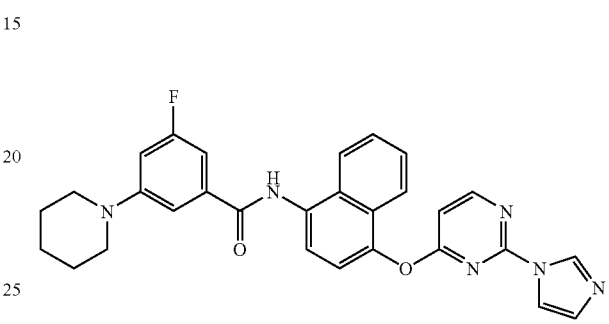

3-Fluoro-N-(4-{[2-(1H-imidazol-1-yl)pyrimidin-4-yl]oxy}-1-naphthyl)-5-piperidin-1-ylbenzamide (Compound B379). Compound is prepared from 3-fluoro-N-[4-(2-methanesulfonyl-pyrimidin-4-yloxy)-naphthalen-1-yl]-5-piperidin-1-yl-benzamide and imidazole according to conditions described in general procedure C. Mp: 175-176° C.; $^1$H NMR (400 MHz, DMSO-d$_6$) δ 1.58-1.60 (m, 6 H), 3.28-3.31 (m, 4 H), 6.96 (d, J=12.4, 1 H), 7.03-7.04 (m, 1 H), 7.10-7.12 (m, 1 H), 7.17 (d, J=8.8 Hz, 1 H), 7.47 (s, 1 H), 7.55-7.67 (m, 5 H), 7.88-7.90 (m, 1 H), 8.03 (d, J=8.4 Hz, 1 H), 8.18-8.19 (m, 1 H), 8.73-8.75 (m, 1 H), 10.49 (s, 1H).

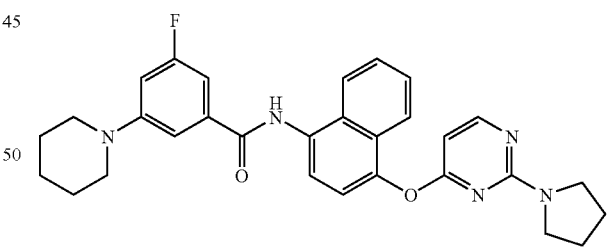

3-Fluoro-5-piperidin-1-yl-N-{4-[(2-pyrrolidin-1-ylpyrimidin-4-yl)oxy]-1-naphthyl}benzamide (Compound B377). Compound is prepared from 3-fluoro-N-[4-(2-methanesulfonyl-pyrimidin-4-yloxy)-naphthalen-1-yl]-5-piperidin-1-yl-benzamide and pyrrolidine according to conditions described in general procedure C. Mp: 111-113° C.; $^1$H NMR (400 MHz, DMSO-d$_6$) δ 1.58 (s, 6 H), 1.81 (bs, 4 H), 3.03-3.40 (m, 8 H), 6.15 (d, J=5.5, 1 H), 6.95 (d, 1 H), 7.15 (d, 1 H), 7.40 (d, J=8.4 Hz,1 H), 7.46 (s, 1 H), 7.50-7.60 (m, 3 H), 7.82-7.86 (m, 1 H), 7.97-7.99 (m, 1 H), 8.21-8.23 (m, 1 H), 10.43 (s, 1 H).

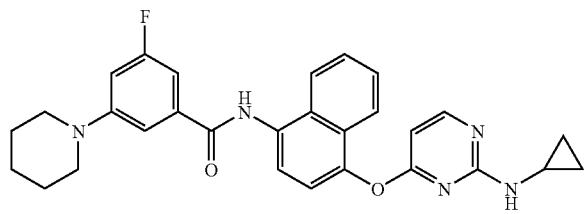

N-(4-{[2-(Cyclopropylamino)pyrimidin-4-yl]oxy}-1-naphthyl)-3-fluoro-5-piperidin-1-ylbenzamide (Compound B382). Compound is prepared from 3-fluoro-N-[4-(2-methanesulfonyl-pyrimidin-4-yloxy)-naphthalen-1-yl]-5-piperidin-1-yl-benzamide and cyclopropylamine according to conditions described in general procedure C. Mp: 157-158° C.; $^1$H NMR (400 MHz, DMSO-d$_6$) δ 0.32-0.48 (m, 4 H), 1.58 (s, 6 H), 3.19-3.31 (m, 4 H), 6.34 (bs, 1 H), 6.96 (d, J=12.4, 1 H), 7.15 (d, J=8.7 Hz, 1 H), 7.34-7.42 (m, 3 H), 7.53-7.63 (m, 3H), 7.81 (d, J=8.0 Hz, 1 H), 7.95 (d, J=8.0 Hz, 1 H), 8.21-8.23 (m, 1 H), 10.40 (s, 1 H).

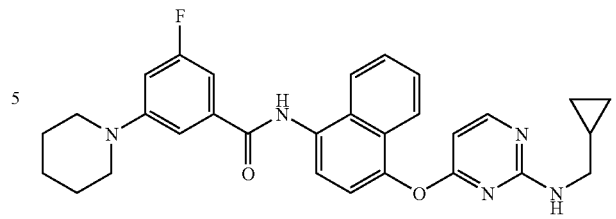

N-[4-({2-[(cyclopropylmethyl)amino]pyrimidin-4-yl}oxy)-1-naphthyl]-3-fluoro-5-piperidin-1-ylbenzamide (Compound B384). Compound is prepared from 3-fluoro-N-[4-(2-methanesulfonyl-pyrimidin-4-yloxy)-naphthalen-1-yl]-5-piperidin-1-yl-benzamide and cyclopropylmethylamine according to conditions described in general procedure C. Mp: 117-119° C.; $^1$H NMR (400 MHz, DMSO-d$_6$) δ 0.10-0.30 (m, 4 H), 0.90 (bs, 1 H), 1.58-1.60 (m, 6H), 3.00 (bs, 2H), 3.27-3.28 (m, 4 H), 6.29 (bs, 1 H), 6.96 (d, 1 H), 7.15 (d, 1 H), 7.20 (s, 1 H), 7.38 (d, J=8.0 Hz, 1 H), 7.45 (s, 1 H), 7.54-7.58 (m, 3 H), 7.80 (d, 1 H), 7.96 (d, 1 H), 8.20 (s, 1 H), 10.41 (s, 1 H).

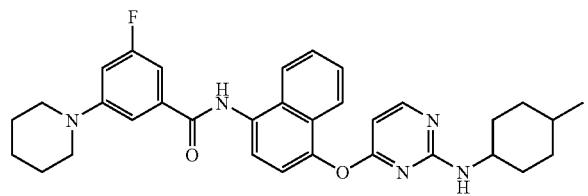

3-Fluoro-N-[4-({2-[(4-methylcyclohexyl)amino]pyrimidin-4-yl}oxy)-1-naphthyl]-5-piperidin-1-ylbenzamide (Compound B388). Compound is prepared from 3-fluoro-N-[4-(2-methanesulfonyl-pyrimidin-4-yloxy)-naphthalen-1-yl]-5-piperidin-1-yl-benzamide and 4-methylcyclohexylamine according to conditions described in general procedure C. Mp: 101-102° C.; $^1$H NMR (400 MHz, DMSO-d$_6$) δ 0.82 (d, J=6.6 Hz, 3 H), 0.86-1.59 (m, 15 H), 3.27-3.36 (m, 5 H), 6.27 (bs, 1 H), 6.96 (d, J=12.8, 2 H), 7.15 (d, J=8.4 Hz,1 H), 7.36-7.39 (m, 1H), 7.43 (s, 1 H), 7.54-7.60 (m, 3 H), 7.79-7.83 (m, 1 H), 7.96 (d, J=7.3 Hz, 1 H), 8.18 (s, 1H), 10.40 (s, 1 H).

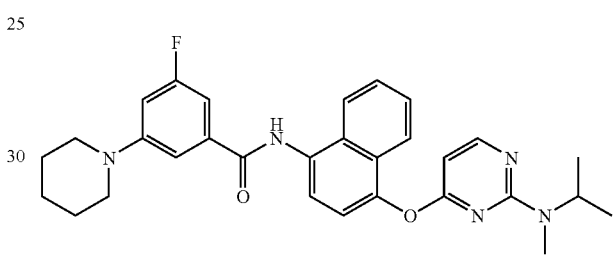

3-Fluoro-N-[4-({2-[isopropyl(methyl)amino]pyrimidin-4-yl}oxy)-1-naphthyl]-5-piperidin-1-ylbenzamide (Compound B385). Compound is prepared from 3-fluoro-N-[4-(2-methanesulfonyl-pyrimidin-4-yloxy)-naphthalen-1-yl]-5-piperidin-1-yl-benzamide and N-isopropylmethylamine according to conditions described in general procedure C. Mp: 102-104° C.; $^1$H NMR (400 MHz, DMSO-d$_6$) δ 0.94 (bs, 6 H), 1.58 (s, 6 H), 2.70 (bs, 1 H), 3.26-3.31 (m, 7 H), 6.19 (d, J=6.0 Hz, 1 H), 6.96 (d, J=12.4 Hz, 1 H), 7.15 (d, J=8.8 Hz, 1 H), 7.40 (d, J=8.0 Hz, 1 H), 7.46 (s, 1 H), 7.51-7.62 (m, 3 H), 7.82 (d, J=7.6 Hz, 1 H), 7.97 (d, J=8.0 Hz, 1H), 8.22-8.24 (m, 1 H), 10.43 (s, 1 H).

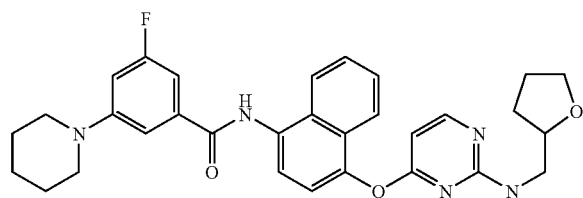

3-Fluoro-5-piperidin-1-yl-N-[4-({2-[(tetrahydrofuran-2-ylmethyl)amino]pyrimidin-4-yl}oxy)-1-naphthyl]benzamide (Compound B386). Compound is prepared from 3-fluoro-N-[4-(2-methanesulfonyl-pyrimidin-4-yloxy)-naphthalen-1-yl]-5-piperidin-1-yl-benzamide and C-(tetrahydrofuran-2-yl)-methylamine according to conditions described in general procedure C. $^1$H NMR (400 MHz, DMSO-d$_6$) δ 1.40-1.65 (m, 10 H), 3.00-3.85 (m, 9 H), 6.327 (bs, 1 H), 6.96 (d, 1 H), 7.15 (d, 1 H), 7.38 (d, J=8.0 Hz, 1 H), 7.43 (s, 1 H), 7.54-7.60 (m, 3 H), 7.78-7.82 (m, 1 H), 7.96 (d, 1 H), 8.20 (s, 1 H), 10.41 (s, 1 H).

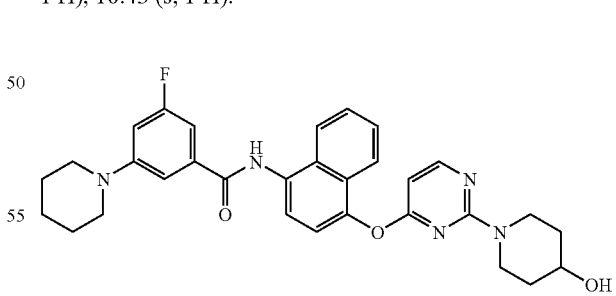

3-Fluoro-N-(4-{[2-(4-hydroxypiperidin-1-yl)pyrimidin-4-yl]oxy}-1-naphthyl)-5-piperidin-1-ylbenzamide (Compound B387). Compound is prepared from 3-fluoro-N-[4-(2-methanesulfonyl-pyrimidin-4-yloxy)-naphthalen-1-yl]-5-piperidin-1-yl-benzamide and piperidin-4-ol according to conditions described in general procedure C. Mp: 182-184° C.; $^1$H NMR (400 MHz, DMSO-d$_6$) δ 1.15 (bs, 2 H), 1.58 (s, 8 H), 3.00 (bs, 2 H), 3.27 (s, 4 H), 3.61 (m, 1 H), 3.95 (bs, 2 H), 4.64 (d, J=4.0 Hz, 1 H), 6.19 (d, J=5.5 Hz, 1 H), 6.96 (d, J=12.8 Hz, 1 H), 7.15 (d, J=8.8 Hz, 1 H), 7.40 (d, J=8.4 Hz, 1 H), 7.46 (s, 1 H), 7.55-7.59 (m, 3 H), 7.82 (d, J=8.0 Hz, 1 H), 7.97 (d, J=8.4 Hz, 1 H), 8.22-8.24 (m, 1 H), 10.43 (s, 1 H).

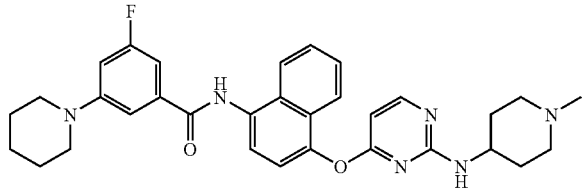

3-Fluoro-N-[4-({2-[(1-methylpiperidin-4-yl)amino]pyrimidin-4-yl}oxy)-1-naphthyl]-5-piperidin-1-ylbenzamide (Compound B409). Compound is prepared from 3-fluoro-N-[4-(2-methanesulfonyl-pyrimidin-4-yloxy)-naphthalen-1-yl]-5-piperidin-1-yl-benzamide and 4-amino-N-methylpiperidine according to conditions described in general procedure C. $^1$H NMR (400 MHz, DMSO-$d_6$) δ 1.41-1.84 (m, 10 H), 2.09 (s, 3 H), 2.54-3.03 (m, 4 H), 2.92 (s, 4 H), 3.63 (s, 1 H), 6.30 (s, 1 H), 6.94-6.98 (m, 2 H), 7.15 (d, J=8.8 Hz, 1 H), 7.37 (d, J=8.0 Hz, 1H), 7.43 (s, 1 H), 7.51-7.61 (m, 3 H), 7.80 (d, J=8.8 Hz, 1 H), 7.97 (d, J=8.4 Hz, 1 H), 8.20 (s, 1 H), 10.42 (s, 1 H).

N-(4-{[2-(4-Ethylpiperazin-1-yl)pyrimidin-4-yl]oxy}-1-naphthyl)-3-fluoro-5-piperidin-1-ylbenzamide (Compound B398). Compound is prepared from 3-fluoro-N-[4-(2-methanesulfonyl-pyrimidin-4-yloxy)-naphthalen-1-yl]-5-piperidin-1-yl-benzamide and N-ethylpiperazine according to conditions described in general procedure C. Mp: 86-87° C.; $^1$H NMR (400 MHz, DMSO-$d_6$) δ 0.96 (s, 3 H), 1.58-1.59 (m, 6 H), 2.26 (bs, 4 H), 3.26-3.31 (m, 8H), 3.46 (bs, 2 H), 6.21 (d, J=5.8 Hz, 1 H), 6.95 (d, J=12.4 Hz, 1 H), 7.15 (d, J=8.8 Hz, 1H), 7.40 (d, J=8.0 Hz, 1 H), 7.45 (s, 1 H), 7.55-7.61 (m, 3 H), 7.81-7.83 (m, 1 H), 7.97 (d, J=7.7 Hz, 1 H), 8.25 (d, J=5.5 Hz, 1 H), 10.43 (s, 1 H).

3-Fluoro-5-piperidin-1-yl-N-[4-({2-[(2-pyrrolidin-1-yl-ethyl)amino]pyrimidin-4-yl}oxy)-1-naphthyl]benzamide (Compound B389). Compound is prepared from 3-fluoro-N-[4-(2-methanesulfonyl-pyrimidin-4-yloxy)-naphthalen-1-yl]-5-piperidin-1-yl-benzamide and 2-pyrrolidin-1-yl-ethylamine according to conditions described in general procedure C. Mp: 92-94° C.; $^1$H NMR (400 MHz, DMSO-$d_6$) δ 1.58 (m, 10 H), 2.20-2.47 (m, 6 H), 2.91 (bs, 2 H), 3.27 (s, 4 H), 6.20-6.32 (m, 1 H), 6.94-6.98 (m, 2 H), 7.15 (d, J=8.4 Hz, 1 H), 7.37 (d, J=8.0 Hz, 1 H), 7.43 (s, 1 H), 7.51-7.61 (m, 3 H), 7.78-7.80 (m, 1 H), 7.96 (d, J=7.3 Hz, 1 H), 8.21 (s 1 H), 10.40 (s, 1 H).

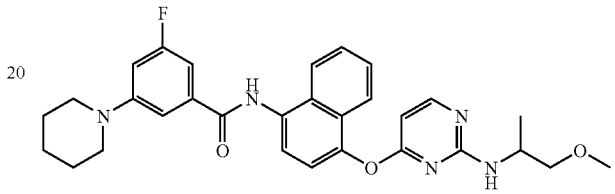

3-Fluoro-N-[4-({2-[(2-methoxy-1-methylethyl)amino]pyrimidin-4-yl}oxy)-1-naphthyl]-5-piperidin-1-ylbenzamide (Compound B392). Compound is prepared from 3-fluoro-N-[4-(2-methanesulfonyl-pyrimidin-4-yloxy)-naphthalen-1-yl]-5-piperidin-1-yl-benzamide and 2-methoxy-1-methylethylamine according to conditions described in general procedure C. Mp: 94-95° C.; $^1$H NMR (400 MHz, DMSO-$d_6$) δ 0.97 (s, 3 H), 1.56-1.61 (m, 6 H), 3.00-3.32 (m, 9H), 4.10 (s, 1 H), 6.31 (s, 1 H), 6.95-7.03 (m, 2 H), 7.15 (d, J=9.1 Hz, 1 H), 7.38 (d, J=8.0 Hz, 1 H), 7.43 (s, 1 H), 7.50-7.62 (m, 3 H), 7.79-7.82 (m, 1 H), 7.95-7.97 (m, 1 H), 8.20 (s 1 H), 10.40 (s, 1 H).

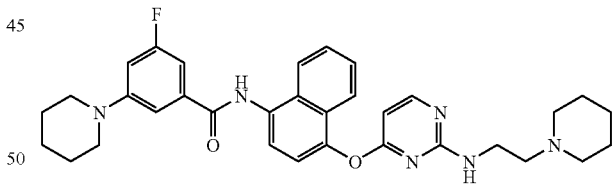

3-Fluoro-5-piperidin-1-yl-N-[4-({2-[(2-piperidin-1-yl-ethyl)amino]pyrimidin-4-yl}oxy)-1-naphthyl]benzamide (Compound B390). Compound is prepared from 3-fluoro-N-[4-(2-methanesulfonyl-pyrimidin-4-yloxy)-naphthalen-1-yl]-5-piperidin-1-yl-benzamide and 2-piperidin-1-yl-ethylamine according to conditions described in general procedure C. Mp: 88-89° C.; $^1$H NMR (400 MHz, DMSO-$d_6$) δ 1.31-1.39 (m, 6 H), 1.58-1.61 (m, 6 H), 1.99-2.27 (m, 6H), 2.90-3.24 (m, 2 H), 3.23-3.29 (m, 4 H), 6.20-6.31 (bd, 1 H), 6.90-6.98 (m, 2 H), 7.15 (d, J=8.8 Hz, 1 H), 7.37 (d, J=8.0 Hz, 1 H), 7.43 (s, 1 H), 7.50-7.62 (m, 3 H), 7.78-7.80 (m, 1 H), 7.96 (d, J=8.0 Hz, 1 H), 8.20 (s 1 H), 10.40 (s, 1 H).

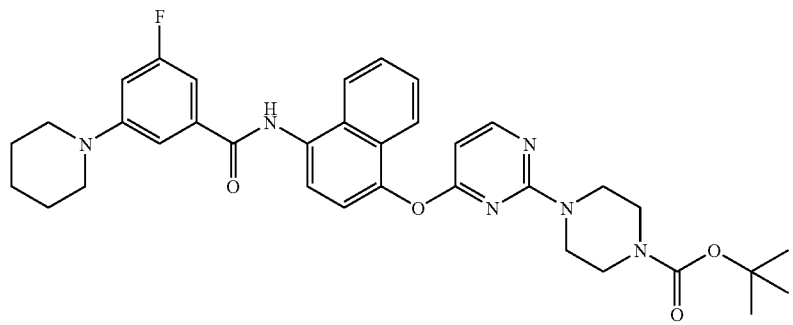

tert-Butyl-4-[4-({4-[(3-fluoro-5-piperidin-1-ylbenzoyl)amino]-1-naphthyl}oxy)pyrimidin-2-yl]piperazine-1-carboxylate (Compound B397). Compound is prepared from 3-fluoro-N-[4-(2-methanesulfonyl-pyrimidin-4-yloxy)-naphthalen-1-yl]-5-piperidin-1-yl-benzamide and N-(tert-butoxy carbonyl)piperazine according to conditions described in general procedure C. Mp: 175-177° C.; $^1$H NMR (400 MHz, DMSO-$d_6$) δ 1.36 (s, 9 H), 1.58-1.59 (m, 6 H), 3.24-3.31 (m, 8 H), 3.47 (s, 4 H), 6.22 (d, J=5.5 Hz, 1 H), 6.96 (d, J=12.4 Hz, 1 H), 7.15 (d, J=9.1 Hz, 1H), 7.41 (d, J=8.0 Hz, 1 H), 7.47 (s, 1 H), 7.50-7.62 (m, 3 H), 7.82-7.84 (m, 1 H), 7.98 (d, J=7.7 Hz, 1 H), 8.27 (d, J=5.5 Hz, 1 H), 10.43 (s, 1 H).

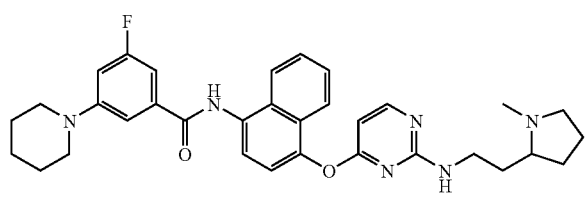

3-Fluoro-N-{4-[(2-{[2-(1-methylpyrrolidin-2-yl)ethyl]amino}pyrimidin-4-yl)oxy]-1-naphthyl}-5-piperidin-1-yl-benzamide (Compound B394). Compound is prepared from 3-fluoro-N-[4-(2-methanesulfonyl-pyrimidin-4-yloxy)-naphthalen-1-yl]-5-piperidin-1-yl-benzamide and 2-(1-methyl-pyrrolidin-2-yl)ethylamine according to conditions described in general procedure C. Mp: 112-114° C.; $^1$H NMR (400 MHz, DMSO-$d_6$) δ 1.30-1.61 (m, 10 H), 1.37-2.10 (m, 5 H), 2.84 (bs, 2 H), 3.11-3.36 (m, 7 H), 6.15-6.30 (m, 1 H), 6.96 (d, J=12.4 Hz, 1 H), 7.08-7.20 (m, 2 H), 7.37 (d, J=8.0 Hz, 1 H), 7.43 (s, 1 H), 7.52-7.59 (m, 3H), 7.79 (d, J =8.4 Hz, 1 H), 7.96 (d, J=7.7 Hz, 1 H), 8.21 (s, 1 H), 10.40 (s, 1 H).

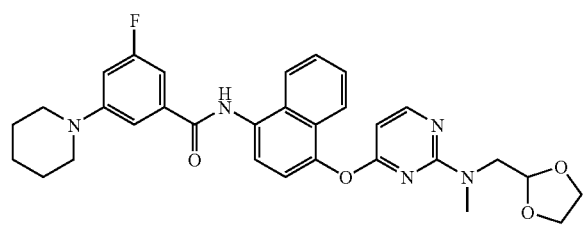

N-[4-({2-[(1,3-Dioxolan-2-ylmethyl)(methyl)amino]pyrimidin-4-yl}oxy)-1-naphthyl]-3-fluoro-5-piperidin-1-yl-benzamide (Compound B395). Compound is prepared from 3-fluoro-N-[4-(2-methanesulfonyl-pyrimidin-4-yloxy)-naphthalen-1-yl]-5-piperidin-1-yl-benzamide and [1,3]dioxolan-2-ylmethylmethylamine according to conditions described in general procedure C. Mp: 125-127° C.; $^1$H NMR (400 MHz, DMSO-$d_6$) δ 1.57-1.61 (m, 6 H), 2.76 (bs, 1 H), 3.04 (bs, 1 H), 3.22-3.32 (m, 7 H), 3.55-3.86 (m, 4 H), 4.74-4.90 (m, 1 H), 6.26 (d, J=5.1 Hz, 1 H), 6.94-6.97 (m, 1 H), 7.15 (d, J=8.8 Hz, 1 H), 7.41 (d, J=8.0 Hz, 1 H), 7.46 (s, 1 H), 7.55-7.60 (m, 3 H), 7.82 (d, J=7.7 Hz, 1 H), 7.96-7.99 (m, 1 H), 8.24 (d, J=5.5 Hz, 1 H), 10.44 (s, 1 H).

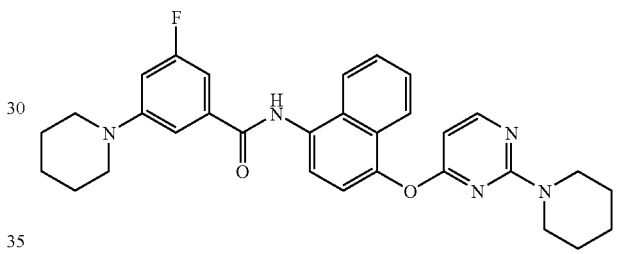

3-Fluoro-5-piperidin-1-yl-N-{4-[(2-piperidin-1-ylpyrimidin-4-yl)oxy]-1-naphthyl}benzamide (Compound B375). Compound is prepared from 3-fluoro-N-[4-(2-methanesulfonyl-pyrimidin-4-yloxy)-naphthalen-1-yl]-5-piperidin-1-yl-benzamide and piperidine according to conditions described in general procedure C. $^1$H NMR (400 MHz, DMSO-$d_6$) δ 1.34-1.58 (m, 12 H), 3.21-3.35 (m, 8 H), 6.18 (d, J=5.5 Hz, 1 H), 6.95 (d, J=12.4 Hz, 1 H), 7.15 (d, J=10.6 Hz, 1 H), 7.40 (d, J=8.0 Hz, 1 H), 7.46 (s, 1 H), 7.55-7.60 (m, 3 H), 7.81-7.83 (m, 1 H), 7.97 (d, J=7.3 Hz, 1 H), 8.24 (d, J=5.5 Hz, 1 H), 10.43 (s, 1 H).

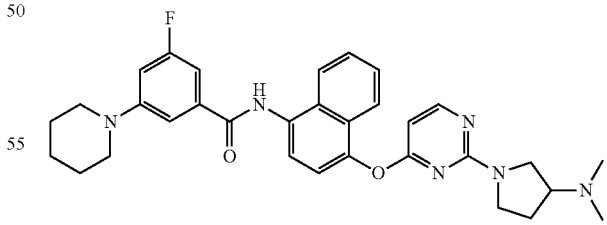

N-[4-({2-[3-(Dimethylamino)pyrrolidin-1-yl]pyrimidin-4-yl}oxy)-1-naphthyl]-3-fluoro-5-piperidin-1-ylbenzamide (Compound B420). Compound is prepared from 3-fluoro-N-[4-(2-methanesulfonyl-pyrimidin-4-yloxy)-naphthalen-1-yl]-5-piperidin-1-yl-benzamide and dimethyl-pyrrolidin-3-yl-amine according to conditions described in general procedure C. Mp: 108-110° C.; $^1$H NMR (400 MHz, CDCl$_3$) δ 1.61-1.77 (m, 6 H), 1.80-2.2.15 (m, 2 H), 2.17-2.27 (m, 6

H), 2.72 (bs, 1 H), 3.20-3.91 (m, 4 H), 3.25-3.27 (m, 4 H), 5.82-5.84 (bd, 1 H), 6.73-6.77 (m, 1 H), 6.97 (d, J=8.0 Hz, 1 H), 7.29-7.34 (m, 2 H), 7.46-7.64 (m, 2 H), 7.88-8.00 (m, 3 H), 8.13-8.20 (m, 2 H), 8.22 (d, J=5.5 Hz, 1 H).

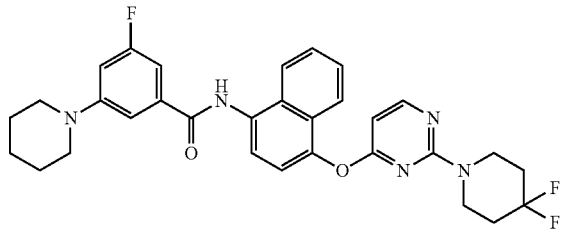

N-(4-{[2-(4,4-Difluoropiperidin-1-yl)pyrimidin-4-yl]oxy}-1-naphthyl)-3-fluoro-5-piperidin-1-ylbenzamide (Compound B423). Compound is prepared from 3-fluoro-N-[4-(2-methanesulfonyl-pyrimidin-4-yloxy)-naphthalen-1-yl]-5-piperidin-1-yl-benzamide and 4,4-difluoropiperidine according to conditions described in general procedure C. Mp: 172-174° C.; $^1$H NMR (400 MHz, CDCl$_3$) δ 1.63-1.71 (m, 6 H), 1.86-1.91 (m, 4 H), 3.28 (t, J=5.8 Hz, 4 H), 3.77 (s, 4 H), 6.07 (d, J=5.8 Hz, 1 H), 6.75-6.79 (m, 1 H), 6.98 (d, J=8.0 Hz, 1 H), 7.29-7.31 (m, 2 H), 7.49-7.60 (m, 2 H), 7.90-7.99 (m, 3 H), 8.12 (s, 1 H), 8.17 (d, J=5.5 Hz, 1 H).

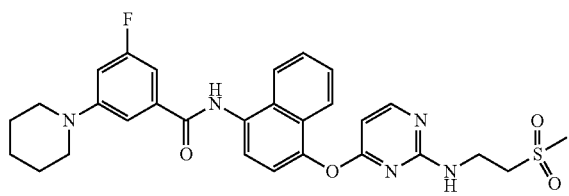

3-Fluoro-N-{4-[(2-{[2-(methylsulfonyl)ethyl]amino}pyrimidin-4-yl)oxy]-1-naphthyl}-5-piperidin-1-yl-benzamide (Compound B422). Compound is prepared from 3-fluoro-N-[4-(2-methanesulfonyl-pyrimidin-4-yloxy)-naphthalen-1-yl]-5-piperidin-1-yl-benzamide and 2-methanesulfonylethylamine according to conditions described in general procedure C. Mp: 102-104° C.; $^1$H NMR (400 MHz, CDCl$_3$) δ 1.62-1.71 (m, 6 H), 2.54-2.64 (m, 5 H), 3.27 (t, J=5.5 Hz, 4 H), 3.50 (s, 2 H), 5.66 (bs, 1 H), 6.31 (d, J=5.5 Hz, 1 H), 6.76 (d, J=11.1 Hz, 1 H), 6.98 (d, J=8.5 Hz, 1 H), 7.23 (d, J=8.0 Hz, 1 H), 7.30 (s, 1 H), 7.47-7.56 (m, 2 H), 7.80-7.91 (m, 3 H), 8.17 (d, J=5.5 Hz, 1 H), 8.25 (s, 1 H).

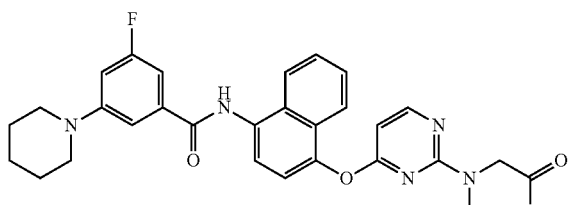

3-Fluoro-N-(4-{[2-(3-oxopiperazin-1-yl)pyrimidin-4-yl]oxy}-1-naphthyl)-5-piperidin-1-ylbenzamide (Compound B421). Compound is prepared from 3-fluoro-N-[4-(2-methanesulfonyl-pyrimidin-4-yloxy)-naphthalen-1-yl]-5-piperidin-1-yl-benzamide and 2-piperazinone according to conditions described in general procedure C. Mp: 140-142° C.; $^1$H NMR (400 MHz, CDCl$_3$) δ 1.62-1.69 (m, 6 H), 3.25-3.28 (m, 6 H), 3.82 (s, 2 H), 4.14 (s, 2 H), 6.20 (d, J=5.5 Hz, 1 H), 6.38 (s, 1 H), 6.76 (d, J=11.7 Hz, 1 H), 7.00 (d, J=8.0 Hz, 1 H), 7.26 (d, J=8.0 Hz, 1 H), 7.32 (s, 1 H), 7.46-7.55 (m, 2 H), 7.83-7.92 (m, 3 H), 8.20-8.21 (m, 1H), 8.36 (s, 1 H).

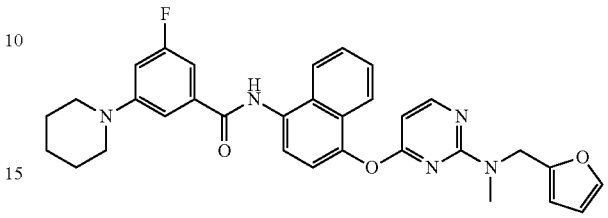

3-Fluoro-N-[4-({2-[(2-furylmethyl)(methyl)amino]pyrimidin-4-yl}oxy)-1-naphthyl]-5-piperidin-1-ylbenzamide (Compound B418). Compound is prepared from 3-fluoro-N-[4-(2-methanesulfonyl-pyrimidin-4-yloxy)-naphthalen-1-yl]-5-piperidin-1-yl-benzamide and furan-2-ylmethylmethylamine according to conditions described in general procedure C. Mp: 155-156° C.; $^1$H NMR (400 MHz, CDCl$_3$) δ 1.61-1.69 (m, 6 H), 3.05 (s, 3 H), 3.25-3.28 (m, 4 H), 4.49 (s, 2 H), 6.12-6.18 (m, 2 H), 6.75 (d, J=11.1 Hz, 1 H), 6.98 (d, J=8.0 Hz, 1 H), 7.25-7.31 (m, 3H), 7.46-7.57 (m, 3 H), 7.88-7.97 (m, 3 H), 8.16-8.21 (m, 2 H).

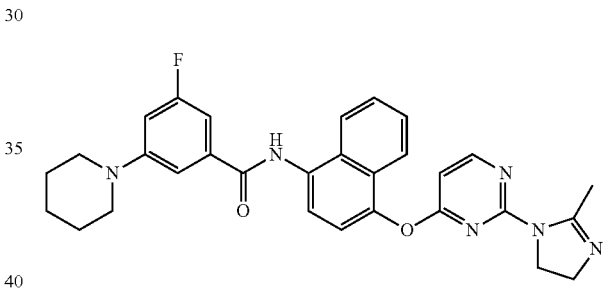

3-Fluoro-N-(4-{[2-(2-methyl-4,5-dihydro-1H-imidazol-1-yl)pyrimidin-4-yl]oxy}-1-naphthyl)-5-piperidin-1-ylbenzamide (Compound B417). Compound is prepared from 3-fluoro-N-[4-(2-methanesulfonyl-pyrimidin-4-yloxy)-naphthalen-1-yl]-5-piperidin-1-yl-benzamide and 2-methyl-4,5-dihydro-1H-imidazole according to conditions described in general procedure C. $^1$H NMR (400 MHz, CDCl$_3$) δ 1.63-1.70 (m, 9 H), 3.29 (t, J=5.5 Hz, 4H), 3.67 (t, J=8.8 Hz, 2 H), 3.83 (t, J=8.8 Hz, 2 H), 6.25-6.53 (m, 1 H), 6.77 (d, J=11.7 Hz, 1 H), 6.99 (d, J=8.0 Hz, 1 H), 7.25-7.31 (m, 2 H), 7.49-7.60 (m, 2 H), 7.88-7.93 (m, 2 H), 8.01 (d, J=8.0 Hz, 1 H), 8.17 (s, 1 H), 8.34-8.36 (m, 1 H).

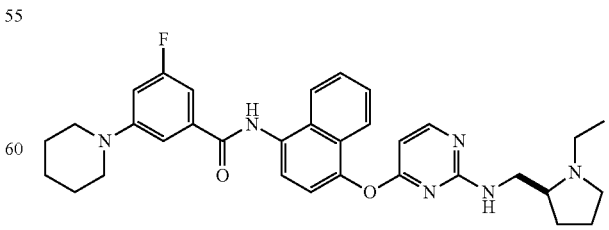

N-(4-{[2-({[(2S)-1-Ethylpyrrolidin-2-yl]methyl}amino)pyrimidin-4-yl]oxy}-1-naphthyl)-3-fluoro-5-piperidin-1-yl-benzamide (Compound B419). Compound is prepared from 3-fluoro-N-[4-(2-methanesulfonyl-pyrimidin-4-yloxy)-naphthalen-1-yl]-5-piperidin-1-yl-benzamide and (2S)-(1-ethyl-pyrrolidin-2-yl)-methylamine according to conditions described in general procedure C. ¹H NMR (400 MHz, CDCl₃) δ 1.02 (s, 3 H), 1.62-1.70 (m, 10 H), 2.00-2.08 (m, 2H), 2.46-2.69 (m, 2H), 3.11 (s, 2 H), 3.26-3.31 (m, 4 H), 3.40-3.60 (m, 1 H), 5.56 (s, 1 H), 6.01 (d, J=5.5 Hz, 1 H), 6.76 (d, J=12.0 Hz, 1 H), 6.99 (d, J=8.0 Hz, 1 H), 7.26-7.30 (m, 2 H), 7.48-7.58 (m, 2 H), 7.89-7.96 (m, 3 H), 8.10 (s, 1 H), 8.17 (s, 1 H).

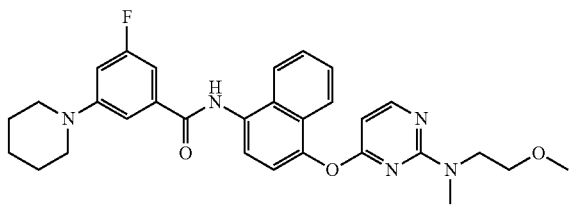

3-Fluoro-N-[4-({2-[(2-methoxyethyl)(methyl)amino]pyrimidin-4-yl}oxy)-1-naphthyl]-5-piperidin-1-ylbenzamide (Compound B414). Compound is prepared from 3-fluoro-N-[4-(2-methanesulfonyl-pyrimidin-4-yloxy)-naphthalen-1-yl]-5-piperidin-1-yl-benzamide and (2-methoxyethyl)methylamine according to conditions described in general procedure C. Mp: 81-82° C.; ¹H NMR (400 MHz, CDCl₃) δ 1.62-1.70 (m, 6 H), 3.06-3.40 (m, 14 H), 6.05 (s, 1 H), 6.76 (d, J=12.0 Hz, 1 H), 6.99 (d, J=7.8 Hz, 1 H), 7.26-7.30 (m, 2 H), 7.47-7.56 (m, 2 H), 7.88-7.96 (m, 3 H), 8.17 (s, 2 H).

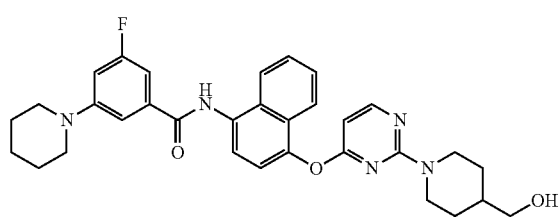

3-Fluoro-N-[4-({2-[4-(hydroxymethyl)piperidin-1-yl]pyrimidin-4-yl}oxy)-1-naphthyl]-5-piperidin-1-ylbenzamide (Compound B415). Compound is prepared from 3-fluoro-N-[4-(2-methanesulfonyl-pyrimidin-4-yloxy)-naphthalen-1-yl]-5-piperidin-1-yl-benzamide and piperidin-4-yl-methanol according to conditions described in general procedure C. ¹H NMR (400 MHz, CDCl₃) δ 1.05-1.14 (m, 2 H), 1.61-1.70 (m, 9 H), 2.74 (t, J=12.0 Hz, 2 H), 3.26 (t, J=5.5 Hz, 4 H), 3.45 (d, J=5.8 Hz, 2 H), 5.92 (d, J=5.5 Hz, 1 H), 6.74-6.77 (m, 1 H), 6.97 (d, J=7.6 Hz, 1 H), 7.25-7.29 (m, 2 H), 7.46-7.56 (m, 2 H), 7.87-7.89 (m, 2 H), 7.98 (d, J=7.7 Hz, 1 H), 8.22 (s, 2 H).

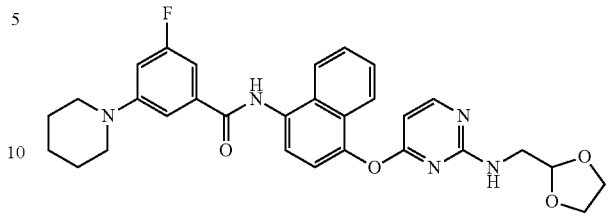

N-[4-({2-[(1,3-Dioxolan-2-ylmethyl)amino]pyrimidin-4-yl}oxy)-1-naphthyl]-3-fluoro-5-piperidin-1-ylbenzamide (Compound B411). Compound is prepared from 3-fluoro-N-[4-(2-methanesulfonyl-pyrimidin-4-yloxy)-naphthalen-1-yl]-5-piperidin-1-yl-benzamide and C-[1,3]dioxolan-2-yl-methylamine according to conditions described in general procedure C. Mp: 96-98° C.; ¹H NMR (400 MHz, DMSO-d₆) δ 1.57-1.61 (m, 6 H), 3.27-3.30 (m, 4 H), 3.60-3.89 (m, 6 H), 4.70-4.89 (bd, 1 H), 6.20-6.34 (bd, 1 H), 6.94-6.99 (m, 1 H), 7.14-7.21 (m, 2 H), 7.40 (d, J=8.0 Hz, 1 H), 7.44 (s, 1 H), 7.52-7.61 (m, 3 H), 7.81 (d, J=7.3 Hz, 1 H), 7.96-7.98 (m, 1H), 8.21 (s, 1 H), 10.42 (s, 1 H).

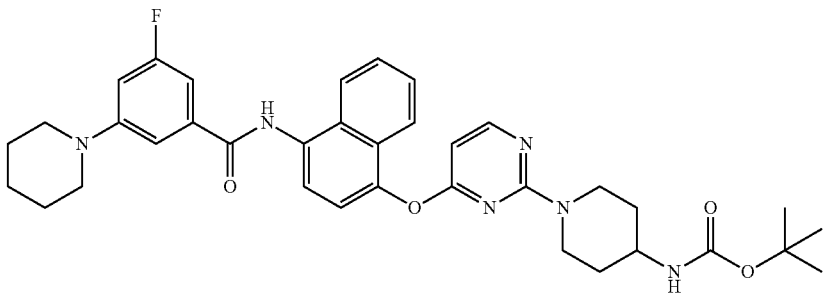

tert-Butyl{1-[4-({4-[(3-fluoro-5-piperidin-1-ylbenzoyl)amino]-1-naphthyl}oxy)pyrimidin-2-yl]piperidin-4-yl}carbamate (Compound B410). Compound is prepared from 3-fluoro-N-[4-(2-methanesulfonyl-pyrimidin-4-yloxy)-naphthalen-1-yl]-5-piperidin-1-yl-benzamide and piperidin-4-yl-carbamic acid tert-butyl ester according to conditions described in general procedure C. Mp: 211-212° C.; ¹H NMR (400 MHz, DMSO-d₆) δ 1.18-1.14 (m, 2 H), 1.34 (s, 9H), 1.57-1.61 (m, 8 H), 2.80 (t, J=12.8 Hz, 2 H), 3.21-3.34 (m, 6 H), 4.19 (bs, 1 H), 6.19 (d, J =5.5 Hz, 1 H), 6.76 (d, J=7.6 Hz, 1 H), 6.94-6.98 (m, 1 H), 7.14 (d, J=9.1 Hz, 1 H), 7.40 (d, J=8.0 Hz, 1 H), 7.46 (s, 1 H), 7.54-7.61 (m, 3 H), 7.81-7.83 (m, 1 H), 7.96-7.99 (m, 1 H), 8.24 (d, J=5.5 Hz, 1 H), 10.44 (s, 1 H)

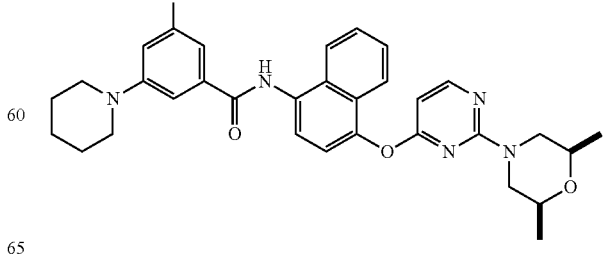

N-[4-({2-[(2R,6S)-2,6-Dimethylmorpholin-4-yl]pyrimidin-4-yl}oxy)-1-naphthyl]-3-fluoro-5-piperidin-1-ylbenza.

mide (Compound B416). Compound is prepared from 3-fluoro-N-[4-(2-methanesulfonyl-pyrimidin-4-yloxy)-naphthalen-1-yl]-5-piperidin-1-yl-benzamide and (2R,6S)-2,6-dimethylmorpholine according to conditions described in general procedure C.

Mp: 174-176° C.; $^1$H NMR (400 MHz, DMSO-d$_6$) δ 1.00 (d, J=5.8 Hz, 6 H), 1.57-1.61 (m, 6H), 2.40 (t, J=11.7 Hz, 2 H), 3.26-3.31 (m, 4 H), 3.39 (bs, 2 H), 4.17 (bs, 2 H), 6.17 (d, J=5.8 Hz, 1 H), 6.94-6.98 (m, 1 H), 7.14 (d, J=8.4 Hz, 1 H), 7.41 (d, J=8.0 Hz, 1 H), 7.45 (s, 1 H), 7.53-7.62 (m, 3 H), 7.80-7.82 (m, 1 H), 7.98 (d, J=7.3 Hz, 1 H), 8.25 (d, J=5.5 Hz, 1 H), 10.43 (s, 1 H).

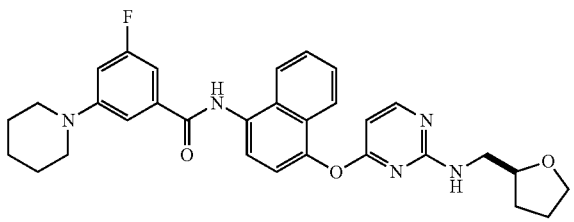

3-Fluoro-5-piperidin-1-yl-N-{4-[(2-{[(2S)-tetrahydrofuran-2-ylmethyl]amino}pyrimidin-4-yl)oxy]-1-naphthyl}benzamide (Compound B412). Compound is prepared from 3-fluoro-N-[4-(2-methanesulfonyl-pyrimidin-4-yloxy)-naphthalen-1-yl]-5-piperidin-1-yl-benzamide and (2S)-(tetrahydro-furan-2-yl)-methylamine according to conditions described in general procedure C. $^1$H NMR (400 MHz, DMSO-d$_6$) δ 1.40-1.72 (m, 10 H), 2.87 (s, 1 H), 3.08 (bs, 1H), 3.27-3.30 (m, 4 H), 3.51 (bs, 1 H), 3.66 (bs, 1 H), 3.89 (bs, 1 H), 6.20-6.32 (bd, 1 H), 6.94-6.99 (m, 1 H), 7.12-7.22 (m, 1 H), 7.38 (d, J=8.0 Hz, 1 H), 7.44 (s, 1 H), 7.51-7.61 (m, 3 H), 7.79-7.81 (m, 1 H), 7.97 (d, J=8.0 Hz, 1 H), 8.20 (bs, 1 H), 10.41 (s, 1 H).

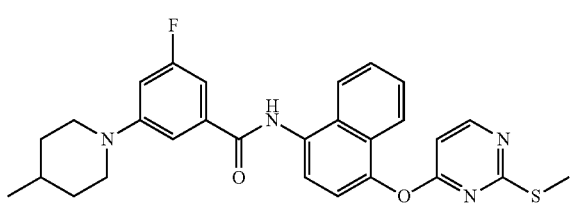

3-Fluoro-5-(4-methylpiperidin-1-yl)-N-(4-{[2-(methylthio)pyrimidin-4-yl]oxy}-1-naphthyl)benzamide (Compound B247). Formed from t-butyl(4-{[2-(methylthio)pyrimidin-4-yl]oxy}-1-naphthyl)carbamate (1.60 g, 4.17 mmol) and 3-fluoro-5-(4-methylpiperidin-1-yl)benzoic acid (1.18 g, 5.01 mmol) according to conditions described in Step 3 of Example 3 (1.025 g); Mp: 142-143° C.; $^1$H NMR (300 MHz, CDCl$_3$) δ 0.99(d, J=6.6 Hz, 3H), 1.25-1.38(m, 2H), 1.57-1.64 (m, 1H), 1.75(d, J=12.6 Hz, 2H), 2.29(s, 3H), 2.78-2.86(m, 2H), 3.76(d, J=12.6 Hz, 2H), 6.52(d, J=5.7 Hz, 1H), 6.77(d, J=12.3 Hz, 1H), 6.98(d, J=8.4 Hz, 1H), 7.29-7.32(m, 2H), 7.48-7.59(m, 2H), 7.90-7.96(m, 3H), 8.18(s, 1H), 8.35(d, J=6.0 Hz, 1H): MS: 503 (M+1).

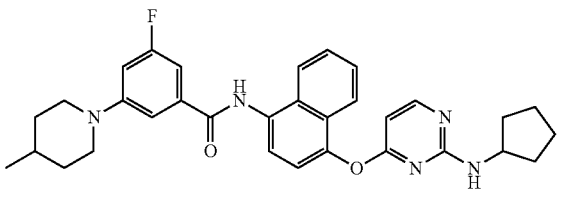

N-(4-{[2-(Cyclopentylamino)pyrimidin-4-yl]oxy}-1-naphthyl)-3-fluoro-5-(4-methylpiperidin-1-yl)benzamide (Compound B266). Compound is prepared from 3-fluoro-5-(4-methylpiperidin-1-yl)-N-(4-{[2-(methylthio)pyrimidin-4-yl]oxy}-1-naphthyl)benzamide (0.2 mmol) and cyclopentylamine (10 mmol) according to conditions described in Step 4 of Example 3 and general procedure C. A yellow solid (13 mg); Mp: 88-90° C.; $^1$H NMR (300 MHz, CDCl$_3$) δ 0.98(d, J=6.6 Hz, 3H), 1.23-1.87(m, 13H), 2.77-2.85(m, 2H), 3.76(d, J=12.3 Hz, 2H), 4.08-4.15(m, 1H), 5.15(bs, 1H), 6.04(s, 1H), 6.76(d, J=12.3 Hz, 1H), 6.98(d, J=8.4 Hz, 1H), 7.26-7.30(m, 2H), 7.49-7.55(m, 2H), 7.87-7.97(m, 3H), 8.07-8.11(m, 1H), 8.20(s, 1H);

MS 540 (M+1).

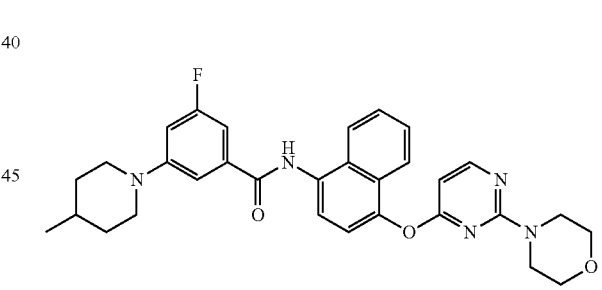

3-Fluoro-5-(4-methylpiperidin-1-yl)-N-{4-[(2-morpholin-4-ylpyrimidin-4-yl)oxy]-1-naphthyl}benzamide (Compound B265). Compound is prepared from 3-fluoro-5-(4-methylpiperidin-1-yl)-N-(4-{[2-(methylthio)pyrimidin-4-yl]oxy}-1-naphthyl)benzamide (0.1 g, 0.2 mmol) and morpholine (10 mmol) according to conditions described in Step 4 of Example 3 and general procedure C. A pink solid is produced (15 mg). Mp: 88-89° C.; $^1$H NMR (300 MHz, CDCl$_3$) δ 0.98(d, J=6.6 Hz, 3H), 1.25-1.38(m, 3H), 1.75 (d, J=12.6 Hz, 2H), 2.78-2.86(m, 2H), 3.64(s, 9H), 3.77(d, J=12 Hz, 1H), 6.07(d, J=5.7 Hz, 1H), 6.77(d, J=12 Hz, 1H), 6.98(d, J=7.8 Hz, 1H), 2.30-7.33(m, 2H), 7.49-7.60(m, 2H), 7.89-7.99(m, 3H), 8.13(s, 1H), 8.18(d, J=5.7 Hz, 1H); MS 542 (M+1).

Example 3a

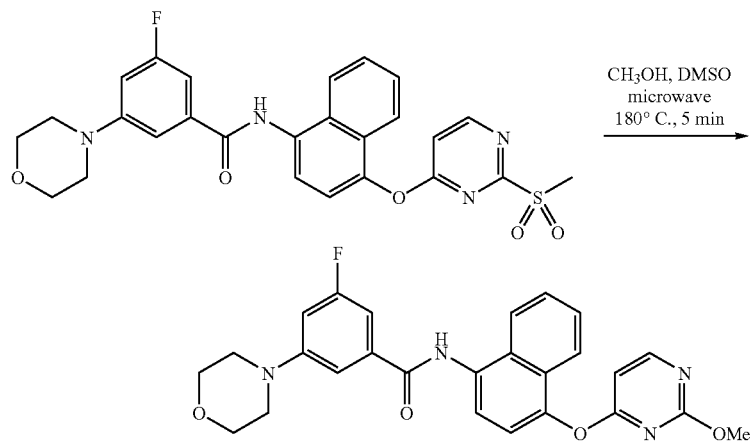

3-Fluoro-N-{4-[(2-methoxypyrimidin-4-yl)oxy]-1-naphthyl}-5-morpholin-4-ylbenzamide (Compound B267). A mixture of 3-fluoro-N-(4-{[2-(methylsulfonyl)pyrimidin-4-yl]oxy}-1-naphthyl)-5-morpholin-4-ylbenzamide (0.1 mmol) and methanol (1.0 ml) in DMSO (0.5 ml) is heated using a microwave source at 180° C. for 5 min. The resulting mixture is diluted with $CH_2Cl_2$ (5 ml), washed with water, dried over $Na_2SO_4$ and concentrated. Purification of the residue by column chromatography on silica gel (50% EtOAc in hexane) gives 3-fluoro-N-{4-[(2-methoxypyrimidin-4-yl)oxy]-1-naphthyl}-5-morpholin-4-ylbenzamide as a white solid (31 mg). Mp: 216-217° C.; $^1$H NMR (300 MHz, CDCl$_3$) δ 3.25(t, J=4.8 Hz, 4H), 3.84(s, 3H), 3.87(t, J=4.8 Hz, 4H), 6.53(d, J=5.7 Hz, 1H), 6.77(d, J=12 Hz, 1H), 7.06(d, J=8.4 Hz, 1H), 7.31-7.34(m, 2H), 7.49-7.60(m, 2H), 7.89-7.97(m, 3H), 8.15(s, 1H), 8.36(d, J=5.7 Hz, 1H);

MS 475 (M+1).

Additional compounds of the invention can be prepared as described in Example 4.

A representative synthetic scheme is shown in Scheme 4, below.

-continued

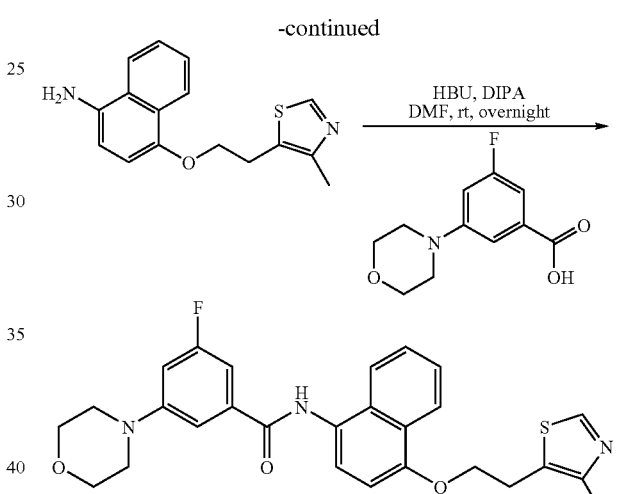

Example 4

General Procedure D

Scheme 4

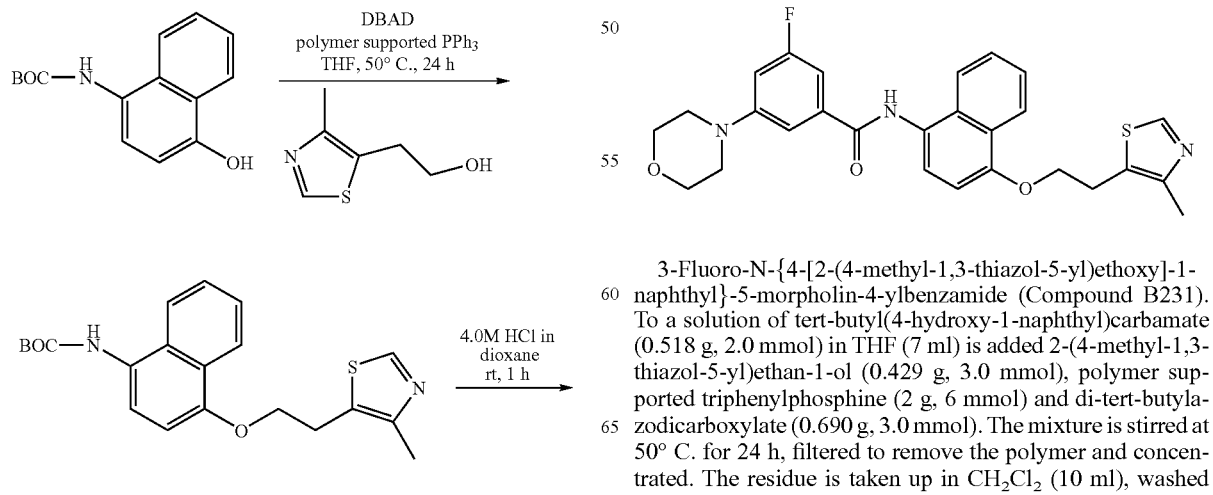

3-Fluoro-N-{4-[2-(4-methyl-1,3-thiazol-5-yl)ethoxy]-1-naphthyl}-5-morpholin-4-ylbenzamide (Compound B231). To a solution of tert-butyl(4-hydroxy-1-naphthyl)carbamate (0.518 g, 2.0 mmol) in THF (7 ml) is added 2-(4-methyl-1,3-thiazol-5-yl)ethan-1-ol (0.429 g, 3.0 mmol), polymer supported triphenylphosphine (2 g, 6 mmol) and di-tert-butylazodicarboxylate (0.690 g, 3.0 mmol). The mixture is stirred at 50° C. for 24 h, filtered to remove the polymer and concentrated. The residue is taken up in $CH_2Cl_2$ (10 ml), washed with 2.0 M Na₂CO₃, water, dried over Na₂SO₄ and evaporated. To the residue is added a solution of 4.0 M HCl in dioxane (5 ml). The resulting mixture is stirred at room temperature for 1 h then concentrated under vacuum. This residue is then taken up in CH₂Cl₂ (10 ml), washed with Na₂CO₃, dried over Na₂SO₄ and concentrated to provide the amine intermediate. To a solution of the amine intermediate in DMF (5 ml) is added 3-fluoro-5-morpholinebenzoic acid (0.270 g, 1.2 mmol), HBTU (0.568 g, 1.5 mmol) and diisopropylamine (0.53 ml, 3.0 mmol). This mixture is stirred at room temperature overnight. Then mixture is diluted with CH₂Cl₂ (15 ml), washed with 0.05 N NaOH, dried over Na₂SO₄ and concentrated. The residue is purified by column chromatography on silica gel (2% methanol in EtOAc) to give 3-fluoro-N-{4-[2-(4-methyl-1,3-thiazol-5-yl)ethoxy]-1-naphthyl}-5-morpholin-4-ylbenzamide as a pink solid (95 mg); Mp: 186-187° C.; ¹H NMR (300 MHz, CDCl₃) δ 2.50(s, 3H), 3.22(bs, 4H), 3.40(t, J=6.3 Hz, 2H), 3.85(t, J=4.2 Hz, 4H), 4.33(t, J=6.0 Hz, 2H), 6.72-6.79(m, 2H), 7.06(d, J=8.1 Hz, 1H), 7.30(s, 1H), 7.49-7.52(m, 2H), 7.67(d, J=7.8 Hz, 1H), 7.81(d, J=8.1 hz, 1H), 8.01(s, 1H), 8.31-8.35(m, 1H), 8.62(s, 1H); MS 492 (M+1).

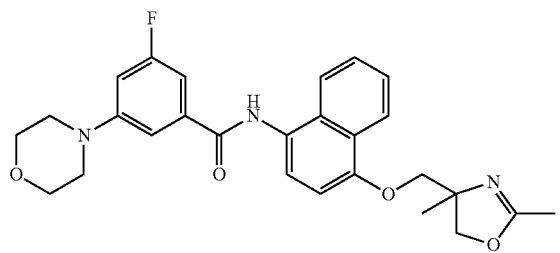

N-{4-[(2,4-Dimethyl-4,5-dihydro-1,3-oxazol-4-yl)methoxy]-1-naphthyl}-3-fluoro-5-morpholin-4-ylbenzamide (Compound B232). Compound is prepared from tert-butyl(4-hydroxy-1-naphthyl)carbamate and (2,4-dimethyl-4,5-dihydro-oxazol-4-yl)-methanol according to conditions described in general procedure D. A pink solid is produced (0.115 g). Mp: 203-206° C.; ¹H NMR (300 MHz, CDCl₃) δ 1.49(s, 3H), 2.06(s, 3H), 3.24(bs, 4H), 3.86(t, J=4.8 Hz, 4H), 3.96-4.06(m, 3H), 4.51(d, J=8.4 Hz, 1H), 6.71-6.77(m, 2H), 7.09(d, J=9.0 Hz, 1H), 7.32(s, 1H), 7.46-7.54(m, 2H), 7.63(d, J=7.8 Hz, 1H), 7.81(d, J=7.8 Hz, 1H), 8.15(s, 1H), 8.18-8.21(m, 1H); MS 478 (M+1).

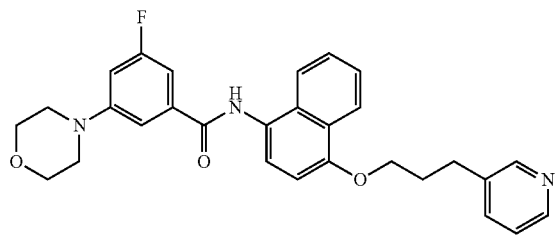

3-Fluoro-5-morpholin-4-yl-N-[4-(3-pyridin-3-ylpropoxy)-1-naphthyl]benzamide (Compound B222). Compound is prepared from tert-butyl(4-hydroxy-1-naphthyl)carbamate and 3-pyridin-3-yl-propan-1-ol according to conditions described in general procedure D. A pink solid is produced(20 mg). Mp: 64-66° C.; ¹H NMR (300 MHz, CDCl₃) δ 2.22-2.31(m, 2H), 2.94 (t, J=7.5 Hz, 2H), 3.18-3.23 (m, 4H), 3.85(bs, 4H), 4.16(t, J=6.0 Hz, 2H), 6.73-6.77(m, 2H), 7.07(d, J=8.1 Hz, 1H), 7.20-7.24(m, 1H), 7.31(s, 1H), 7.51-7.57(m, 3H), 7.65(d, J=8.1 Hz, 1H), 7.82(d, J=8.7 Hz, 1H), 8.08(s, 1H), 8.30-8.33(m, 1H), 8345-8.47(m, 1H), 8.51 (s, 1H); MS 486 (M+1).

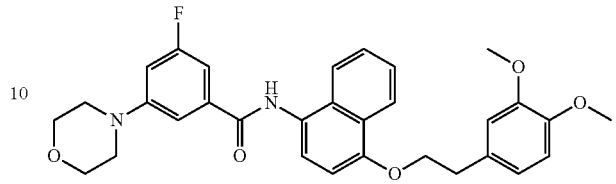

N-{4-[2-(3,4-Dimethoxyphenyl)ethoxy]-1-naphthyl}-3-fluoro-5-morpholin-4-ylbenzamide (Compound B189). Compound is prepared from tert-butyl(4-hydroxy-1-naphthyl)carbamate and 2-(3,4-Dimethoxy-phenyl)-ethanol according to conditions described in general procedure D. A red solid is produced (12 mg). Mp: 73-75° C.; ¹H NMR (300 MHz, CDCl₃) δ 3.01(t, J=7.2 Hz, 1H), 3.20(t, J=6.9 Hz, 1H), 3.24(s, 4H), 3.80-3.87(m, 10H), 4.35(t, J=6.9 Hz, 1H), 4.51(t, J=7.2 Hz, 1H), 6.73-6.92(m, 4H), 7.00-7.08(m, 1H), 7.31(s, 1H), 7.47-7.57(m, 3H), 7.69(d, J=7.8 Hz, 1H), 7.80-7.82(m, 1H), 7.91(s, 1H), 8.33(d, J=7.5 Hz, 1H); MS 531 (M+1).

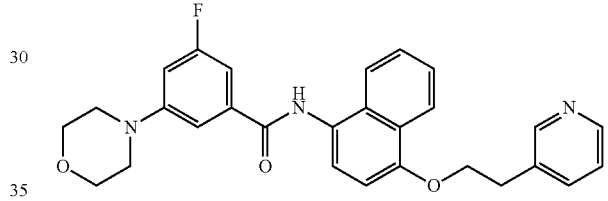

3-Fluoro-5-morpholin-4-yl-N-[4-(3-pyridin-4-ylethoxy)-1-naphthyl]benzamide (Compound B190). Compound is prepared from tert-butyl(4-hydroxy-1-naphthyl)carbamate and 2-pyridin-3-yl-ethanol according to conditions described in general procedure D. A red solid is produced (12 mg). Mp: 80-82° C.; ¹H NMR (300 MHz, CDCl₃) δ 3.21-3.27(m, 6H), 3.82-3.86(m, 4H), 4.36(t, J=6.0 Hz, 2H), 6.71-6.79(m, 2H), 7.06(d, J=8.7 Hz, 1H), 7.28-7.30(m, 1H), 7.48-7.52(m, 3H), 7.65(d, J=7.8 Hz, 1H), 7.72(d, J=7.5 Hz, 1H), 7.79(d, J=7.2 Hz, 1H), 8.09(s, 1H), 8.22-8.25(m, 1H), 8.50(d, J=7.5 Hz, 1H), 8.65(s, 1H); MS 472 (M+1).

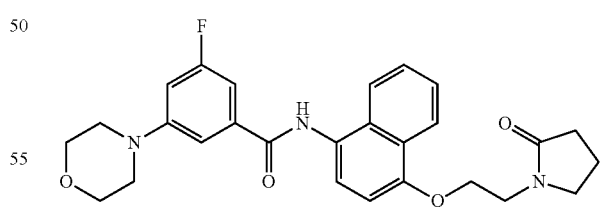

3-Fluoro-5-morpholin-4-yl-N-{4-[2-(2-oxopyrrolidin-1-yl)ethoxy]-1-naphthyl}benzamide (Compound B224). Compound is prepared from tert-butyl(4-hydroxy-1-naphthyl)carbamate and 1-(2-hydroxy-ethyl)-pyrrolidin-2-one according to conditions described in general procedure D. A pink solid is produced (12 mg). Mp: 172-173° C.; ¹H NMR (300 MHz, CDCl₃) δ 2.04(t, J=7.2 Hz, 2H), 2.41(t, J=8.1 Hz, 2H), 3.25(s, 4H), 3.65(t, J=7.2 Hz, 2H), 3.85(s, 6H), 4.26(t, J=4.5 Hz, 2H), 6.74-6.79(m, 1H), 7.09(d, J=8.4 Hz, 1H), 7.33(s, 1H), 7.52-

7.56(m, 2H), 7.67(d, J=7.5 Hz, 1H), 7.83(d, J=7.2 Hz, 1H), 8.03(s, 1H), 8.26 (d, J=7.5 Hz, 1H); MS 478 (M+1).

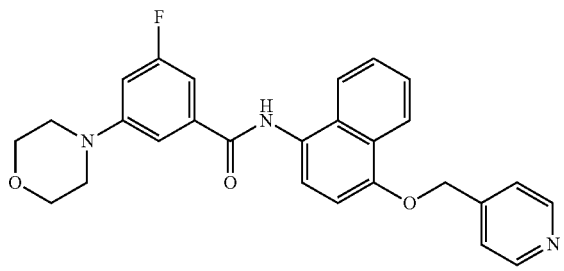

3-Fluoro-5-morpholin-4-yl-N-[4-(pyridin-4-ylmethoxy)-1-naphthyl]benzamide (Compound B191). Compound is prepared from tert-butyl(4-hydroxy-1-naphthyl)carbamate and pyridin-4-yl-methanol according to conditions described in general procedure D. A white solid is produced (12 mg). Mp: 157-159° C.; $^1$H NMR (300 MHz, DMSO-$d_6$) δ 3.19-3.23(m, 4H), 3.83-3.87(m, 4H), 5.28(s, 2H), 6.72-6.82(m, 2H), 7.04-7.09(m, 1H), 7.31-7.34(m, 1H), 7.46(d, J=5.7 Hz, 1H), 7.53-7.61(m, 2H), 7.67(d, J=8.1 Hz, 1H), 7.83-7.86(m, 1H), 8.13 (s, 1H), 8.39-8.42(m, 1H), 8.64-8.66(m, 3H); MS 458 (M+1).

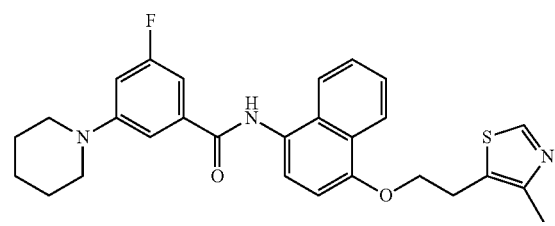

3-Fluoro-N-{4-[2-(4-methyl-1,3-thiazol-5-yl)ethoxy]-1-naphthyl}-5-piperidin-1-ylbenzamide (Compound B424). Compound is prepared from tert-butyl(4-hydroxy-1-naphthyl)carbamate, 3-fluoro-5-piperidin-1-yl-benzoic acid and 2-(4-methylthiazol-5-yl)-ethanol according to conditions described in general procedure D. A pink solid is produced (12 mg). Mp: 221-222° C.; $^1$H NMR (300 MHz, CDCl$_3$) δ 1.62-1.69(m, 6H), 2.50(s, 3H), 3.20-3.27(m, 5H), 3.40(t, J=6.3 Hz, 1H), 4.34(t, J=6.0 Hz, 1H), 4.46(t, J=6.6 Hz, 1H), 6.73-6.82(m, 2H), 6.98(d, J=8.1 Hz, 1H), 7.06-7.10(m, 1H), 7.31-7.35(m, 1H), 7.50-7.59(m, 2H), 7.73(d, J=9.3 Hz, 1H), 7.83(d, J=7.8 Hz, 1H), 7.93(s, 1H), 8.32-8.35(m, 1H), 8.60-8.62(m, 1H); MS 490 (M+1).

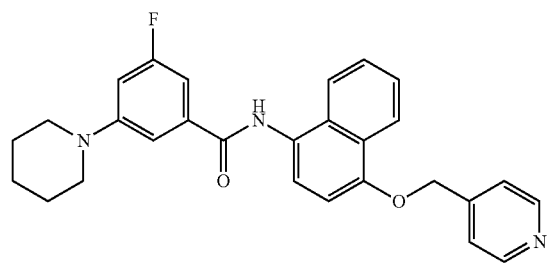

3-Fluoro-5-piperidin-1-yl-N-[4-(pyridin-4-ylmethoxy)-1-naphthyl]benzamide (Compound B230). Compound is prepared from tert-butyl(4-hydroxy-1-naphthyl)carbamate, 3-fluoro-5-piperidin-1-yl-benzoic acid and 1-(2-hydroxyethyl)-pyrrolidin-2-one according to conditions described in general procedure D. A pink solid is produced (38 mg). Mp: 69-71° C.; $^1$H NMR (300 MHz, DMSO-$d_6$) δ 1.58(s, 6H), 3.28(s, 4H), 5.42(s, 2H), 6.95(d, J=8.4 Hz, 1H), 7.06(d, J =8.1 Hz, 1H), 7.15(d, J=6.9 Hz, 1H), 7.44(s, 1H), 7.55-7.60(m, 4H), 7.85-7.92(m, 1H), 8.30-8.38(m, 1H), 8.60-8.63(m, 1H), 10.26(s, 1H); MS 456 (M+1).

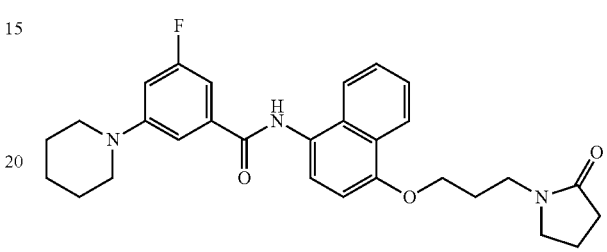

3-Fluoro-N-{4-[3-(2-oxopyrrolidin-1-yl)propoxy]-1-naphthyl}-5-piperidin-1-ylbenzamide (Compound B182). Compound is prepared from tert-butyl(4-hydroxy-1-naphthyl)carbamate, 3-fluoro-5-piperidin-1-yl-benzoic acid and 1-(3-hydroxy-propyl)-pyrrolidin-2-one according to conditions described in general procedure D. A pink solid is produced (42 mg). Mp: 88-89° C.; $^1$H NMR (300 MHz, CDCl$_3$) δ 1.69(s, 6H), 1.95-2.04(m, 2H), 2.10-2.18(m, 2H), 2.34-2.39 (m, 2H), 3.26(s, 4H), 3.37-3.45(m, 2H), 3.50-3.55(m, 2H), 4.09-4.13(m, 2H), 6.72-6.77(m, 2H), 7.03(d, J=8.4 Hz, 1H), 7.33(s, 1H), 7.46-7.55(m, 2H), 7.63(d, J=7.8 Hz, 1H), 7.82(d, J=7.5 Hz, 1H), 8.23(s, 1H), 8.27-8.30 (m, 1H); MS 490 (M+1).

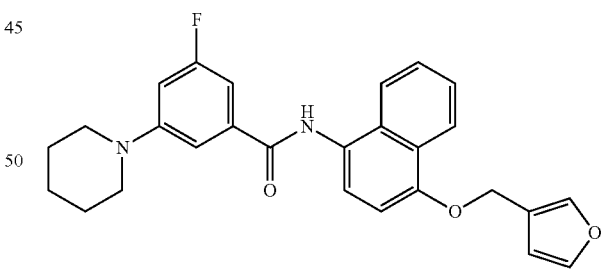

3-Fluoro-N-[4-(3-furylmethoxy)-1-naphthyl]-5-piperidin-1-ylbenzamide (Compound B180). Compound is prepared from tert-butyl(4-hydroxy-1-naphthyl)carbamate, 3-fluoro-5-piperidin-1-yl-benzoic acid and furan-3-yl-methanol according to conditions described in general procedure D. A pink solid is produced (12 mg). Mp: 152-153° C.; $^1$H NMR (300 MHz, CDCl$_3$) δ 1.63-1.69(m, 6H), 3.20-3.27 (m, 2H), 5.13(s, 2H), 6.58(s, 1H), 6.75(d, J=12.6 Hz, 1H), 6.89(d, J=8.4 Hz, 1H), 6.98(d, J=9.0 Hz, 1H), 7.30(s, 1H), 7.47-7.59(m, 4H), 7.12(d, J=8.1 Hz, 1H), 7.83(d, J=8.4 Hz, 1H), 7.95(s, 1H), 8.32(d, J=8.1 Hz, 1H); MS 445 (M+1).

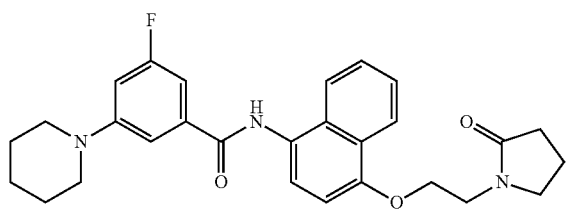

3-Fluoro-N-{4-[2-(2-oxopyrrolidin-1-yl)ethoxy]-1-naphthyl}-5-piperidin-1-ylbenzamide (Compound B181). Compound is prepared from tert-butyl(4-hydroxy-1-naphthyl)carbamate, 3-fluoro-5-piperidin-1-yl-benzoic acid and 1-(2-hydroxyethyl)-pyrrolidin-2-one according to conditions described in general procedure D. A white solid is produced (27 mg). Mp: 161-162° C.; $^1$H NMR (300 MHz, CDCl$_3$) δ 1.62-1.70(m, 6H), 1.99-2.09(m, 2H), 2.35-2.44(m, 2H), 3.16-3.27(m, 2H), 3.63-3.68(m, 2H), 3.84(d, J=5.1 Hz, 2H), 4.26 (d, J=4.8 Hz, 2H), 6.73-6.79(m, 2H), 6.70(d, J=8.4 Hz, 1H), 7.32(s, 1H), 7.49-7.58(m, 2H), 7.68(d, J=8.1 Hz, 1H), 7.84(d, J=7.8 Hz, 1H), 8.03(s, 1H), 8.24-8.27(m, 1H); MS 476 (M+1).

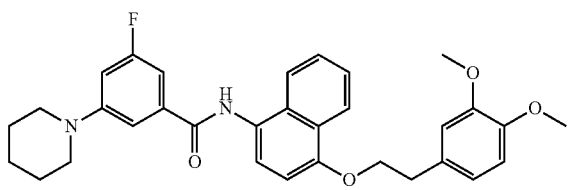

N-{4-[2-(3,4-Dimethoxyphenyl)ethoxy]-1-naphthyl}-3-fluoro-5-piperidin-1-ylbenzamide (Compound B179). Compound is prepared from tert-butyl(4-hydroxy-1-naphthyl)carbamate, 3-fluoro-5-piperidin-1-yl-benzoic acid and 2-(3,4-Dimethoxy-phenyl)-ethanol according to conditions described in general procedure D. A deep pink solid is produced (42 mg). Mp: 158-160° C.; $^1$H NMR (300 MHz, CDCl$_3$) δ 1.60-1.68(m, 6H), 3.00(d, J=6.3 Hz, 1H), 3.18-3.27 (m, 5H), 3.85-3.87(m, 6H), 4.35(d, J=6.6 Hz, 1H), 4.48(d, J=7.2 Hz, 1H), 6.71-6.91(m, 4H), 6.98(d, J=7.8 Hz, 1H), 7.08(d, J=8.4 Hz, 1H), 7.30-7.34(m, 1H), 7.46-7.56(m, 2H), 7.69(d, J =7.8 Hz, 1H), 7.82(d, J=7.8 Hz, 1H), 7.94(s, 1H), 8.33(d, J=9.0 Hz, 1H); MS 529 (M+1).

Additional compounds of the invention can be prepared as described in Example 5.

Example 5

General Procedure E

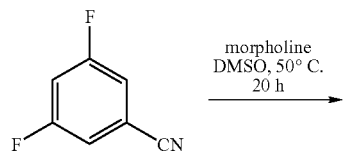

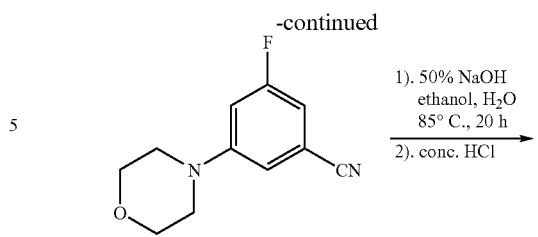

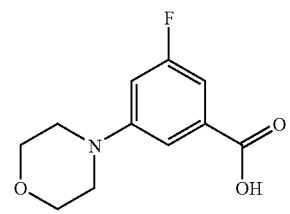

3-Fluoro-5-morpholin-1-ylbenzoic acid. A mixture of 3,5-difluorobenzonitrile (20 g, 143 mmol) and morpholine (85 ml, 863 mmol) in DMSO (30 ml) is heated at 50° C. for 20 h. The resulting reaction mixture is diluted with CHCl$_3$ (100 ml), washed with water (50 ml×2), dried over Na$_2$SO$_4$ and concentrated to yield 3-fluoro-5-morpholinbenzonitrile. This is then mixed with 50% NaOH (300 ml), ethanol (300 ml) and water (100 ml). The mixture is heated at 85° C. for 20 h then cooled to 0° C. To this cold mixture is added concentrated HCl dropwise at 0° C. until pH<1. The mixture is extracted with EtOAc (1000 ml×2) and the organic layer washed with water (200 ml), brine (200 ml) and dried over Na$_2$SO$_4$. Concentration gives 3-fluoro-5-morpholin-1-ylbenzoic acid (25.3 g) as a white solid. Mp: 177-178° C.; $^1$H NMR (300 MHz, CDCl$_3$) δ 3.19(t, J=5.1 Hz, 4H), 3.73(t, J=4.8 Hz, 4H), 7.02-7.06(m, 2H), 7.29(s, 1H), 7.54-7.57(m, 1H); MS 226 (M+1).

General Procedure F

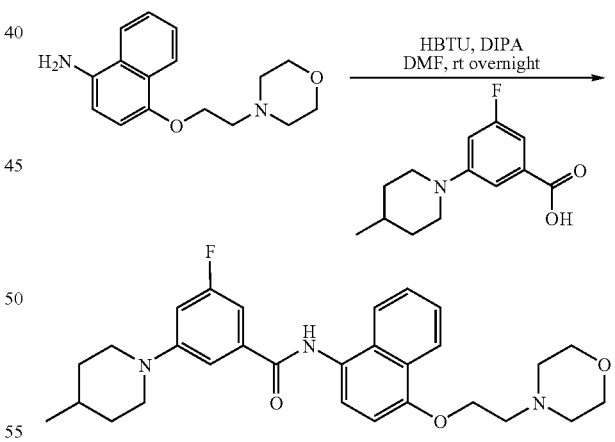

3-Fluoro-5-(4-methylpiperidin-1-yl)-N-[4-(2-morpholin-4-ylethoxy)-1-naphthyl]benzamide (Compound B184). To a solution of [4-(2-morpholin-4-ylethoxy)-1-naphthyl]amine (0.60 g, 2.2 mmol) in DMF (2 ml) is added 3-fluoro-5-(4-methylpiperidin-1-yl)benzoic acid (0.63 g, 2.64 mmol), prepared from 4-methylpiperidine according to conditions described in general procedure E, HBTU (1.25 g, 3.3 mmol) and diisopropylamine (1.15 ml, 6.6 mmol). This mixture is stirred at room temperature overnight and diluted with CH$_2$Cl$_2$ (5 ml), washed with 0.05 N NaOH, dried over Na$_2$SO$_4$ and concentrated. The residue is purified by column chromatography on silica gel (90% EtOAc in hexane) to give 3-fluoro-5-(4-methylpiperidin-1-yl)-N-[4-(2-morpholin-4-ylethoxy)-1-naphthyl]benzamide as a white solid (0.53 g). Mp: 116-118° C.; $^1$H NMR (300 MHz, DMSO-d$_6$) δ 0.91(d, 6.3 Hz, 3H), 1.15-1.25(m, 2H), 1.67(d, J=12 Hz, 2H), 2.55 (bs, 4H), 2.74(t, J=12.3 Hz, 2H), 2.86(s, 2H), 3.59(t, J=4.5 Hz, 4H), 3.82(d, J=12.9 Hz, 2H), 4.29(t, J=5.7 Hz, 2H), 6.93(d, J=12.6 Hz, 1H), 7.00(d, J=8.1 Hz, 1H), 7.12(d, J=8.7 Hz, 1H), 7.37-7.43(m, 2H), 7.51-7.55(m, 2H), 7.81-7.84 (m, 1H), 8.17-8.20(m, 1H), 10.21 (s, 1H); MS 492 (M+1).

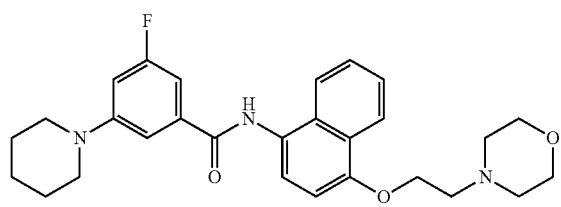

3-Fluoro-N-[4-(2-morpholin-4-ylethoxy)-1-naphthyl]-5-piperidin-1-ylbenzamide (Compound B66). Compound is prepared from [4-(2-morpholin-4-ylethoxy)-1-naphthyl]amine (0.11 g, 0.40 mmol) and 3-fluoro-5-piperidin-1-ylbenzoic acid (0.10 g, 0.40 mmol) according to conditions described in general procedures E and F. A light pink solid is produced (67 mg). Mp: 150-151° C.; $^1$H NMR (300 MHz, DMSO-d$_6$) δ 1.60 (bs, 6H), 2.49-2.57 (m, 4H), 2.89 (bs, 2H), 3.30 (bs, 4H), 3.61 (bs, 4H), 4.32 (bs, 2H), 3.96 (d, J=12.6 Hz, 1H), 7.03 (d, J=8.4 Hz, 1H), 7.15 (d, J=9.3 Hz, 1H), 7.40-7.45 (m, 2H), 7.54-7.57 (m, 2H), 7.83-7.87 (m, 1H), 8.23 (s, 1H), 10.24 (s, 1H); MS 478 (M+1).

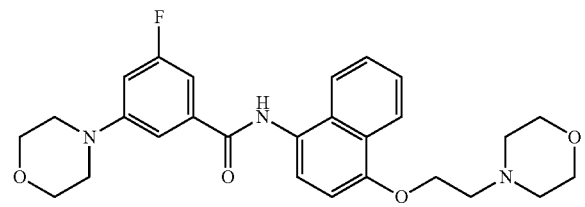

3-Fluoro-5-morpholin-4-yl-N-[4-(2-morpholin-4-ylethoxy)-1-naphthyl]benzamide (Compound B206). Compound is prepared from [4-(2-morpholin-4-ylethoxy)-1-naphthyl]amine (0.11 g, 0.40 mmol) and 3-fluoro-5-morpholin-1-ylbenzoic acid (90 mg, 0.40 mmol) according to conditions described in general procedures E and F. A light pink solid is produced (0.124 g). Mp: 123-124° C.; $^1$H NMR (300 MHz, CDCl$_3$) δ 2.67 (t, J=4.5 Hz, 4H), 2.98 (t, J=5.7 Hz, 2H), 3.25 (s, 4H), 3.75 (t, J=4.5 Hz, 4H), 3.85-3.88 (m, 4H), 4.32 (t, J=5.7 Hz, 2H), 6.76 (d, J=11.7 Hz, 1H), 6.84 (d, J=8.1 Hz, 1H), 7.07 (d, J=8.1 Hz, 1H), 7.31 (s, 1H), 7.50-7.59 (m, 2H), 7.72 (d, J=8.1 Hz, 1H), 7.82 (d, J=7.8 Hz, 1H), 7.89 (s, 1H), 8.33 (dd, J=1.8 and 7.8 Hz, 1H); MS 480 (M+1).

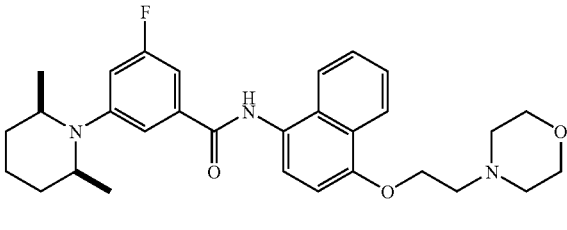

3-(2,6-Dimethylpiperidin-1-yl)-5-fluoro-N-[4-(2-morpholin-4-ylethoxy)-1-naphthyl]benzamide (Compound B205). Compound is prepared from [4-(2-morpholin-4-ylethoxy)-1-naphthyl]amine (0.11 g, 0.40 mmol) and 3-fluoro-5-(2,6-dimethylpiperidin)-1-ylbenzoic acid (0.40 mmol) according to conditions described in general procedures E and F. A light pink solid is produced (45 mg). Mp: 105-107° C.; $^1$H NMR (300 MHz, CDCl$_3$) δ 0.94 (d, J =6.0 Hz, 3H), 1.00 (d, J=6.3 Hz, 3H), 1.80-1.85 (m, 3H), 2.10 (bs, 1H), 2.31 (t, J=11.7 Hz, 2H), 2.68 (t, J=4.5 Hz, 4H), 2.98 (t, J=5.4 Hz, 2H), 3.75 (t, J=4.5 Hz, 6H), 4.30 (t, J=5.1 Hz, 2H), 6.72-6.81 (m, 2H), 6.95 (d, J=7.5 Hz, 1H), 7.30 (s, 1H), 7.47-7.56 (m, 2H), 7.67 (d, J =7.5 Hz, 1H), 7.81 (d, J=8.1 Hz, 1H), 8.00 (d, J=9.6 Hz, 1H), 8.29 (d, J=7.8 Hz, 1H); MS 506 (M+1).

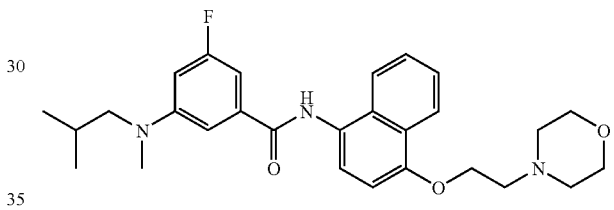

3-Fluoro-5-[isobutyl(methyl)amino]-N-[4-(2-morpholin-4-ylethoxy)-1-naphthyl]benzamide (Compound B210). Compound is prepared from [4-(2-morpholin-4-ylethoxy)-1-naphthyl]amine (0.11 g, 0.40 mmol) and 3-fluoro-5-isobutyl-methylamino-1-ylbenzoic acid (0.40 mmol) according to conditions described in general procedures E and F. A pink solid is produced (58 mg). Mp: 126-128° C.; $^1$H NMR (300 MHz, CDCl$_3$) δ 0.93 (d, J=6.6 Hz, 6H), 2.00-2.20 (m, 1H), 2.68 (t, J=4.5 Hz, 4H), 2.93-3.01 (m, 5H), 3.15 (d, J=7.5 Hz, 2H), 3.74 (t, J=4.8 Hz, 4H), 4.29 (t, J=5.4 Hz, 2H), 6.49 (d, J=12.9 Hz, 1H), 6.78-6.84 (m, 2H), 7.04 (s, 1H), 7.47-7.53 (m, 2H), 7.69 (d, J=8.4 Hz, 1H), 7.80 (d, J=7.2 Hz, 1H), 8.02 (s, 1H), 8.27-8.30 (m, 1H); MS 480 (M+1).

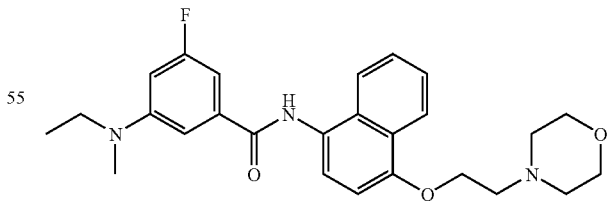

3-[Ethyl(methyl)amino]-5-fluoro-N-[4-(2-morpholin-4-ylethoxy)-1-naphthyl]benzamide (Compound B207). Compound is prepared from [4-(2-morpholin-4-ylethoxy)-1-naphthyl]amine (0.11 g, 0.40 mmol) and 3-fluoro-5-ethylmethylamino-1-ylbenzoic acid (0.40 mmol) according to conditions described in general procedures E and F. A deep pink solid is produced (17 mg). Mp: 126-128° C.; $^1$H NMR (300 MHz, CDCl$_3$) δ 1.16 (t, J=6.9 Hz, 3H), 2.68 (t, J=4.8 Hz, 4H), 2.93-3.00 (m, 5H), 3.44 (q, J=7.2 Hz, 2H), 3.75 (t, J=4.5 Hz, 4H), 4.32 (t, J=5.7 Hz, 2H), 6.53 (d, J=12.3 Hz, 1H), 6.81-6.87 (m, 2H), 7.08 (s, 1H), 7.49-7.58 (m, 2H), 7.74 (d, J=8.1 Hz, 1H), 7.83 (d, J=7.8 Hz, 1H), 7.94 (s, 1H), 8.29-8.32 (m, 1H); MS 452 (M+1).

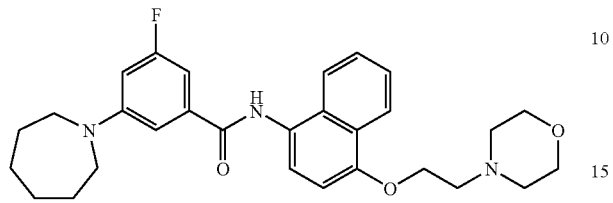

3-Azepan-1-yl-5-fluoro-N-[4-(2-morpholin-4-ylethoxy)-1-naphthyl]benzamide (Compound B67). Compound is prepared from [4-(2-morpholin-4-ylethoxy)-1-naphthyl]amine (0.11 g, 0.40 mmol) and 3-fluoro-5-azepan-1-ylbenzoic acid (0.40 mmol) according to conditions described in general procedures E and F. A pink solid is produced (78 mg). Mp: 142-144° C.; $^1$H NMR (300 MHz, DMSO-d$_6$) δ 1.48 (bs, 4H), 1.74 (bs, 4H), 3.33 (bs, 2H), 3.51 (t, J=5.7 Hz, 4H), 3.53-3.76 (m, 6H), 4.01 (bs, 2H), 4.56 (t, J=4.2 Hz, 2H), 6.67 (d, J=13.2 Hz, 1H), 6.99-7.01 (m, 1H), 7.07 (d, J=8.1 Hz, 1H), 7.17 (s, 1H), 7.46 (d, J=8.1 Hz, 1H), 7.56-7.61 (m, 2H), 7.85-7.88 (m, 1H), 8.30-8.33 (m, 1H), 10.22 (s, 1H); MS 492 (M+1).

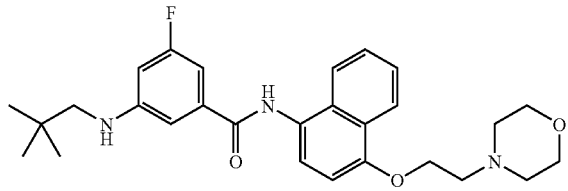

3-[(2,2-Dimethylpropyl)amino]-5-fluoro-N-[4-(2-morpholin-4-ylethoxy)-1-naphthyl]benzamide (Compound B209). Compound is prepared from [4-(2-morpholin-4-ylethoxy)-1-naphthyl]amine (0.11 g, 0.40 mmol) and 3-fluoro-5-(2,2-dimethylpropylamino)-1-ylbenzoic acid (0.40 mmol) according to conditions described in general procedures E and F. A light pink solid is produced (25 mg). Mp: 85-87° C.; $^1$H NMR (300 MHz, CDCl$_3$) δ 0.99 (s, 9H), 2.68 (bs, 4H), 2.94-3.00 (m, 4H), 3.73 (bs, 4H), 4.30 (bs, 2H), 6.46 (d, J=10.2 Hz, 1H), 6.79-6.82 (m, 2H), 6.99 (s, 1H), 7.46-7.52 (m, 3H), 7.66 (d, J=7.8 Hz, 1H), 7.79 (d, J=7.8 Hz, 1H), 7.98 (d, J=8.4 Hz, 1H), 8.27 (d, J=6.6 Hz, 1H); MS 480 (M+1).

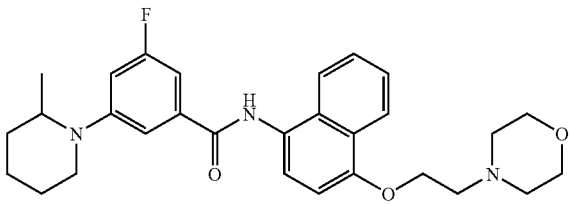

3-Fluoro-5-(2-methylpiperidin-1-yl)-N-[4-(2-morpholin-4-ylethoxy)-1-naphthyl]benzamide (Compound B201). Compound is prepared from [4-(2-morpholin-4-ylethoxy)-1-naphthyl]amine (0.11 g, 0.40 mmol) and 3-fluoro-5-(2-methylpiperidin)-1-ylbenzoic acid (0.40 mmol) according to conditions described in general procedures E and F. A deep pink solid is produced (12 mg). Mp: 75-78° C.; $^1$H NMR (300 MHz, CDCl$_3$) δ 1.08 (d, J=6.6 Hz, 3H), 1.62-1.82 (m, 6H), 2.68 (t, J=4.8 Hz, 4H), 2.98 (t, J=5.4 Hz, 2H), 3.25-3.45 (m, 2H), 3.75 (t, J=4.5 Hz, 4H), 4.18 (bs, 1H), 4.31 (t, J=5.7 Hz, 2H), 6.73 (d, J=11.7 Hz, 1H), 6.80 (d, J=8.1 Hz, 1H), 6.96 (d, J=8.4 Hz, 1H), 7.29 (s, 1H), 7.48-7.57 (m, 2H), 7.69 (d, J=9.0 Hz, 1H), 7.82 (d, J=7.8 Hz, 1H), 8.00 (d, J=6.9 Hz, 1H), 8.29 (d, J=4.8 Hz, 1H); MS 492 (M+1).

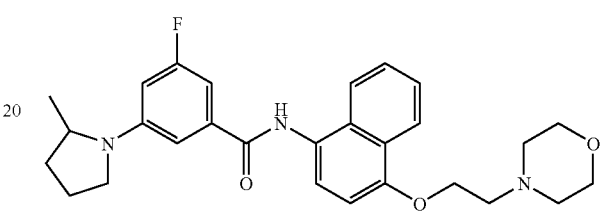

3-Fluoro-5-(2-methylpyrrolidin-1-yl)-N-[4-(2-morpholin-4-ylethoxy)-1-naphthyl]benzamide (Compound B208). Compound is prepared from [4-(2-morpholin-4-ylethoxy)-1-naphthyl]amine (0.11 g, 0.40 mmol) and 3-fluoro-5-(2-methylpyrrolidin)-1-ylbenzoic acid (0.40 mmol) according to conditions described in general procedures E and F. A pink solid is produced (53 mg). Mp: 108-111° C.; $^1$H NMR (300 MHz, CDCl$_3$) δ 1.19 (d, J=6.0 Hz, 3H), 2.00-2.10 (m, 4H), 2.67 (t, J=4.5 Hz, 4H), 2.95 (t, J=5.4 Hz, 2H), 3.15-3.22 (m, 1H), 3.40-3.45 (m, 1H), 3.74 (t, J=4.5 Hz, 4H), 3.91 (bs, 1H), 4.30 (t, J=5.4 Hz, 2H), 6.40 (d, J=11.7 Hz, 1H), 6.79-6.84 (m, 2H), 6.94 (s, 1H), 7.47-7.55 (m, 2H), 7.69 (d, J=8.4 Hz, 1H), 7.81 (d, J=7.5 Hz, 1H), 8.04 (s, 1H), 8.28 (dd, J=2.1 and 6.9 Hz, 1H); MS 478 (M+1).

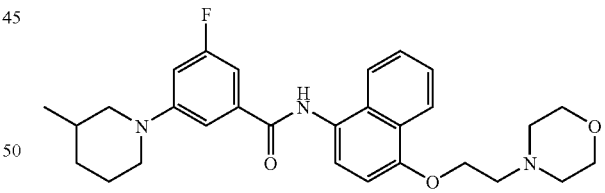

3-Fluoro-5-(3-methylpiperidin-1-yl)-N-[4-(2-morpholin-4-ylethoxy)-1-naphthyl]benzamide (Compound B202). Compound is prepared from [4-(2-morpholin-4-ylethoxy)-1-naphthyl]amine (0.11 g, 0.40 mmol) and 3-fluoro-5-(3-methylpiperidin)-1-ylbenzoic acid (0.40 mmol) according to conditions described in general procedures E and F. A pink solid is produced (40 mg). Mp: 145-148° C.; $^1$H NMR (300 MHz, CDCl$_3$) δ 0.95 (d, J=6.6 Hz, 3H), 1.00-1.18 (m, 1H), 1.60-1.90 (m, 4H), 2.30-2.50 (m, 2H), 2.71 (t, J=4.8 Hz, 4H), 3.01 (t, J=5.4 Hz, 2H), 3.63-3.68 (m, 2H), 3.76 (t, J=4.5 Hz, 4H), 4.32 (t, J=5.7 Hz, 2H), 6.75 (d, J=12.0 Hz, 1H), 6.81 (d, J=8.4 Hz, 1H), 6.95 (d, J=8.4 Hz, 1H), 7.30 (s, 1H), 7.50-7.55 (m, 2H), 7.69 (d, J=7.8 Hz, 1H), 7.81 (d, J=8.4 Hz, 1H), 7.96 (s, 1H), 8.27-8.30 (m, 1H); MS 492 (M+1).

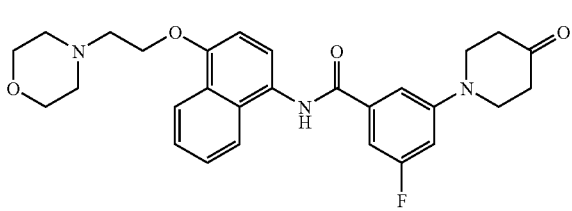

3-Fluoro-N-[4-(2-morpholin-4-yl-ethoxy)-naphthalen-1-yl]-5-(4-oxo-piperidin-1-yl)-benzamide (Compound B198). Compound is prepared from [4-(2-morpholin-4-ylethoxy)-1-naphthyl]amine (0.11 g, 0.40 mmol) and 3-fluoro-5-(4-oxo-piperidin-yl)-1-ylbenzoic acid (0.40 mmol) according to conditions described in general procedures E and F. A pink solid is produced (40 mg). $^1$H NMR (300 MHz, DMSO-d$_6$) δ 10.27 (s, 1H), 8.21 (m, 1H), 7.88 (m, 1H), 7.58 (m, 2H), 7.51 (s, 1H), 7.42 (d, 1H), 7.20 (d, 1H), 7.05 (m, 2H), 4.31 (t, 2H), 3.73 (m, 4H), 3.60 (m, 4H), 2.88 (t, 2H), 2.57 (m, 4H), 2.50 (m, 4H). MS: 492.2 (M+1).

Additional compounds of the invention can be prepared as described in Example 6.

Example 6

General Procedure G

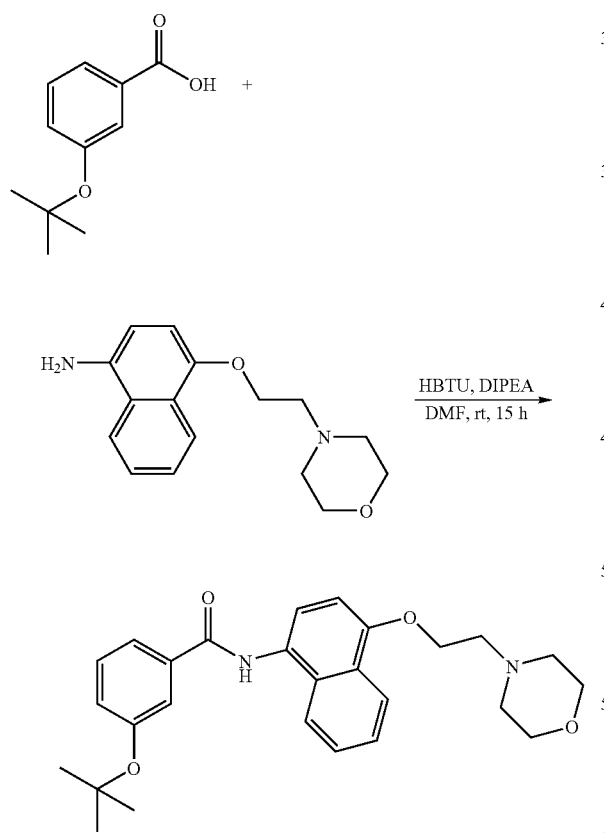

3-tert-Butoxy-N-[4-(2-morpholin-4-yl-ethoxy)-naphthalen-1-yl]-benzamide (Compound B65). To a solution of 3-tert-butoxy-benzoic acid (0.15 g, 0.774 mmol) in dimethylformamide (5 ml) is added HBTU (0.44 g, 1.5 eq) followed by the addition of diisopropylethylamine (0.296 ml, 3.0 eq). The mixture is stirred at room temperature for five minutes. A solution of 4-(2-morpholin-4-yl-ethoxy)-naphthalen-1-ylamine (0.21 g) in dimethylformamide (2 ml) is then added. This mixture is stirred at room temperature for 15 h, diluted with water and extracted with ethyl acetate. The organic layer is washed with water, dried over Na$_2$SO$_4$ and evaporated. The residue is purified by column chromatography on silica gel (ethyl acetate) to give 3-tert-butoxy-N-[4-(2-morpholin-4-yl-ethoxy)-naphthalen-1-yl]-benzamide (0.146 g). Mp: 50-51° C. $^1$H NMR (300 MHz, DMSO-d$_6$) δ 10.25 (s, 1H), 8.22 (m, 1H), 7.85 (m, 2H), 7.66 (s, 1H), 7.55 (m, 2H), 7.23 (d, J=7.5 Hz, 1H), 7.03 (d, J=8.1 Hz, 1H), 4.31 (t, J=5.1 Hz, 2H), 3.61 (t, J=4.2 Hz, 4H), 2.89 (brs, 2H), 2.58 (brs, 4H), 1.35 (s, 9H). MS: 449 (M+1).

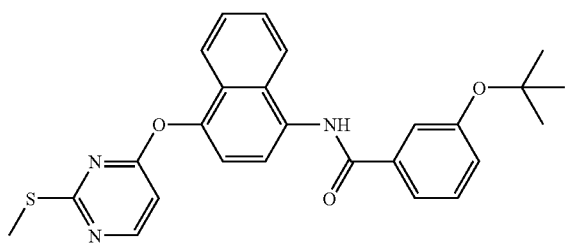

3-tert-Butoxy-N-[4-(2-methylsulfanyl-pyrimidin-4-yloxy)-naphthalen-1-yl]-benzamide (Compound B306). Compound is prepared from 3-tert-butoxy-benzoic acid and 4-(2-methylsulfanyl-pyrimidin-4-yloxy)-naphthalen-1-ylamine according to conditions described in general procedure G. (0.130 g) (46%). Mp: 135-136° C. $^1$H NMR (300 MHz, DMSOd$_6$) 10.49 (s, 1H), 8.56 (d, J=4.2 Hz, 1H), 8.04 (d, J=6.3 Hz, 1H), 7.83 (brd, 2H), 7.68-7.47 (m, 6H), 7.25 (d, J=5.7 Hz, 1H), 6.93 (d, J=4.5 Hz, 1H), 2.27 (s, 3H), 1.36 (s, 9H). MS: 460 (M+1).

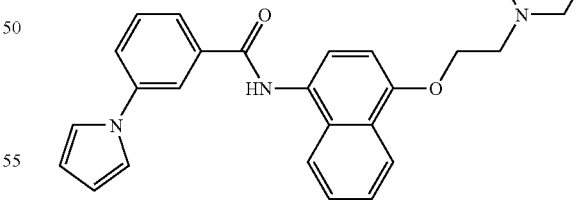

N-[4-(2-Morpholin-4-yl-ethoxy)-naphthalen-1-yl]-3-pyrrol-1-yl-benzamide (Compound B57). Compound is prepared from 3-pyrrol-1-yl-benzoic acid and 4-(2-morpholin-4-yl-ethoxy)-naphthalen-1-ylamine according to conditions described in general procedure G. (96 mg) (40%). Mp: 142-143° C. $^1$H NMR (300 MHz, DMSO-d$_6$) δ 10.38 (s, 1H), 8.25 (m, 2H), 7.90 (m, 2H), 7.83 (d, J=8.1, 1H), 7.66-7.47 (m, 6H), 7.06 (d, J=8.4 Hz, 1H), 6.32 (brs, 2H), 4.33 (t, J=5.4, 2H), 3.62 (brt, 4H), 2.93 (brs, 2H), 2.62 (brs, 4H). MS: 442 (M+1).

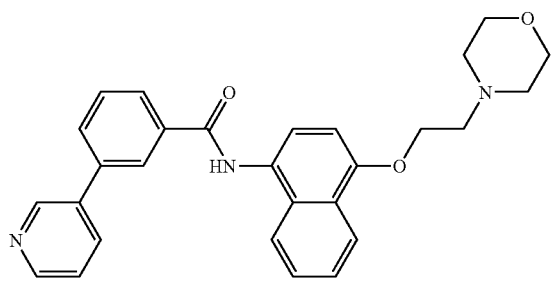

N-[4-(2-Morpholin-4-yl-ethoxy)-naphthalen-1-yl]-3-pyridin-3-yl-benzamide (Compound B58). Compound is prepared from 3-pyridin-3-yl-benzoic acid and 4-(2-morpholin-4-yl-ethoxy)-naphthalen-1-ylamine according to conditions described in general procedure G. (0.218 g) (63%). Mp: 77-78° C. $^1$H NMR (300 MHz, DMSOd$_6$) 10.42 (s, 1H), 9.06 (s, 1H), 8.63 (d, J=3.9 Hz, 1H), 8.48 (s, 1H), 8.22 (d, J=8.1 Hz, 2H), 8.10 (d, J=7.5 Hz, 1H), 7.98 (m, 2H), 7.69 (t, J=7.5 Hz, 1H), 7.56-7.47 (m, 4H), 7.04 (d, J=8.4 Hz, 1H), 4.33 (brt, 2H), 3.60 (brs, 4H), 2.88 (brs, 2H), 2.57 (brs, 4H). MS: 454 (M+1).

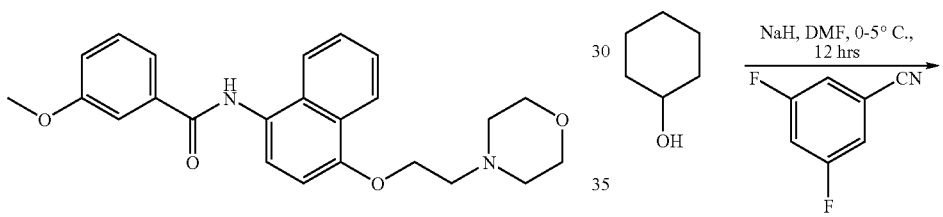

3-Methoxy-N-[4-(2-morpholin-4-ylethoxy)-1-naphthyl] benzamide (Compound B60). Compound is prepared from 3-methoxybenzoic acid and 4-(2-morpholin-4-yl-ethoxy)-naphthalen-1-ylamine according to conditions described in general procedure G. Mp: 105-107° C.; $^1$H NMR (300 MHz, DMSO-d$_6$) δ 2.57 (t, J=4.8 Hz, 4H), 2.88 (t, J=5.7 Hz, 2H), 3.60 (t, J=4.5 Hz, 4H), 3.85 (s, 3H), 4.31 (t, J=5.4 Hz, 2H), 7.02 (d, J=8.1 Hz, 1H), 7.17 (dd, J=2.4 and 8.4 Hz, 1H), 7.42-7.68 (m, 5H), 7.85-7.89 (m, 1H), 8.19-8.22 (m, 1H), 10.24 (s, 1H); MS 407 (M+1).

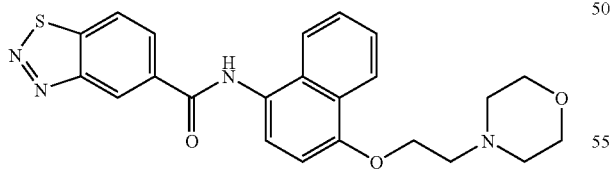

N-[4-(2-Morpholin-4-ylethoxy)-1-naphthyl]-1,2,3-benzothiadiazole-5-carboxamide (Compound B50). Compound is prepared from benzo[1,2,3]thiadiazole-5-carboxylic acid and 4-(2-morpholin-4-yl-ethoxy)-naphthalen-1-ylamine according to conditions described in general procedure G. Mp: 188-190° C.; $^1$H NMR (300 MHz, CDCl$_3$) δ 2.70 (t, 4H), 3.00 (t, 2H), 3.78 (t, 4H), 4.30 (t, 2H), 6.82 (d, 1H), 7.58 (m, 2H), 7.65 (d, 1H), 7.88 (d, 1H), 8.15 (d, 1H), 8.25 (d, 2H), 8.40 (s, 1H), 9.18 (s, 1H); MS 435 (M+1).

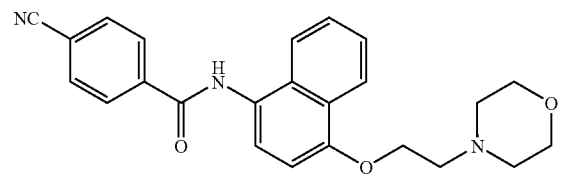

4-Cyano-N-[4-(2-morpholin-4-ylethoxy)-1-naphthyl] benzamide (Compound B36). Compound is prepared from 4-cyanobenzoic acid and 4-(2-morpholin-4-yl-ethoxy)-naphthalen-1-ylamine according to conditions described in general procedure G. Mp: 213-214° C.; $^1$H NMR (300 MHz, CDCl$_3$) δ 2.70 (m, 4H), 3.00 (t, 2H), 3.78 (t, 4H), 4.35 (t, 2H), 6.80 (d, 1H), 7.50-7.70 (m, 5H), 7.80 (d, 1H), 7.95 (d, 2H), 8.31 (s, 2H); MS 402 (M+1).

Additional compounds of the invention can be prepared as described in Example 7.

A representative synthetic scheme is shown in Scheme 5, below.

Scheme 5

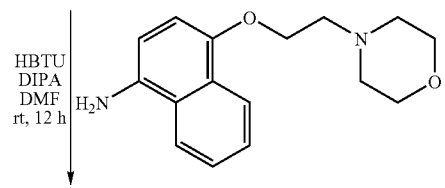

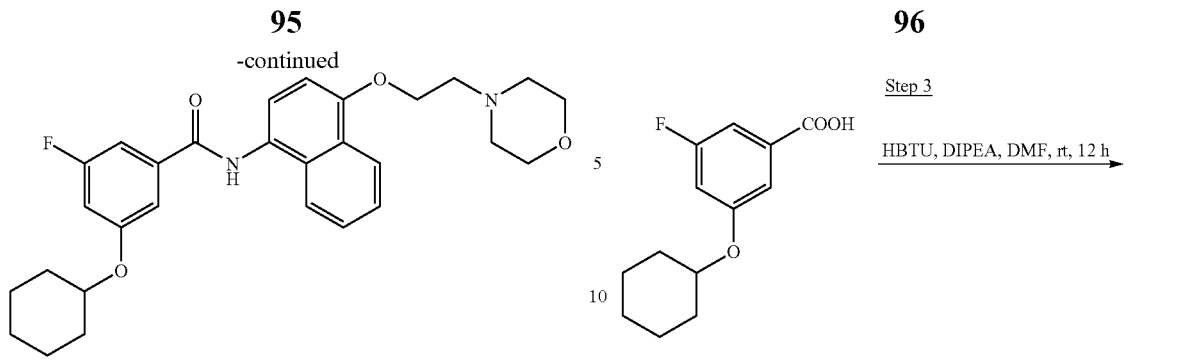

Example 7

General Procedure H

Step 1

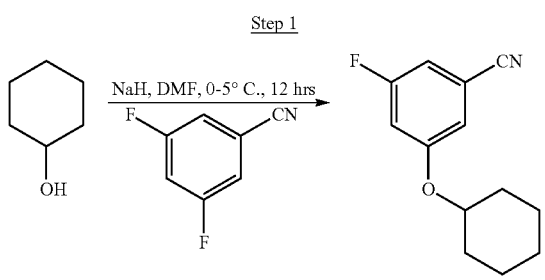

3-Fluoro-5-cyclohexyloxybenzonitrile: Sodium hydride (1.92 g, 48.0 mmol) is slowly added to a stirred solution of cyclohexanol (4.01 g, 40.0 mmol) in DMF (30 ml) at 0-5° C. under nitrogen. After 2.5 hours, 3,5-difluorobenzonitrile (5.56 g, 40.0 mmol) is slowly added over 5 min. The mixture is allowed to warm to room temperature and stirred for an additional 12 hours. The mixture is diluted with ether (150 ml), washed with water, brine (30 ml), dried over $Na_2SO_4$ and evaporated. The residue is purified by column chromatography on silica gel eluting with ethyl acetate:hexanes (1:10) to provide 3-fluoro-5-cyclohexyloxybenzonitrile as a yellow oil. MS: 220 (M+1).

Step 2

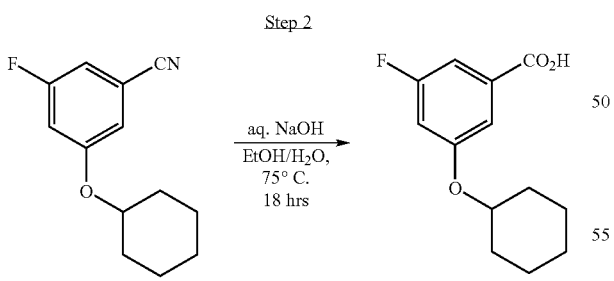

3-Fluoro-5-cyclohexyloxybenzoic acid: A mixture of 3-fluoro-5-hexyloxybenzonitrile (1.0 g, 4.56 mmol), ethanol (12 ml), water (12 ml), and aq. NaOH (50%, 12 ml) is heated at 75° C. for 18 hours. The mixture is then cooled in an ice bath and acidified with concentrated HCl to pH 1. The mixture is extracted with ethyl acetate and the organic layer washed with brine, dried over $Na_2SO_4$, and concentrated to afford 3-fluoro-5-cyclohexyloxybenzoic acid as a yellow solid. MS: 239.11(M+1).

3-(Cyclohexyloxy)-5-fluoro-N-[4-(2-morpholin-4-ylethoxy)-1-naphthyl]benzamide (Compound B195). 3-Fluoro-5-cyclohexyloxybenzoic acid (100 mg, 420 μmol), 4-amino-1-(2-morpholinoethoxy)naphthalene (103 mg, 378 μmol), HBTU (238 mg, 630 μmol), DIPEA (220 μl, 1.26 mmol), and DMF (1.5 ml) are stirred for 12 hours at room temperature. $CH_2Cl_2$ (2 ml) is added to the mixture, and it is then washed with $H_2O$, $NaHCO_3$ solution, and brine. The organic layer is dried over $Na_2SO_4$ and concentrated. The residue is purified by column chromatography on silica gel eluting with ethyl acetate to provide 3-(cyclohexyloxy)-5-fluoro-N-[4-(2-morpholin-4-ylethoxy)-1-naphthyl]benzamide as a brown solid (50 mg). Mp: 116-118° C.; $^1$H NMR (DMSO-$d_6$) δ 10.29 (s, 1H), 8.21 (m, 1H), 7.87 (m, 1H), 7.57 (m, 2H), 7.52 (s, 1H), 7.42 (m, 2H), 7.07 (m, 2H), 4.51 (m, 1H), 4.31 (t, 2H), 3.61 (t, 4H), 2.89 (m, 2H), 2.62 (t, 4H), 1.93 (m, 2H), 1.72 (m, 2H), 1.46 (m, 6H); MS 493.32 (M+1).

3-[(4-Ethylcyclohexyl)oxy]-5-fluoro-N-[4-(2-morpholin-4-ylethoxy)-1-naphthyl]benzamide (Compound B194). Compound is prepared from 4-amino-1-(2-morpholinoethoxy)naphthalene and 4-ethyl cyclohexanol according to conditions described in general procedure H. Mp: 102-105° C.; $^1$H NMR (CDCl$_3$) δ 8.31 (d, 1H), 7.95 (s, 2H), 7.82 (d, 1H), 7.69 (m, 1H), 7.54 (m, 2H), 7.30 (s, 1H), 7.20 (d, 1H), 6.83 (m, 2H), 4.33 (m, 3H), 3.76 (m, 4H), 3.02 (t, 2H), 2.71 (t, 4H), 2.16 (m, 2H), 1.87 (m, 2H), 1.44 (m, 3H), 1.27 (m, 4H), 0.90 (t, 3H); MS 521.27 (M+1).

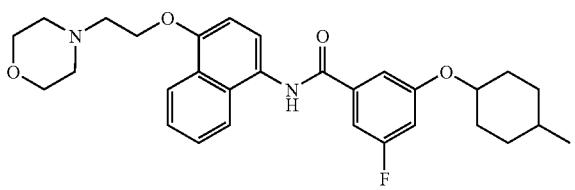

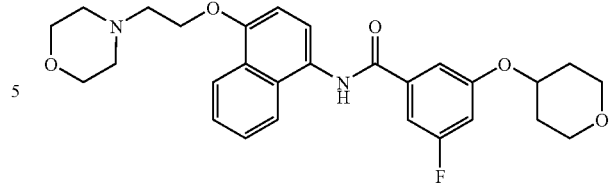

3-Fluoro-5-[(4-methylcyclohexyl)oxy]-N-[4-(2-morpholin-4-ylethoxy)-1-naphthyl]benzamide (Compound B234). Compound is prepared from 4-amino-1-(2-morpholinoethoxy)naphthalene and 4-methylcyclohexanol according to conditions described in general procedure H. Mp: 98-100° C.; $^1$H NMR (CDCl$_3$) δ 8.31 (d, 1H), 7.85 (t, 2H), 7.75 (d, 1H), 7.55 (m, 2H), 7.30 (s, 1H), 7.21 (d, 1H), 6.83 (m, 2H), 4.34 (t, 2H), 4.23 (s, 1H), 3.76 (t, 4H), 2.99 (t, 2H), 2.69 (t, 4H), 2.10 (m, 2H), 1.78 (m, 2H), 1.67 (m, 2H), 1.47 (m, 2H), 1.10 (m, 1H), 0.93 (d, 3H); MS 493.26 (M+1).

3-Fluoro-N-[4-(2-morpholin-4-ylethoxy)-1-naphthyl]-5-(tetrahydro-2H-pyran-4-yloxy)benzamide (Compound B226). Compound is prepared from 4-amino-1-(2-morpholinoethoxy)naphthalene and tetrahydropyran-4-ol according to conditions described in general procedure H. Mp: 75-77° C.; $^1$H NMR (CDCl$_3$) δ 8.30 (d, 1H), 8.06 (s, 1H), 7.80 (d, 1H), 7.67 (d, 1H), 7.52 (m, 2H), 7.33 (s, 1H), 7.22 (d, 1H), 6.81 (t, 2H), 4.56 (s, 1H), 4.31 (t, 2H), 3.99 (m, 2H), 3.75 (t, 4H), 3.59 (t, 2H), 2.03 (m, 2H), 1.82 (m, 2H), 1.30 (m, 4H); MS 495.56 (M+1).

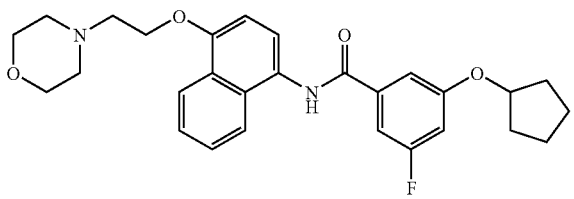

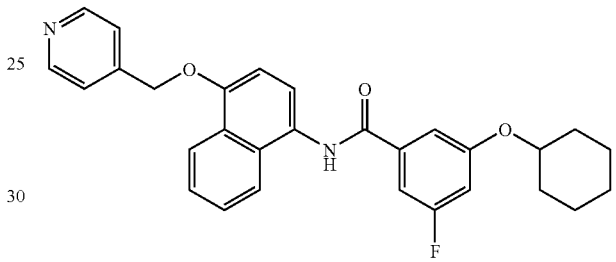

3-(Cyclopentyloxy)-5-fluoro-N-[4-(2-morpholin-4-ylethoxy)-1-naphthyl]benzamide (Compound B225). Compound is prepared from 4-amino-1-(2-morpholinoethoxy)naphthalene and cyclopentanol according to conditions described in general procedure H. Mp: 117-119° C.; $^1$H NMR (CDCl$_3$) δ 8.30(m, 1H), 8.00 (d, 1H), 7.80 (d, 1H), 7.68 (d, 1H), 7.51 (m, 2H), 7.27 (s, 1H), 7.20 (d, 1H), 6.79 (t, 2H), 4.80 (s, 1H), 4.31 (t, 2H), 3.75 (t, 4H), 2.98 (t, 2H), 2.67 (t, 4H), 1.80 (m, 8H); MS 479.33 (M+1).

3-(Cyclohexyloxy)-5-fluoro-N-[4-(pyridin-4-ylmethoxy)-1-naphthyl]benzamide (Compound B235). Compound is prepared from 4-(pyridin-4-ylmethoxy)-naphthalen-1-ylamine and cyclohexanol according to conditions described in general procedure H. Mp: 176-178° C.; $^1$H NMR (CDCl$_3$) δ 8.71 (m, 2H), 8.43 (m, 1H), 7.95 (s, 1H), 7.86 (d, 1H), 7.75 (d, 1H), 7.60 (m, 2H), 7.46 (m, 2H), 7.31 (s, 1H), 7.21 (d, 1H), 6.84 (t, 2H), 5.31 (s, 2H), 4.33 (Compound B, 1H), 2.00 (m, 2H), 1.81 (m, 2H), 1.46 (m, 6H); MS 471.18 (M+1).

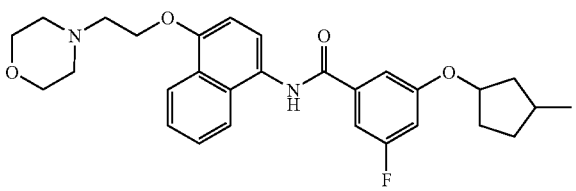

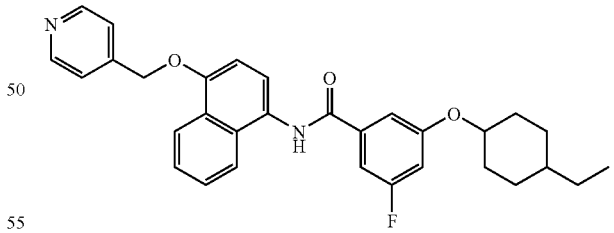

3-Fluoro-5-[(3-methylcyclopentyl)oxy]-N-[4-(2-morpholin-4-ylethoxy)-1-naphthyl]benzamide (Compound B227). Compound is prepared from 4-amino-1-(2-morpholinoethoxy)naphthalene and 3-methylcyclopentanol according to conditions described in general procedure H. Mp: 65-66° C.; $^1$H NMR (CDCl$_3$) δ 8.29 (m, 1H), 8.07 (s, 1H), 7.80 (d, 1H), 7.65 (d, 1H), 7.51 (m, 2H), 7.25 (s, 1H), 7.18 (d, 1H), 6.77 (t, 2H), 4.75 (m, 1H), 4.30 (t, 2H), 3.75 (t, 4H), 2.94 (t, 2H), 2.67 (t, 4H), 1.98 (m, 4H), 1.85 (m, 1H), 1.41 (m, 2H), 1.18 (m, 3H); MS 493.58 (M+1).

3-[(4-Ethylcyclohexyl)oxy]-5-fluoro-N-[4-(pyridin-4-ylmethoxy)-1-naphthyl]benzamide (Compound B228). Compound is prepared from 4-ethyl cyclohexanol and 4-(pyridin-4-ylmethoxy)-naphthalen-1-ylamine according to conditions described in general procedure H. Mp: 93-95° C. $^1$H NMR (CDCl$_3$) δ 8.65 (d, 2H), 8.40 (m, 1H), 8.11 (s, 1H), 7.85 (d, 1H), 7.69 (d, 1H), 7.58 (m, 2H), 7.46 (m, 2H), 7.29 (s, 1H), 7.21 (d, 1H), 6.81 (m, 2H), 5.28 (s, 2H), 4.22 (m, 1H), 2.00 (m, 4H), 1.39 (m, 4H), 1.25 (m, 3H), 0.90 (t, 3H); MS 499.26 (M+1).

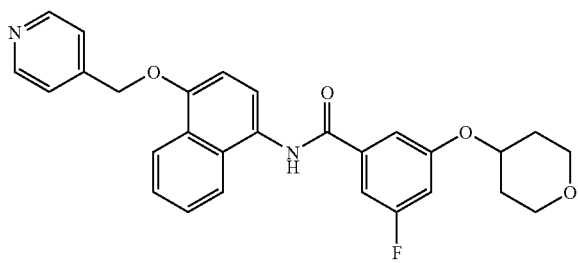

3-Fluoro-N-[4-(pyridin-4-ylmethoxy)-1-naphthyl]-5-(tetrahydro-2H-pyran-4-yloxy)benzamide (Compound B229). Compound is prepared from tetrahydropyran-4-ol and 4-(pyridin-4-ylmethoxy)-naphthalen-1-ylamine according to conditions described in general procedure H. Mp: 182-184° C.; $^1$H NMR (CDCl$_3$) δ 8.67 (m, 2H), 8.43 (m, 1H), 8.00 (s, 1H), 7.86 (d, 1H), 7.73 (d, 1H), 7.61 (m, 2H), 7.46 (d, 2H), 7.34 (s, 1H), 7.27 (m, 1H), 6.84 (d, 2H), 5.31 (s, 2H), 4.58 (m, 1H), 4.00 (m, 2H), 3.60 (m, 2H), 2.04 (m, 2H), 1.82 (m, 2H); MS 473.19 (M+1).

Additional compounds of the invention can be prepared as described in Example 8.

Example 8

General Procedure I

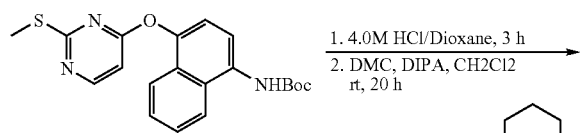

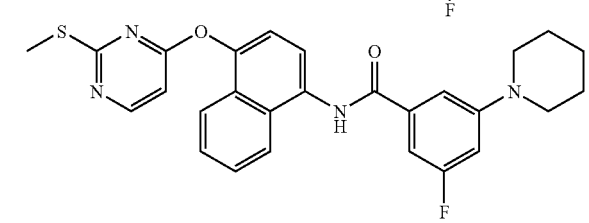

3-Fluoro-N-(4-{[2-(methylthio)pyrimidin-4-yl]oxy}-1-naphthyl)-5-piperidin-1-ylbenzamide (Compound B311). A solution of tert-butyl(4-{[2-(methylthio)pyrimidin-4-yl]oxy}-1-naphthyl)carbonate (100 mg, 0.261 mmol) in 4.0 M HCl in dioxane (4 ml) is stirred at room temperature for 2 h. The mixture is concentrated under vacuum and the residue dissolved in CH$_2$Cl$_2$ (3 ml) containing diisopropylethylamine (0.227 ml, 1.305 mmol). To this mixture is added a solution of 3-fluoro-5-piperidin-1-ylbenzoic acid (0.21 g, 0.313 mmol), 2-chloro-1,3-dimethylimidazolinium chloride (0.53 g, 0.313 mmol) and diisopropylethylamine (0.045 ml, 0.261 mmol) in CH$_2$Cl$_2$ (1 ml) at room temperature. The mixture is stirred at room temperature for 20 h washed with satd. NaHCO$_3$ solution, brine, dried over Na$_2$SO$_4$ and concentrated. The residue is purified by column chromatography on silica gel (10-60% EtOAc in hexane) to give 3-fluoro-N-(4-{[2-(methylthio)pyrimidin-4-yl]oxy}-1-naphthyl)-5-piperidin-1-ylbenzamide as an off-white solid (70 mg). Mp: 170-172° C.; $^1$H NMR (300 MHz, CDCl$_3$) δ 8.35 (d, 1H), 8.09 (s, 1H), 8.03 (d, 1H), 7.93 (d, 2H), 7.64-7.51 (m, 2H), 7.33 (m, 2H), 6.98 (d, 1H), 6.77 (dt, 1H), 6.53 (d, 1H), 3.30 (t, 4H), 2.30 (s, 3H), 1.72-1.63 (m, 6H); MS 489.16 (M+1).

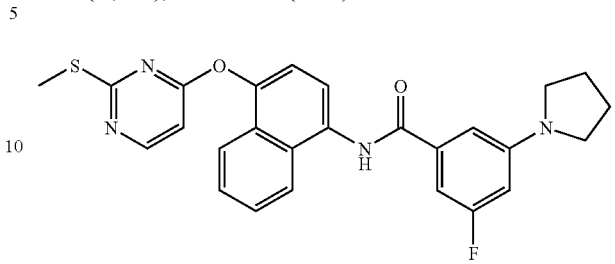

3-Fluoro-N-(4-{[2-(methylthio)pyrimidin-4-yl]oxy}-1-naphthyl)-5-pyrrolidin-1-ylbenzamide (Compound B264). Compound is prepared from tert-butyl(4-{[2-(methylthio)pyrimidin-4-yl]oxy}-1-naphthyl)carbonate and 3-fluoro-5-pyrrolidin-1-yl-benzoic acid according to conditions described in general procedure I. Mp: 180-181° C.; $^1$H NMR (300 MHz, DMSO-d$_6$) δ 10.44 (s, 1H), 8.57 (d, 1H), 8.02 (d, 1H), 7.82 (d, 2H), 7.63-7.56 (m, 3H), 7.48 (d, 1H), 7.06 (d, 2H), 6.56 (d, 1H), 3.33 (t, 4H), 2.27 (s, 3H), 2.01-1.97 (m, 6H); MS 475.15 (M+1).

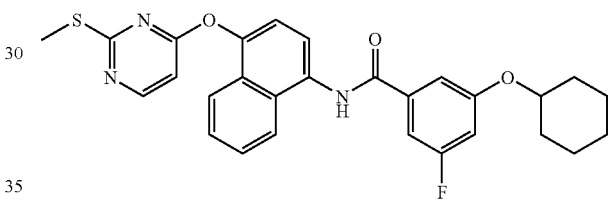

3-(Cyclohexyloxy)-5-fluoro-N-(4-{[2-(methylthio)pyrimidin-4-yl]oxy}-1-naphthyl)benzamide (Compound B303). Compound is prepared from tert-butyl(4-{[2-(methylthio)pyrimidin-4-yl]oxy}-1-naphthyl)carbonate and 3-cyclohexyloxy-5-fluoro-benzoic acid according to conditions described in general procedure I. Mp: 130-132° C.; $^1$H NMR (300 MHz, CDCl$_3$) δ 8.36 (d, 1H), 8.14 (s, 1H), 7.99 (d, 1H), 7.93 (dd, 2H), 7.60 (t, H), 7.53 (t, 1H), 7.32 (d, 2H), 7.21 (d, 1H), 6.83 (d, 1H), 6.53 (d, 1H), 4.34 (m, 1H), 2.29 (s, 3H), 2.02 (m, 2H), 1.82 (m, 2H), 1.61-1.53 (m, 4H), 1.45-1.32 (m, 2H); MS 504.19 (M+1).

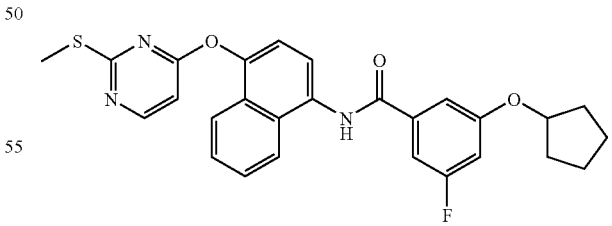

3-(Cyclopentyloxy)-5-fluoro-N-(4-{[2-(methylthio)pyrimidin-4-yl]oxy}-1-naphthyl)benzamide (Compound B304). Compound is prepared from tert-butyl(4-{[2-(methylthio)pyrimidin-4-yl]oxy}-1-naphthyl)carbonate and 3-cyclopentyloxy-5-fluoro-benzoic acid according to conditions described in general procedure I. Mp: 115-116° C.; $^1$H NMR (300 MHz, CDCl$_3$) δ 8.37 (d, 1H), 8.13 (s, 1H), 7.99 (d, 1H), 7.93 (dd, 2H), 7.60 (t, H), 7.53 (t, 1H), 7.33 (d, 1H), 7.29 (s, 1H), 7.22

(d, 1H), 6.81 (m, 1H), 6.53 (dd, 1H), 4.83 (m, 1H), 2.29 (s, 3H), 1.98-1.80 (m, 6H), 1.68-1.65 (m, 2H); MS 490.16 (M+1).

Additional compounds of the invention can be prepared as described in Example 9.

Example 9

General Procedure J

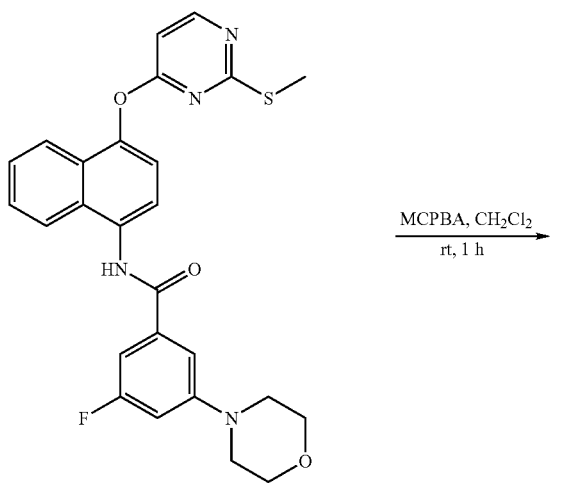

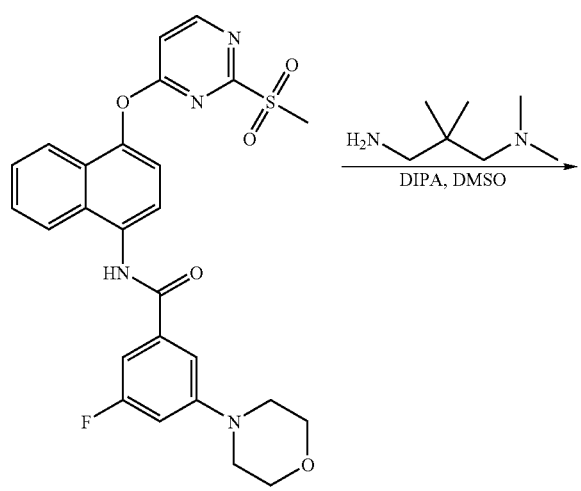

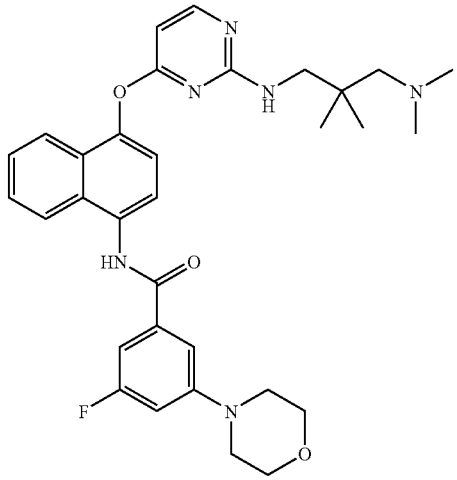

N-{4-[2-(3-Dimethylamino-2,2-dimethyl-propylamino)-pyrimidin-4-yloxy]-naphthalen-1-yl}-3-fluoro-5-morpholin-4-yl-benzamide (Compound B317). 3-Fluoro-N-[4-(2-methylsulfanyl-pyrimidin-4-yloxy)-naphthalen-1-yl]-5-morpholin-4-yl-benzamide (457 mg, 0.908 mmol) and MCPBA (447 mg, 1.998 mmol) in CHCl$_3$ (5 ml) is stirred at room temperature for 1 h. The mixture is diluted with CHCl$_3$ (5 ml) washed with sat'd NaHCO$_3$ solution (5 ml), water (5 ml), dried over Na$_2$SO$_4$ and concentrated to give a yellow solid. The yellow solid is mixed with N,N,2,2-tetramethyl-1,3-propanediamine (1.18 g, 9.08 mmol) and DIPA (1.58 ml, 9.08 mmol) in DMSO (2 ml), and heated to 85° C. for 4 h. The resulting mixture is diluted with CH$_2$Cl$_2$ (2 ml), washed with 0.01 N NaOH, dried over Na$_2$SO$_4$, concentrated. The residue is purified by column chromatography on silica gel (EtOAc) to give N-{4-[2-(3-dimethylamino-2,2-dimethyl-propylamino)-pyrimidin-4-yloxy]-naphthalen-1-yl}-3-fluoro-5-morpholin-4-yl-benzamide as a white solid (60 mg). $^1$H NMR (400 MHz, CDCl$_3$) δ 8.19 (s, 1H), 8.08 (s, 1H), 8.01 (d, 1H), 7.92 (m, 2H), 7.57 (t, H), 7.51 (t, 1H), 7.30 (d, 2H), 7.21 (d, 1H), 6.82 (dt, 1H), 5.87 (s, 1H), 4.33 (m, 1H), 3.23 (s, 1H), 2.27 (s, 6H), 2.21 (m, 2H), 2.02 (m, 2H), 1.82 (m, 2H), 1.57 (m, 3H), 1.39 (m, 3H), 0.98 (s, 6H); MS 586.37 (M+1).

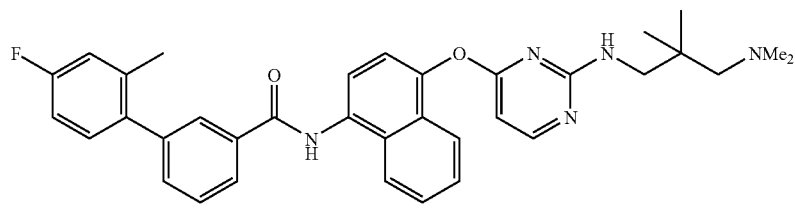

4'-Fluoro-2'-methyl-biphenyl-3-carboxylic acid{4-[2-(3-dimethylamino-2,2-dimethyl-propylamino)-pyrimidin-4-yloxy]-naphthalen-1-yl}-amide (Compound B314). Compound is prepared from 4'-fluoro-2'-methyl-biphenyl-3-carboxylic acid[4-(2-methylsulfanyl-pyrimidin-4-yloxy)-naphthalen-1-yl]-amide and N,N,2,2-tetramethyl-1,3-propanediamine according to conditions described in general procedure J. (23 mg). $^1$H NMR (400 MHz, CDCl$_3$) δ 8.01-8.1(m, 4H), 7.88(dd, 1H, J=0.8 and 8 Hz), 7.5-7.65(m, 5H), 7.26-7.33(m, 2H), 6.98-7.08(m, 2H), 6.21(d, 1H, J=6 Hz), 2.3(s, 3H), 2.0-2.2(brm, 10H), 0.6-0.9(brs, 6H).

Additional compounds of the invention can be prepared as described in Example 10.

A representative synthetic scheme is shown in Scheme 6, below.

4-[2-(4-Nitro-naphthalen-1-yloxy)-ethyl]-morpholine. A mixture of 4-nitro-1-hydroxynaphthalene (10 g, 52.8 mmol), 4-(2-chloroethyl)-morpholine hydrochloride (13.77 g, 74.0 mmol), sodium hydroxide (3.0 g, 74.0 mmol), potassium carbonate (17.53 g, 126.8 mmol) and 1-methyl-2-pyrrolidinone (400 ml) is heated to 90°-100° C. for 2-3 hours. The mixture is cooled to 40° C. and water (300 ml) added. The mixture is then cooled to 0° C. and held for 4 hours. The product is precipitated and collected by filtration, washed with water, cyclohexane and dried under vacuum to yield 4-[2-(4-nitro-naphthalen-1-yloxy)-ethyl]-morpholine (14.73 g, 92.6%). $^1$H NMR 300 MHz (CDCl$_3$) 8.80(d, 1H), 8.38(t, 2H), 7.75(t, 1H), 7.63(t, 1H), 6.84(d, 1H), 4.40(t, 2H), 3.75(t, 4H), 3.01(t, 2H), 2.66(t, 4H). MS: 303 (M+1).

Scheme 6

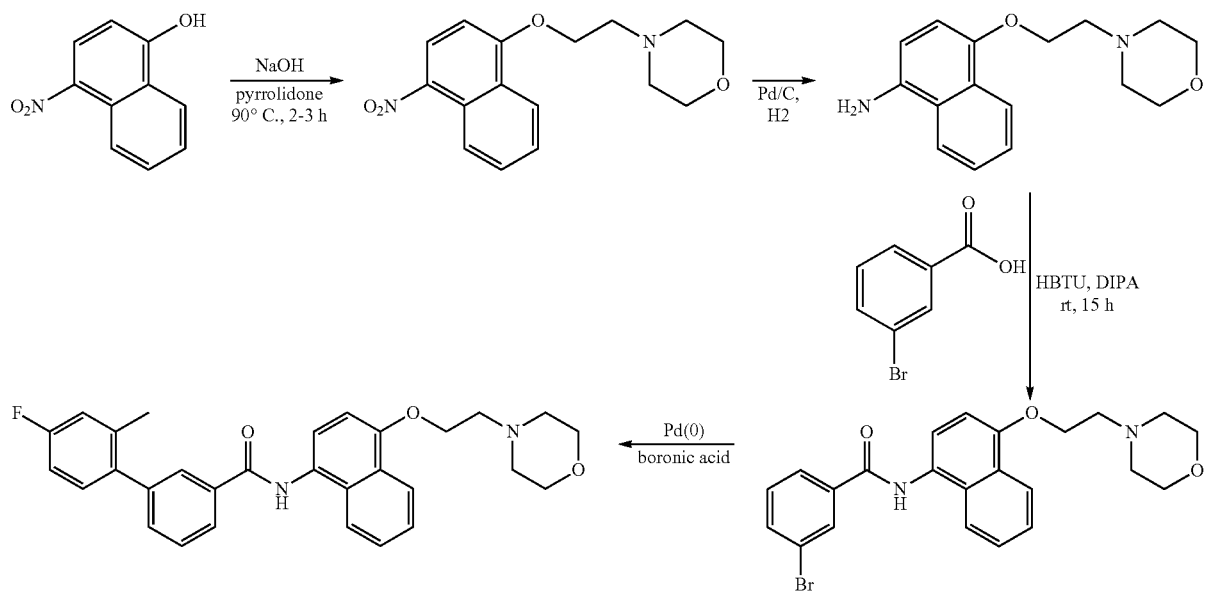

Example 10

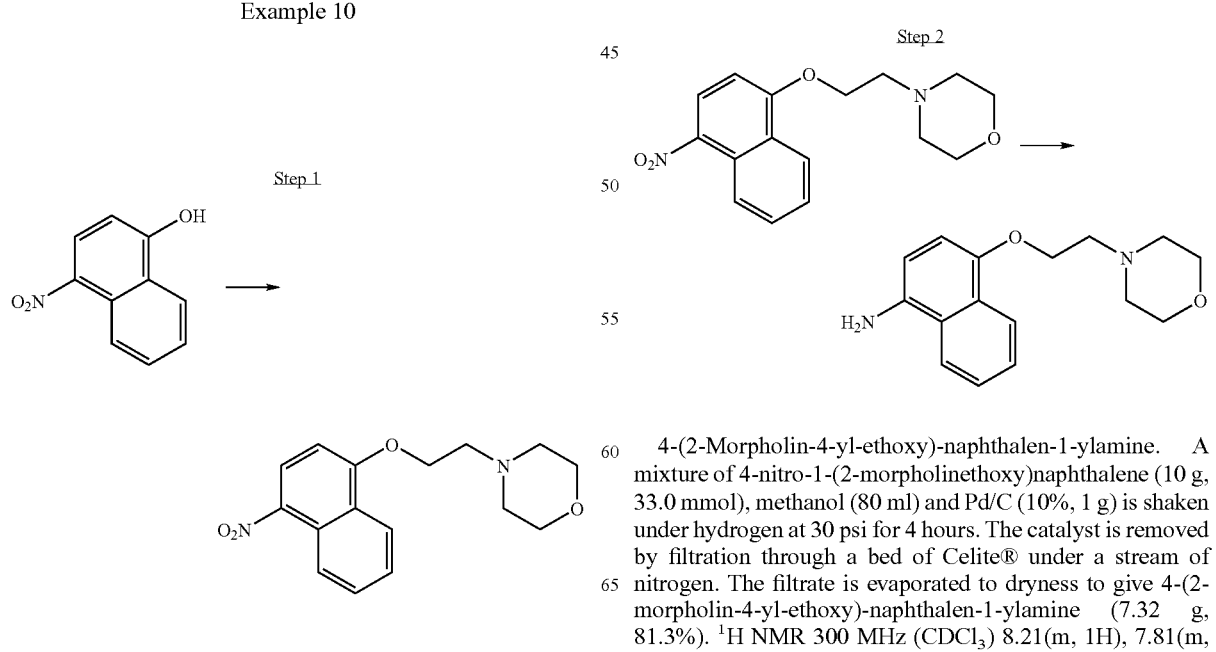

4-(2-Morpholin-4-yl-ethoxy)-naphthalen-1-ylamine. A mixture of 4-nitro-1-(2-morpholinethoxy)naphthalene (10 g, 33.0 mmol), methanol (80 ml) and Pd/C (10%, 1 g) is shaken under hydrogen at 30 psi for 4 hours. The catalyst is removed by filtration through a bed of Celite® under a stream of nitrogen. The filtrate is evaporated to dryness to give 4-(2-morpholin-4-yl-ethoxy)-naphthalen-1-ylamine (7.32 g, 81.3%). $^1$H NMR 300 MHz (CDCl$_3$) 8.21(m, 1H), 7.81(m, 1H), 7.49(m, 2H), 6.69(s, 2H), 4.23(t, 2H), 3.76(t, 4H), 2.92 (t, 2H), 2.65(t, 4H). MS: 273 (M+1).

Step 3

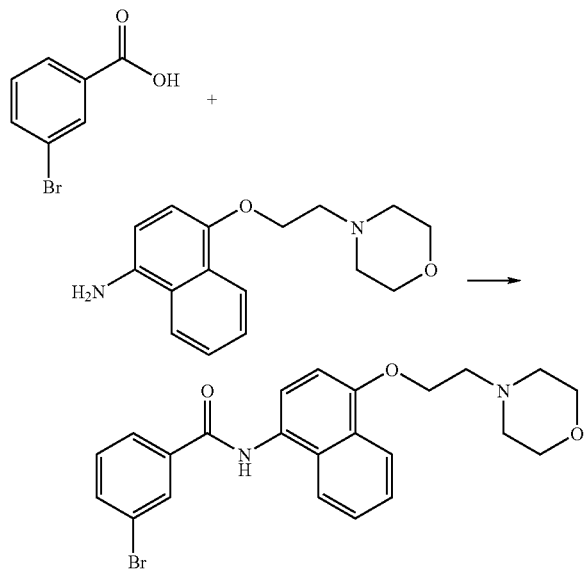

3-Bromo-N-[4-(2-morpholin-4-yl-ethoxy)-naphthalen-1-yl]-benzamide. 3-Bromobenzoic acid (1.66 g, 8.2 mmol), 4-amino-1-(2-morpholinethoxy)naphthalene (1.5 g, 5.5 mmol) and HBTU (3.13 g, 8.2 mmol) are dissolved in anhydrous dimethylformamide (2 ml). Diisopropylethyl amine (2.0 ml, 11.0 mmol) is then added and the mixture agitated at room temperature overnight. The mixture is diluted with ethyl acetate (50 ml) and water (50 ml), separated and the organic layer is washed with brine (50 ml). The aqueous layer is extracted with ethyl acetate (50 ml) and the organic layers combined. After drying with anhydrous sodium sulfate and evaporating to dryness the residue is purified by column chromatography on silica gel to give 3-bromo-N-[4-(2-morpholin-4-yl-ethoxy)-naphthalen-1-yl]-benzamide as a purple powder (1.217 g). Mp: 90-93° C.

General Procedure K

Step 4

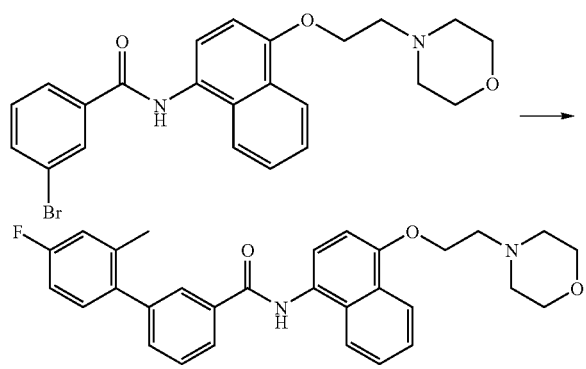

4'-Fluoro-2'-methyl-biphenyl-3-carboxylic acid[4-(2-morpholin-4-yl-ethoxy)-naphthalen-1-yl]-amide (Compound B105). 3-Bromo-N-[4-(2-morpholin-4-yl-ethoxy)-naphthalen-1-yl]-benzamide (600 mg, 1.31 mmol), 4-fluoro-2-methylphenyl boronic acid (271 mg, 1.98 mmol), cesium carbonate (730 mg, 2.24 mmol) and tetrakis triphenylphosphine palladium(0) (25 mg) in dioxane (10 ml) are heated to 100° C. under a nitrogen atmosphere for 16 hours. The mixture is cooled to room temperature then poured into ethyl acetate (100 ml). The organic layer is washed with water (100 ml), dried over anhydrous sodium sulfate and evaporated to dryness. The residue is then purified by column chromatography on silica gel to give 4'-fluoro-2'-methyl-biphenyl-3-carboxylic acid[4-(2-morpholin-4-yl-ethoxy)-naphthalen-1-yl]-amide as pale purple needles (0.44 g). Mp: 95-7° C. $^1$H NMR 300 MHz (CDCl$_3$) δ 8.35(d, 1H, J=7.5 Hz), 7.85-8.1 (m, 5H), 7.75(d, 1H, J=7.5 Hz), 7.5-7.63(m, 4H), 7.2(m, 1H), 6.9-7.05(m, 2H), 6.85(d, 1H, J=12 Hz), 4.3(t, 2H), 3.75(m, 4H), 2.98(t, 2H), 2.6(m, 4H), 2.3(s, 3H).

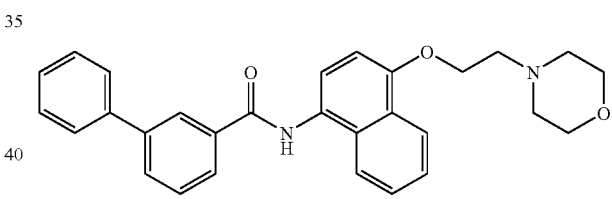

4'-Trifluoromethoxy-biphenyl-3-carboxylic acid[4-(2-morpholin-4-yl-ethoxy)-naphthalen-1-yl]amide (Compound B87). Compound is prepared from 3-bromo-N-[4-(2-morpholin-4-yl-ethoxy)-naphthalen-1-yl]-benzamide and 4-trifluoromethoxyphenyl boronic acid according to conditions described in general procedure K. $^1$H NMR 300 MHz (DMSO-d$_6$) δ 10.4(s, 1H), 8.4(s, 1H), 8.2(m, 1H), 8.05(d, 1H, J=7.2 Hz), 7.9(m, 3H), 7.4-7.7(m, 7H), 7.0(d, 1H, J=10.1 Hz), 4.3(m, 2H), 3.6(m, 4H), 2.9(m, 2H), 2.6(m, 4H).

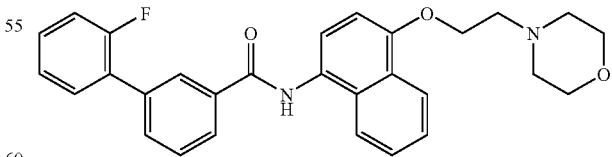

Biphenyl-3-carboxylic acid[4-(2-morpholin-4-yl-ethoxy)-naphthalen-1-yl]-amide (Compound B84). Compound is prepared from 3-bromo-N-[4-(2-morpholin-4-yl-ethoxy)-naphthalen-1-yl]-benzamide and phenyl boronic acid according to conditions described in general procedure K. $^1$H NMR 300 MHz (DMSO-d$_6$) δ 10.4(s, 1H), 8.4(s, 1H), 8.2(m, 1H), 8.05(d, 1H, J=7.2 Hz), 7.9(m, 2H), 7.8(m, 2H), 7.4-7.7(m, 7H), 7.0(d, 1H, J=10.1 Hz), 4.3(m, 2H), 3.6(s, 4H), 2.9(m, 2H), 2.6(m, 4H).

2'-Fluoro-biphenyl-3-carboxylic acid[4-(2-morpholin-4-yl-ethoxy)-naphthalen-1-yl]-amide (Compound B278). Compound is prepared from 3-bromo-N-[4-(2-morpholin-4-yl-ethoxy)-naphthalen-1-yl]-benzamide and 2-fluorophenyl boronic acid according to conditions described in general procedure K. $^1$H NMR 300 MHz (CDCl$_3$) δ 8.3(d, 1H), 8.15

(s, 1H), 7.18-8.05(m, 11H), 6.8(d, 1H, J=10 Hz), 4.3(t, 2H), 3.75(m, 4H), 3.0(t, 2H), 2.6(m, 4H).

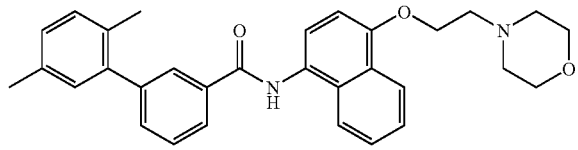

2',5'-dimethyl-biphenyl-3-carboxylic acid[4-(2-morpholin-4-yl-ethoxy)-naphthalen-1-yl]-amide (Compound B287). Compound is prepared from 3-bromo-N-[4-(2-morpholin-4-yl-ethoxy)-naphthalen-1-yl]-benzamide and 2,5-dimethylphenyl boronic acid according to conditions described in general procedure K. $^1$H NMR 300 MHz (CDCl$_3$) δ 8.3(d, 1H), 7.4-8.05(m, 9H), 7.2(d, 1H), 7.1(d, 2H), 6.8(d, 1H), 4.3(t, 2H), 3.75(m, 4H), 3.0(t, 2H), 2.7(m, 4H), 2.4(s, 3H), 2.3(s, 3H).

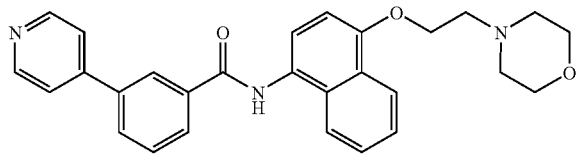

N-[4-(2-Morpholin-4-yl-ethoxy)-naphthalen-1-yl]-3-pyridin-4-yl-benzamide (Compound B86). Compound is prepared from 3-bromo-N-[4-(2-morpholin-4-yl-ethoxy)-naphthalen-1-yl]-benzamide and pyridyl-4-boronic acid according to conditions described in general procedure K. $^1$H NMR 300 MHz (DMSO-d$_6$) δ 10.4(s, 1H), 8.7(d, 2H), 8.5(s, 1H), 8.22(m, 1H), 8.15(d, 1H), 8.05(d, 1H), 7.9(m, 1H), 7.85(d, 2H), 7.7(t, 1H), 7.5(m, 2H), 7.45(d, 1H), 7.0(d, 1H), 4.3(t, 2H), 3.6(m, 4H), 2.9(t, 2H), 2.55(m, 4H).

3'-Trifluoromethyl-biphenyl-3-carboxylic acid[4-(2-morpholin-4-yl-ethoxy)-naphthalen-1-yl]-amide (Compound B88). Compound is prepared from 3-bromo-N-[4-(2-morpholin-4-yl-ethoxy)-naphthalen-1-yl]-benzamide and 3-trifluoromethylphenyl boronic acid according to conditions described in general procedure K. $^1$H NMR 300 MHz (DMSO-d$_6$) δ 10.4(s, 1H), 8.4(s, 1H), 8.2 (m, 1H), 8.05(s, 2H), 8.03(d, 1H), 8.0(d, 1H), 7.9(m, 1H), 7.4-7.75(m, 6H), 7.0(d, 1H), 4.3(t, 2H), 3.6(m, 4H), 2.9(t, 2H), 2.55(m, 4H).

Additional compounds of the invention can be prepared as described in Example 11.

A representative synthetic scheme is shown in Scheme 7, below.

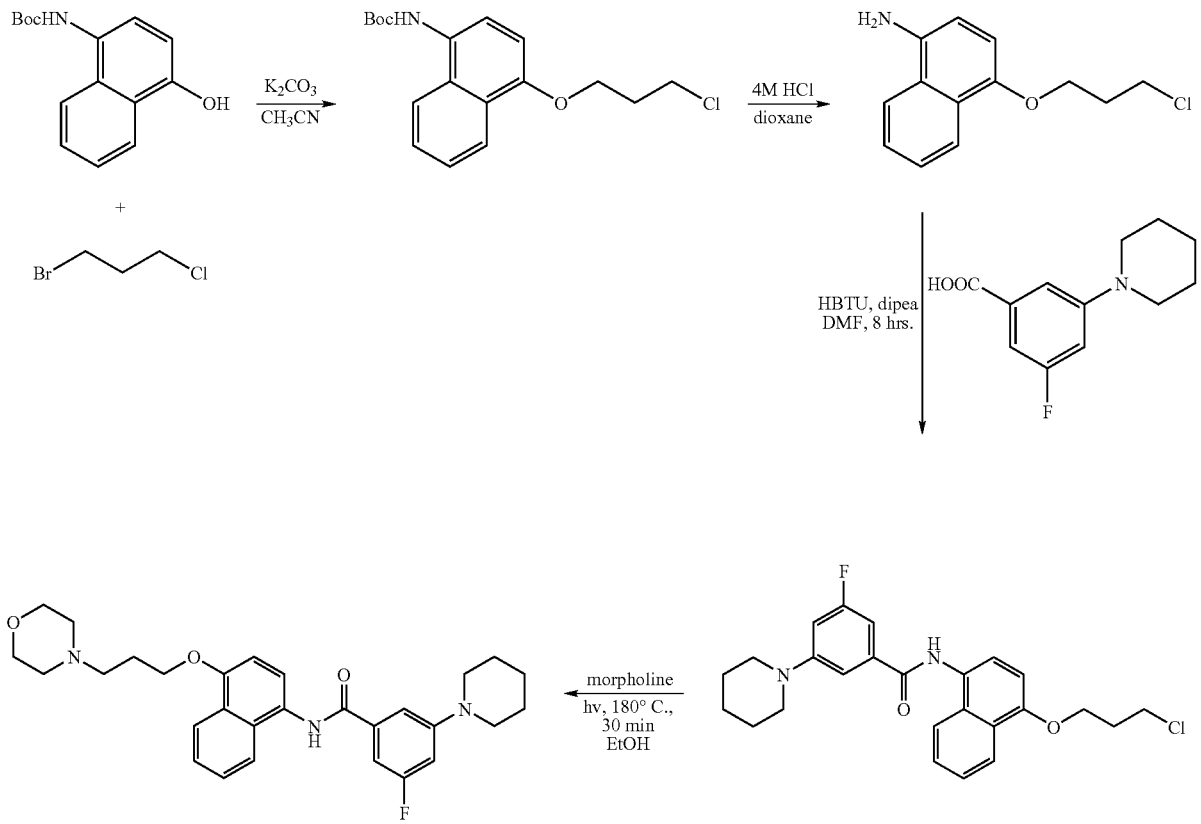

Example 11

Step 1

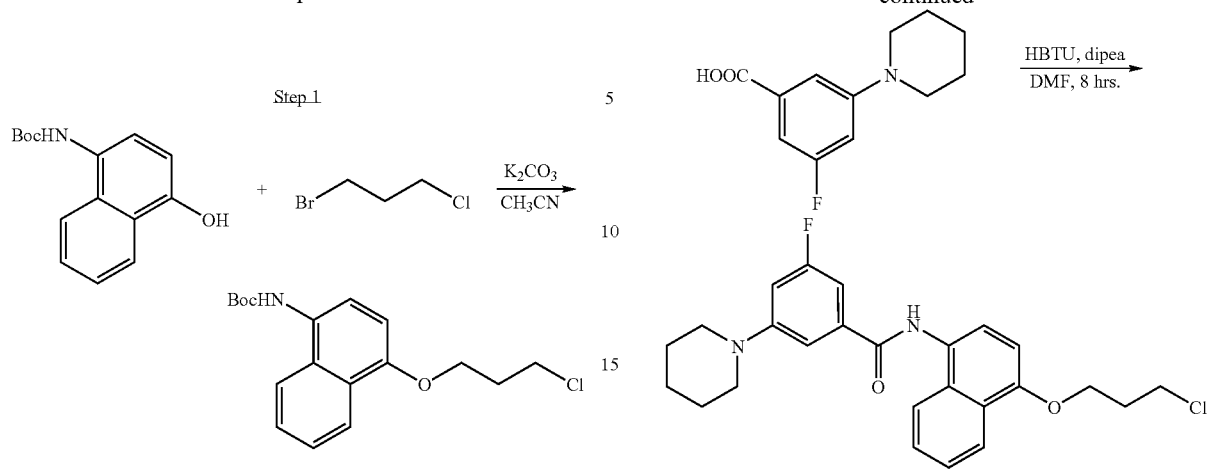

[4-(3-Chloropropoxy)-naphthalen-1-yl]-carbamic acid tert-butyl ester. Tert-butyl(4-hydroxy-1-naphthyl)carbamate (3.93 g, 15.1 mmol), 1-bromo-3-chloropropane (5.5 g, 34.8 mmol), and $K_2CO_3$ (10.0 g, 75.8 mmol) in acetonitrile (50 ml) are heated to 80° C. with agitation for 8 h. After cooling to room temperature the mixture is filtered and concentrated under vacuum. The residue is purified by column chromatography on silica gel to yield [4-(3-chloropropoxy)-naphthalen-1-yl]-carbamic acid tert-butyl ester. 4 g, 78% is produced as an off-white solid. MS: 336.2 (M+1).

Step 2

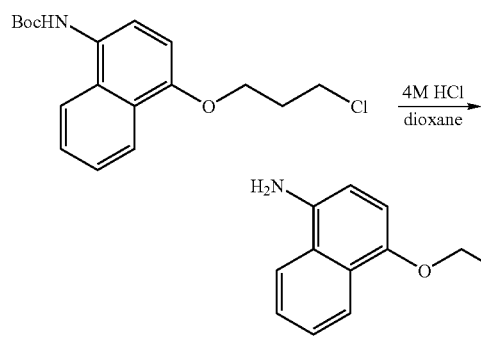

4-(3-Chloropropoxy)-naphthalen-1-ylamine. To a solution of tert-butyl[4-(3-chloropropoxy)-1-naphthyl]carbamate (4 g, 11.9 mmol) in dioxane (20 ml) is added a solution of 4M HCl in dioxane (30 ml). The mixture is stirred at room temperature until the consumption of tert-butyl(4-hydroxy-1-naphthyl)carbamate is complete. The mixture is then diluted with diethylether (200 ml) and 4-(3-chloropropoxy)-naphthalen-1-ylamine isolated by filtration as its HCl salt, as a white solid (2.85 g, 89%). MS: 236.2 (M+1).

Step 3

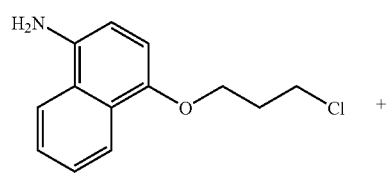

N-[4-(3-Chloropropoxy)-naphthalen-1-yl]-3-fluoro-5-piperidin-1-yl-benzamide. To a solution of 4-(3-chloropropoxy)naphthalen-1-amine (2.85 g, 10.5 mmol) and 3-fluoro-5-piperidin-1-ylbenzoic acid (3.52 g, 15.7 mmol), in DMF (30 ml) is added HBTU (7.1 g, 18.9 mmol), and Hunig's base (6.0 ml, 33.6 mmol). The mixture is stirred overnight at room temperature then diluted with ethyl acetate (200 ml) and washed with water (3×100 ml). The organic layer is dried over $Na_2SO_4$ and evaporated. The residue is purified by column chromatography on silica gel to yield N-[4-(3-chloropropoxy)-naphthalen-1-yl]-3-fluoro-5-piperidin-1-yl-benzamide as a white solid (3.0 g, 65%). Mp: 181-182° C. $^1$H NMR (300 MHz, DMSO-$d_6$) δ 10.25 (s, 1H), 8.26 (m, 1H), 7.87 (m, 1H), 7.55 (m, 2H), 7.46 (s, 1H), 7.43 (d, J=8.1 Hz, 1H), 7.17 (d, J=9.3 Hz, 1H), 7.04 (d, J=8.4 Hz, 1H), 6.97 (d, J=10.5 Hz, 1H), 4.33 (t, J=6.0 Hz, 2H), 3.96(t, J=6.6, Hz, 2H), 3.29 (m, 4H), 2.34 (m, 6H), 1.59 (m, 6H). MS: 441.3 (M+1).

General Procedure L

Step 4

3-Fluoro-N-[4-(3-morpholin-4-yl-propoxy)-naphthalen-1-yl]-5-piperidin-1-yl-benzamide (Compound B161). A solution of N-[4-(3-chloropropoxy)-naphthalen-1-yl]-3-fluoro-5-piperidin-1-yl-benzamide (0.125 g, 0.283 mmol) and morpholine (0.123 g, 1.4 mmol) in EtOH (3 ml) is heated at 180° C. for 30 min by microwave. The mixture is then concentrated under vacuum and the residue purified by column chromatography on silica gel (5% MeOH in EtOAc) to give 3-fluoro-N-[4-(3-morpholin-4-yl-propoxy)-naphthalen-1-yl]-5-piperidin-1-yl-benzamide as a white powder (90 mg, 64%). Mp: 70-72° C. ¹H NMR (300 MHz, DMSO-$d_6$) δ 10.23 (s, 1H), 8.23 (m, 1H), 7.86 (m, 1H), 7.56 (m, 2H), 7.45 (s, 1H), 7.42 (d, J=8.1, Hz, 1H), 7.16 (d, J=9.0 Hz, 1H), 7.01 (d, J=8.1 Hz, 1H), 6.93 (s, 1H), 4.23 (t, J=6.3 Hz, 2H), 3.60 (t, J=4.5 Hz, 4H), 3.29 (m, 4H), 2.55 (m, 2H), 2.42 (bs, 4H), 2.04 (q, J=6.6 Hz, 2H), 1.60 (bs, 6H). MS: 492.4 (M+1).

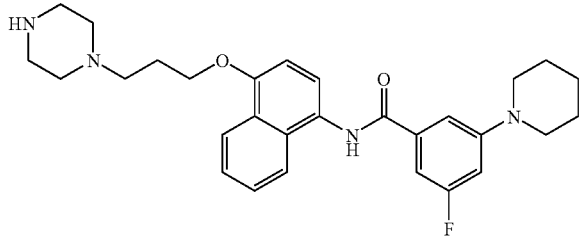

3-Fluoro-N-[4-(3-piperazin-1-yl-propoxy)-naphthalen-1-yl]-5-piperidin-1-yl-benzamide (Compound B183). Compound is prepared from N-[4-(3-chloropropoxy)-naphthalen-1-yl]-3-fluoro-5-piperidin-1-yl-benzamide and piperazine according to conditions described in general procedure L. A yellow powder is produced (0.194 g, 69%). Mp: 70-72° C. ¹H NMR (300 MHz, DMSO-$d_6$) δ 10.24 (s, 1H), 8.23 (m, 1H), 7.86 (m, 1H), 7.55 (m, 2H), 7.45 (s, 1H), 7.42 (d, J=8.1 Hz, 1H), 7.16 (d, J=9.0 Hz, 1H), 7.01 (d, J=8.4 Hz, 1H), 6.93 (s, 1H), 4.21 (t, J=6.0 Hz, 2H), 3.32 (m, 4H), 2.71 (t, J=4.5, 4H), 2.53 (m, 2H), 2.35 (brs, 4H), 2.02 (m, J=7.2 Hz, 2H), 1.60 (brs, 6H). MS: 491.2 (M+1).

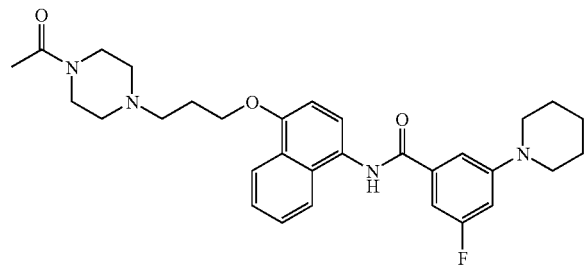

N-{4-[3-(4-Acetyl-piperazin-1-yl)-propoxy]-naphthalen-1-yl}-3-fluoro-5-piperidin-1-yl-benzamide (Compound B165). Compound is prepared from N-[4-(3-chloropropoxy)-naphthalen-1-yl]-3-fluoro-5-piperidin-1-yl-benzamide and N-acetylpiperizine according to conditions described in general procedure L. A white powder (0.13 g, 75.5%). Mp: 210-211° C. ¹H NMR (300 MHz, DMSO-$d_6$) δ 10.23 (s, 1H), 8.22 (br s, 1H), 7.84 (br s, 1H), 7.55 (m, 2H), 7.44 (m, 2H), 7.15 (br s, 1H), 6.98 (br s, 2H), 4.23 (br s, 2H), 3.42 (br s, 4H), 3.30 (br s, 4H), 2.57 (br s, 2H), 2.42 (m, 4H), 2.04 (m, 2H), 1.98 (s, 3H), 1.60 (br s, 6H). MS: 533.5 (M+1).

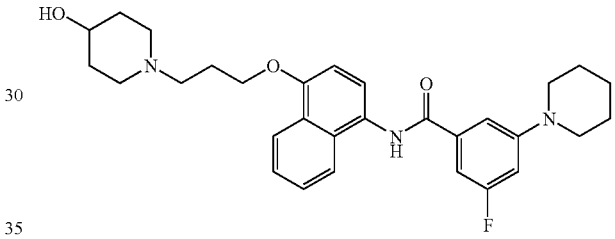

3-Fluoro-N-{4-[3-(4-hydroxy-piperidin-1-yl)-propoxy]-naphthalen-1-yl}-5-piperidin-1-yl-benzamide (Compound B162). Compound is prepared from N-[4-(3-chloropropoxy)-naphthalen-1-yl]-3-fluoro-5-piperidin-1-yl-benzamide and 4-hydroxypiperidine according to conditions described in general procedure L. A yellow powder is produced (0.137 g, 80%). MS: 506 (M+1).

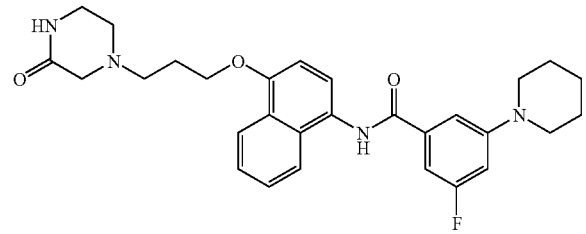

3-Fluoro-N-{4-[3-(3-oxo-piperazin-1-yl)-propoxy]-naphthalen-1-yl}-5-piperidin-1-yl-benzamide (Compound B175). Compound is prepared from N-[4-(3-chloropropoxy)-naphthalen-1-yl]-3-fluoro-5-piperidin-1-yl-benzamide and 2-piperazinone according to conditions described in general procedure L. A white powder is produced (0.102 g, 60%). Mp: 90-92° C. ¹H NMR (300 MHz, DMSO-$d_6$) δ 10.23 (s, 1H), 8.24 (d, J=6.3 Hz, 1H), 7.86 (d, J=8.7 Hz, 1H), 7.75 (s, 1H), 7.56 (m, 2H), 7.45 (s, 1H), 7.42 (d, J=8.1, Hz, 1H), 7.16 (d, J=9.6 Hz, 1H), 7.01 (d, J=8.7 Hz, 1H), 6.93 (s, 1H), 4.22 (br s, 2H), 3.31 (m, 4H), 3.17 (br s, 2H), 2.98 (s, 2H), 2.61 (m, 4H), 2.06 (m, 2H), 1.60 (brs, 6H). MS: 505.2 (M+1).

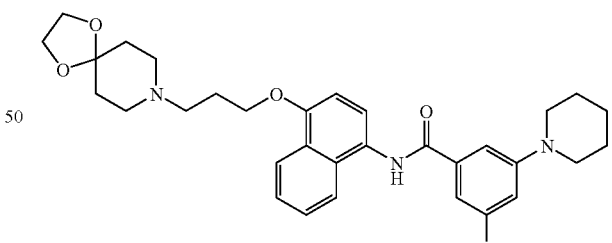

N-{4-[3-(1,4-Dioxa-8-aza-spiro[4.5]dec-8-yl)-propoxy] naphthalen-1-yl}-3-fluoro-5-piperidin-1-yl-benzamide (Compound B166). Compound is prepared from N-[4-(3-chloropropoxy)-naphthalen-1-yl]-3-fluoro-5-piperidin-1-yl-benzamide and 1,4-dioxa-8-aza-spiro[4.5] according to conditions described in general procedure L. A yellow powder is produced (0.137 g, 80%). Mp: 70-72° C. MS 548.2 (M+1).

Additional compounds of the invention can be prepared as described in Example 12.

A representative synthetic scheme is shown in Scheme 8, below.

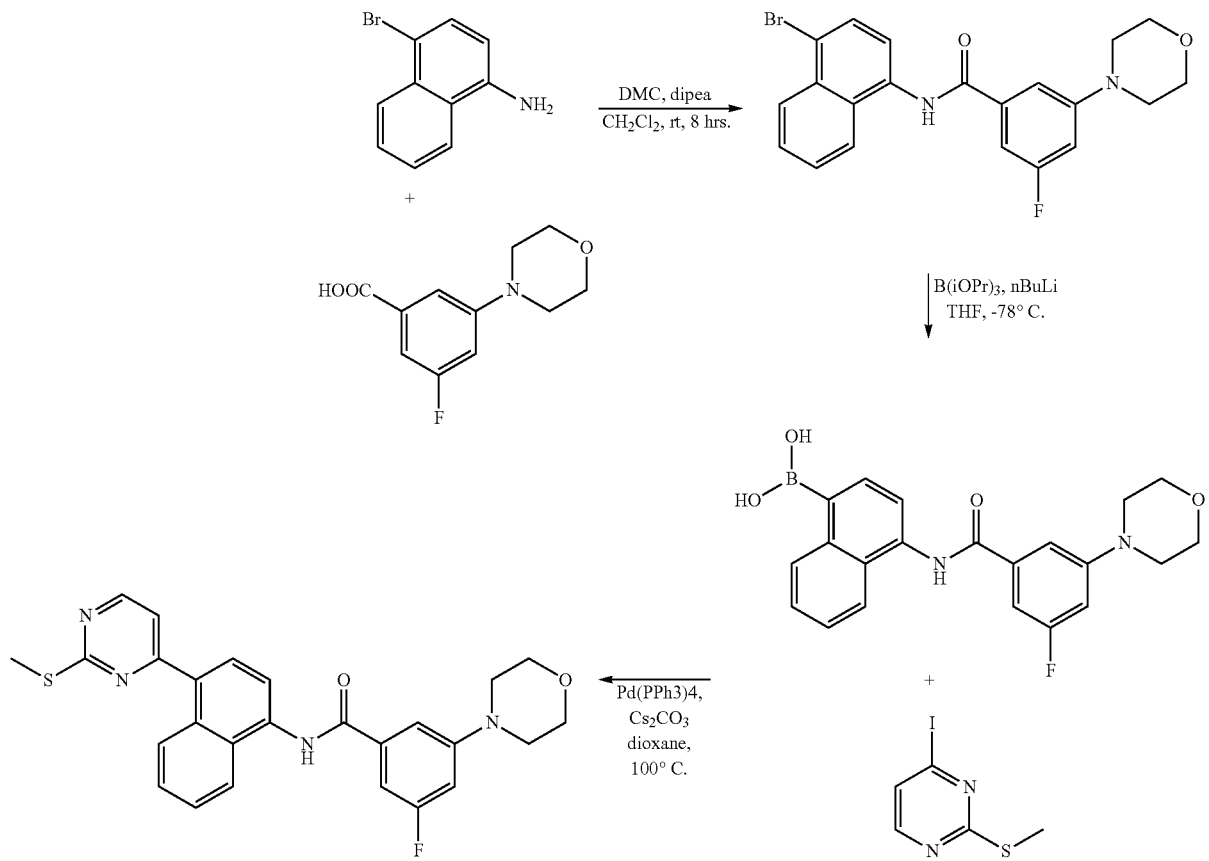

Example 12

Step 1

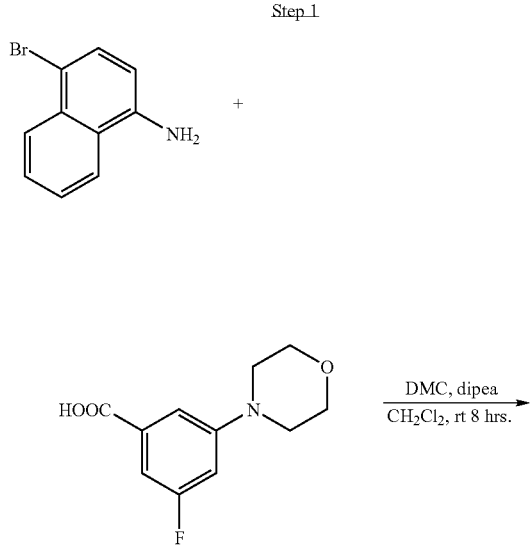

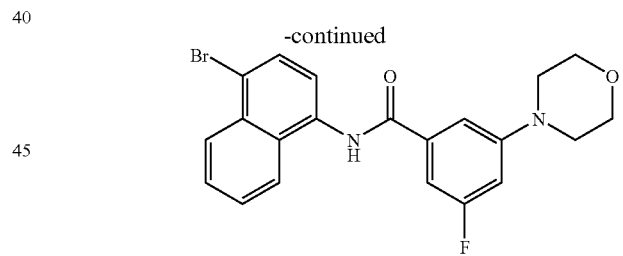

N-(4-Bromo-naphthalen-1-yl)-3-fluoro-5-morpholin-4-yl-benzamide. To a solution of 3-fluoro-5-morpholin-4-yl-benzoic acid (1.01 g, 4.4 mmol) in methylenechloride (30 ml) is added DMC (0.908 g, 5.4 mmol) and the mixture is stirred for 10 minutes. To this mixture is added 4-bromonaphthalen-1-amine (1.0 g, 4.50 mmol) and Hunig's base (3.21 ml). The mixture is stirred vigorously overnight at room temperature. The mixture is poured into water (200 ml) and extracted with EtOAc (2×100 ml). The organic layers are combined, dried over $Na_2SO_4$, filtered and concentrated. The residue is recrystalized from EtOH (50 ml) to give N-(4-bromo-naphthalen-1-yl)-3-fluoro-5-morpholin-4-yl-benzamide as white crystals (1.26 g, 65%). Mp: 187-189° C. $^1$H NMR (400 MHz, DMSO-$d_6$): δ 10.48 (s, 1H), 8.18 (d, J=6.3 Hz, 1H), 8.02 (d, J=6.0 Hz, 1H), 7.93 (d, J=5.7 Hz, 1H), 7.72 (t, J=5.1 Hz, 1H), 7.67 (t, J=5.4 Hz, 1H), 7.51 (d, J=5.7 Hz, 1H), 7.45 (s, 1H), 7.24 (d, J=6.3 Hz, 1H), 7.04 (d, J=9.3 Hz, 1H), 3.74 (t, J=3.3 Hz, 4H), 3.24 (t, J=3.9 Hz, 4H). MS 429 (M+1).

Step 2

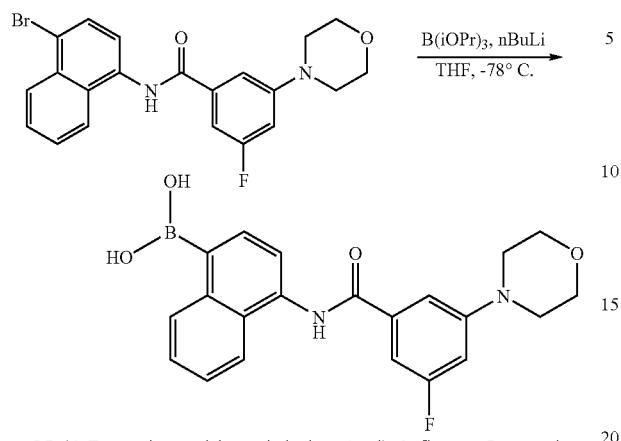

N-(4-Boronic acid-naphthalen-1-yl)-3-fluoro-5-morpholin-4-yl-benzamide. To a −78° C. solution of N-(4-bromo-naphthalen-1-yl)-3-fluoro-5-morpholin-4-yl-benzamide (1.0 g, 2.33 mmol) in dry THF (30 ml) under a stream of argon is added nBuLi (1.6M in THF, 3.2 ml, 5.14 mmol). The mixture is stirred for 5 minutes before adding triisopropylborate (0.646 ml, 2.80 mmol). The mixture is allowed to warm to room temperature and quenched with 1M NaOH (1 ml) and water (100 ml). The mixture is extracted with EtOAc (2×50 ml), the organic layers combined, dried over Na₂SO₄, filtered and concentrated. The residue is purified by column chromatography on silica gel (EtOAc) to give N-(4-boronic acid-naphthalen-1-yl)-3-fluoro-5-morpholin-4-yl-benzamide as a yellow powder (0.29 g, 34%). MS 395 (M+1).

Step 3

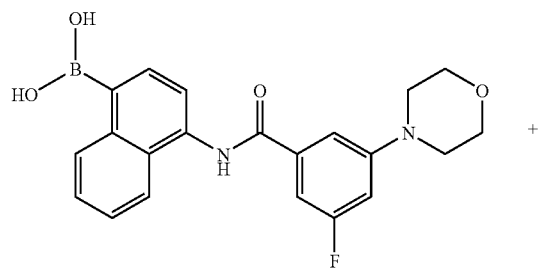

+

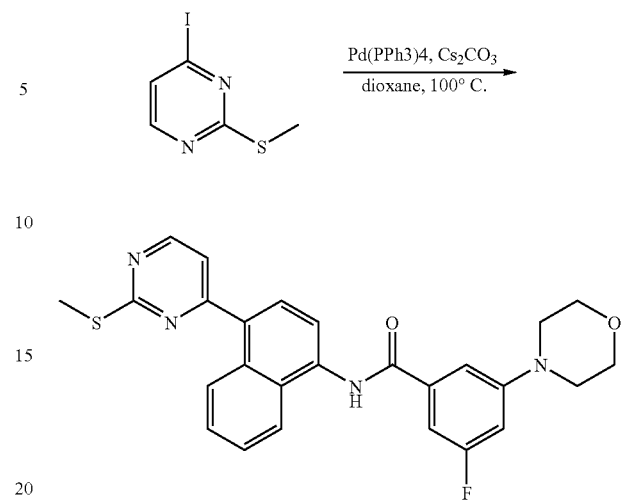

3-Fluoro-N-[4-(2-methylsulfanyl-pyrimidin-4-yl)-naphthalen-1-yl]-5-morpholin-4-yl-benzamide (Compound B270) A mixture of N-(4-boronic acid-naphthalen-1-yl)-3-fluoro-5-morpholin-4-yl-benzamide (0.1 g, 0.253 mmol), 4-iodo-2-(methylsulfanyl)pyrimidine (0.07 g, 0.279 mmol), Pd(PPh₃)₄ (30 mg), Cs₂CO₃ (0.124 g, 0.38 mmol) in dry dioxane (40 ml) is heated to 100° C. with vigorous stirring for 8 hours. The mixture is cooled, filtered through Celite®, and concentrated under vacuum. The residue is purified by column chromatography on silica gel (20-50% EtOAc in hexane) to give 3-fluoro-N-[4-(2-methylsulfanyl-pyrimidin-4-yl)-naphthalen-1-yl]-5-morpholin-4-yl-benzamide (43 mg, 35%). Mp: 135-138° C. ¹H NMR (400 MHz, DMSO-d₆) δ 10.58 (s, 1H), 8.78 (d, J=4.8 hz, 1H), 8.26 (m, 1H), 8.10(m, 1H), 7.79 (d, J=7.6 Hz, 1H), 7.72 (d, J=8.0 Hz, 1H), 7.63 (m, 2H), 7.54 (d, J=5.2 Hz, 1H), 7.48 (s, 1H), 7.28 (d, J=8.8 Hz, 1H), 7.06 (d, J=12.4 Hz, 1H), 3.75 (t, J=4.0 Hz, 4H), 3.27 (t, J=4.4 Hz, 4H), 2.55 (s, 3H). MS 475 (M+1).

Additional compounds of the invention can be prepared as described in Example 13.

A representative synthetic scheme is shown in Scheme 9, below.

Scheme 9

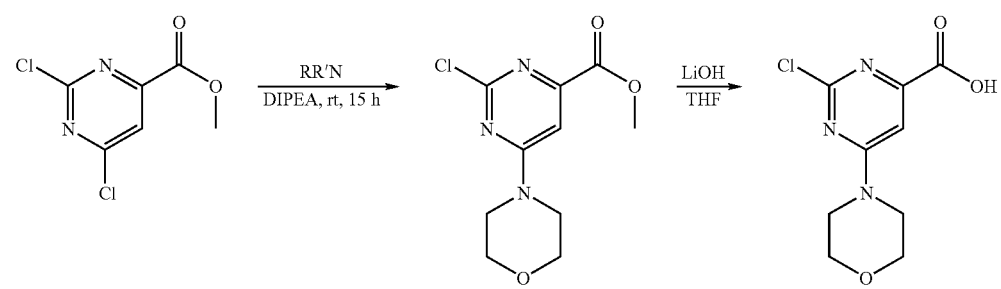

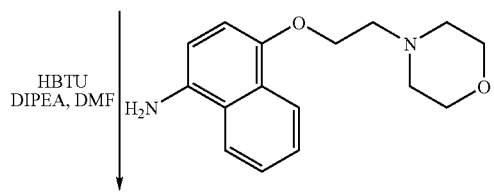

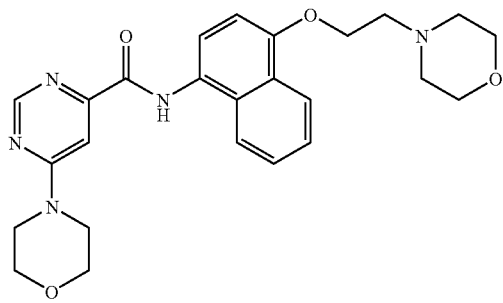

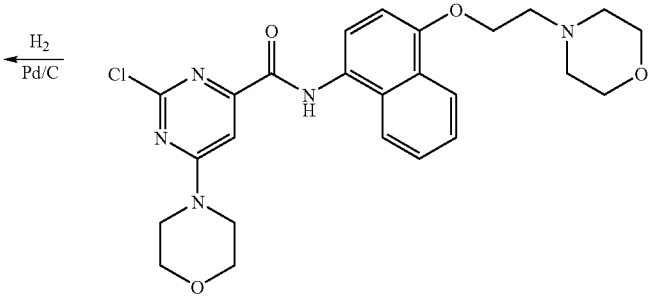

Example 13

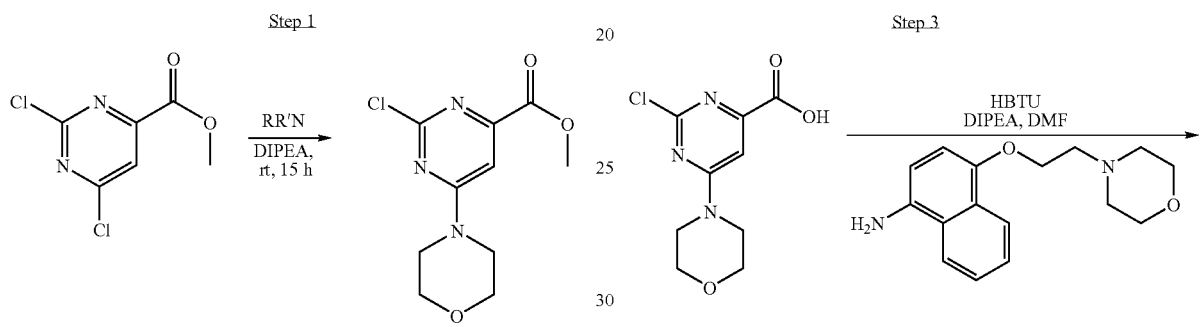

Methyl 2-chloro-6-morpholin-4-ylpyrimidine-4-carboxylate: To a solution of 2,6-dichloropyrimidine-4-carboxylic acid methyl ester (300 mg, 1.45 mmol) in dimethylsulfoxide (2 ml) is added morpholine (0.126 g, 1.0 eq) followed by diisopropylethylamine (0.285 ml, 1.1 eq). The mixture is stirred at room temperature for 15 h before being diluted with water and extracted with ethyl acetate (2×20 ml). The combined organic layers are washed with water, dried over $Na_2SO_4$ and evaporated to dryness. The residue is purified by column chromatography on silica gel, eluted with ethyl acetate:hexane (1:1) to provide methyl 2-chloro-6-morpholin-4-ylpyrimidine-4-carboxylate as a white solid (0.30 g). Mp: 135-138° C., $^1$H NMR (300 MHz, DMSO-$d_6$) δ 7.34 (s, 1H), 3.86 (s, 3H), 3.67 (brs, 8H). MS: 257 (M+1).

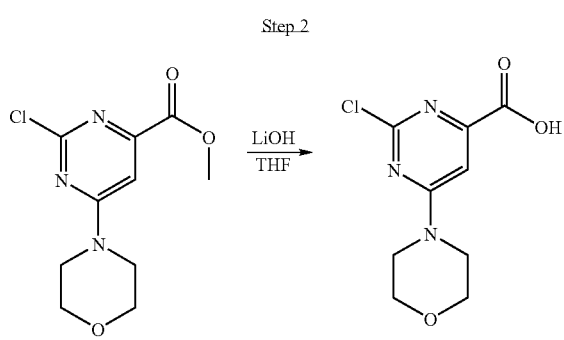

2-Chloro-6-morpholin-4-ylpyrimidine-4-carboxylic acid: A suspension of methyl 2-chloro-6-morpholin-4-ylpyrimidine-4-carboxylate (0.30 g, 1.16 mmol) in a mixture of THF: $H_2O$:MeOH (12 ml, 4:1:1) is stirred at room temperature for 24 hrs with lithium hydroxide (28 mg, 1.0 eq). The mixture is then evaporated to dryness to give 2-chloro-6-morpholin-4-ylpyrimidine-4-carboxylic acid as a solid (280 mg).

2-Chloro-6-morpholin-4-yl-pyrimidine-4-carboxylic acid [4-(2-morpholin-4-yl-ethoxy)-naphthalen-1-yl]-amide (Compound B42). 2-Chloro-6-morpholin-4-ylpyrimidine-4-carboxylic acid (0.280 g, 1.15 mmol) in DMF (5 ml) is treated with HBTU (0.466 g, 1.5 eq) and diisopropylethylamine (0.367 ml). The mixture is stirred at room temperature for 5-10 min. 4-(2-Morpholin-4-yl-ethoxy)-naphthalen-1-ylamine (0.224 g, 0.82 mmol) is then added. The mixture is stirred at room temperature for an additional 15 h, diluted with water and extracted with ethyl acetate. The organic layer is dried over $Na_2SO_4$ and evaporated to dryness. The residue is purified by column chromatography on silica gel eluted with 2% MeOH in ethyl acetate to provide 2-chloro-6-morpholin-4-yl-pyrimidine-4-carboxylic acid[4-(2-morpholin-4-yl-ethoxy)-naphthalen-1-yl]-amide as a solid (0.342 g). Mp: 95-93° C., 1H NMR (300 MHz, DMSOd$_6$) δ 10.43 (s, 1H), 8.20 (m, 1H), 7.79 (s, 1H), 7.56 (m, 3H), 7.39 (s, 1H), 7.03 (d, J=8.1 Hz, 1H), 4.31 (t, J=6.3 Hz, 2H), 3.60 (brt, 8H) 2.88 (t, 2H), 2.56 (brt, 8H). MS: 498 (M+1).

Step 4

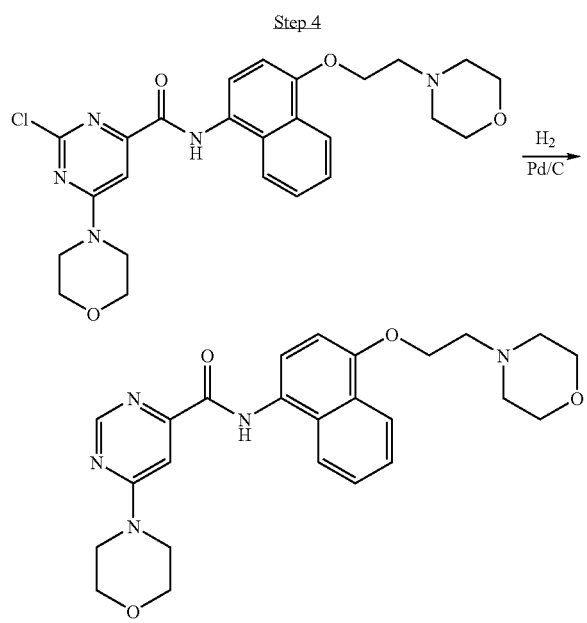

6-Morpholin-4-yl-pyrimidine-4-carboxylic acid[4-(2-morpholin-4-yl-ethoxy)-naphthalen-1-yl]-amide (Compound B54). To a mixture of 2-chloro-6-morpholin-4-yl-pyrimidine-4-carboxylic acid[4-(2-morpholin-4-yl-ethoxy)-naphthalen-1-yl]-amide (95 mg) and 10% Pd/C (10 mg) in ethyl acetate (4 ml) is added a few drops of triethylamine. The mixture is then shaken at room temperature under hydrogen at 50 psi for 8 h. The solvent is then removed under reduced pressure and the residue purified by column chromatography on silica gel eluted with ethyl acetate: hexane (1:1) to 100% ethyl acetate to provide 6-morpholin-4-yl-pyrimidine-4-carboxylic acid[4-(2-morpholin-4-yl-ethoxy)-naphthalen-1-yl]-amide as a solid (22 mg). Mp: 50-51° C. $^1$H NMR (300 MHz, DMSO-$d_6$) δ 10.62 (s, 1H), 8.70 (s, 1H), 8.22 (d, J=7.2 Hz, 1H), 7.83 (d, J=8.1 Hz, 1H), 7.66 (d, J=8.1 Hz, 1H), 7.57 (m, 2H), 7.42 (s, 1H), 7.04 (d, J=8.1 Hz, 1H), 4.30 (t, J=5.7, 2H), 3.70 (m, 10H), 3.60 (t, J=4.5 Hz, 2H) 2.87 (t, J=5.7 Hz, 2H), 2.56 (brm, 4H). MS: 463 (M+1).

Additional compounds of the invention can be prepared as described in Example 14.

A representative synthetic scheme is shown in Scheme 10, below.

Scheme 10

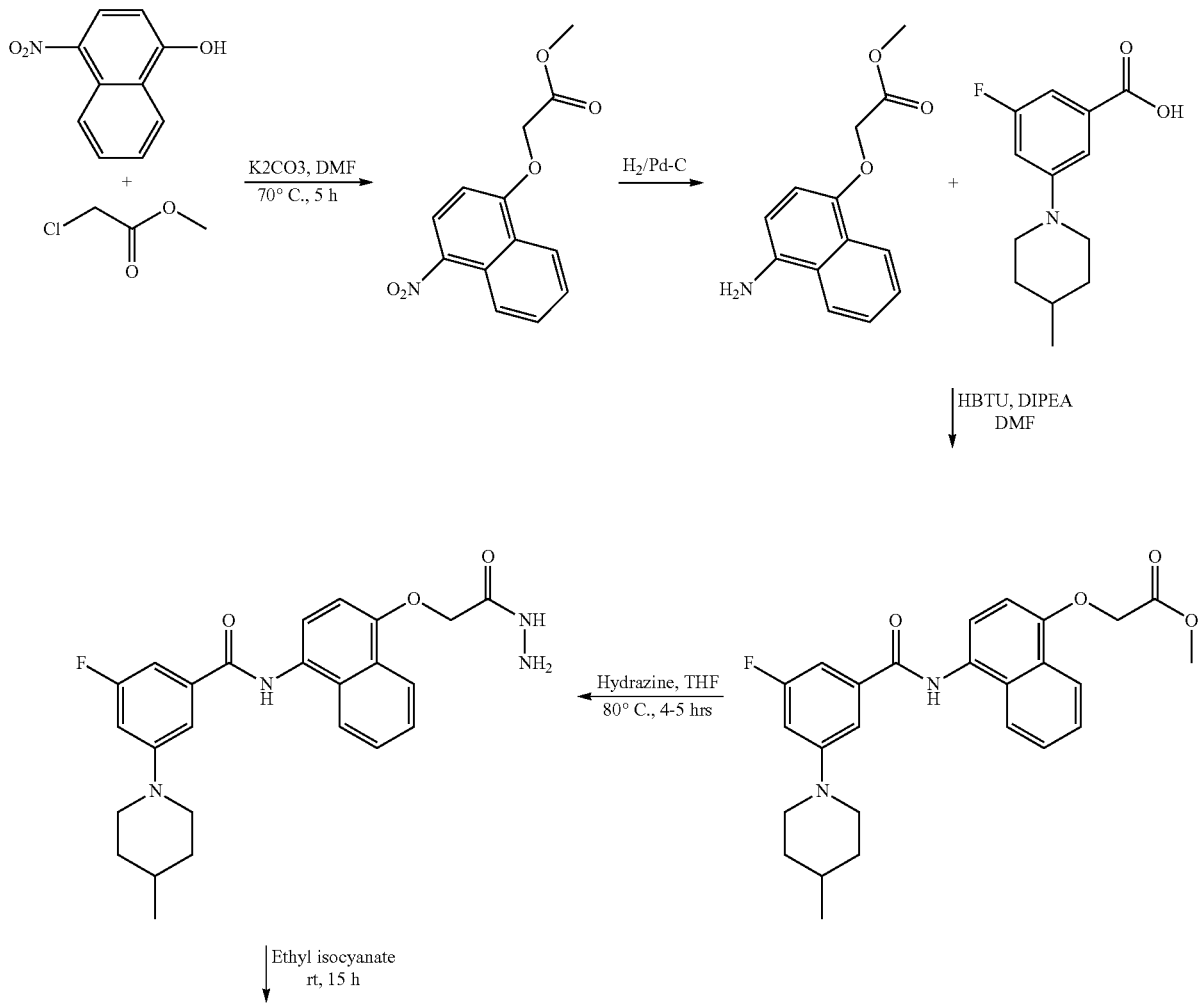

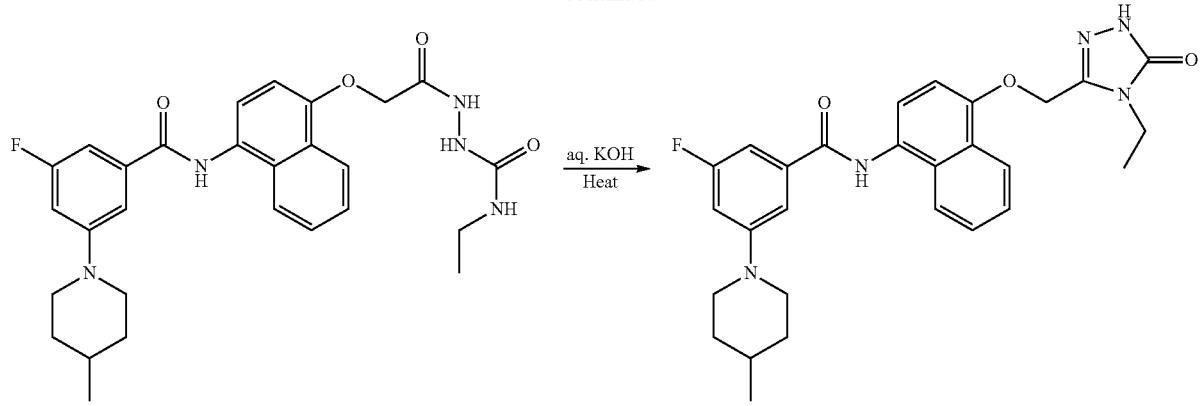

Example 14

Step 1

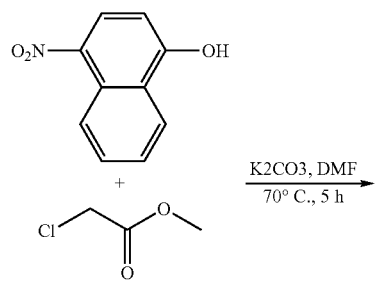

(4-Nitronaphthalen-1-yloxy)-acetic acid methyl ester. 4-Nitronaphthalen-1-ol (0.70 g, 3.7 mmol) in N-methylpyrrolidine (6 ml) is treated with potassium carbonate (1.0 g) and methyl bromoacetate (0.169 g, 1.1 eq). The mixture is stirred at 70° C. for 5 h. The mixture is then diluted with water and extracted with ethyl acetate. The organic layer is repeatedly washed with water, dried over $Na_2SO_4$, and evaporated to dryness to provide (4-nitronaphthalen-1-yloxy)-acetic acid methyl ester (0.94 g). MS: 262 (M+1).

Step 2

(4-Amino-naphthalen-1-yloxy)-acetic acid methyl ester. (4-Nitro-naphthalen-1-yloxy)-acetic acid methyl ester (0.90 g) and 10% Pd/C (90 mg) in MeOH (150 ml) is stirred at room temperature under 1 atmosphere of hydrogen for 4 h. The mixture is then filtered through Celite® and evaporated to dryness to provide (4-amino-naphthalen-1-yloxy)-acetic acid methyl ester (0.72 g). MS 232 (M+1).

Step 3

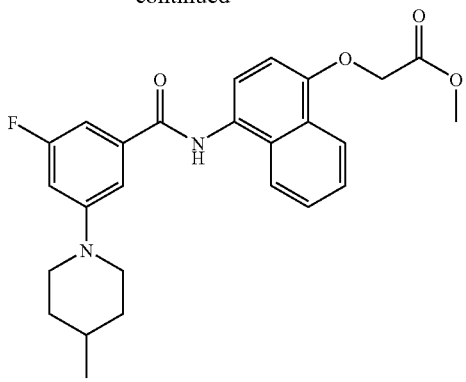

{4-[3-Fluoro-5-(4-methylpiperidin-1-yl)-benzoylamino]-naphthalen-1-yloxy}-acetic acid methyl ester. A solution of 3-fluoro-5-(4-methylpiperidin-1-yl)-benzoic acid (0.650 g, 2.7 mmol) in dimethylformamide (5 ml) is treated with HBTU (1.7 g, 1.7 eq) and diisopropylethylamine (1.6 ml, 3.5 eq). The mixture is stirred for five minutes at room temperature before a solution of (4-aminonaphthalen-1-yloxy)-acetic acid methyl ester (0.696 g, 1.1 eq) in DMF (2 ml) is added. The mixture is then stirred at room temperature for an additional 15 h before being diluted with water and extracted with ethyl acetate. The organic layer is washed with water, dried over Na$_2$SO$_4$ and evaporated to dryness. The residue is purified by column chromatography on silica gel, eluted with ethyl acetate in hexane (10-30%) to give {4-[3-fluoro-5-(4-methylpiperidin-1-yl)-benzoylamino]-naphthalen-1-yloxy}-acetic acid methyl ester as a solid (1.0 g). Mp: 50-51° C. $^1$H NMR (300 MHz, DMSO-d$_6$) δ 10.25 (s, 1H), 8.26 (m, 1H), 7.87 (m, 1H), 7.58 (m, 2H), 7.41 (m, 2H), 7.14 (d, J=8.7 Hz, 1H), 6.96 (m, 3H), 5.05 (s, 2H), 3.84 (d, J=12.6 Hz, 1H), 3.74 (s, 3H) 2.77 (t, J=11.7 Hz, 2H), 1.68 (brd, 2H), 1.60 (m, 1H), 1.20 (m, 2H), 0.94 (d, J=6.3 Hz, 3H). MS: 451 (M+1).

Step 4

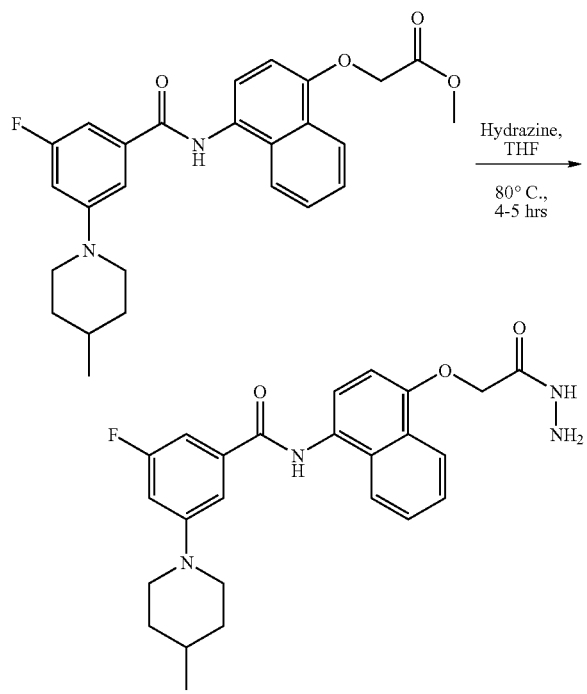

3-Fluoro-N-(4-hydrazinocarbonylmethoxy-naphthalen-1-yl)-5-(4-methylpiperidin-1-yl)-benzamide. {4-[3-Fluoro-5-(4-methylpiperidin-1-yl)-benzoylamino]-naphthalen-1-yloxy}-acetic acid methyl ester (0.40 g, 0.88 mmol) in a solution of 1M hydrazine in tetrahydrofuran (10 ml) is heated at 80° C. for five hours. After cooling to room temperature the mixture is evaporated to dryness to give 3-fluoro-N-(4-hydrazinocarbonylmethoxy-naphthalen-1-yl)-5-(4-methylpiperidin-1-yl)-benzamide (0.40 g). MS: 451 (M+1).

General Procedure M

Step 5

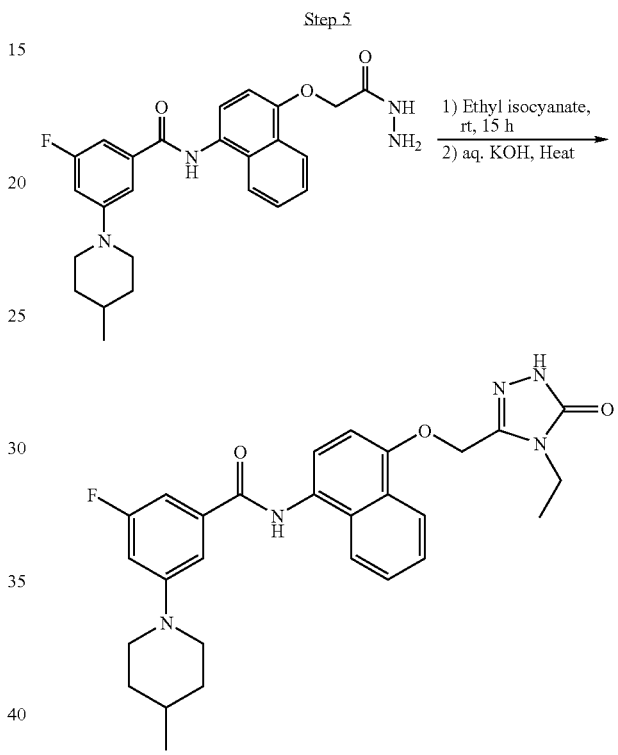

N-[4-(4-Ethyl-5-oxo-4,5-dihydro-1H-[1,2,4]triazol-3-ylmethoxy)-naphthalen-1-yl]-3-fluoro-5-(4-methyl-piperidin-1-yl)-benzamide (Compound B220). To a solution of 3-fluoro-N-(4-hydrazinocarbonylmethoxy-naphthalen-1-yl)-5-(4-methyl-piperidin-1-yl)-benzamide (0.35 g, 0.77 mmol) in tetrahydrofuran (10 ml) is added ethylisocyanate (60 mg, 1.1 eq). The mixture is stirred at room temperature for 15 hours before being evaporated to dryness to give the urea intermediate as a solid (0.34 g). MS: 522 (M+1). Urea intermediate (0.1 g, 0.19 mmol) in 5% NaOH (2 ml) is heated at 100° C. for five hours. The mixture is then extracted with ethyl acetate, washed with water, dried over Na$_2$SO$_4$ and evaporated to dryness. The residue is purified by column chromatography on silica gel eluted with ethyl acetate then ethyl acetate containing a few drops of ammonium hydroxide to give N-[4-(4-ethyl-5-oxo-4,5-dihydro-1H-[1,2,4]triazol-3-ylmethoxy)-naphthalen-1-yl]-3-fluoro-5-(4-methyl-piperidin-1-yl)-benzamide as a white solid (21 mg). Mp: 240-241° C. $^1$H NMR (300 MHz, DMSO-d$_6$) δ 11.88 (s, 1H), 10.27 (s, 1H), 8.16 (d, J=5.1 Hz, 1H), 7.88 (d, J=4.5 Hz, 1H), 7.57-6.95 (m, 7H), 5.27 (s, 2H), 3.78 (m, 4H), 2.77 (t, J=11.4 Hz, 2H) 1.68 (m, 3H), 1.20 (brs, 6H), 0.95 (brs, 3H). MS: 504 (M+1).

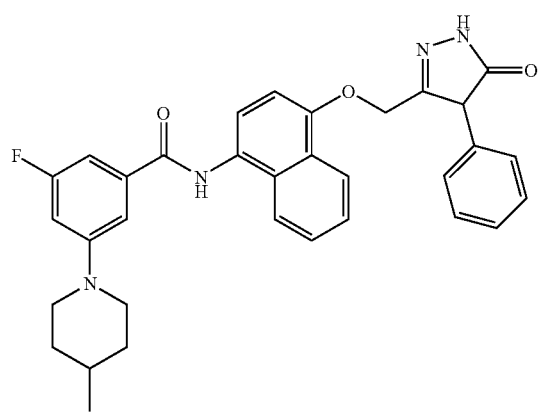

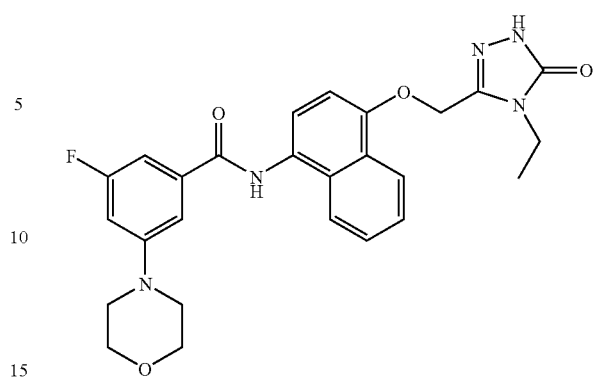

3-Fluoro-5-(4-methyl-piperidin-1-yl)-N-[4-(5-oxo-4-phenyl-4,5-dihydro-1H-[1,2,4]triazol-3-ylmethoxy)-naphthalen-1-yl]benzamide (Compound B263). Compound is prepared from 3-fluoro-N-(4-hydrazinocarbonylmethoxy-naphthalen-1-yl)-5-(4-methyl-piperidin-1-yl)-benzamide and phenylisocyanate according to conditions described in general procedure M. Mp: 140-143° C. $^1$H NMR (300 MHz, DMSO-$d_6$) δ 12.16 (s, 1H), 10.22 (s, 1H), 7.79 (d, J=6.6 Hz, 1H), 7.64 (d, J=6.3 Hz, 1H), 7.81-7.35 (m, 9H), 7.12 (d, J=6.3 Hz, 1H), 7.09 (d, J=6.3 Hz, 1H), 6.96 (d, J=9.3 Hz, 1H), 5.21 (s, 2H), 3.83 (d, J=9.3 Hz, 2H), 2.77 (t, J=9.3 Hz, 2H) 1.69 (d, J=8.4 Hz, 2H), 1.20 (brm, 1H), 1.22 (m, 2H), 0.94 (d, J=4.8 Hz, 3H). MS 552 (M+1).

N-[4-(4-Ethyl-5-oxo-4,5-dihydro-1H-[1,2,4]triazol-3-yl-methoxy)-naphthalen-1-yl]-3-fluoro-5-morpholin-4-yl-benzamide (Compound B255). Compound is prepared from (4-aminonaphthalen-1-yloxy)-acetic acid methyl ester, 3-fluoro-5-(morpholin-1-yl)-benzoic acid and ethylisocyanate according to conditions described in Example 14, Steps 3 and 4 and general procedure M. Mp: 260° C. $^1$H NMR (300 MHz, DMSO-$d_6$) M1.88 (s, 1H), 10.29 (s, 1H), 8.16 (d, J=7.8 Hz, 1H), 7.88 (d, J=7.5 Hz, 1H), 7.57-7.45 (m, 4H), 7.22 (t, J=8.7 Hz, 2H), 7.0 (d, J=11.7 Hz, 1H), 5.28 (s, 2H), 3.74 (brs, 6H), 3.25 (brs, 4H) 1.21 (t, J=6.6 Hz, 3H). MS 492 (M+1).

Additional compounds of the invention can be prepared as described in Example 15.

A representative synthetic scheme is shown in Scheme 11, below.

Scheme 11

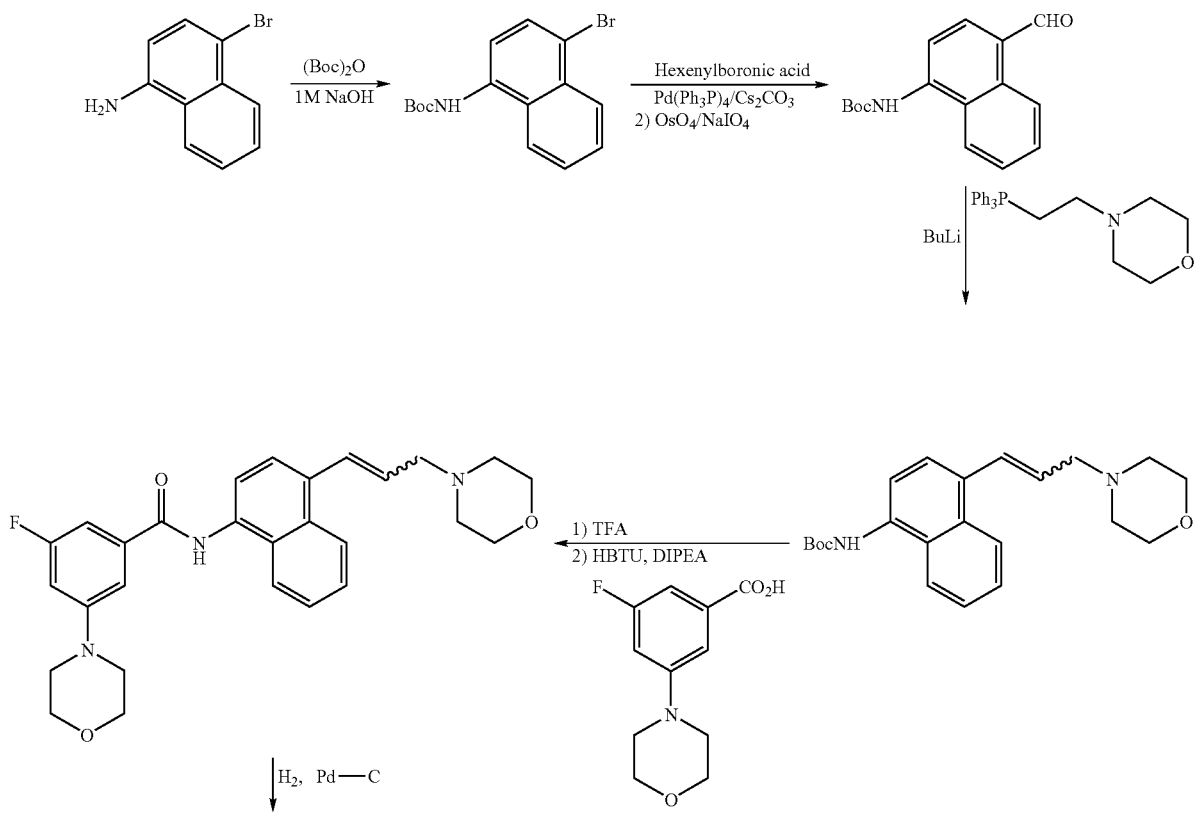

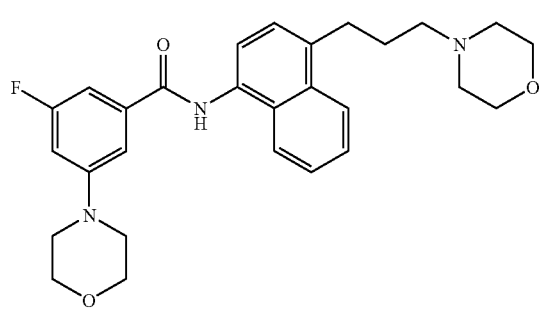

-continued

Example 15

Step 1

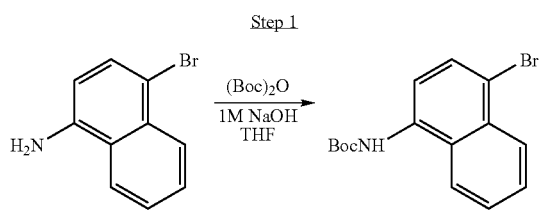

(4-Bromo-naphthalen-1-yl)-carbamic acid tert-butyl ester. 4-Bromo-1-naphthylamine (5.0 g, 22.5 mmol) and ditertbutyldicarbonate (7.4 g, 33.9 mmol) in tetrahydrofuran (75 ml) and 1M sodium hydroxide (75 ml) are stirred at room temperature for 4 days. The mixture is then poured into ethyl acetate (250 ml) and washed with water (300 ml). The ethyl acetate layer is dried over anhydrous sodium sulfate and evaporated to dryness. The residue is purified by column chromatography on silica gel eluted with 10% ethyl acetate in hexanes then recrystalized from ethyl acetate and hexanes to yield (4-bromo-naphthalen-1-yl)-carbamic acid tert-butyl ester (3.669 g).

Step 2

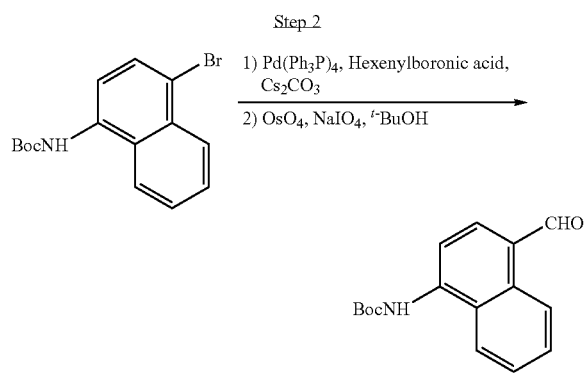

(4-Formyl-naphthalen-1-yl)-carbamic acid tert-butyl ester. 4-Bromo-naphthalen-1-yl)-carbamic acid tert-butyl ester (3.669 g, 11.4 mmol), 1-hexeneylboronic acid (2.18 g, 17.1 mmol), cesium carbonate (7.4 g, 22.8 mmol) and tetrakistriphenylphosphine palladium(0) (50 mg) in dioxane (35 ml) are heated to 100° C. under a nitrogen atmosphere for 24 hours. The mixture is then cooled to room temperature and poured into ethyl acetate (300 ml) and washed with water (2×200 ml). The ethyl acetate layer is dried over anhydrous sodium sulfate and evaporated to dryness. The residue is taken up in dioxane (40 mol), t-butanol (40 ml) and water (10 ml) and osmium tetroxide 2.5%wt in t-butanol (0.1 ml) added. Sodium periodate (10 g) is then added in portions over 15 mins and the mixture allowed to stir at room temperature for 24 hours. The mixture is then poured into ethyl acetate (250 ml) and washed with water (300 ml). The ethyl acetate layer is dried over anhydrous sodium sulfate and evaporated to dryness. The residue is purified by column chromatography on silica gel eluted with 7.5% ethyl acetate in hexanes to give (4-formyl-naphthalen-1-yl)-carbamic acid tert-butyl ester as a light brown solid (923 mg). $^1$H NMR 300 MHz (CDCl$_3$) 10.25(s, 1H), 9.4(d, 1H, J=8.7 Hz), 8.35(d, 1H, J=5.7 Hz), 7.95(d, 1H, J=5.7 Hz), 7.9(d, 1H, J=8.7 Hz), 7.6-7.75(m 2H), 7.3(s, 1H), 1.5(s, 9H).

Step 3

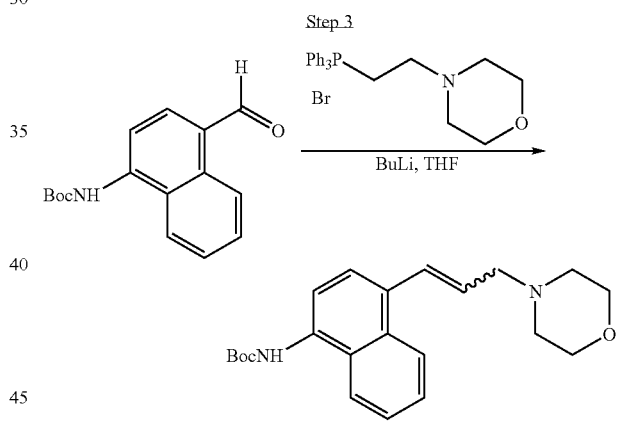

[4-(3-Morpholin-4-yl-propenyl)-naphthalen-1-yl]-carbamic acid tert-butyl ester. To a solution of 2-(morpholin-1-yl)ethyltriphenylphosphonium bromide (3.1 g, 6.8 mmol) in anhydrous tetrahydrofuran (25 ml) at room temperature is added a solution of n-butyl lithium (2.5 M in hexanes) (2.7 ml, 6.8 mmol). After 15 min, a solution of (4-formyl-naphthalen-1-yl)-carbamic acid tert-butyl ester (923 mg, 3.4 mmol) in anhydrous tetrahydrofuran (5 ml) is added dropwise and the resulting mixture stirred at room temperature for 2 days. The mixture is then poured into ethyl acetate (200 ml) and washed with saturated sodium chloride solution (100 ml). The organic layer is dried over anhydrous sodium sulfate and evaporated to dryness. The residue is purified by column chromatography on silica gel eluted with ethyl acetate to give [4-(3-morpholin-4-yl-propenyl)-naphthalen-1-yl]-carbamic acid tert-butyl ester as a white solid (367 mg). $^1$H NMR 300 MHz (CDCl$_3$) 8.1(m, 1H), 7.9(m, 2H), 7.42-7.7(m, 4H), 6.8 (m, 1H), 6.15(m, 0.66H), 6.0(m, 0.33H), 3.8(m, 2.66H), 3.7 (m, 1.33H), 3.25(d, 1.33H, J=5.7 Hz), 3.15(d, 0.66H, J=5.7 Hz), 2.6(s, 2.66H), 2.35(s, 1.33H), 1.5(s, 9H).

Step 4

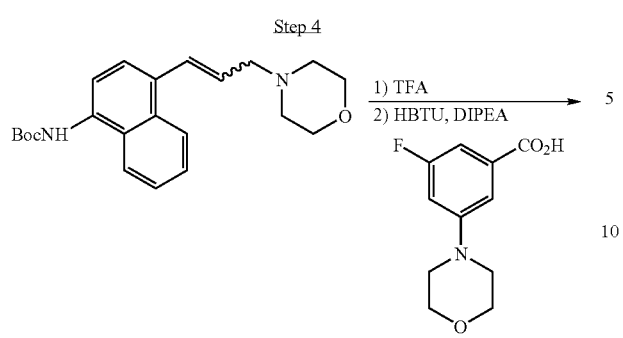
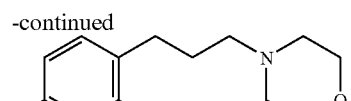

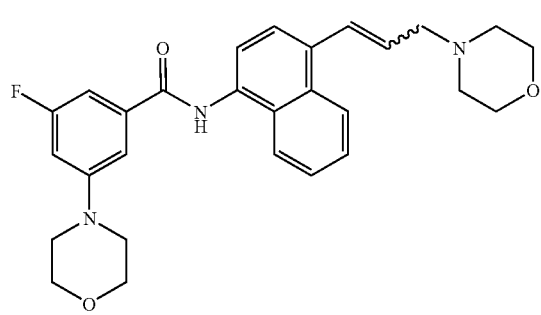

3-Fluoro-5-morpholin-4-yl-N-[4-(3-morpholin-4-yl-propenyl)-naphthalen-1-yl]-benzamide. [4-(3-Morpholin-4-yl-propenyl)-naphthalen-1-yl]-carbamic acid tert-butyl ester (367 mg, 1.0 mmol) is stirred at room temperature in dichloromethane (10 ml) and trifluoroacetic acid (5 ml) for 2 hours. The mixture is then evaporated to dryness. The residue, 3-fluoro-5-morpholinyl benzoic acid (337 mg, 1.5 mmol), HBTU (758 mg, 2.0 mmol) and diisopropylethylamine (0.87 ml, 5.0 mmol) are stirred at room temperature in a mixture of tetrahydrofuran (5 ml) and dimethylformamide (1 ml) for 16 hours. The mixture is then poured into ethyl acetate (100 ml) and washed with water (100 ml). The organic layer is dried over anhydrous sodium sulfate and evaporated to dryness. The residue is purified by column chromatography on silica gel eluted with 50% ethyl acetate in hexanes followed by 2.5% methanol in ethyl acetate to give 3-fluoro-5-morpholin-4-yl-N-[4-(3-morpholin-4-yl-propenyl)-naphthalen-1-yl]-benzamide as a pale yellow oil (56 mg).

Step 5

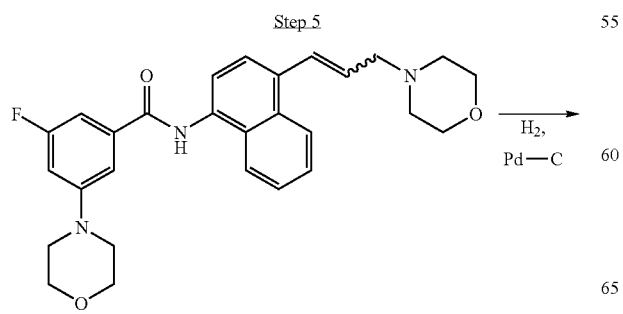

3-Fluoro-5-morpholin-4-yl-N-[4-(3-morpholin-4-yl-propyl)-naphthalen-1-yl]-benzamide (Compound B240). 3-Fluoro-5-morpholin-4-yl-N-[4-(3-morpholin-4-yl-propenyl)-naphthalen-1-yl]-benzamide (56 mg, 117 μmol), is stirred under 1 atmosphere of hydrogen with 10% palladium on carbon (50 mg) in methanol (15 ml) at room temperature for 1 day. Celite° (1 g) is then added and the mixture filtered through a pad of Celite® and washed with methanol (2×10 ml). The filtrate is evaporated to dryness and the purified by column chromatography on silica gel eluted with 5% methanol in ethyl acetate to give 3-fluoro-5-morpholin-4-yl-N-[4-(3-morpholin-4-yl-propyl)-naphthalen-1-yl]-benzamide as a white powder (26 mg). $^1$H NMR 300 MHz (CDCl$_3$) 8.04(d, 1H, J=11.5 Hz), 7.95(s, 1H), 7.7-7.8(m, 2H), 7.5(m, 2H), 7.35(d, 1H, J=8.6 Hz), 7.3(s, 1H), 7.0(d, 1H, J=10.1 Hz), 6.7 (d, 1H, J=13.0 Hz), 3.8(t, 4H, J=5.7 Hz), 3.7(m, 4H), 3.2(m, 4H), 3.1(t, 2H, J=7.2 Hz), 2.45(s, 6H), 1.9(m, 2H).

Additional compounds of the invention can be prepared as described in Example 16.

Example 16

3-Fluoro-5-morpholin-4-yl-N-[4-(2-morpholin-4-yl-ethylamino)-naphthalen-1-yl]-benzamide. N$^4$-(2-morpholin-4-yl-ethyl)-naphthalene-1,4-diamine (190 mg, 701 μmol), 3-fluoro-5-morpholinyl benzoic acid (236 mg, 1.05 mmol), HBTU (531 mg, 1.4 mmol) and diisopropylethylamine (0.37 ml, 2.1 mmol) are stirred at room temperature in dimethylformamide (10 ml) for 12 hours. The mixture is poured into ethyl acetate (100 mL) and washed with water (100 ml). The organic layer is dried over anhydrous sodium sulfate and evaporated to dryness. The residue is purified by column chromatography on silica gel eluted with 5% methanol in ethyl acetate to give 3-fluoro-5-morpholin-4-yl-N-[4-(2-morpholin-4-yl-ethylamino)-naphthalen-1-yl]-benzamide (72 mg). $^1$H NMR 300 MHz (CDCl$_3$) 7.7-8.0(m, 3H), 7.4-7.6 (m, 3H), 7.3(m, 1H), 7.05(m, 1H), 6.7(m, 1H), 6.6(m, 1H), 5.35(m, 1H), 3.65-4.0(m, 8H), 3.2-3.4(m, 6H), 2.8(m, 2H), 2.4-2.55(m, 4H).

Additional compounds of the invention can be prepared as described in Example 17.

A representative synthetic scheme is shown in Scheme 12, below.

[4-(2-Chloro-ethoxy)-naphthalen-1-yl]-carbamic acid tert-butyl ester. N-tert-butyloxycarbonyl-4-amino-1-naphthol (2.0 g, 7.72 mmol), potassium carbonate (5.34 g, 38.6 mmol) and 1-bromo-2-chloroethane (1.28 ml, 15.4 mmol) are heated to 80° C. in anhydrous acetonitrile (40 ml) under a nitrogen atmosphere for 1 day. The mixture is poured into ethyl acetate (250 ml) and washed with water (500 ml). The aqueous layer is re-extracted with ethyl acetate (2×100 ml), the organic layers combined and dried over anhydrous sodium sulfate. The organic layers are evaporated to dryness and the residue purified by column chromatography on silica gel eluted with 20% ethyl acetate in hexanes to give [4-(2-chloro-ethoxy)-naphthalen-1-yl]-carbamic acid tert-butyl ester (1.448 g).

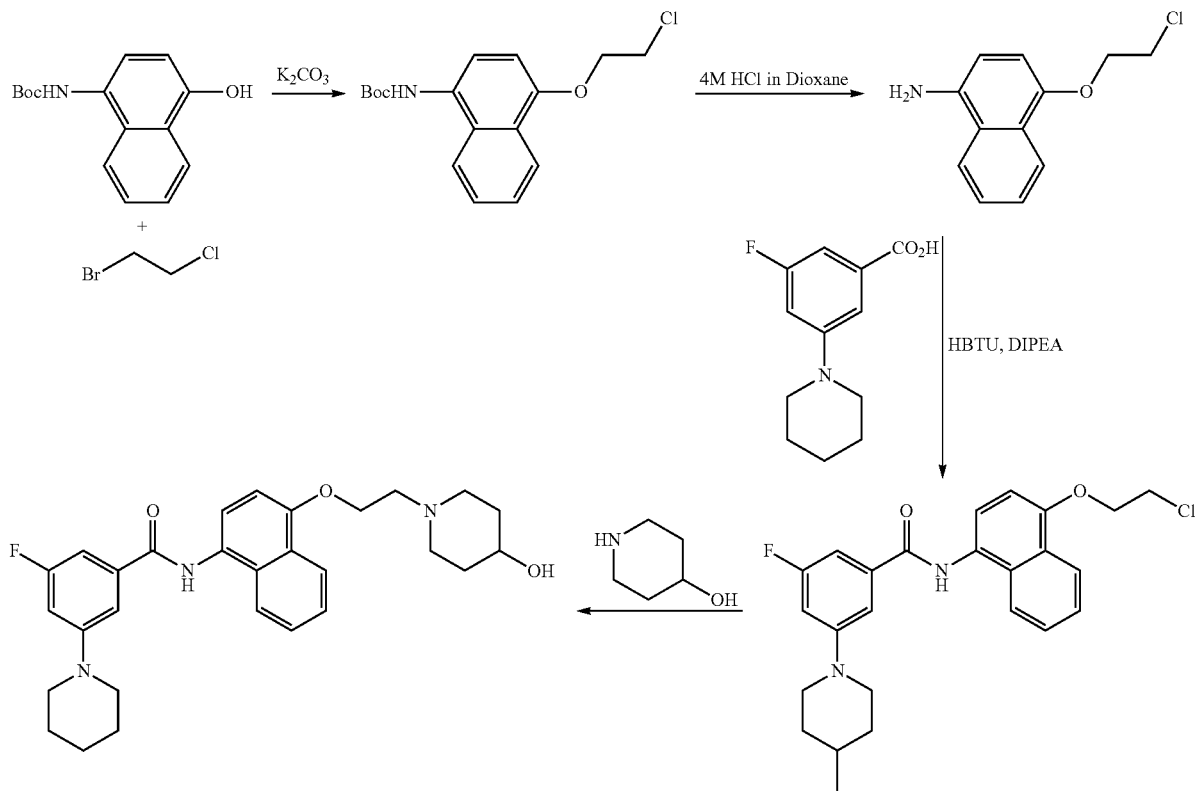

Scheme 12

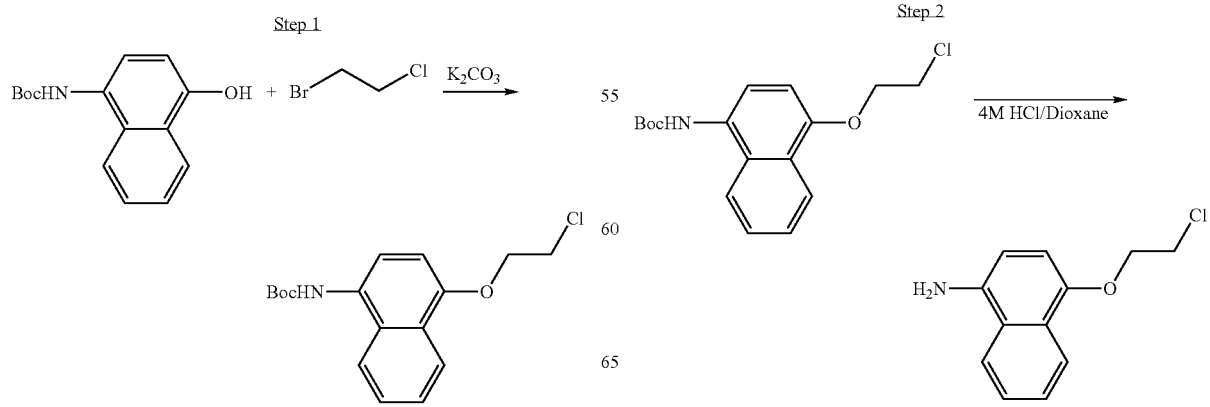

Example 17

4-(2-Chloroethoxy)-naphthalen-1-ylamine hydrochloride salt. To a stirred solution of [4-(2-chloro-ethoxy)-naphthalen-1-yl]-carbamic acid tert-butyl ester (1.387 g, 4.3 mmol) in anhydrous dioxane (10 ml) at room temperature is added a solution of 4M HCl in dioxane (15 ml). After 18 hours diethyl ether (150 ml) is added and 4-(2-chloroethoxy)-naphthalen-1-ylamine hydrochloride salt filtered off as a pink solid (1.081 g).

Step 3

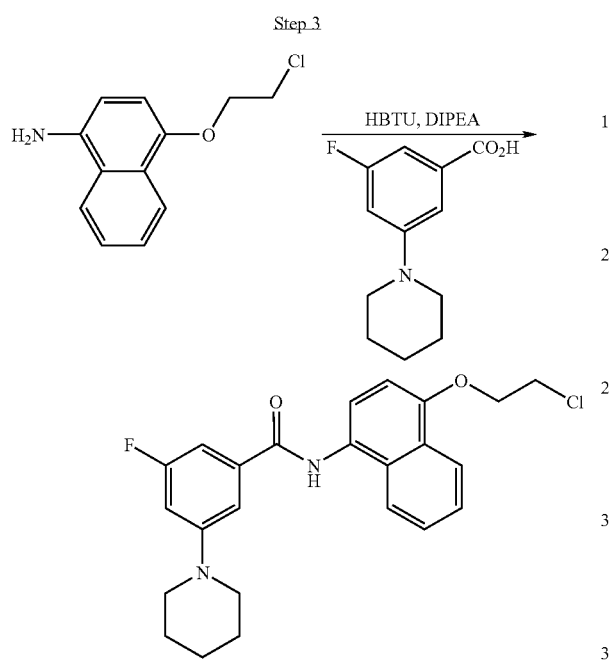

N-[4-(2-Chloroethoxy)-naphthalen-1-yl]-3-fluoro-5-piperidin-1-yl-benzamide. 4-(2-Chloroethoxy)-naphthalen-1-ylamine hydrochloride salt (482 mg, 1.86 mmol), 3-fluoro-5-piperidinylbenzoic acid (500 mg, 2.2 mmol), diisopropylethylamine (1.14 ml, 6.7 mmol) and HBTU (1.06 g, 2.8 mmol) are stirred at room temperature in anhydrous dimethylformamide (10 ml) for 1 day. The mixture is poured into ethyl acetate (200 ml) and washed with water (3×100 ml). The organic layer is dried over anhydrous sodium sulfate and evaporated to dryness. The residue is purified by column chromatography on silica gel eluted with 20% ethyl acetate in hexanes to give N-[4-(2-chloroethoxy)-naphthalen-1-yl]-3-fluoro-5-piperidin-1-yl-benzamide as a tan solid (650 mg).

General Procedure N

Step 4

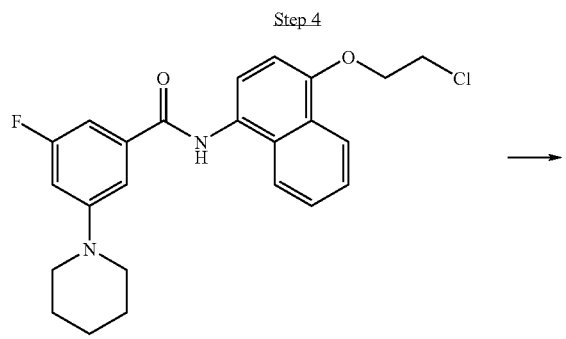

-continued

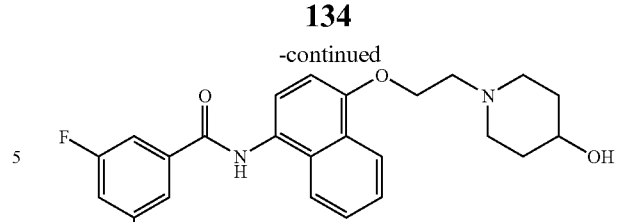

3-Fluoro-N-{4-[2-(4-hydroxypiperidin-1-yl)-ethoxy]-naphthalen-1-yl}-5-piperidin-1-yl-benzamide (Compound B158). N-[4-(2-Chloroethoxy)-naphthalen-1-yl]-3-fluoro-5-piperidin-1-yl-benzamide (100 mg, 234 mmol) and 4-hydroxypiperidine (118 mg, 1.17 mmol) in acetone (3 ml) and dimethylsulfoxide (1 ml) are heated to 180° C. with microwave irradiation for 20 min. After cooling to room temperature the mixture is poured into ethyl acetate (100 ml) and washed with water (100 ml). The organic layer is dried over anhydrous sodium sulfate and evaporated to dryness. The residue is purified by column chromatography on silica gel eluted with ethyl acetate followed by 10% methanol in dichloromethane to give 3-fluoro-N-{4-[2-(4-hydroxypiperidin-1-yl)-ethoxy]-naphthalen-1-yl}-5-piperidin-1-yl-benzamide as a colorless foam (85 mg). $^1$H NMR 300 MHz (CDCl$_3$) 8.31(dd, 1H, J=1.8 and 8.4 Hz), 7.9(s, 1H), 7.83(d, 1H, J=7.2 Hz), 7.71(d, 1H, J=8.4 Hz), 7.53(m, 2H), 7.31(s, 1H), 6.98(d, 1H, J=9 Hz), 6.83(d, 1H, J=8.4 Hz), 6.76(d, 1H, J=12.3 Hz), 4.23(t, 2H, J=5.7 Hz), 3.74(m, 1H), 3.01(s, 4H), 2.98(m, 4H), 2.42(t, 2H, J=9.5 Hz), 1.95(m, 2H), 1.57-1.71 (m, 8H).

N-{4-[2-(1,4-Dioxa-8-aza-spiro[4.5]dec-8-yl)-ethoxy]-naphthalen-1-yl}-3-fluoro-5-piperidin-1-yl-benzamide (Compound B159). Compound is prepared from N-[4-(2-chloroethoxy)-naphthalen-1-yl]-3-fluoro-5-piperidin-1-yl-benzamide and 1,4-dioxa-8-aza-spiro[4.5]decane according to conditions described in general procedure N. $^1$H NMR 300 MHz (CDCl$_3$) 8.32(dd, 1H, J=1.8 and 8.7 Hz), 7.9(s, 1H), 7.83(d, 1H, J=7.8 Hz), 7.73(d, 1H, J=8.4 Hz), 7.53(m, 2H), 7.31(s, 1H), 6.99(d, 1H, J=8.4 Hz), 6.84(d, 1H, J=8.4 Hz), 6.76(d, 1H, J=11.7 Hz), 4.31(t, 2H, J=5.7 Hz), 3.97(s, 4H), 3.28(m, 4H), 3.02(t, 2H, J=6.9 Hz), 2.76(m, 4H), 1.8(t, 4H, J=5.7 Hz), 1.62-1.67(m, 6H).

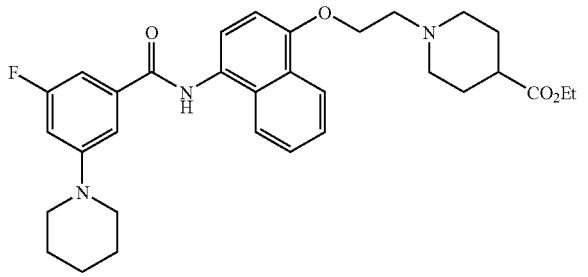

1-{2-[4-(3-Fluoro-5-piperidin-1-yl-benzoylamino)-naphthalen-1-yloxy]-ethyl}-piperidine-4-carboxylic acid ethyl ester (Compound B160). Compound is prepared from N-[4-(2-chloroethoxy)-naphthalen-1-yl]-3-fluoro-5-piperidin-1-yl-benzamide and piperidine-4-carboxylic acid ethyl ester according to conditions described in general procedure N. $^1$H NMR 300 MHz (CDCl$_3$) 8.31(dd, 1H, J=1.2 and 8.4 Hz), 7.88(s, 1H), 7.83(d, 1H, J=7.5 Hz), 7.73(d, 1H, J=8.1 Hz), 7.54(m, 2H), 7.31(s, 1H), 6.98(d, 1H, J=7.8 Hz), 6.84(d, 1H, J=8.4 Hz), 6.76(d, 1H, J=11.7 Hz), 4.31(t, 2H, J=5.7 Hz), 4.14(q, 2H, J=6.9 Hz), 3.28(m, 4H), 3.05(m, 2H), 2.97 (t, 2H, J=5.7 Hz), 2.24-2.32 (m, 3H), 1.64-1.97(m, 10H), 1.25(t, 3H, J=7.5 Hz).

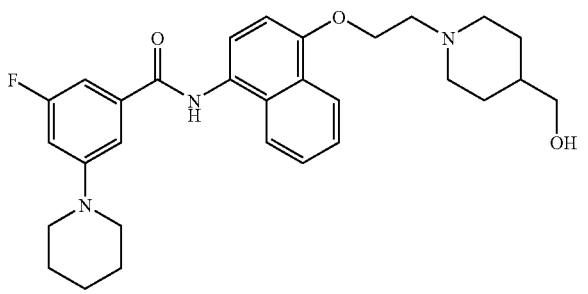

3-Fluoro-N-{4-[2-(4-hydroxymethyl-piperidin-1-yl)-ethoxy]-naphthalen-1-yl}-5-piperidin-1-yl-benzamide (Compound B163). Compound is prepared from N-[4-(2-chloroethoxy)-naphthalen-1-yl]-3-fluoro-5-piperidin-1-yl-benzamide and 4-hydroxymethylpiperidine according to conditions described in general procedure N. $^1$H NMR 300 MHz (CDCl$_3$) 8.32(dd, 1H, J=1.5 and 8.4 Hz), 7.88(s, 1H), 7.83(d, 1H, J=8.4 Hz), 7.73(d, 1H, J=8.1 Hz), 7.54(m, 2H), 7.31(s, 1H), 6.98(d, 1H, J=8.4 Hz), 6.84(d, 1H, J=7.8 Hz), 6.76(d, 1H, J=11.7 Hz), 4.32(t, 2H, J=5.7 Hz), 3.51(d, 2H, J=6.3 Hz), 3.28(m, 4H), 3.1(m, 2H), 2.99 (t, 2H, J=5.7 Hz), 2.23(dt, 2H, J=2.7 and 11.4 Hz), 1.32-1.8(m, 11H).

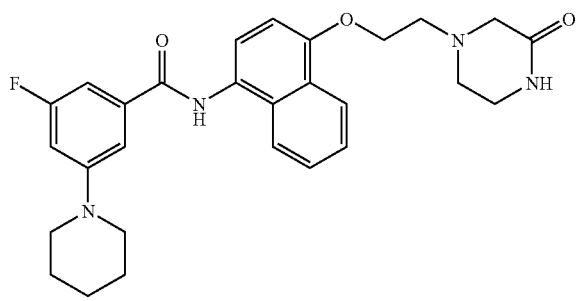

3-Fluoro-N-{4-[2-(3-oxo-piperazin-1-yl)-ethoxy]-naphthalen-1-yl}-5-piperidin-1-yl-benzamide (Compound B164). Compound is prepared from N-[4-(2-chloroethoxy)-naphthalen-1-yl]-3-fluoro-5-piperidin-1-yl-benzamide and 2-piperidinone according to conditions described in general procedure N. $^1$H NMR 300 MHz (CDCl$_3$) 8.31(dd, 1H, J=1.8 and 7.5 Hz), 7.9(s, 1H), 7.84(d, 1H, J=7.5 Hz), 7.74(d, 1H, J=8.7 Hz), 7.54(m, 2H), 7.31(s, 1H), 6.99(d, 1H, J=7.5 Hz), 6.84(d, 1H, J=8.4 Hz), 6.76(d, 1H, J=12.3 Hz), 4.33(t, 2H, J=5.4 Hz), 3.39(m, 4H), 3.28(m, 4H), 3.06 (t, 2H, J=5.4 Hz), 2.91(t, 2H, J=5.7 Hz), 1.58-1.78(m, 6H).

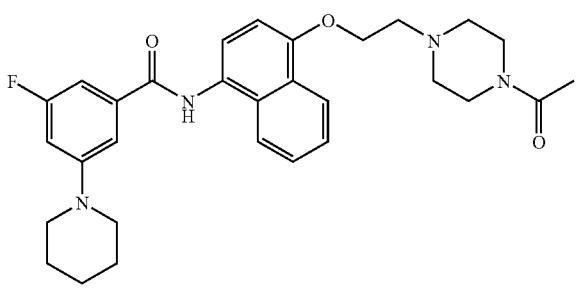

N-{4-[2-(4-Acetyl-piperazin-1-yl)-ethoxy]-naphthalen-1-yl}-3-fluoro-5-piperidin-1-yl-benzamide (Compound B167). Compound is prepared from N-[4-(2-chloroethoxy)-naphthalen-1-yl]-3-fluoro-5-piperidin-1-yl-benzamide and 4-acetylpiperizine according to conditions described in general procedure N. $^1$H NMR 300 MHz (CDCl$_3$) 8.3(dd, 1H, J=1.8 and 8.7 Hz), 7.9(s, 1H), 7.84(d, 1H, J=7.5 Hz), 7.74(d, 1H, J=8.7 Hz), 7.54(m, 2H), 7.31(s, 1H), 6.99(d, 1H, J=7.5 Hz), 6.84(d, 1H, J=8.1 Hz), 6.76(d, 1H, J=11.7 Hz), 4.32(t, 2H, J=5.7 Hz), 3.66(t, 2H, J=5.4), 3.5(t, 2H, J=5.4 Hz), 3.28 (m, 4H), 3.0 (t, 2H, J=5.7 Hz), 2.65(m, 4H), 2.05(s, 3H), 1.62-1.8(m, 6H).

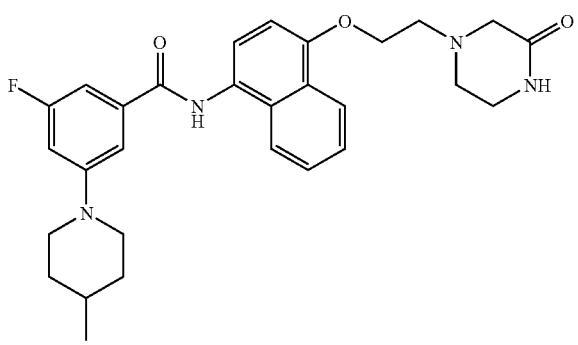

3-Fluoro-5-(4-methyl-piperidin-1-yl)-N-{4-[2-(3-oxo-piperazin-1-yl)-ethoxy]-naphthalen-1-yl}-benzamide (Compound B197). Compound is prepared from 4-(2-chloroethoxy)-naphthalen-1-ylamine hydrochloride salt, 3-fluoro-5-(4-methylpiperidin-1-yl)benzoic acid and 2-piperidinone according to conditions described in Example 17, Step 3 and general procedure N. $^1$H NMR 300 MHz (CDCl$_3$) 8.31(d, 1H, J=8.1 Hz), 7.74-7.9(m, 3H), 7.55(m, 2H), 7.31(s, 1H), 6.97 (m, 1H), 6.84(d, 1H, J=7.5 Hz), 6.77(d, 1H, J=12.3 Hz), 4.33(t, 2H, J=4.8 Hz), 3.77(m, 2H), 3.39(m, 4H), 3.07 (t, 2H, J=4.8 Hz), 2.92(t, 2H, J=5.1 Hz), 2.82(t, 2H, J=13.2 Hz), 1.78(m, 2H), 1.23-1.4(m, 3H).

Additional compounds of the invention can be prepared as described in Example 18.

A representative synthetic scheme is shown in Scheme 13, below.

Scheme 13

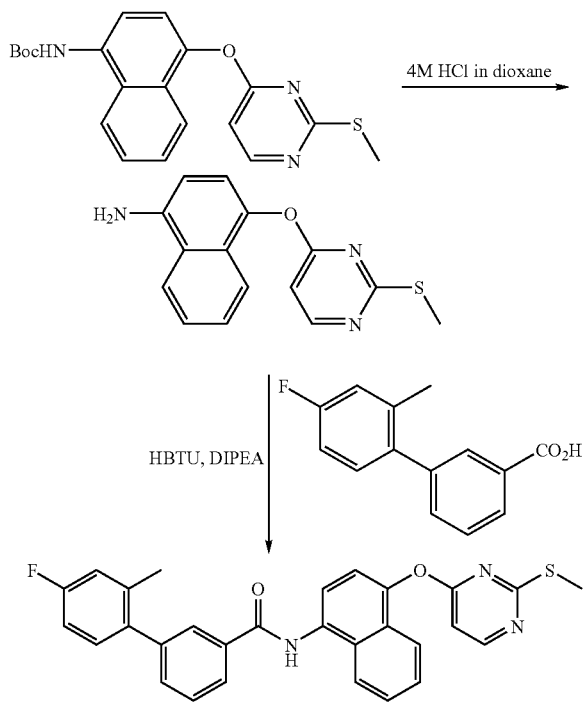

Example 18

Step 1

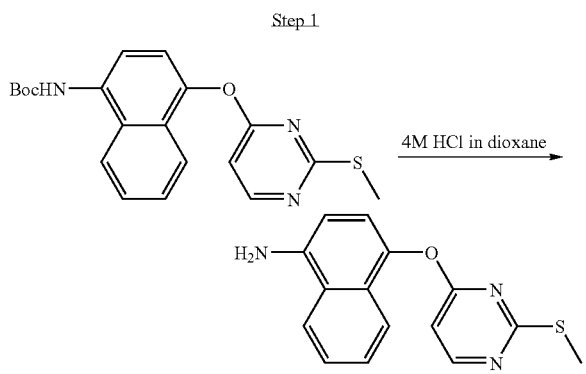

4-(2-Methylsulfanylpyrimidin-4-yloxy)-naphthalen-1-ylamine. To a stirred solution of [4-(2-methylsulfanylpyrimidin-4-yloxy)-naphthalen-1-yl]-carbamic acid tert-butyl ester (1.375 g, 3.6 mmol) in anhydrous dioxane (10 ml) at room temperature is added 4M HCl in dioxane (12 ml, 48 mmol). After 1 day the mixture is evaporated to dryness to give 4-(2-methylsulfanylpyrimidin-4-yloxy)-naphthalen-1-ylamine as a light purple powder (1.547 g).

Step 2

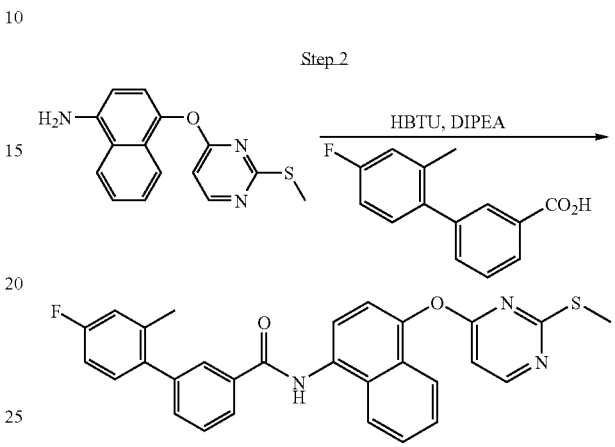

4'-Fluoro-2'-methyl-biphenyl-3-carboxylic acid[4-(2-methylsulfanylpyrimidin-4-yloxy)-naphthalen-1-yl]-amide (Compound B269). 4-(2-Methylsulfanylpyrimidin-4-yloxy)-naphthalen-1-ylamine (320 mg, 1 mmol), 3-(4-fluoro-2-methylphenyl)benzoic acid (230 mg, 1.0 mmol), HBTU (569 mg, 1.5 mmol) and diisopropylethylamine (0.53 ml, 3.0 mmol) are stirred at room temperature in anhydrous dimethylformamide (5 ml) for 1 day. The mixture is then poured into ethyl acetate (100 ml) and washed with water (100 ml). The organic layer is then dried over anhydrous sodium sulfate and evaporated to dryness. The residue is purified by column chromatography on silica gel eluted with 20-30-40% ethyl acetate in hexanes to give product as a pink solid recrystalized from ethyl acetate/hexanes to give 4'-fluoro-2'-methyl-biphenyl-3-carboxylic acid[4-(2-methylsulfanylpyrimidin-4-yloxy)-naphthalen-1-yl]-amide as pink crystals (67 mg). $^1$H NMR 400 MHz (CDCl$_3$) 8.30(d, 1H, J=6 Hz), 8.14(s, 1H), 8.0(d, 1H, J=8 Hz), 7.86-7.92(m, 4H), 7.44-7.56(m, 4H), 7.28(d, 1H, J=8.4), 7.18(m, 1H), 6.9-6.97(m, 2H), 6.46(d, 1H, J=5.6 Hz), 2.23(d, 6H).

Additional compounds of the invention can be prepared as described in Example 19.

A representative synthetic scheme is shown in Scheme 14, below.

Scheme 14

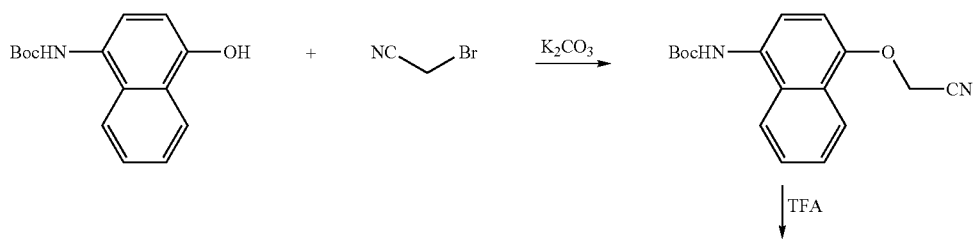

TFA

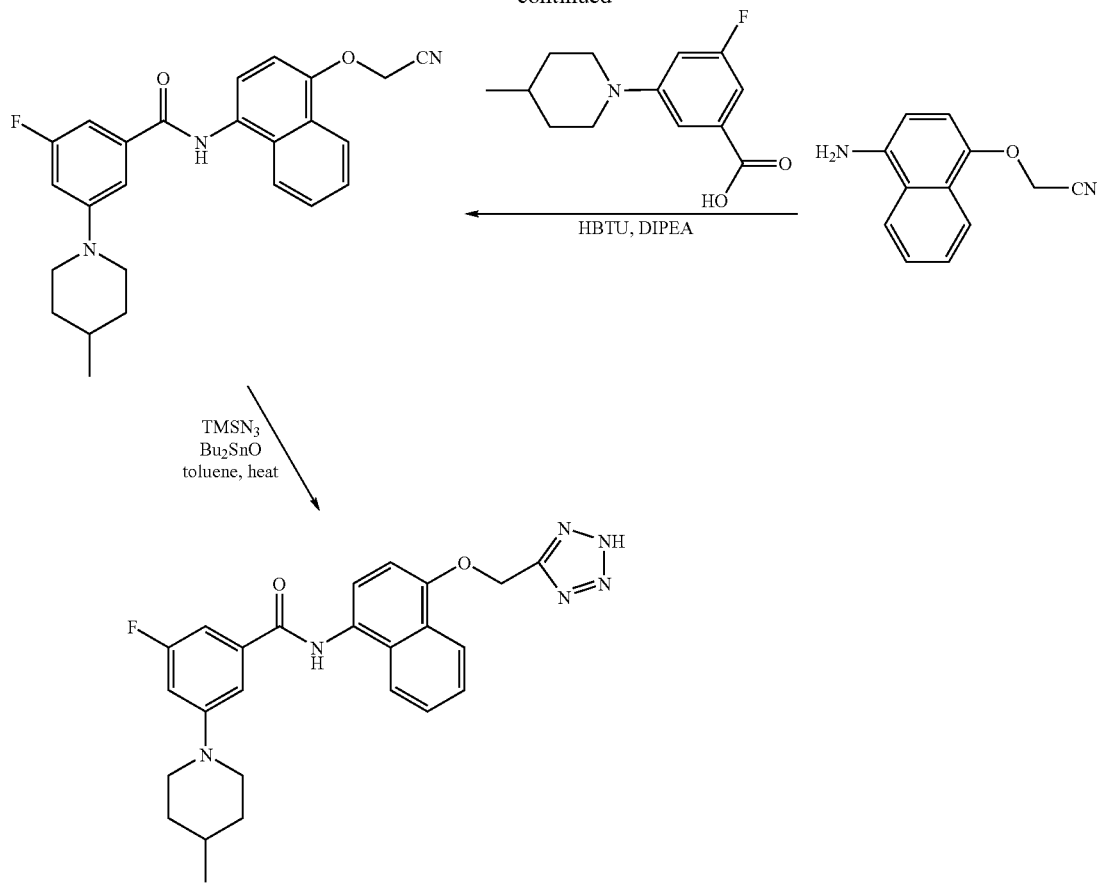

Example 19

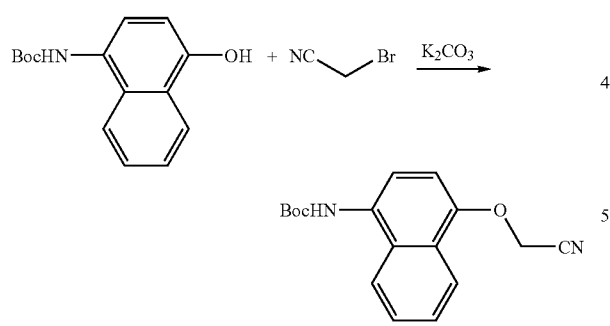

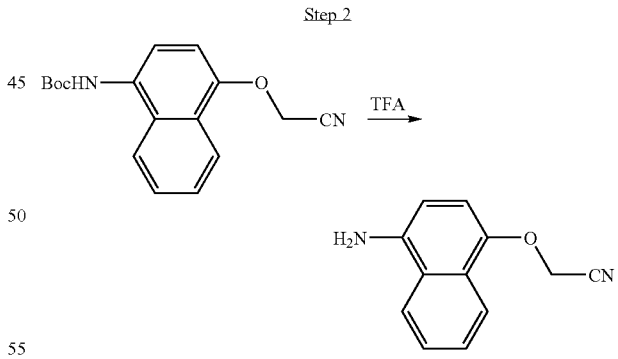

(4-Cyanomethoxynaphthalen-1-yl)-carbamic acid tert-butyl ester. N-tertbutyloxycarbonyl-4-amino-1-naphthol (1.0 g, 3.86 mmol), potassium carbonate (1.06 g, 7.7 mmol) and bromoacetonitrile (0.4 ml, 5.8 mmol) in anhydrous dimethylformamide (10 ml) are stirred at room temperature for 5 hours. The mixture is poured into ethyl acetate (100 ml) and washed with water (2×100 ml). The organic layer is then dried over anhydrous sodium sulfate and evaporated to dryness to give (4-cyanomethoxynaphthalen-1-yl)-carbamic acid tert-butyl ester as a red brown solid (1.132 g). $^1$H NMR 300 MHz (CDCl$_3$) 8.2(d, 1H, J=11.5 Hz), 7.85(d, 1H, J=11.5 Hz), 7.55-7.75(m, 3H), 6.9(d, 1H, J=14 Hz), 6.62(s, 1H), 4.95(s, 2H), 1.5(s, 9H).

(4-Aminonaphthalen-1-yloxy)-acetonitrile. To a stirred solution of (4-cyanomethoxynaphthalen-1-yl)-carbamic acid tert-butyl ester (1.13 g, 3.8 mmol) in anhydrous dichloromethane (15 ml) at room temperature is added trifluoroacetic acid (5 ml). After 4 hours the mixture is poured into ethyl acetate (100 ml) and washed with saturated sodium bicarbonate solution (150 ml). The organic layer is then dried over anhydrous sodium sulfate and evaporated to dryness to give (4-aminonaphthalen-1-yloxy)-acetonitrile as a red brown solid.

Step 3

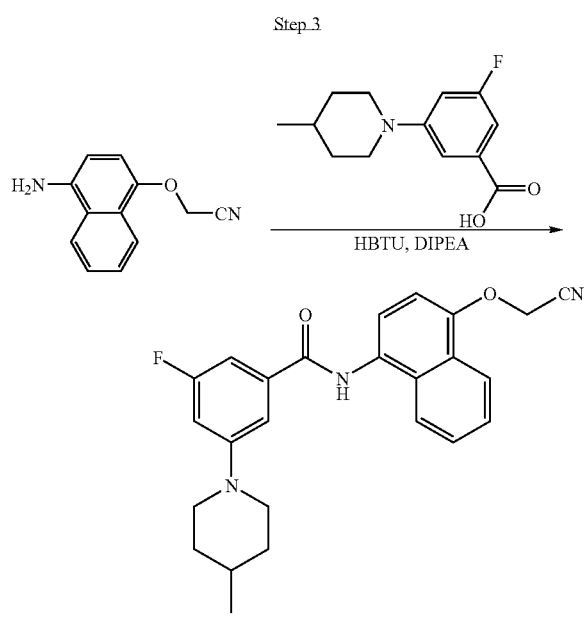

Step 4

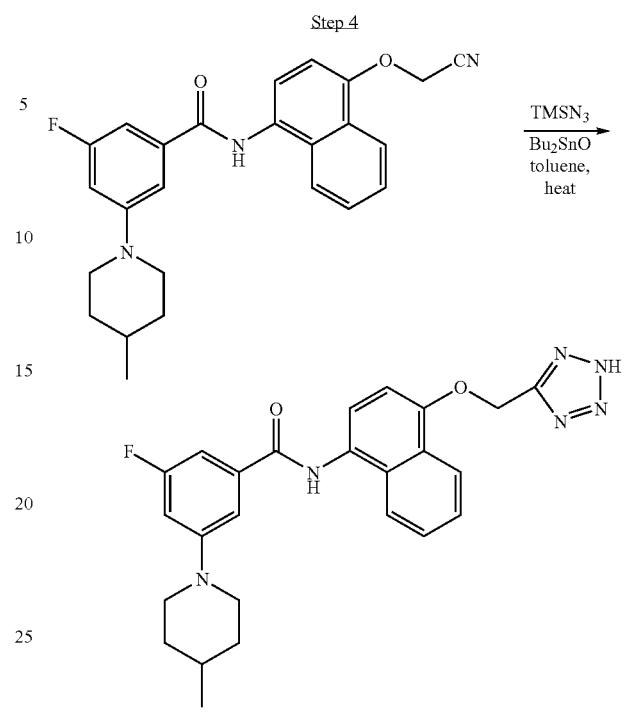

N-(4-Cyanomethoxynaphthalen-1-yl)-3-fluoro-5-(4-methylpiperidin-1-yl)-benzamide (Compound B186). (4-Aminonaphthalen-1-yloxy)-acetonitrile (1.068 g, 5.4 mmol), 3-fluoro-5-(4-methylpiperidin-1-yl)-benzoic acid (1.27 g, 5.4 mmol), diisopropylethylamine (3 ml) and HBTU (2.45 g, 6.5 mmol) are stirred at room temperature in anhydrous dimethylformamide (20 ml) for 1 day. The mixture is then poured into ethyl acetate (200 ml) and washed with water (2×200 ml). The organic layer is then dried over anhydrous sodium sulfate and evaporated to dryness. The residue is purified by column chromatography on silica gel eluted with 25-30% ethyl acetate in hexanes to give a pale purple solid. This is then recrystalized from ethyl acetate/methanol to give N-(4-cyanomethoxynaphthalen-1-yl)-3-fluoro-5-(4-methylpiperidin-1-yl)-benzamide as a pale purple solid (303 mg). $^1$H NMR 300 MHz (CDCl$_3$) 8.27(d, 1H, J=7.5 Hz), 7.94(s, 1H), 7.86(t, 2H, J=9.6 Hz), 7.6(m, 2H), 7.3(s, 1H), 6.97(m, 2H), 6.77(d, 1H, J=11.4 Hz), 5.0(s, 1H), 3.77(m, 2H), 2.83(m, 2H), 1.75 (m, 2H), 1.25-1.4(m, 3H), 1.0(d, 3H).

3-Fluoro-5-(4-methylpiperidin-1-yl)-N-[4-(2H-tetrazol-5-ylmethoxy)-naphthalen-1-yl]-benzamide (Compound B193). N-(4-Cyanomethoxynaphthalen-1-yl)-3-fluoro-5-(4-methylpiperidin-1-yl)-benzamide (54 mg, 129 mmol), trimethylsilylazide (0.1 ml, 760 mmol) and dibutyltin oxide (5 mg) are heated to reflux in anhydrous toluene (3 ml) for 5 hours. After cooling to room temperature methanol (5 ml) is then added and the mixture stirred at room temperature for 30 min. The mixture is then evaporated to dryness and the residue recrystalized from ethyl acetate/hexanes to give 3-fluoro-5-(4-methylpiperidin-1-yl)-N-[4-(2H-tetrazol-5-ylmethoxy)-naphthalen-1-yl]-benzamide as a grey powder (22 mg). $^1$H NMR 300 MHz (DMSO-d6) 10.3(s, 1H), 8.32(dd, 1H, J=8.7 and 2.7 Hz), 7.87(d, 1H, J=9.3 Hz), 7.54-7.62(m, 2H), 7.42-7.5(m, 2H), 7.17(dd, 1H, J=15.9 and 9.3 Hz), 6.97 (d, 1H, J=13.2 Hz), 5.7(s, 2H), 3.85(d, 2H, J=19.8 Hz), 2.77 (m, 2H), 1.5-1.78(m, 3H), 1.25(m, 2H), 0.95(d, 3H, J=6.6 Hz).

Example 20

Scheme 15

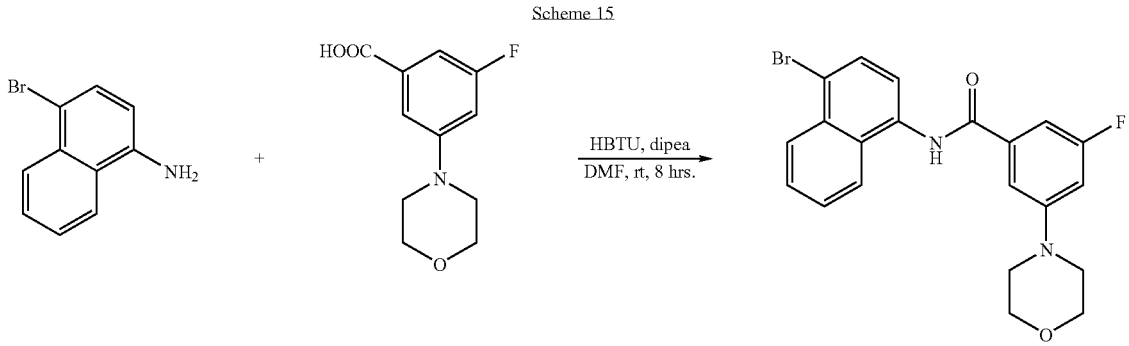

Pd(Ph$_3$)$_4$, Cs$_2$CO$_3$
Hexenyl boronic acid

143
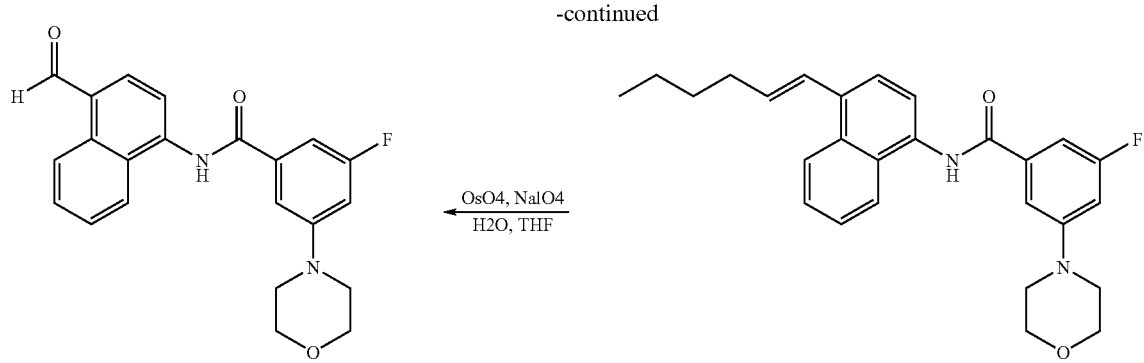
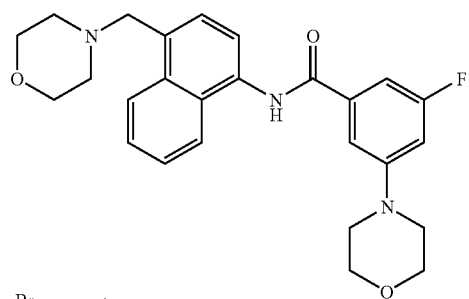
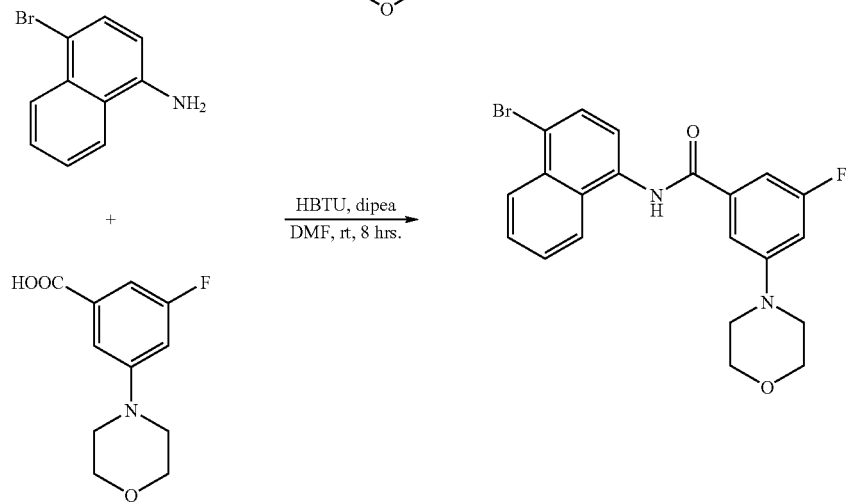
144
-continued
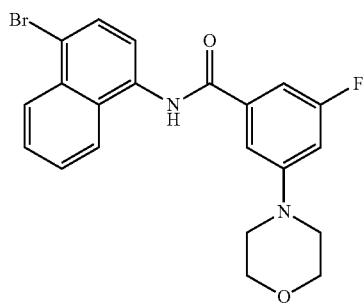
Step 1
-continued
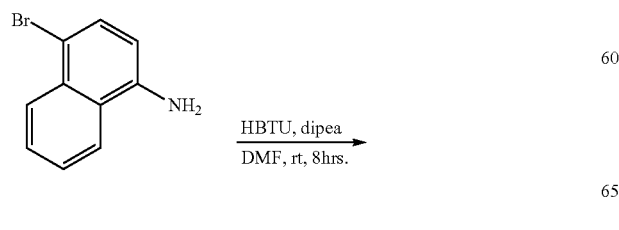

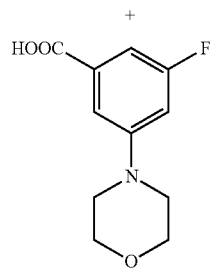

N-(4-Bromo-naphthalen-1-yl)-3-fluoro-5-morpholin-4-yl-benzamide. 3-Fluoro-5-morpholin-4-yl-benzoic acid (4.45 g, 19.8 mmol) and HBTU (8.19 g, 21.6 mmol) are stirred at room temperature in dry DMF (40 ml) for 1 hour. 4-Bromo-naphthalen-1-ylamine (4.0 g, 18.0 mmol) and diisopropylethylamine (4.8 ml, 27 mmol) are then added and the mixture is stirred at room temperature for 16 hours. The mixture is poured into ethyl acetate (300 ml) and washed with water (250 ml). The organic layer is dried over anhydrous sodium sulfate and evaporated to dryness. The residue is crystallized from ethyl acetate and hexanes to give N-(4-bromo-naphthalen-1-yl)-3-fluoro-5-morpholin-4-yl-benzamide as a pink powder (1.688 g). Mp: 195-6° C. $^1$H NMR 300 MHz (DMSO-$d_6$) δ 10.5(s, 1H), 8.19(d, 1H, J=6 Hz), 8.04(d, 1H, J=8.4 Hz), 7.94(d, 1H, J=8.4 Hz), 7.71(m, 2H), 7.53(d, 1H, J=8.1 Hz), 7.47(s, 1H), 7.25(d, 1H, J=8.4 Hz), 7.05(d, 1H, J=12.3 Hz), 3.76(s, 4H), 3.26(s, 4H). MS: 429 (M+1).

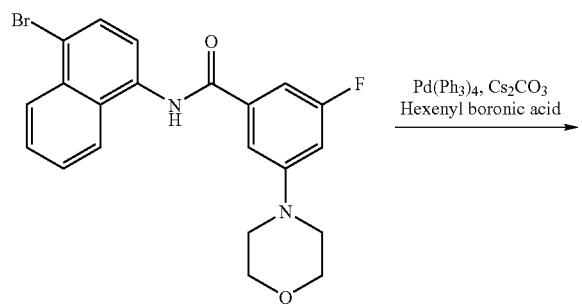

3-Fluoro-N-(4-hex-1-enyl-naphthalen-1-yl)-5-morpholin-4-yl-benzamide. N-(4-Bromo-naphthalen-1-yl)-3-fluoro-5-morpholin-4-yl-benzamide (2.5 g, 5.8 mmol), 1-hexenyl boronic acid (1.06 g, 8.3 mmol), cesium carbonate (3.04 g, 9.34 mmol) and tetrakis triphenylphosphine palladium(0) (100 mg) in dioxane (22 ml) are heated to 100° C. under nitrogen for 24 hours. The mixture is then poured into ethyl acetate (200 ml) and washed with water (2×100 ml). The organic layer is dried over anhydrous sodium sulfate and evaporated to dryness to give 3-fluoro-N-(4-hex-1-enyl-naphthalen-1-yl)-5-morpholin-4-yl-benzamide as a brown solid (2.7 g).

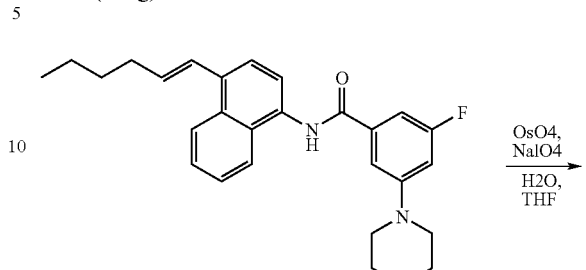

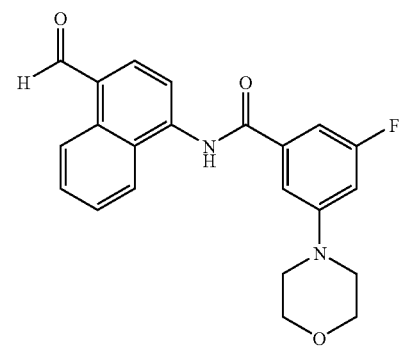

3-Fluoro-N-(4-formyl-naphthalen-1-yl)-5-morpholin-4-yl-benzamide. To a stirred room temperature solution of 3-fluoro-N-(4-hex-1-enyl-naphthalen-1-yl)-5-morpholin-4-yl-benzamide (2.7 g, 6.25 mmol) THF (15 ml) and water (5 ml) is added osmium tetroxide (2.5% in t-butanol) (1000 and sodium periodate (6 g) in portions over 30 minutes. After 1.5 hours, the mixture is diluted with ethyl acetate (200 ml) and washed with water (2×100 ml). The organic layer is dried over anhydrous sodium sulfate and evaporated to dryness. The residue is purified by column chromatography on silica gel eluting with 25-30% ethyl acetate in hexanes to give 3-fluoro-N-(4-formyl-naphthalen-1-yl)-5-morpholin-4-yl-benzamide as a tan powder (1.072 g). Mp: 204-5° C. $^1$H NMR 400 MHz (CDCl$_3$) δ 10.3(s, 1H), 9.41(d, 1H, J=8.8 Hz), 8.47(d, 2H, J=7.6 Hz), 8.02(d, 1H, J=8 Hz), 7.92(d, 1H, J=8.4 Hz), 7.65-7.76(m, 2H), 7.31(s, 1H), 7.05(d, 1H, J=8 Hz), 6.79(d, 1H, J=11.6 Hz), 3.88(t, 4H, J=5.2 Hz), 3.27(t, 4H, J=5.2 Hz). MS: 379 (M+1).

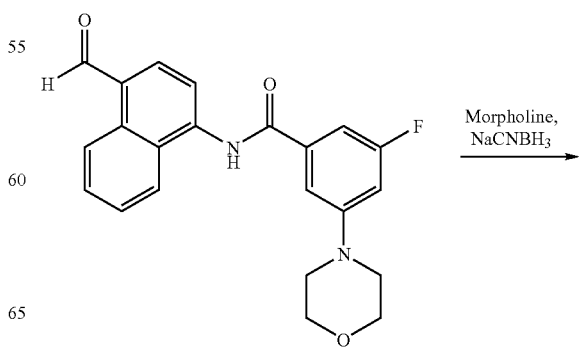

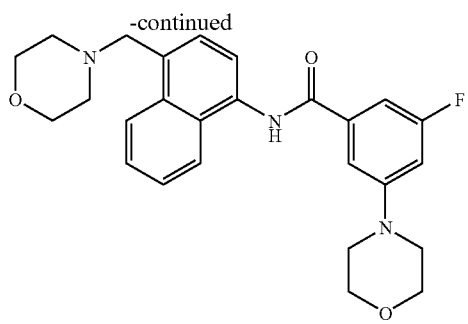

3-Fluoro-5-morpholin-4-yl-N-(4-morpholin-4-ylmethyl-naphthalen-1-yl)-benzamide (Compound B316). 3-Fluoro-N-(4-formyl-naphthalen-1-yl)-5-morpholin-4-yl-benzamide (100 mg, 264 μmol) in morpholine (2.5 ml) is heated to 100° C. for 2.5 hours. Sodium cyanoborohydride (200 mg) is then added and the mixture heated at 100° C. for an additional 2 hours. The mixture is cooled to room temperature poured into ethyl acetate (100 ml), washed with water (2×50 ml) and brine (50 ml). The organic layer is dried over anhydrous sodium sulfate and evaporated to dryness. The residue is purified by column chromatography on silica gel eluting with 70% ethyl acetate in hexanes to give product as a white solid (64 mg). Mp: 192-3° C. $^1$H NMR 400 MHz (CDCl$_3$) δ 8.32(m, 1H), 8.03(s, 1H), 7.83(m, 2H), 7.5(m, 2H), 7.39(d, 1H, J=7.6 Hz), 7.24(s, 1H), 6.98(d, 1H, J=8 Hz), 6.70(d, 1H, J=11.6 Hz), 3.8(m, 6H), 3.62(t, 4H, J=4.4 Hz), 3.19(t, 4H, J=4.8 Hz), 2.45(s, 4H). MS: 450 (M+1).

Example 21

Compounds of the invention are screened for the ability to inhibit ATF2 phosphorylation by p38 MAP Kinase in vitro. The ability of compounds to inhibit ATF2 phosphorylation in this in vitro assay is correlated with the inhibition of p38 MAP Kinase and TNFα expression in vivo, and is therefore an indicator of potential in vivo therapeutic activity (Raingeaud, J., et al, J. Biol. Chem., 270: 7420-7426, 1995, Brinkman, M. N., et al, J. Biol. Chem. 274: 30882-30886, 1999 and Fuchs, S. Y. et al, J. Biol. Chem. 275: 12560-12564, 2000).

Materials: All kinases and the substrate ATF2 are acquired from Upstate Biotechnology Inc. p38 MAP Kinases are recombinant human full-length proteins with an amino-terminal GST fusion, expressed in and purified from E. coli. ATF2 is a GST fusion protein containing amino acids 19-96 of human ATF2 expressed in E. coli. All proteins are aliquoted and stored at −80° C.

Methods: p38 MAP Kinase assays are performed using an assay buffer containing 25 mM HEPES, pH 7.5, 10 mM MgCl$_2$, 2 mM DTT, 20 mM β-glycerophosphate, 0.1 mM Na$_3$VO$_4$, 40 μM ATP and 1.25 μM of ATF2 and in the absence or presence of 1% human serum albumin, Method I and II, respectively, with 0.4-6 ng of protein depending on the kinase used. Compounds are serially diluted in DMSO and 2 μL of test compound at 25× final concentration is used. The vehicle control receives DMSO only. Test compounds are pre-incubated with 20 μl of enzyme in kinase buffer (25 mM HEPES, pH 7.5, 10 mM MgCl$_2$, 2 mM DTT, 20 mM β-glycerophosphate, 0.1 mM Na$_3$VO$_4$ in the absence or presence of 1% human serum albumin, Method I and II, respectively) at room temperature for 15 minutes. Reactions are initiated by addition of 30 μl substrate solution to yield a final concentration of 40 μM ATP and 1.25 μM ATF2 in kinase buffer. The reactions are incubated for 30 minutes at 37° C. and terminated by the addition of 18 μl of 200 mM EDTA. An ELISA method (I or II) is used to measure the phosphorylation of ATF2 at Thr 69. Method I: 96-well high binding plates (Corning 3369) are coated with 50 μl of kinase reaction for 1 hour at 37° C. The coated plates are washed with 200 μl washing buffer (25 mM Tris HCl, pH 8.3, 192 mM glycine, 0.1%SDS and 0.05% Tween-20) three times. The plates are then washed three times with SuperBlock in TBS (Pierce, 37535). After blocking, plates are incubated with 50 μl of rabbit anti-phospho-ATF2 antibody (Cell Signaling, 9221L, 1:500) for 30 minutes at 37° C. Plates are washed three times with washing buffer prior to incubation with 50 μl HRP-conjugated goat anti-rabbit antibody (Cell Signaling, 7074, 1:500) for 30 minutes at 37° C. Plates are then washed three times with washing buffer before incubation with 50 μl of Ultra TMB-ELISA (Pierce, 34028) for 8 minutes at room temperature. Finally, 50 ul of phosphoric acid (1 M) is added to stop reactions and plate absorbance is read at 450 nm on a SpectraMax 250 plate reader. Method II: 96-well high binding plates (Corning 3369) are coated with 400 ng of monoclonal antibody against GST-tag (Cell signaling) in 100 μl containing sodium borate (pH 8.3) for 90 minutes at 37° C. The plates are washed with 200 μl washing buffer (25 mM Tris HCl, pH 7.2, 150 mM NaCl and Tween-20) three times and blocked with 200 μl of 5% nonfat milk for 30 minutes at room temperature. The plates are washed three times with washing buffer, 50 μl of stopped kinase reaction are added to each well and incubated for 80 minutes at 37° C. The plates are washed three times with 200 μl washing buffer, and the plates are incubated with 50 μl of rabbit anti-phospho-ATF2 antibody (Cell Signaling, 9221L, 1:500) for 30 minutes at 37° C. Plates are washed three times with washing buffer prior to incubation with 50 μl HRP-conjugated goat anti-rabbit antibody (Cell Signaling, 7074, 1:500) for 30 minutes at 37° C. Plates are washed three times with washing buffer before incubation with 50 μl of Ultra TMB-ELISA (Pierce, 34028) for 25 minutes at room temperature. Finally, 50 μl of phosphoric acid (1 M) is added to stop reactions and plate absorbance is read at 450 nm on a SpectraMax 250 plate reader.

Results: Results of the p38α assay for certain compounds of the invention are shown in Table 1. It is found that compounds of the invention inhibit the phosphorylation of ATF2 in this in vitro assay. Preferred compounds exhibit IC$_{50}$ values of less than 500 nM, more preferably less than 100 nM, and still more preferably less than 20 nM.

Example 22

Compounds of the invention are screened for the ability to inhibit TNFα and IL-1β release from THP-1 cells stimulated with lipopolysaccharide (LPS) in vitro. The ability of compounds to inhibit TNFα and IL-1β release in this in vitro assay is correlated with the inhibition of p38 activity and TNFα and IL-1β expression in vivo, and is therefore an indicator of potential in vivo therapeutic activity (Lee J. C. et al, Ann. N.Y. Acad. Sci. 696: 149-170, 1993 and Nature, 372: 739-746, 1994).

Materials: THP-1 cells from ATCC (TIB202) are maintained at 37° C., 5% CO$_2$ in RPMI 1640 media (available from MediaTech, Herndon, Va.) containing 4.5 g/L glucose, supplemented with 10% fetal bovine serum, 1% penicillin/streptomycin and 50 μM β-mercaptoethanol.

Methods: Test compounds are initially dissolved in RPMI media with 1% DMSO (v/v). Compounds are then serially diluted in RPMI media for all subsequent dilutions. The assay is performed under sterile conditions. THP-1 cells at a culture density of 6-8×10$^5$ cells/ml are collected and resuspended in the RPMI media at $10^6$ cells/ml containing 10% fetal bovine serum, no serum or 1% human serum albumin (HSA). 100 µl of resuspended cells are added to each well, which contain 100 µl of a test compound. Test compounds are prepared at twice the final concentration. Final DMSO concentration is no more than 0.5% (v/v). Cells are preincubated with compound for 30 minutes at 37° C., 5% $CO_2$ prior to stimulation with lipopolysaccharide (LPS) (Sigma L-2880, 4 mg/ml stock in PBS). The final LPS concentration in each well is 10 or 30 µg/ml for TNFα and IL-1β release, respectively. Unstimulated control cell suspensions receive PBS vehicle only. Cell mixtures are incubated for 18 or 48 hours for TNFα and IL-1β release, respectively. 150 µl of supernatants are taken and transferred to a fresh plate and stored at −20° C. until further analysis. TNFα and IL-1β levels are measured using ELISA kits from Biosource (Catalog no. KHC3012 for TNFα; KAC1192 for IL-1β). A SpectraMAX 250 is used as the plate reader. Analysis is performed by non-linear regression to generate a dose response curve. The calculated $IC_{50}$ value is the concentration of the test compound that causes a 50% decrease in TNFα or IL-1β levels.

Results: Compounds of the invention inhibit the release of TNFα and/or IL-1β release, respectively in this in vitro assay. The TNFα inhibition data for certain compounds of the invention are shown in Table 1. Preferred compounds exhibit $IC_{50}$ values for TNFα and/or IL-1β of less than 1000 nM, more preferably less than 200 nM, still more preferably less than 100 nM, and still more preferably less than 20 nM Example 23

Compounds of the invention are screened for the ability to inhibit the release of TNFα in an in vivo animal model. (See, e.g., Griswold D. E. et al, Drugs Exp. Clin. Res. 19: 243-248, 1993, Badger, A. M. et al, J. Pharmacol. Exp. Ther., 279: 1453-1461, 1996, Dong, C. et al, Annu. Rev. Immunol., 20: 55-72, 2002 (and references cited therein), Ono, K. and Han, J., Cellular Signaling, 12: 1-13, 2000 (and references cited therein) and Griffiths, J. B. et al, Curr. Rheumatol. Rep., 1: 139-148, 1999).

Without being bound by any particular theory, it is believed that inhibition of TNFα in this model is due to inhibition of p38 MAP kinase by the compound.

In Vivo LPS Challenge Study

Male Sprague-Dawley rats (0.2-0.35 kg), female Lewis rats (0.13-0.15 kg) or male Swiss Webster mice (20-25 gm) are randomly divided into groups of six or more and are dosed intravenously by infusion or bolus injection, or are dosed orally with test compounds in a suitable formulation in each case. Thirty minutes following end of infusion or bolus injection, and 1-2 hr following oral administration, lipopolysaccharide *E. coli*/0127:B8 (0.8-2 mg/kg) is administered IV. Blood samples are collected 1.5 hours post-treatment with LPS.

Serum TNFα levels are determined using the ELISA kit from Biosource (KRC3011C) and compared to that from vehicle-treated control.

Results: Preferred compounds of the invention inhibit the release of TNFα in this in vivo assay. Preferred compounds delivered intravenously exhibit an $ED_{50}$ value of less than 30 mg/kg, more preferably less than 10 mg/kg, and still more preferably less than 5 mg/kg. Preferred compounds delivered orally exhibit an $ED_{50}$ value of less than 100 mg/kg, more preferably less than 20 mg/kg, and still more preferably less than 1 mg/kg.

The contents of all references cited herein are hereby incorporated by reference.

Although specific embodiments of this invention have been described herein, it will be understood that these embodiments are merely illustrative of the principles of the invention. Other variations and modifications will be apparent to one of ordinary skill in the art in view of the present teachings without departing from the spirit and scope of the invention.

TABLE 1

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| (structure) | B2 | | >10.0000 | >10.0000 |
| (structure) | B3 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 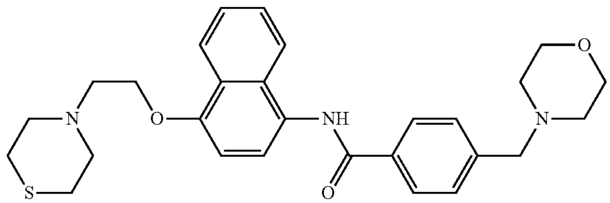 | B4 | | >100.0000 | >10.0000 |
| 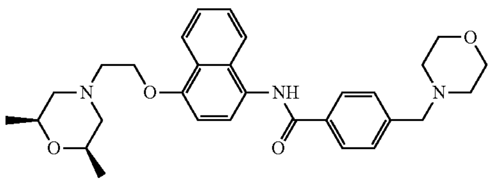 | B5 | | >10.0000 | >10.0000 |
| 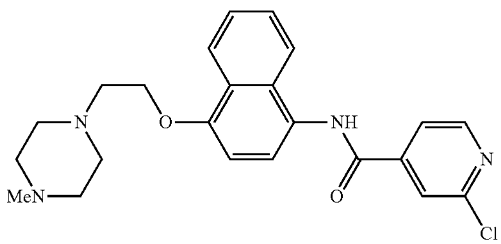 | B6 | 7.5 | | |
| 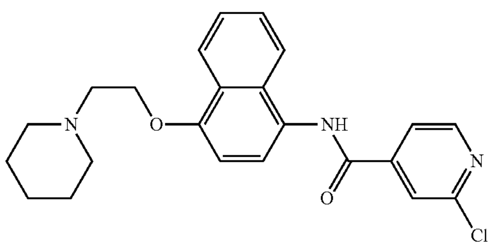 | B7 | 21 | | |
| 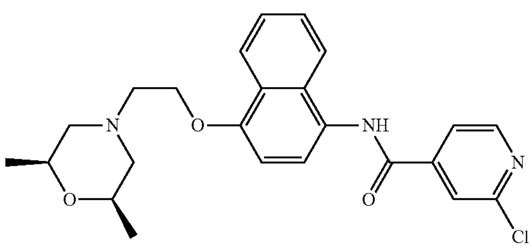 | B8 | 36.5 | | |
| 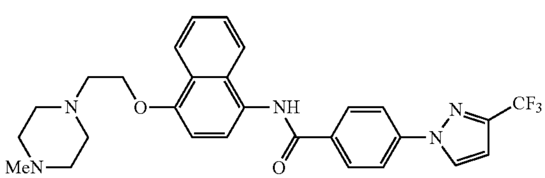 | B9 | 21 | | |
| 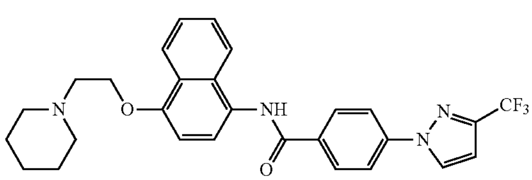 | B10 | 12.5 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
| --- | --- | --- | --- | --- |
| 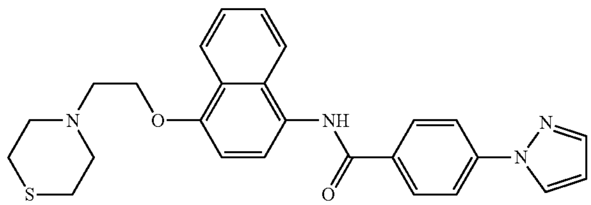 | B11 | 24 | | |
| 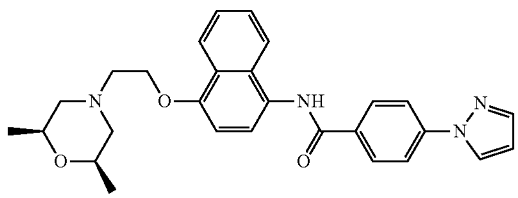 | B12 | 16.5 | | |
| 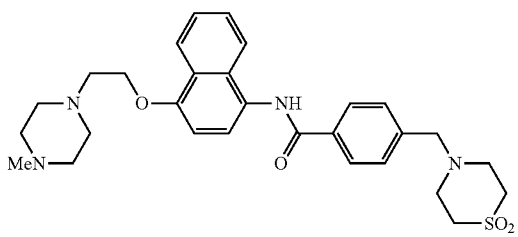 | B13 | 11.5 | | |
| 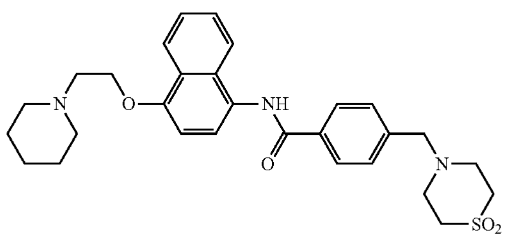 | B14 | 6 | | |
| 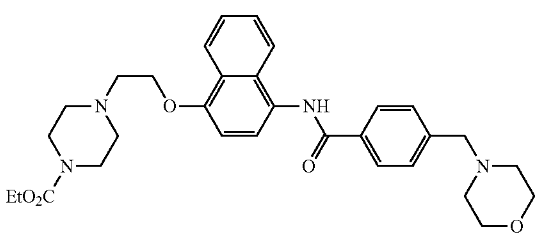 | B15 | 18 | | |
| 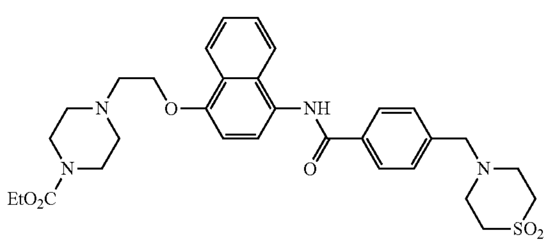 | B16 | 27.5 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 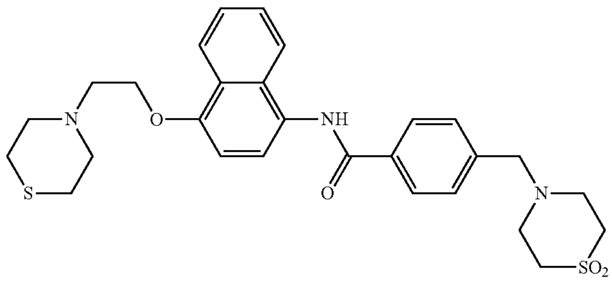 | B17 | 30.5 | | |
| 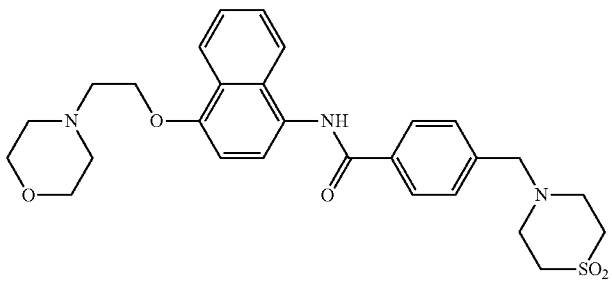 | B18 | 10.5 | | |
| 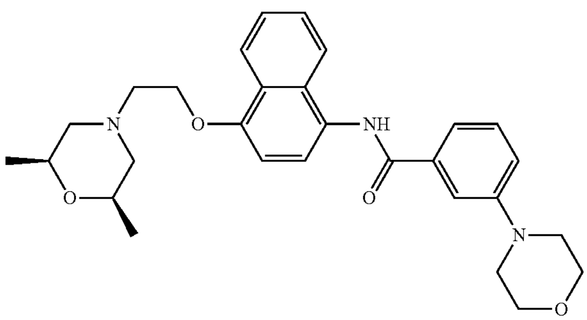 | B19 | 65 | 8.9638 | >10.0000 |
| 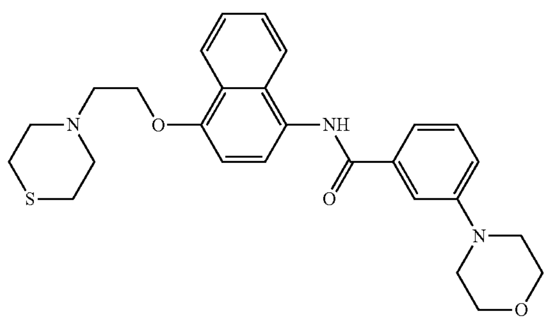 | B20 | 73.5 | 5.5526 | >10.0000 |
| 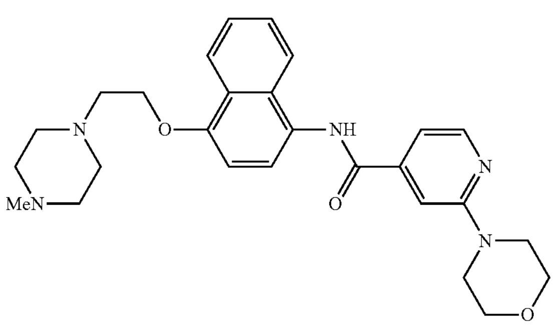 | B21 | 19.5 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 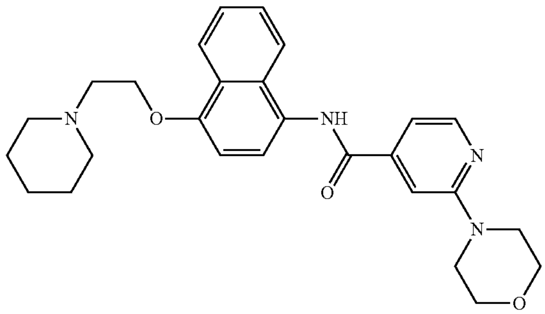 | B22 | 12.5 | | |
| 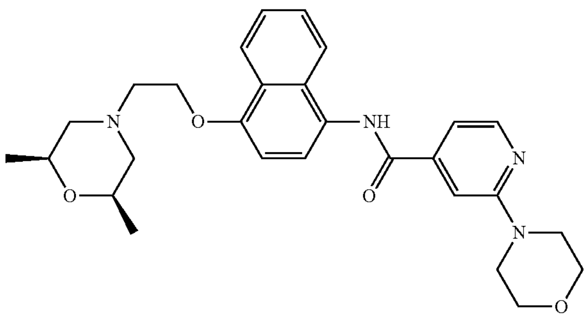 | B23 | 38 | | |
| 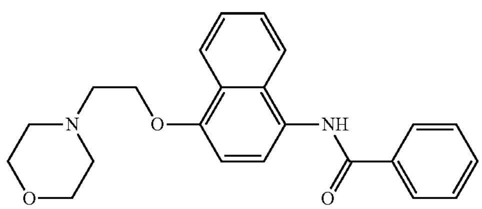 | B26 | | 21.7791 | >10.0000 |
| 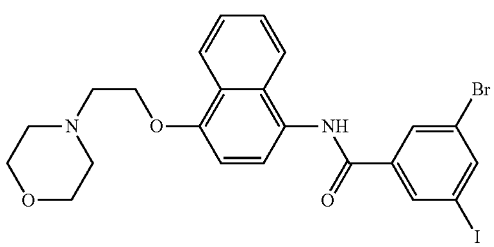 | B27 | | >100.0000 | >10.0000 |
| 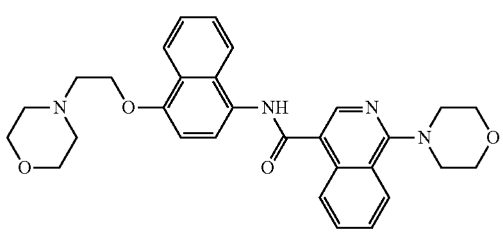 | B28 | | >100.0000 | >10.0000 |
| 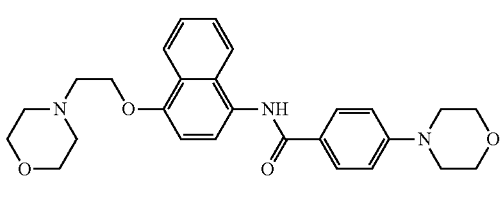 | B29 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 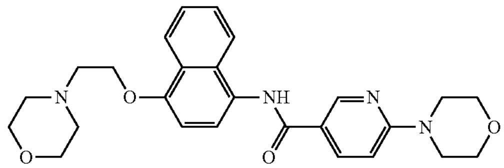 | B30 | | >10.0000 | >10.0000 |
| 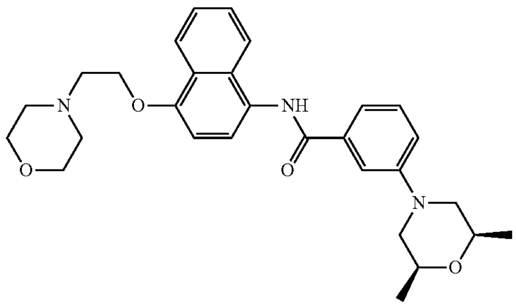 | B31 | | 10.0142 | >10.0000 |
| 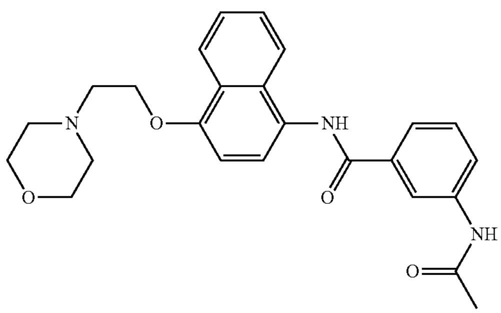 | B32 | | 7.4887 | >10.0000 |
| 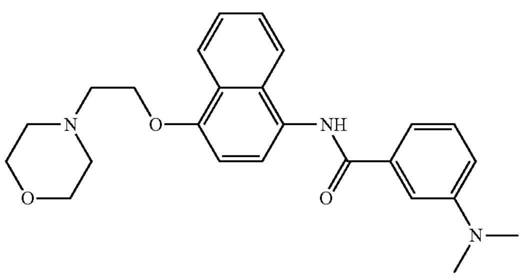 | B33 | | 29.7602 | >10.0000 |
| 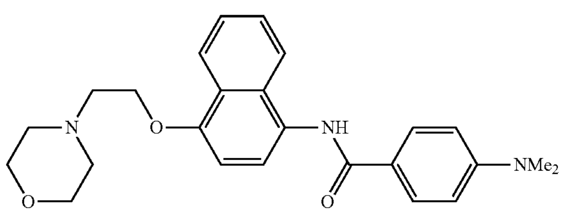 | B34 | | 10.6719 | >10.0000 |
| 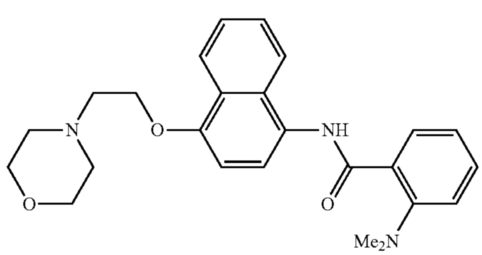 | B35 | | >100.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 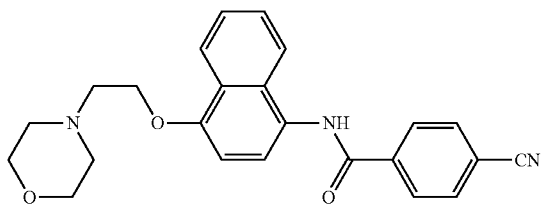 | B36 | | 5.0944 | 6.6185 |
| 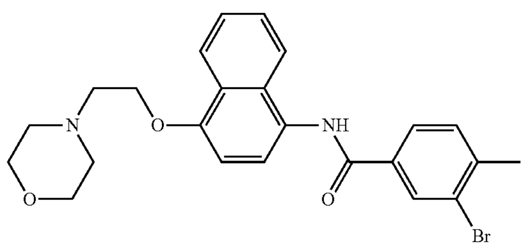 | B37 | | >100.0000 | >10.0000 |
| 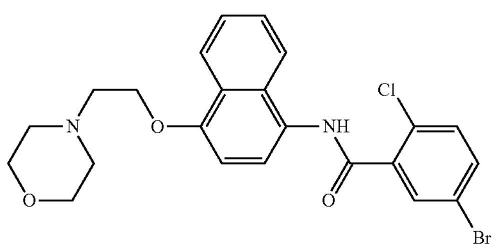 | B38 | | >10.0000 | >10.0000 |
| 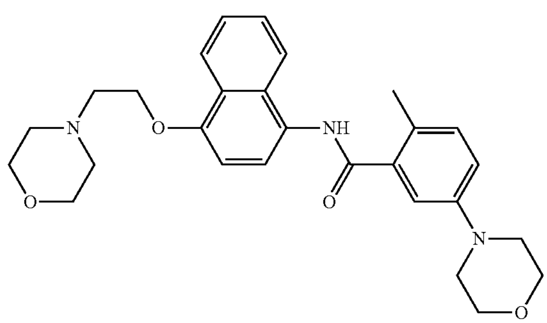 | B39 | | 2.46 | 2.7604 |
| 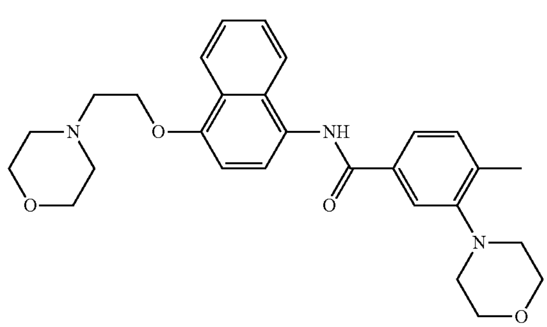 | B40 | | 2.49 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 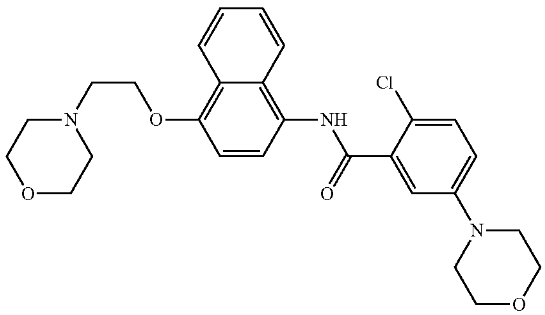 | B41 | | >10.0000, >10.0000 | >10.0000 |
| 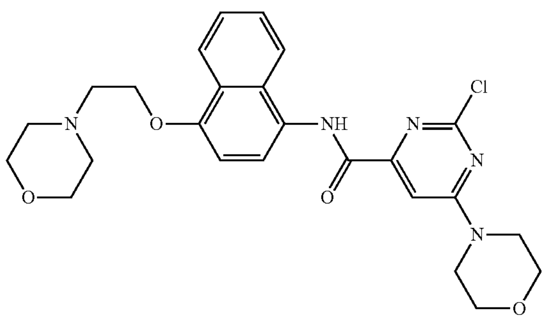 | B42 | | 6.3417 | >1.0000 |
| 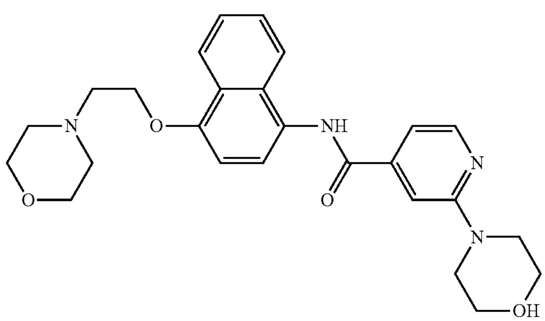 | B43 | | >10.0000 | 2.7234 |
| 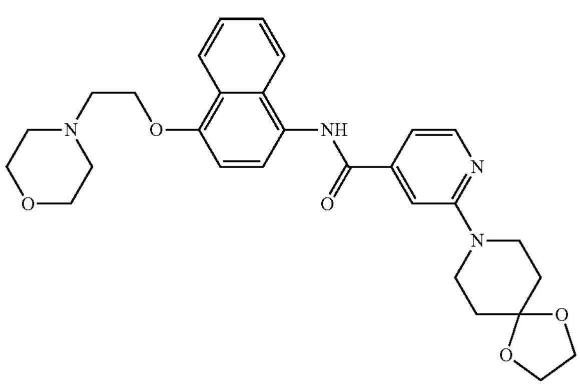 | B44 | | >10.0000 | 1.0075 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 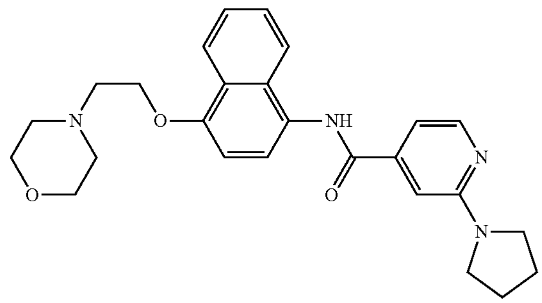 | B45 | | 2.1217 | 1.19 |
| 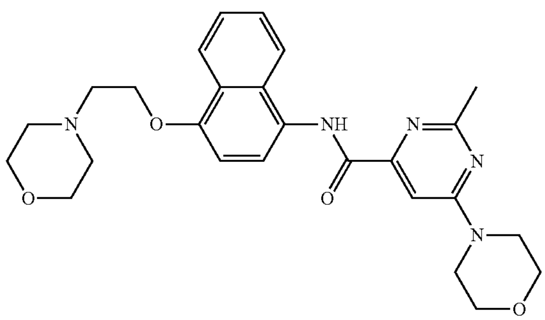 | B46 | | >10.0000, >10.0000, >10.0000 | 0.6849 |
| 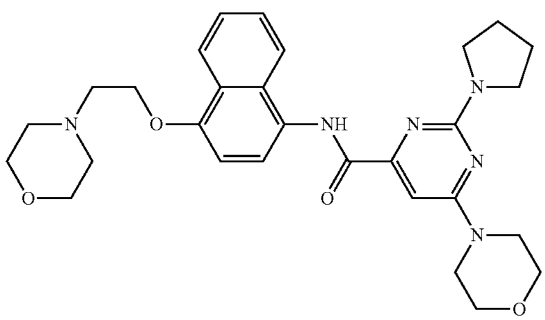 | B47 | | >10.0000, >10.0000, >10.0000 | 0.8425 |
| 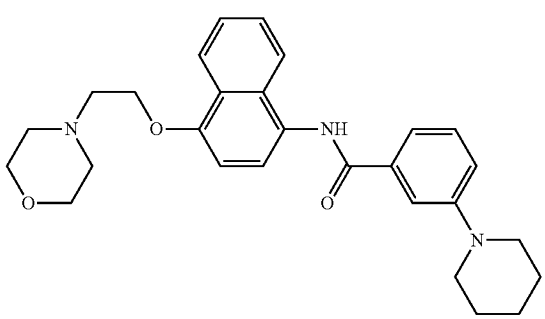 | B48 | | 0.4637 | 7.6495 |
| 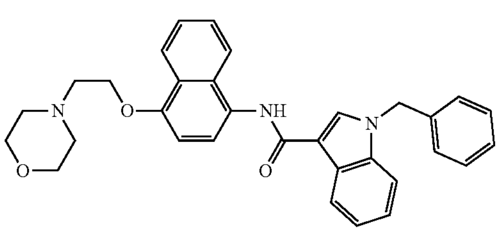 | B49 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 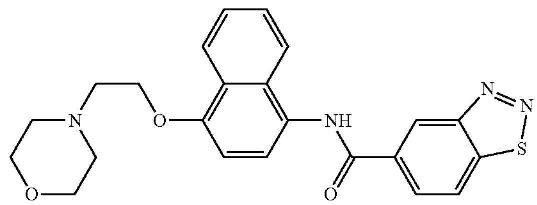 | B50 | | 1.2392 | 9.1791 |
| 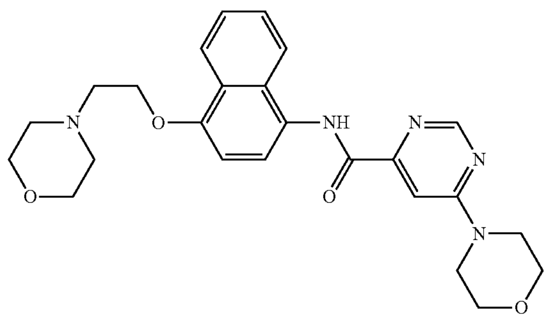 | B54 | | >10.0000 | >10.0000 |
| 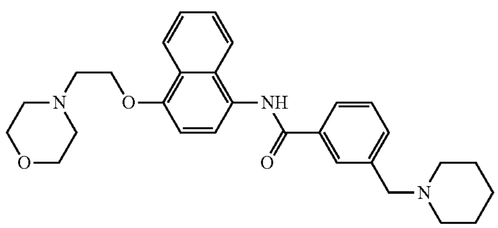 | B55 | | >10.0000 | >10.0000 |
| 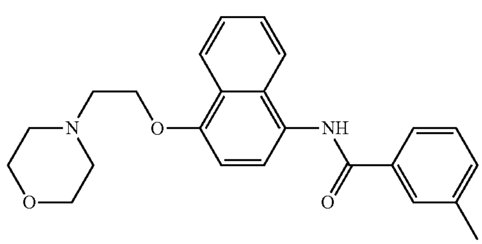 | B56 | | >10.0000 | >10.0000 |
| 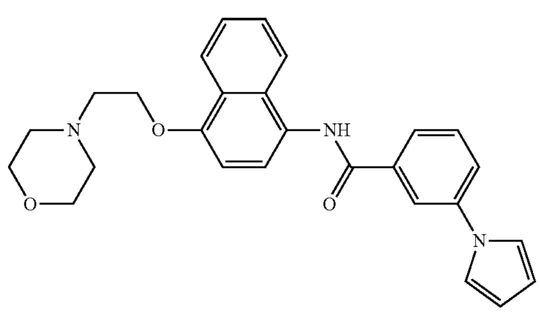 | B57 | | 1.1897 | 2.6522 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 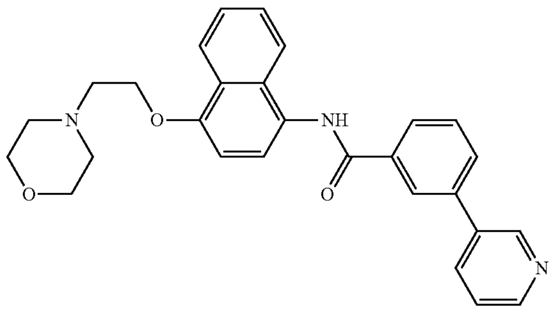 | B58 | | 8.8088 | >10.0000 |
| 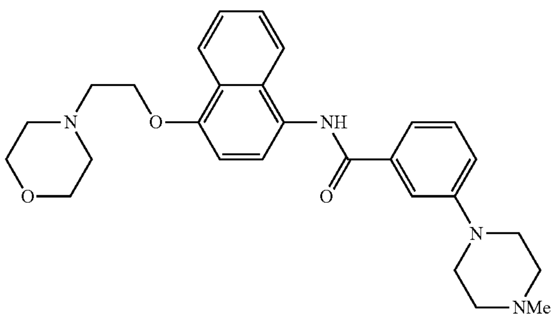 | B59 | | >10.0000 | >10.0000 |
| 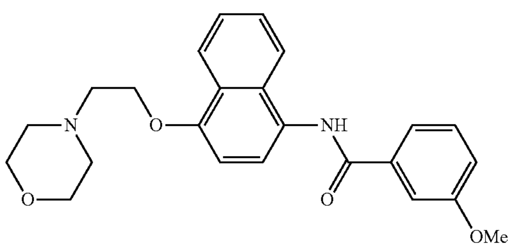 | B60 | | 7.8121 | >10.0000 |
| 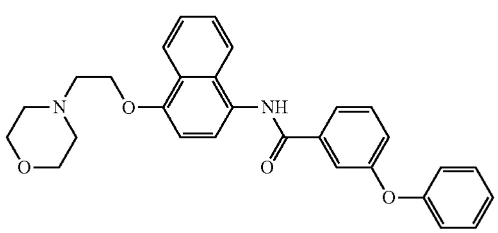 | B61 | | 2.2954 | >10.0000 |
| 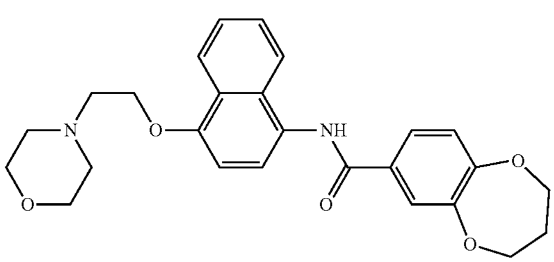 | B62 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 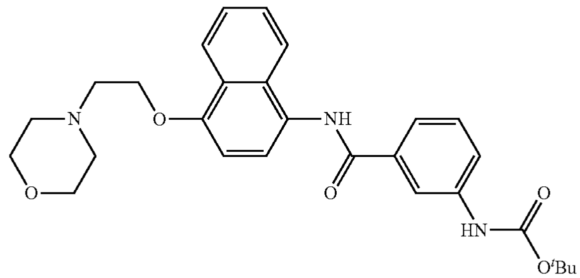 | B63 | | >10.0000 | >10.0000 |
| 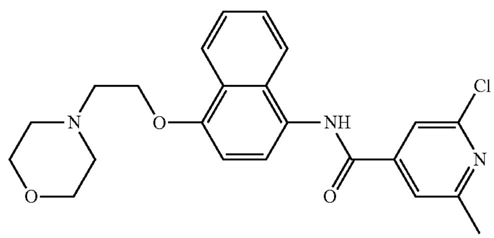 | B64 | 3 | | |
| 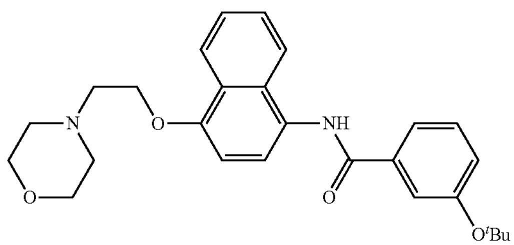 | B65 | | 0.614 | 3.42 |
| 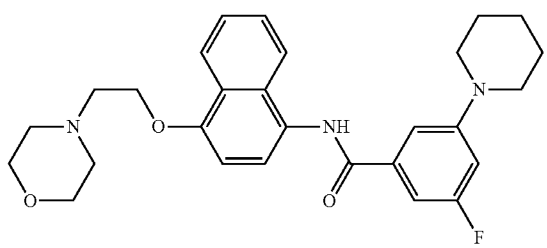 | B66 | | 0.112 | 6.05 |
| 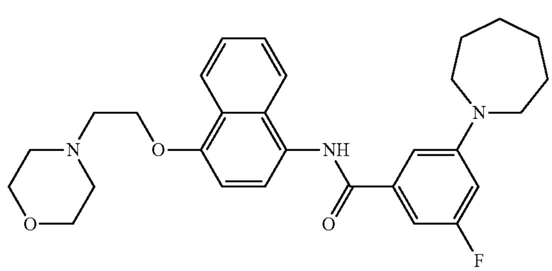 | B67 | 85 | 0.62 | 9.08 |
| 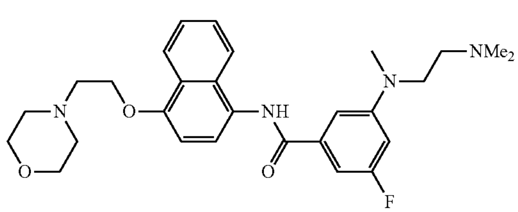 | B68 | 10 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 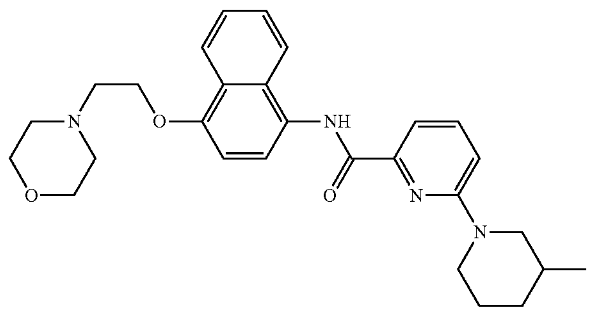 | B69 | 34 | | |
| 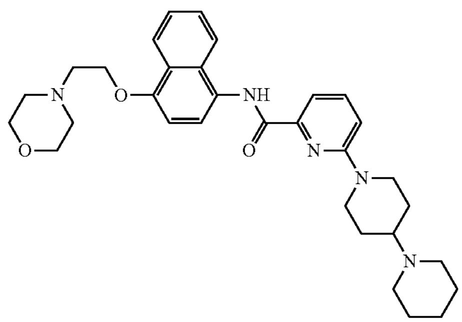 | B70 | 14 | | |
| 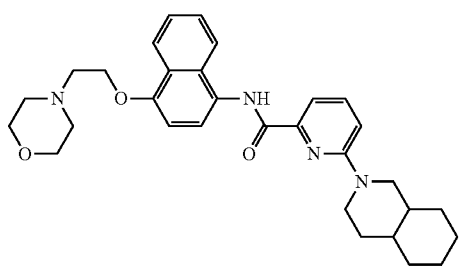 | B71 | | >10.0000 | >10.0000 |
| 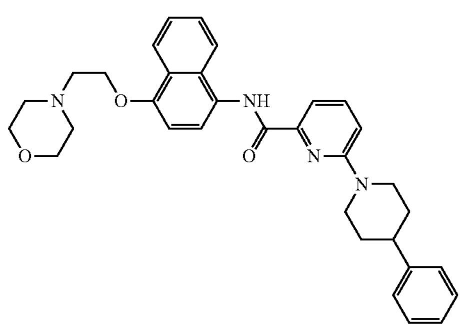 | B72 | 0 | | |
| 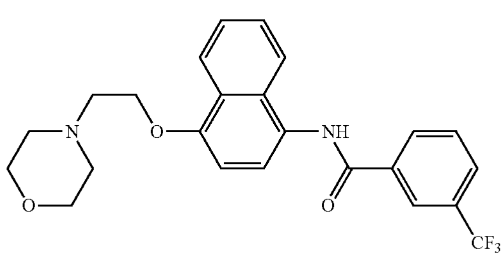 | B73 | 10 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 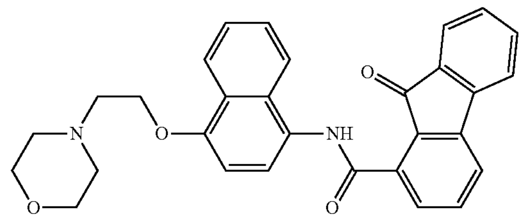 | B74 | 31 | | |
| 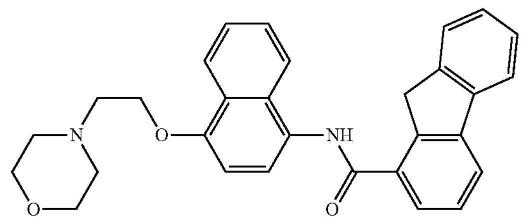 | B75 | 27 | >10.0000 | |
| 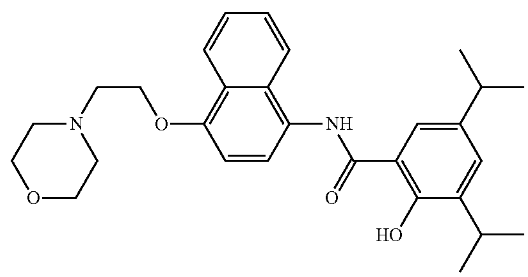 | B76 | 0 | | |
| 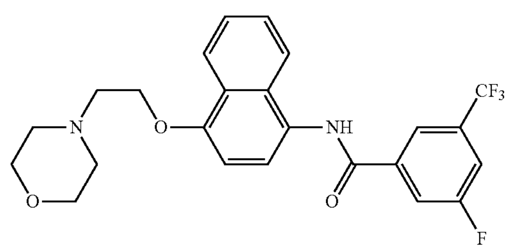 | B77 | 28 | | |
| 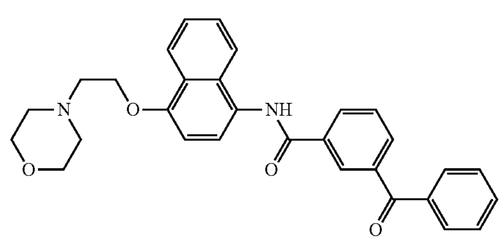 | B78 | 34 | >10.0000 | |
| 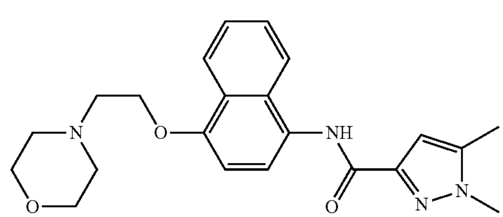 | B79 | 1 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 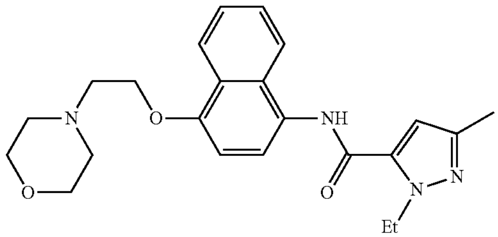 | B80 | 9 | | |
| 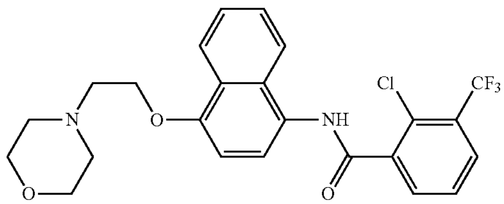 | B81 | 6 | | |
| 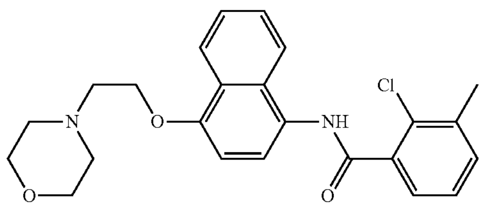 | B82 | 41.3 | | 10.7449 |
| 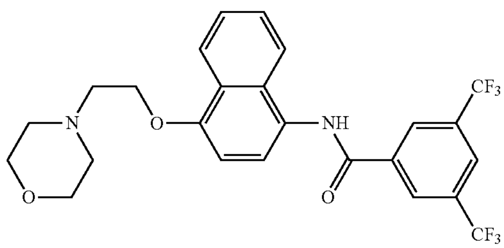 | B83 | 18 | | |
| 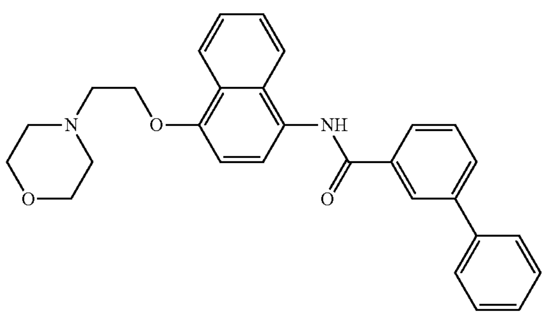 | B84 | 88 | 0.4513 | 2.0329 |
| 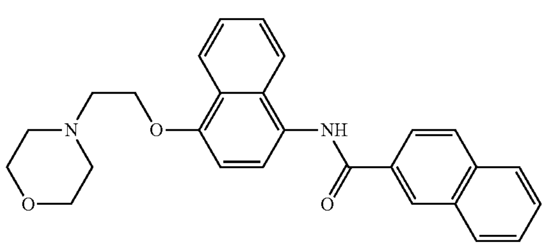 | B85 | 66 | 3.1771 | 4.0289 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 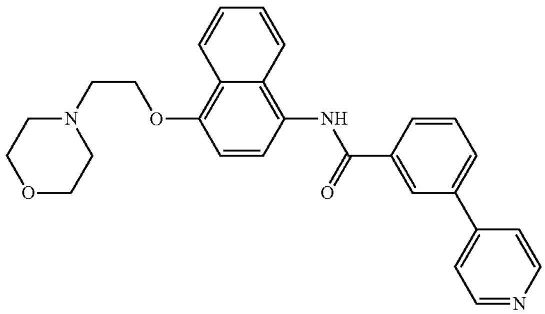 | B86 | 67 | 4.1624 | 2.7131 |
| 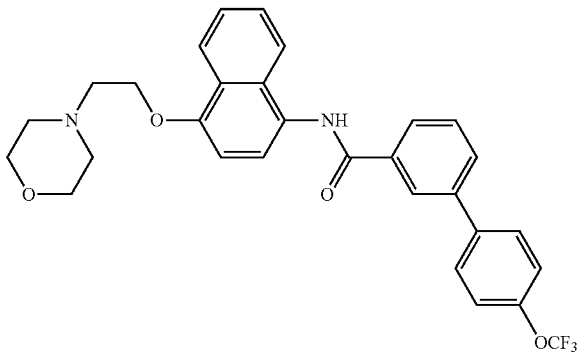 | B87 | 29 | >100.0000 | |
| 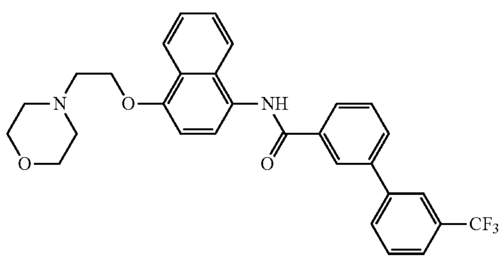 | B88 | 59 | 1.8512 | 3.6048 |
| 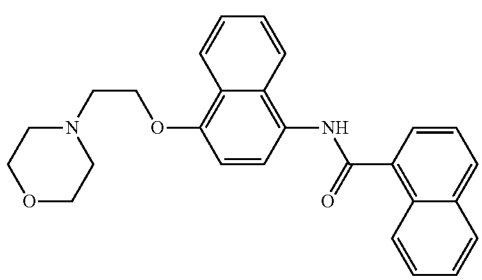 | B89 | 29 | | |
| 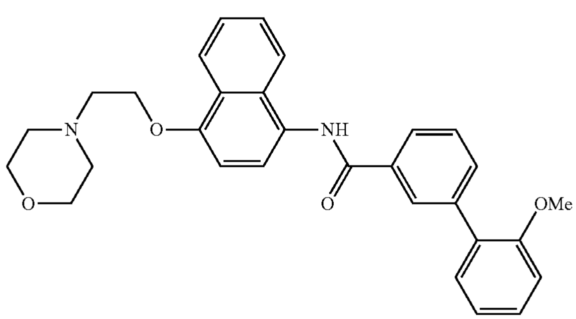 | B90 | 78 | 1.3256 | 5.2509 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 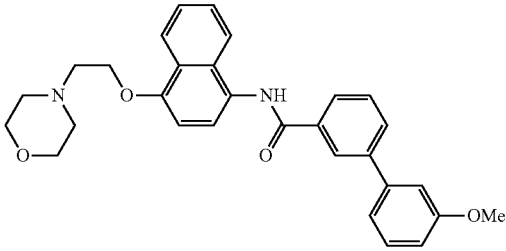 | B91 | 78 | 0.9004 | 3.5527 |
| 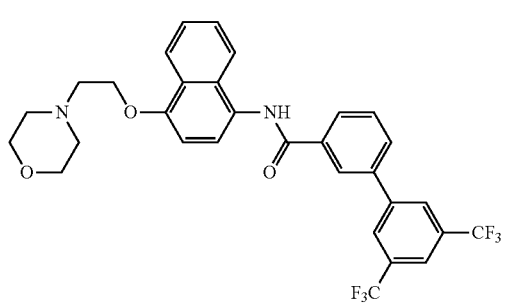 | B92 | 0 | | |
| 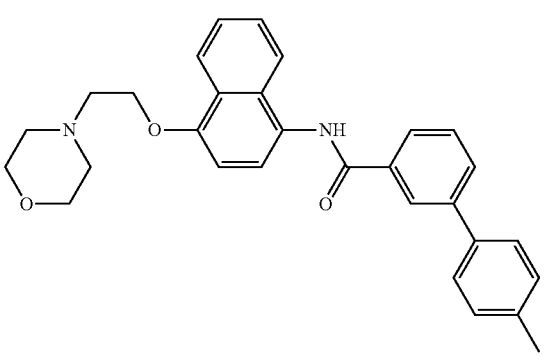 | B93 | 34 | >10.0000 | |
| 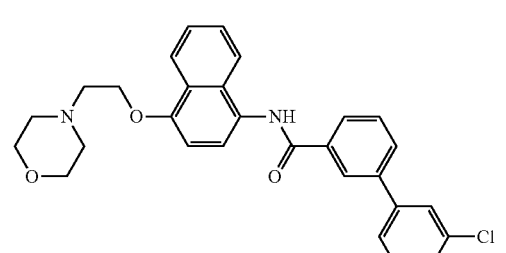 | B94 | 71 | 1.1411 | |
| 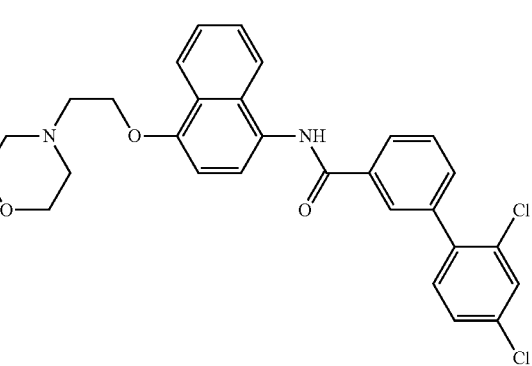 | B95 | 58 | 1.7468 | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 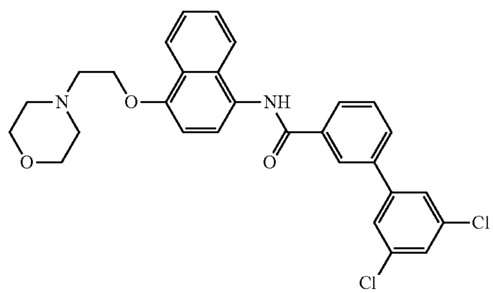 | B96 | 31 | >100.0000 | |
| 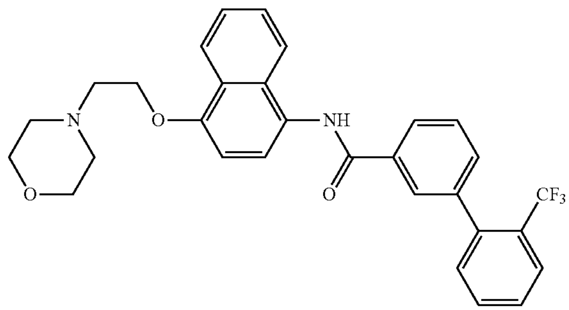 | B97 | 31 | >10.0000 | |
| 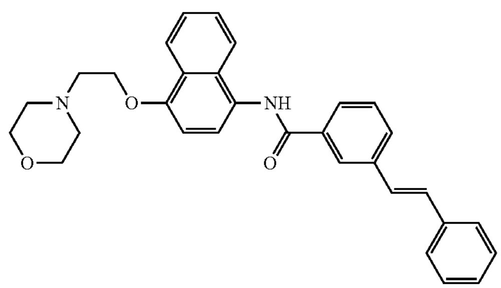 | B98 | 15 | >10.0000 | |
| 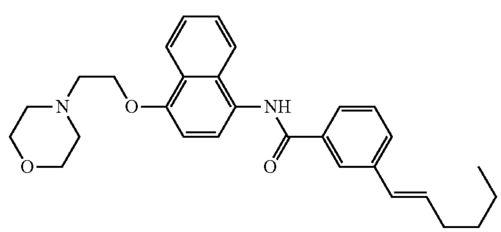 | B99 | 45 | >10.0000 | 5.5732 |
| 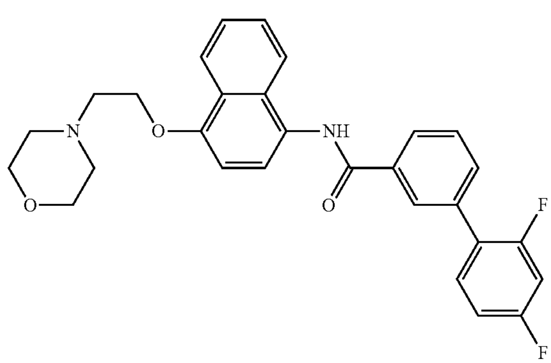 | B100 | 86 | 0.7437 | 1.5866 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 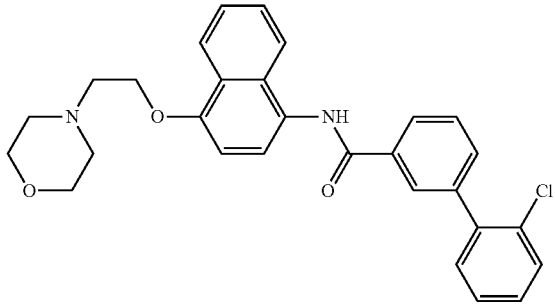 | B101 | 87 | 0.8639 | 2.0345 |
| 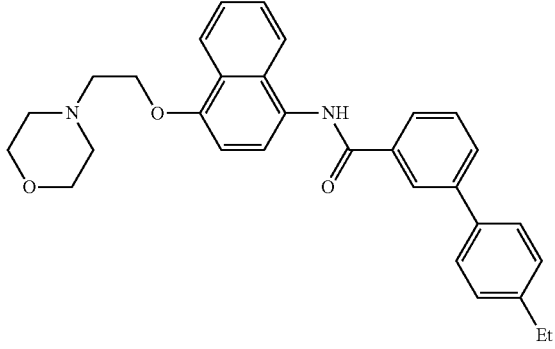 | B102 | 21 | >100.0000 | |
| 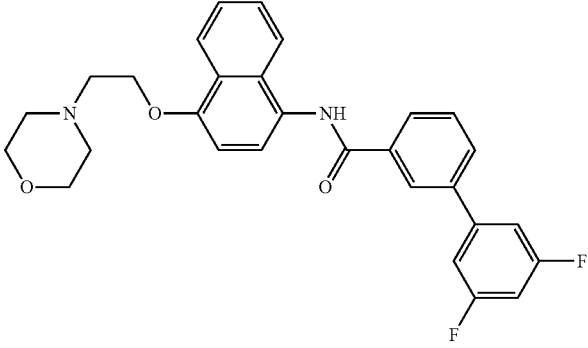 | B103 | 68 | 1.6314 | |
| 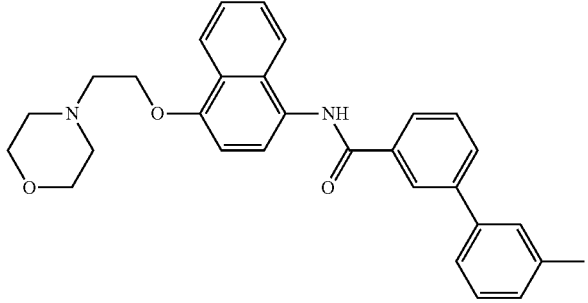 | B104 | 66 | 0.9651 | 4.4422 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 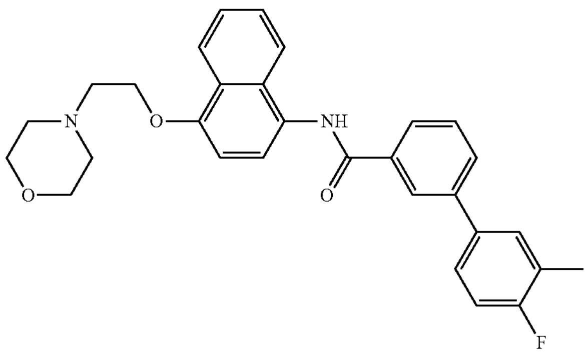 | B105 | 83 | 0.4875 | 3.6428 |
| 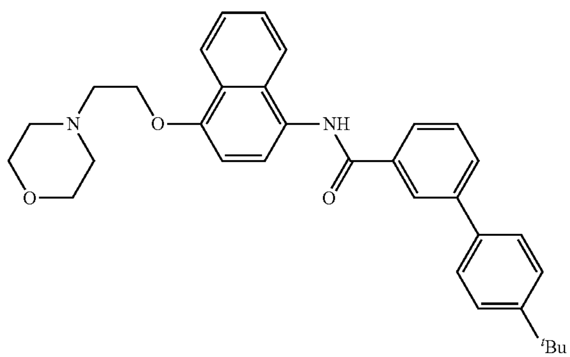 | B106 | 0 | | |
| 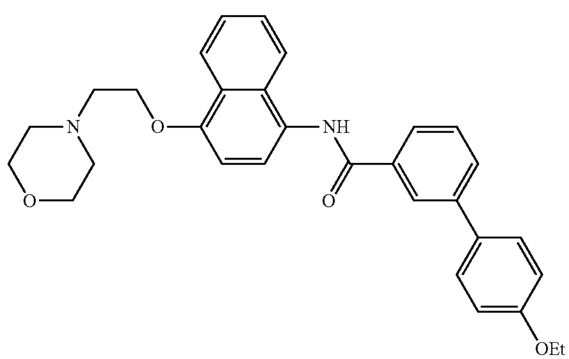 | B107 | 2 | | |
| 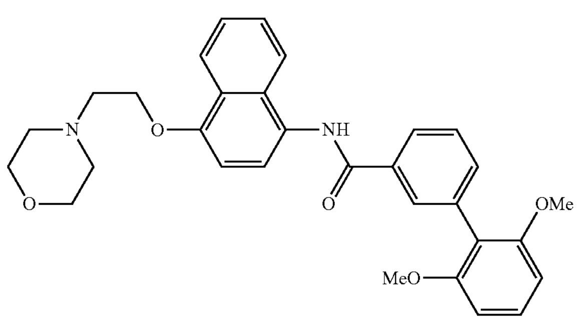 | B108 | 42 | >10.0000 | 2.2632 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 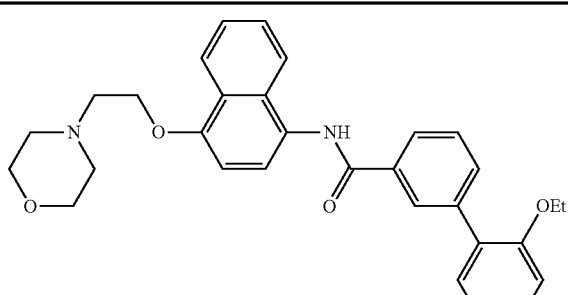 | B109 | 52 | 4.0671 | |
| 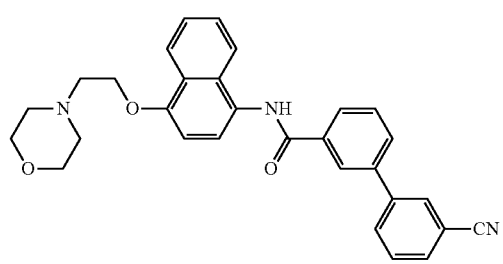 | B110 | 61 | >1.0000 | 6.4313 |
| 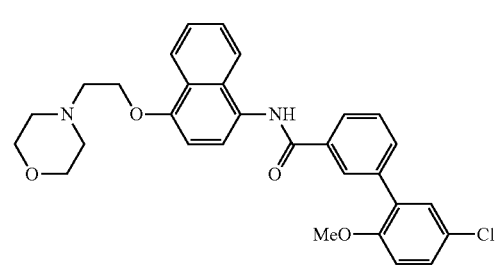 | B111 | 50 | 5.062 | |
| 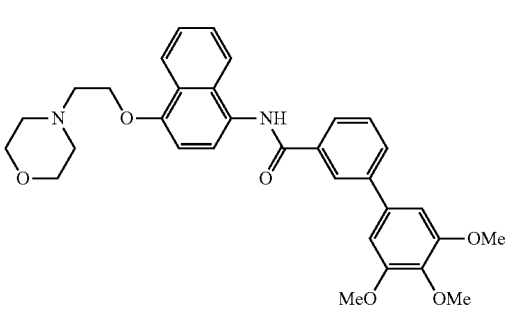 | B112 | 15 | >100.0000 | |
| 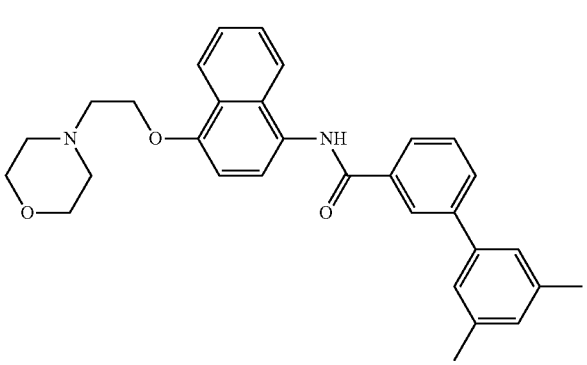 | B113 | 29 | >10.0000 | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 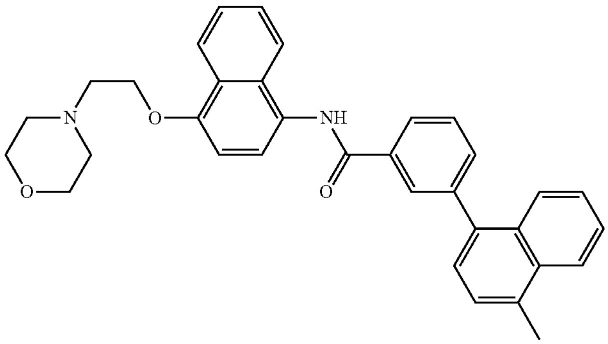 | B114 | 11.3 | | |
| 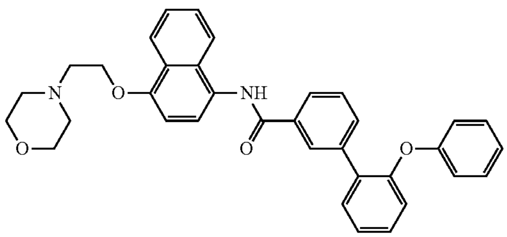 | B115 | 10 | | |
| 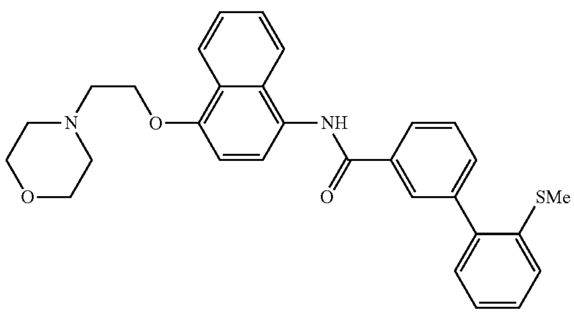 | B116 | 54 | 2.741 | |
| 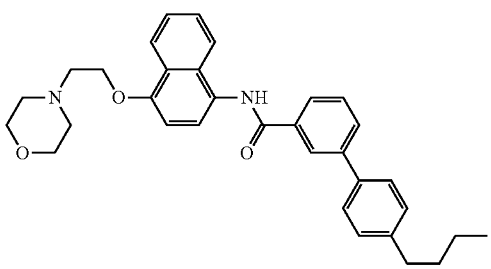 | B117 | 4 | | |
| 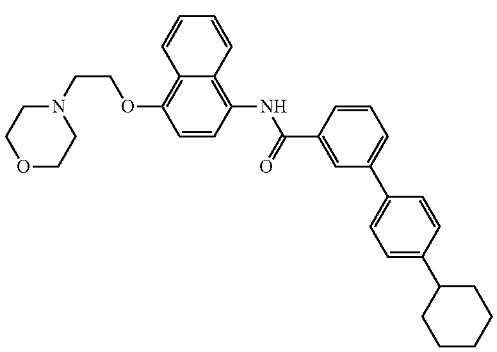 | B118 | 0 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 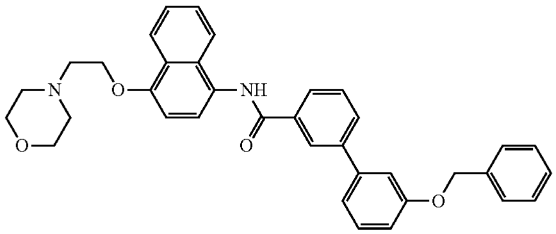 | B119 | 11 | >100.0000 | |
| 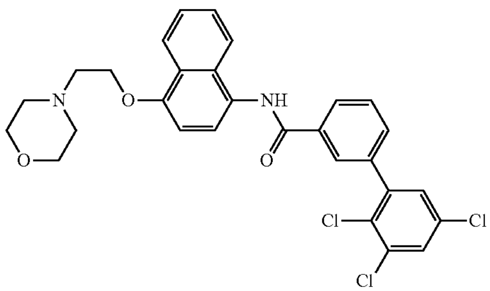 | B120 | 39 | >100.0000 | |
| 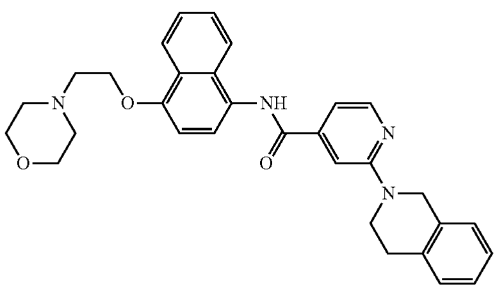 | B121 | 31.5 | | |
| 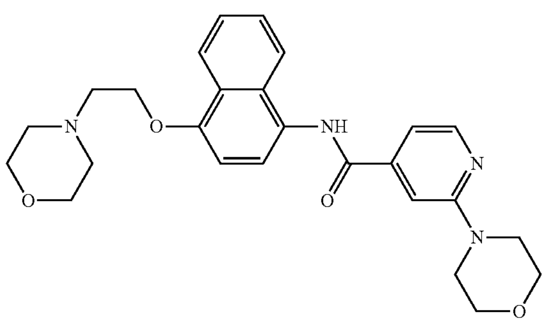 | B122 | 73.5 | 3.5228 | 2.1039 |
| 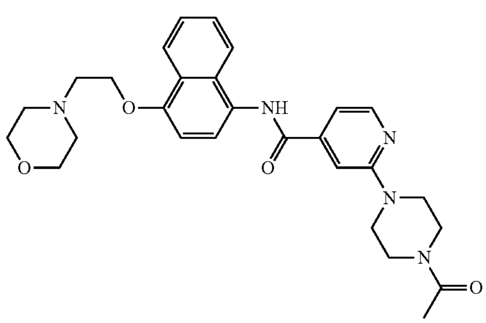 | B123 | 50.5 | 5.7537 | 6.1506 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 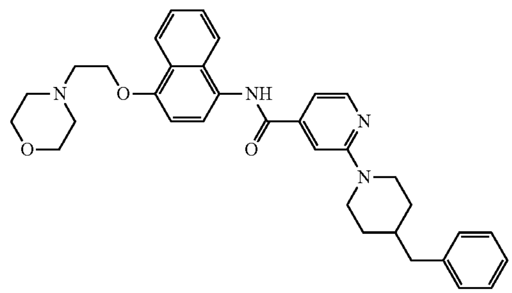 | B124 | 7 |  |  |
| 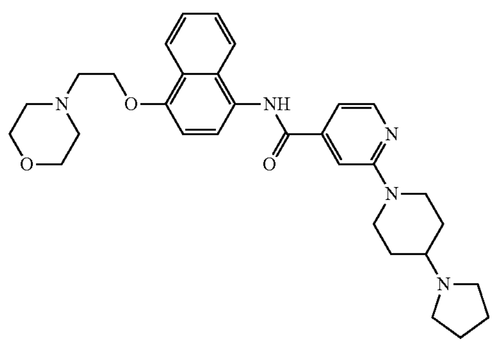 | B125 | 23.5 |  |  |
| 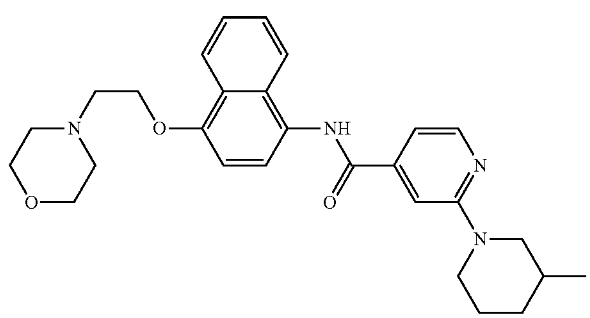 | B126 | 85 | 0.4507 | 0.934 |
| 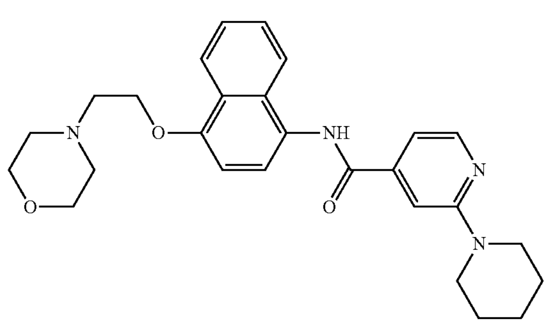 | B127 | 68.5 | 1.8775 | 0.7821 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 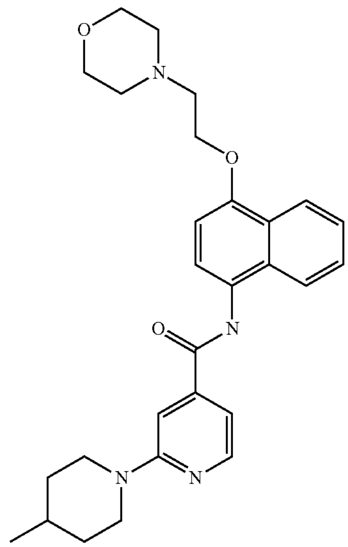 | B128 | 82 | 1.1531 | 8.7095 |
| 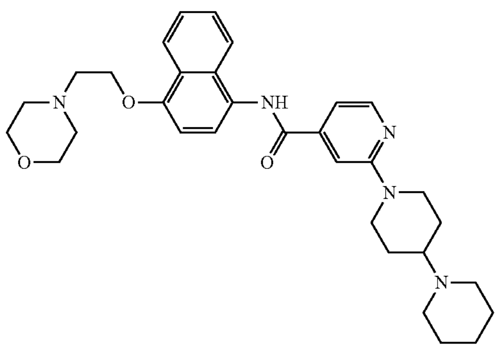 | B129 | 19.5 | | |
| 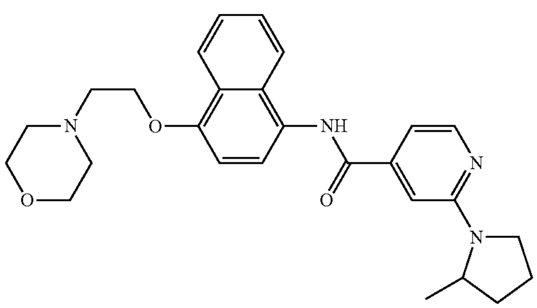 | B130 | 88.5 | 0.8221 | 2.3391 |
| 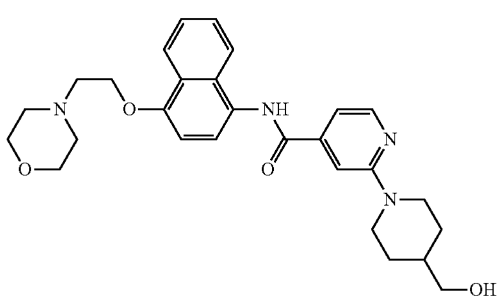 | B131 | 34 | | |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 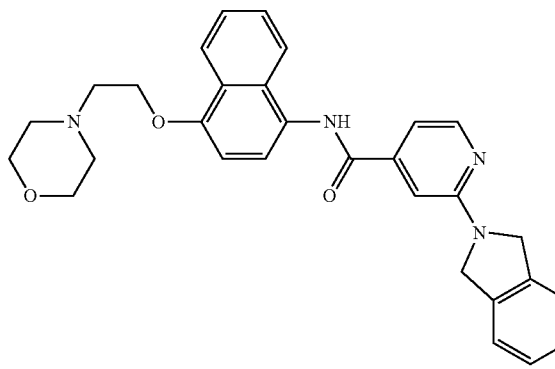 | B132 | 36 | | |
| 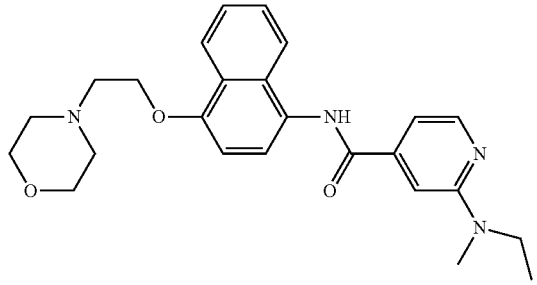 | B133 | 52 | 7.6809 | 8.4978 |
| 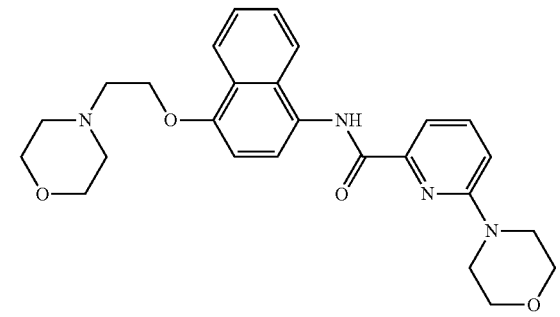 | B134 | 20 | | |
| 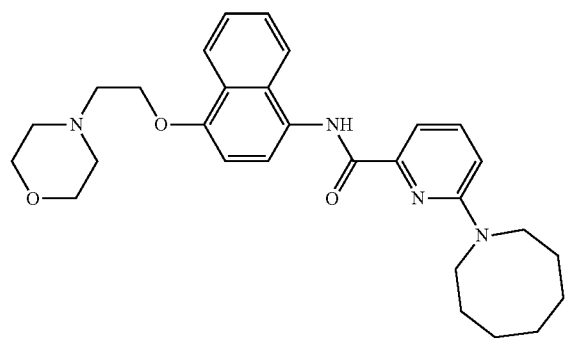 | B135 | 20 | >100.0000 | |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 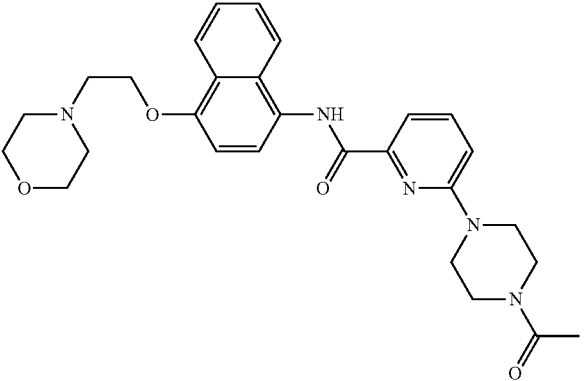 | B136 | 10 | | |
| 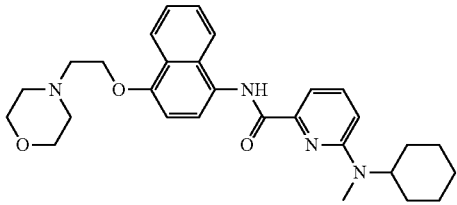 | B137 | 32 | >100.0000 | |
| 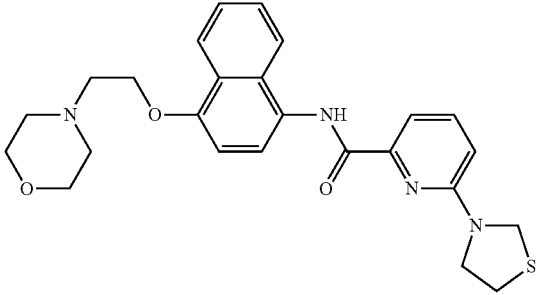 | B138 | −36 | | |
| 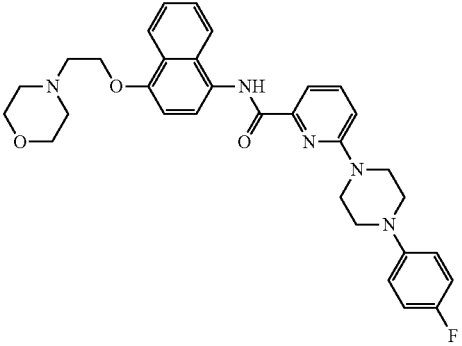 | B139 | 7 | | |
| 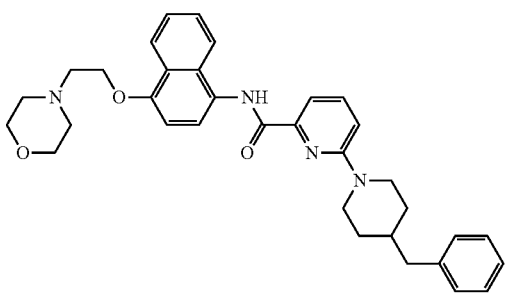 | B140 | 4 | | |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 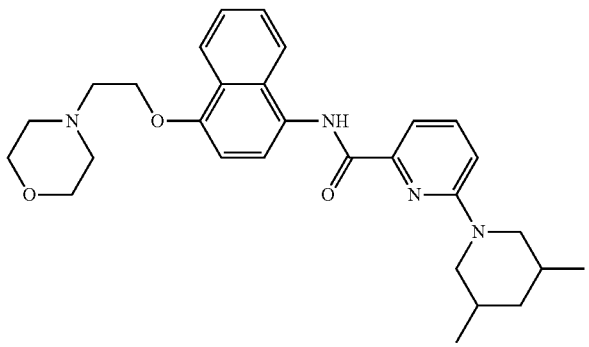 | B141 | 13 | | |
| 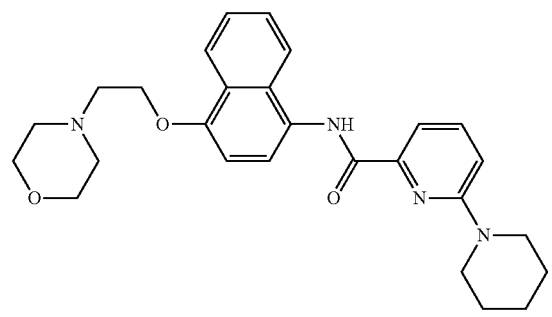 | B142 | 33 | >100.0000 | |
| 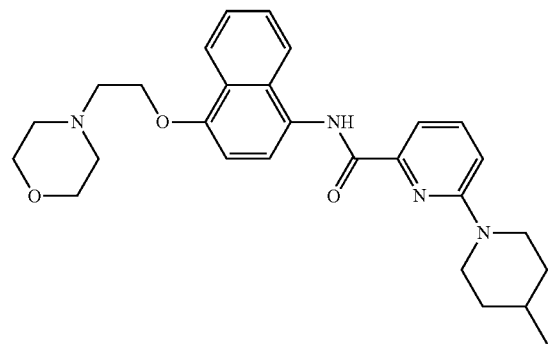 | B143 | 32 | >100.0000 | |
| 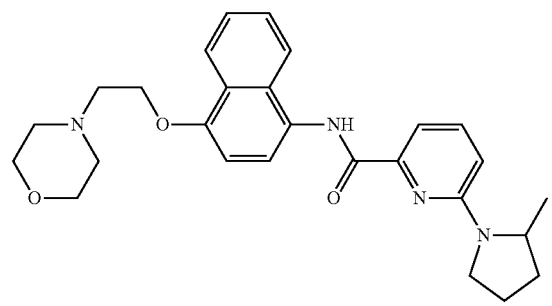 | B144 | 17 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 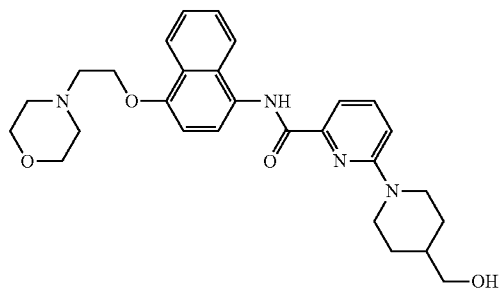 | B145 | 11 | | |
| 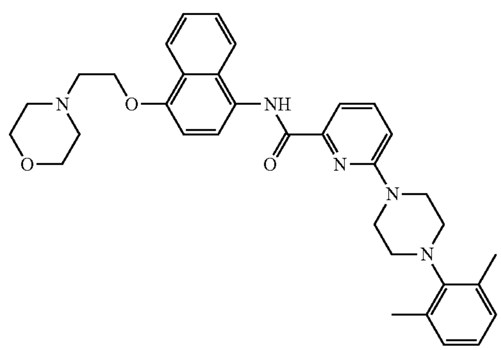 | B146 | 7.5 | | |
| 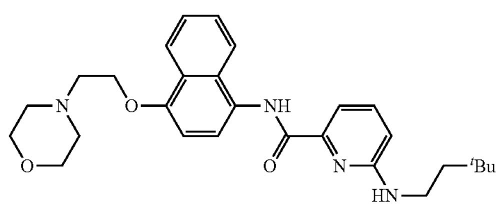 | B147 | 12 | | |
| 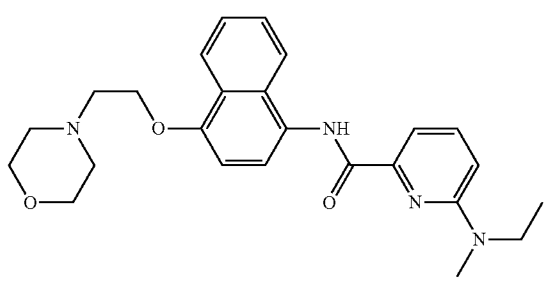 | B148 | 15.5 | | |
| 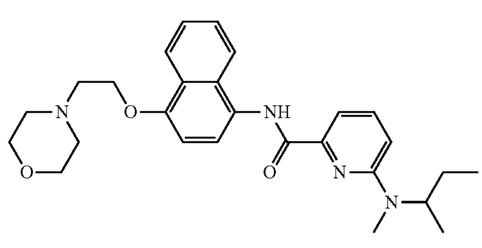 | B149 | 8.5 | | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 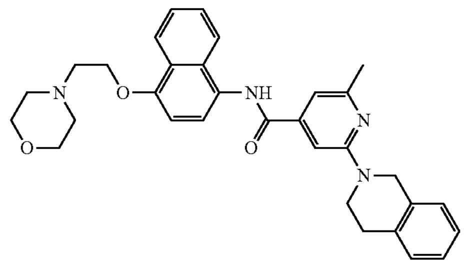 | B150 | 15 | >100.0000 | |
| 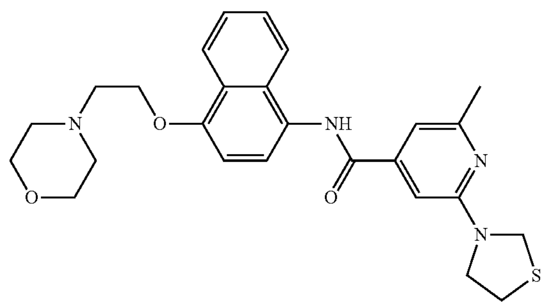 | B151 | 0 | | |
| 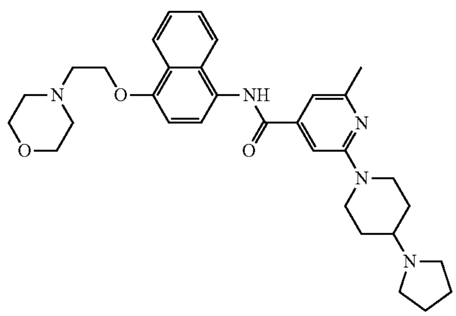 | B152 | 0 | | |
| 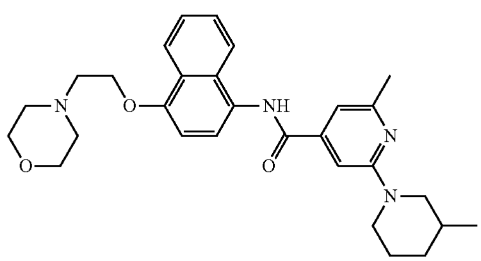 | B153 | 88 | 0.6218 | 1.029 |
| 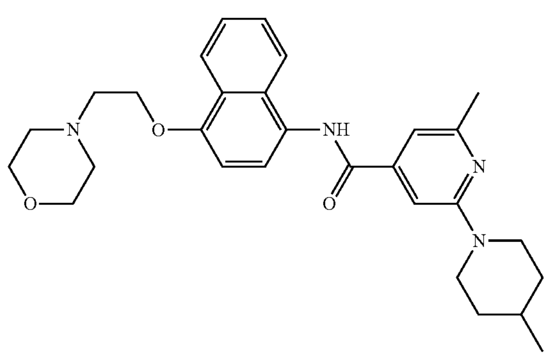 | B154 | 71 | 2.7175 | 2.528 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 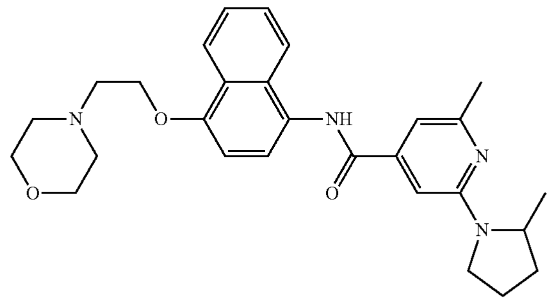 | B155 | 89 | 0.7446 | 2.4471 |
| 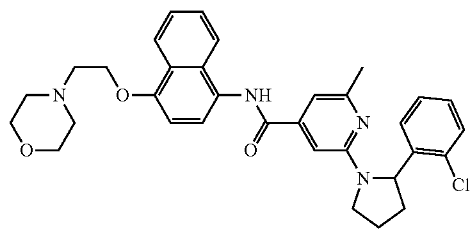 | B156 | 19 | >100.0000 | |
| 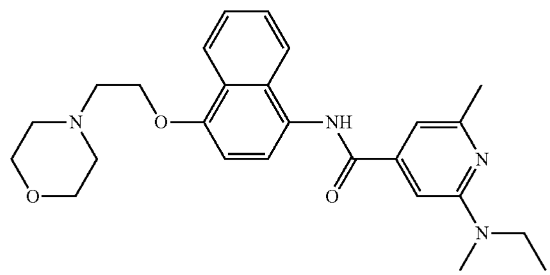 | B157 | 8 | | |
| 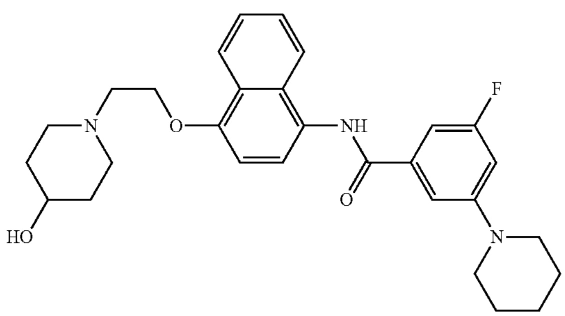 | B158 | 72 | 2.6703 | >10.0000 |
| 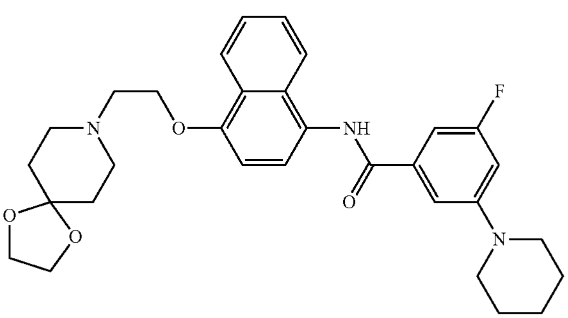 | B159 | 72.5 | 1.0856 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 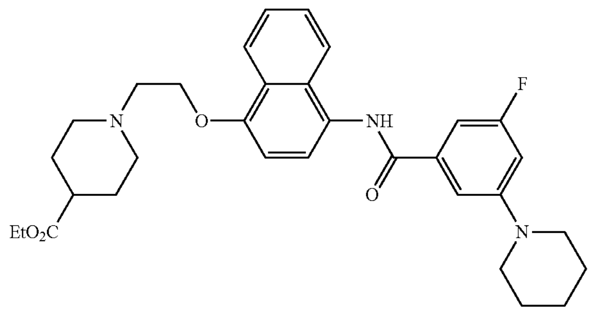 | B160 | 58.5 | 1.8152 | >10.0000 |
| 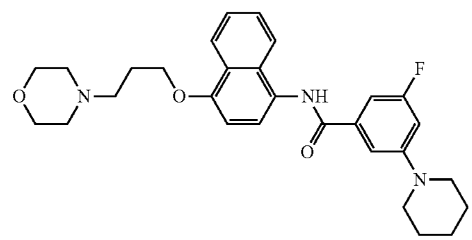 | B161 | 84 | 1.1042 | >10.0000 |
| 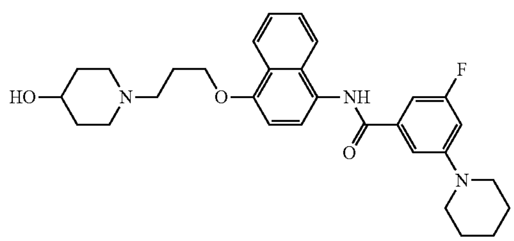 | B162 | 59.5 | 9.8921 | >10.0000 |
| 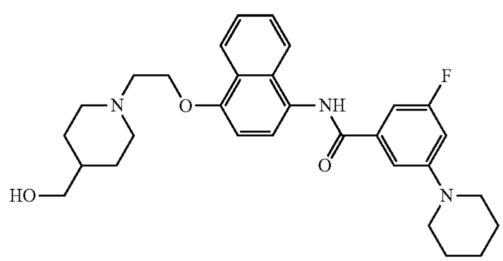 | B163 | 57 | 4.8379 | >10.0000 |
| 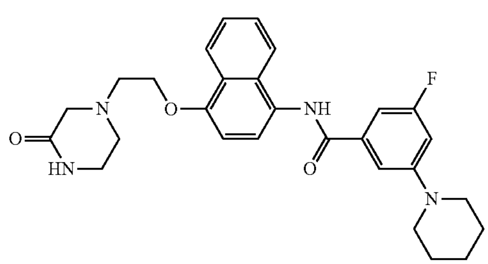 | B164 | 83.5 | 0.4358, 0.3063 | >15.0000, 6.3331 |
| 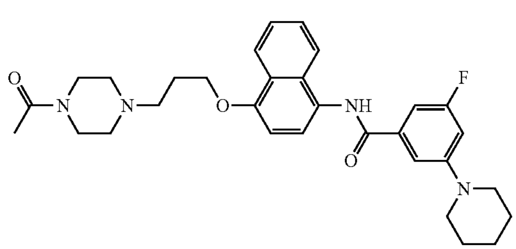 | B165 | 84 | 0.9968 | >10.0000 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 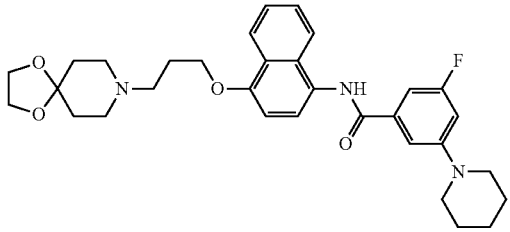 | B166 | | 4.8075 | |
| 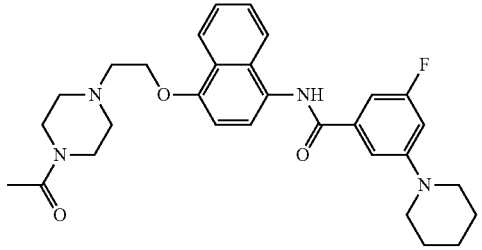 | B167 | | 0.8512 | >10.0000 |
| 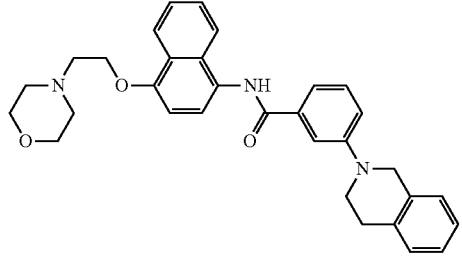 | B168 | 36 | | |
| 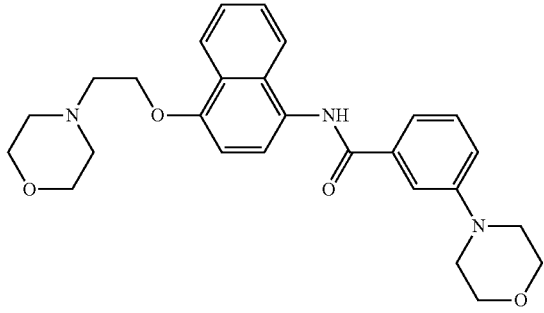 | B169 | 77.5 | 2.072 | 1.3278 |
| 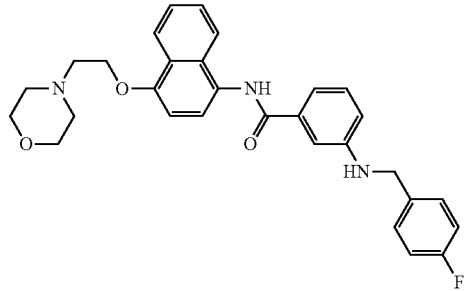 | B170 | 46 | | |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 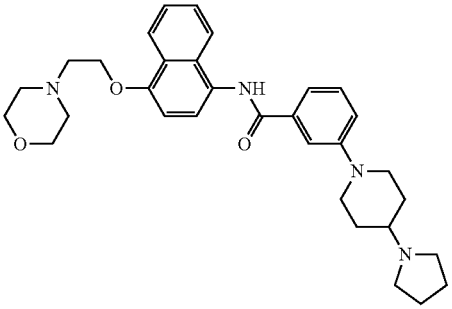 | B171 | 16 | | |
| 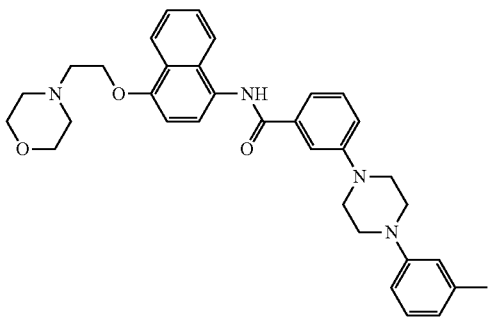 | B172 | 25 | | |
| 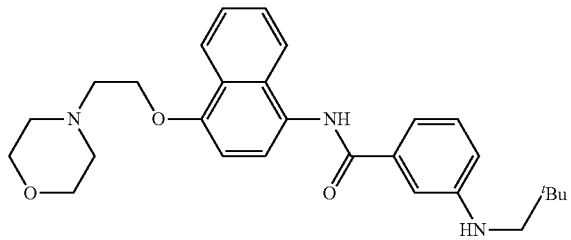 | B173 | 89.5 | 0.7347 | 2.2845 |
| 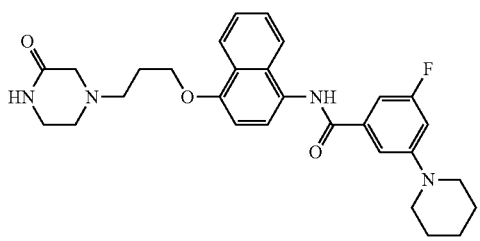 | B175 | | 1.1108 | >10.0000 |
| 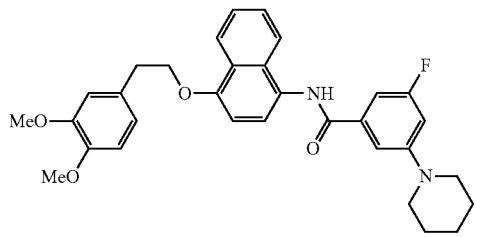 | B179 | | 1.0585 | 2.0488 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 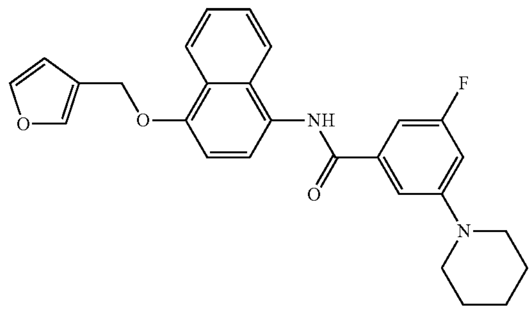 | B180 | | 4.0366 | |
| 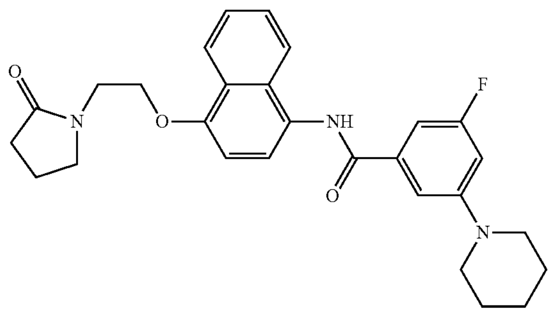 | B181 | | 2.3464 | |
| 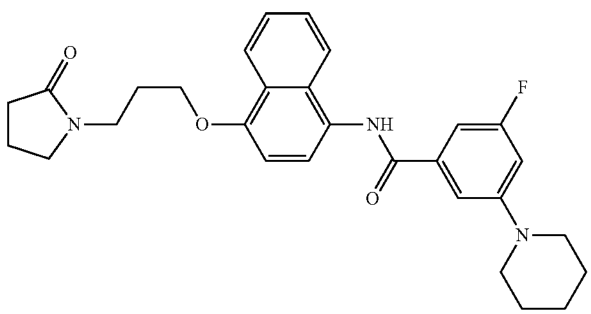 | B182 | | 0.587 | >10.0000 |
| 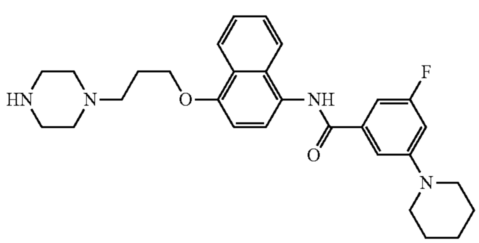 | B183 | | 1.1379 | >10.0000 |
| 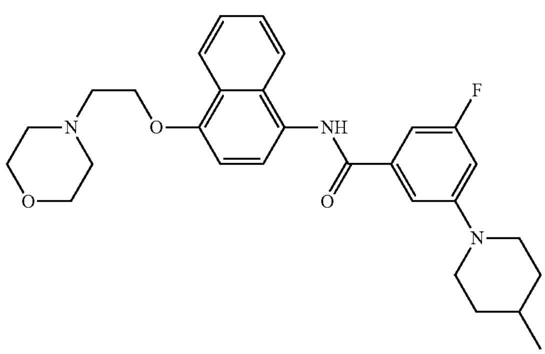 | B184 | | 1.07 | 6.99 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 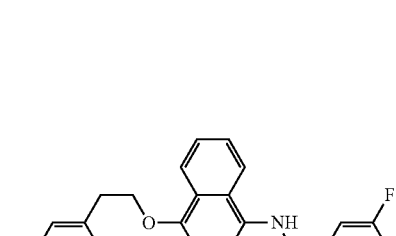 | B187 | | >10.0000 | |
| 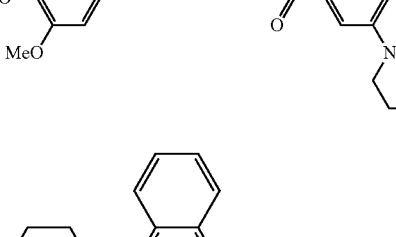 | B189 | | 0.4408 | 2.6057 |
| 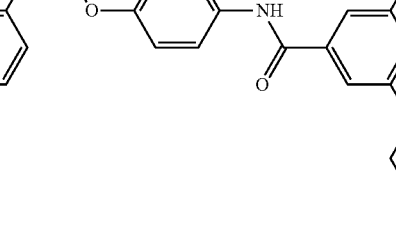 | B190 | | 0.8257 | 7.5233 |
| 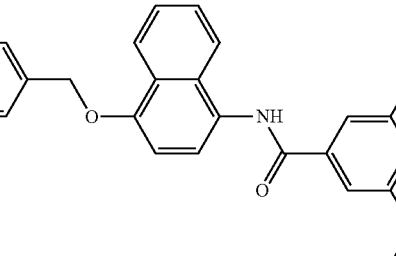 | B191 | | 0.0527, 0.0610 | 1.0484, 0.4122 |
| 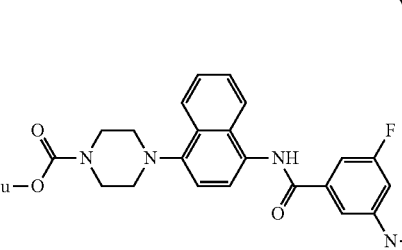 | B192 | | >10.0000 | 4.7216 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 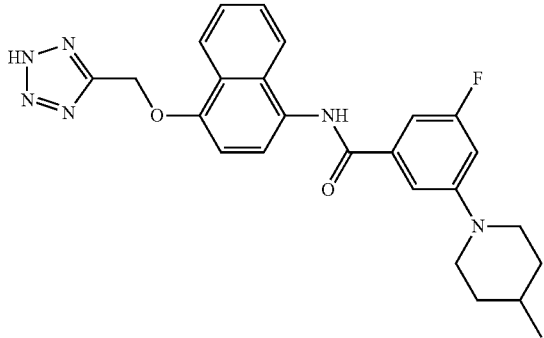 | B193 | | 3.8398 | >10.0000 |
| 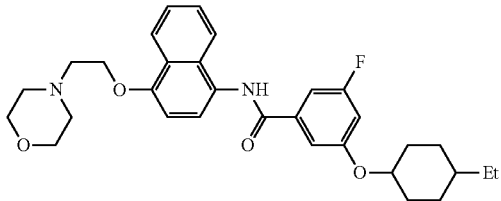 | B194 | | 9.2771 | >10.0000 |
| 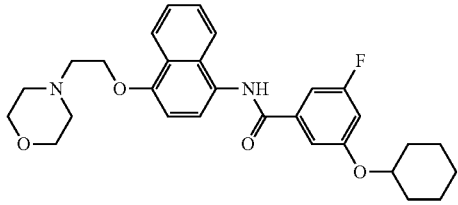 | B195 | | 0.4126 | >10.0000 |
| 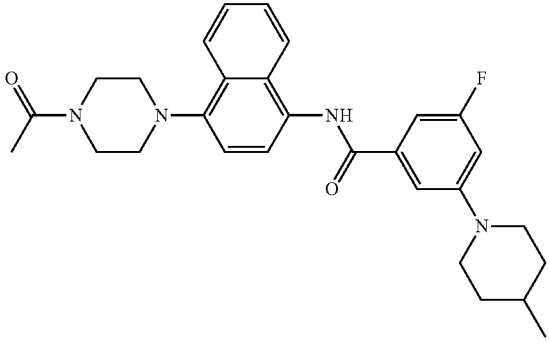 | B196 | | 3.1896 | >10.0000 |
| 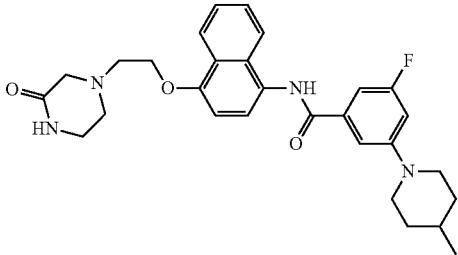 | B197 | | 1.4204 | 6.6267 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 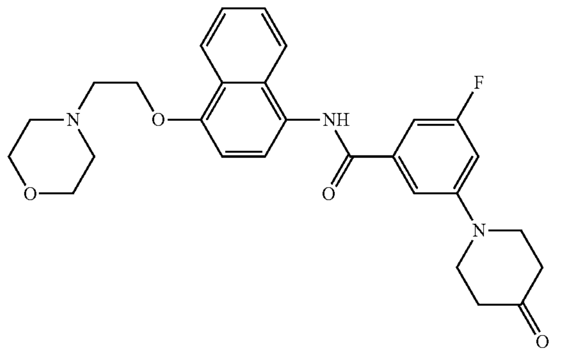 | B198 | | 1.772 | 8.4957 |
| 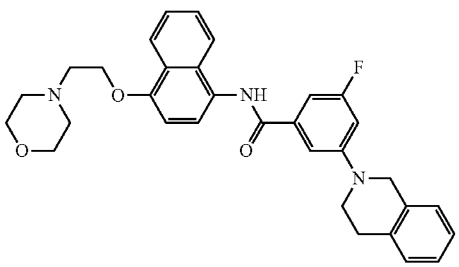 | B200 | | >10.0000 | >10.0000 |
| 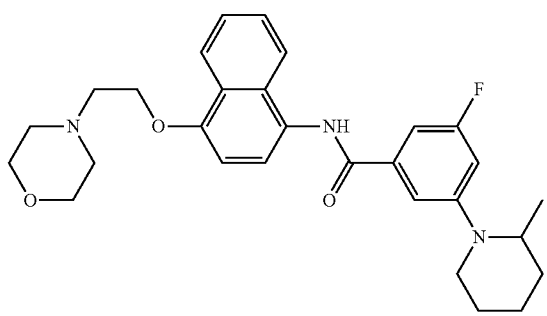 | B201 | | 0.3226 | 4.7302 |
| 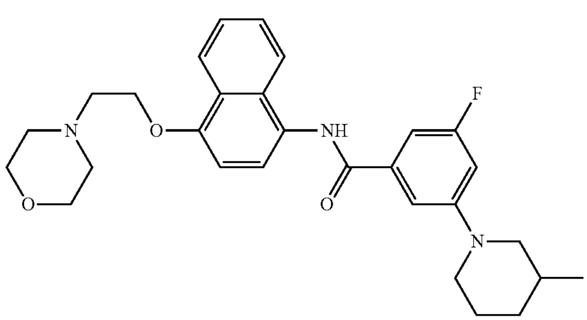 | B202 | | 0.2912 | 9.3276 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 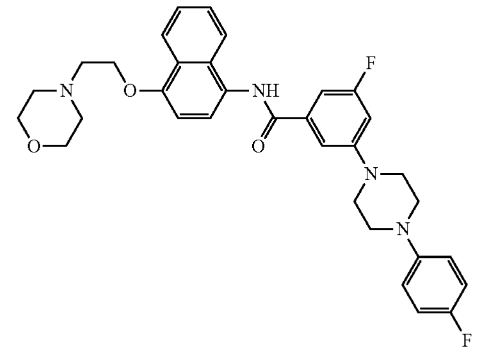 | B203 | | >10.0000 | >10.0000 |
| 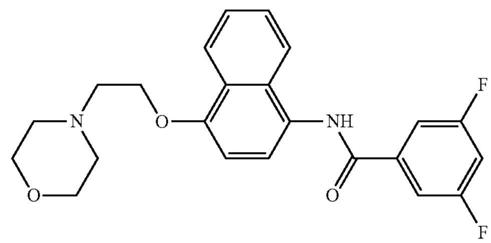 | B204 | | >10.0000 | >10.0000 |
| 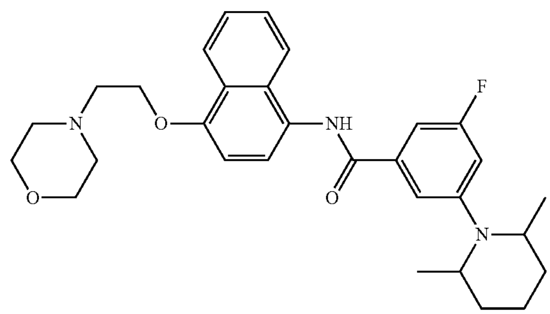 | B205 | | 1.6781 | >10.0000 |
| 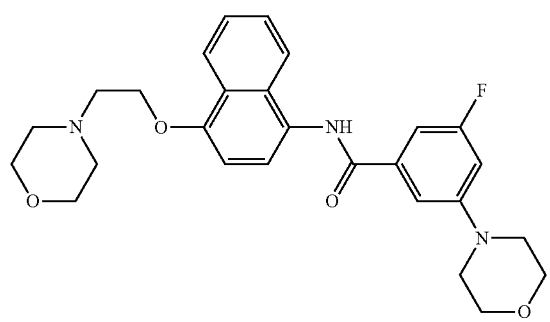 | B206 | | 1.0169 | 4.2279 |
| 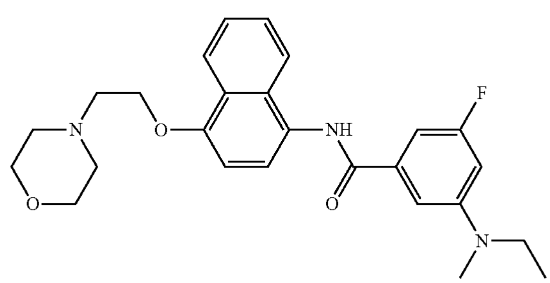 | B207 | | 1.116 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 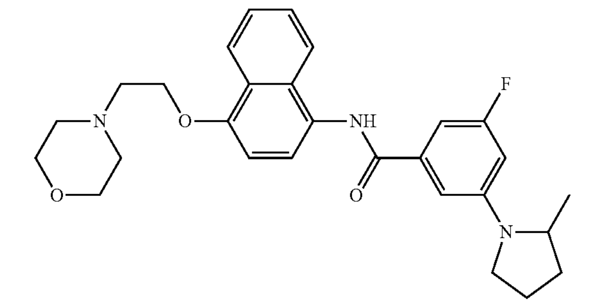 | B208 | | 0.1667 | 3.6355 |
| 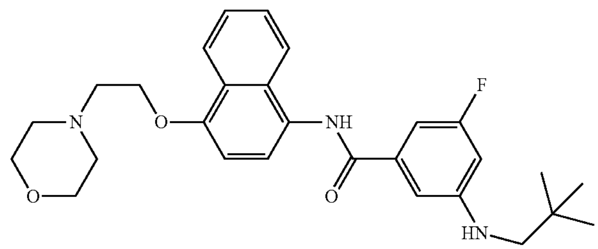 | B209 | | 0.5127 | >10.0000 |
| 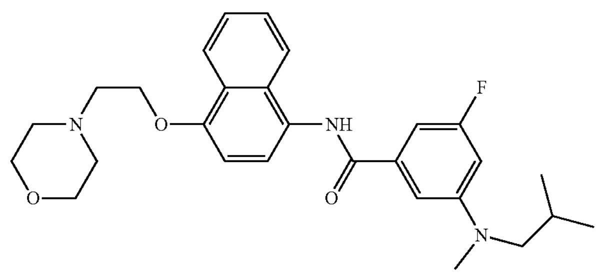 | B210 | | 1.302 | >10.0000 |
| 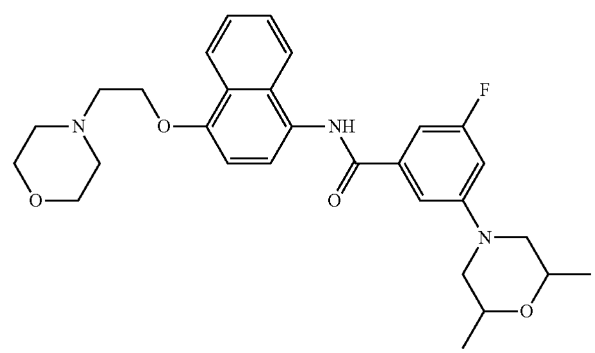 | B211 | | >10.0000 | >10.0000 |
| 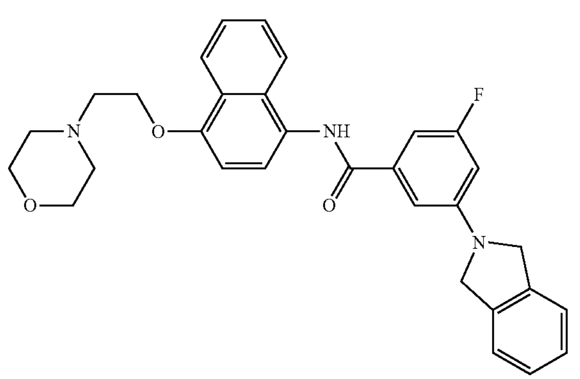 | B212 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 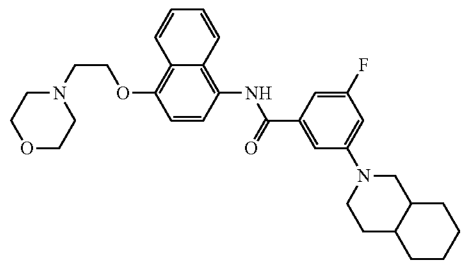 | B213 | | >10.0000 | >10.0000 |
| 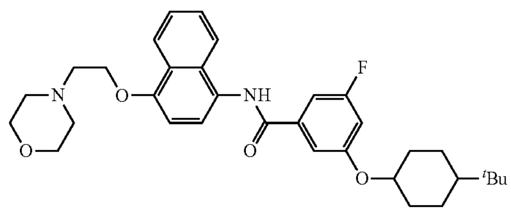 | B216 | | >10.0000 | |
| 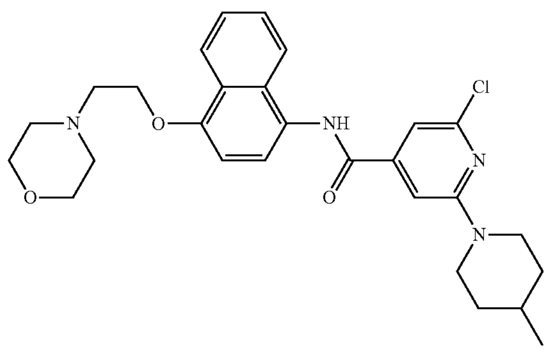 | B218 | | 0.8762 | 3.5795 |
| 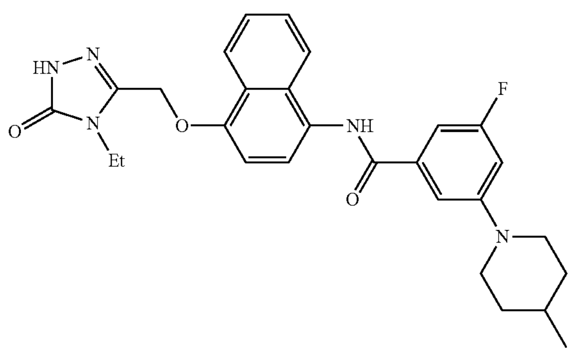 | B220 | | 0.145 | 2.8724 |
| 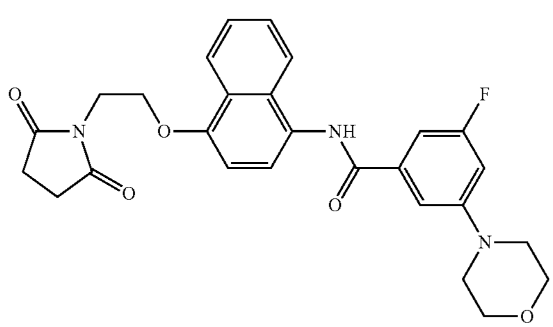 | B221 | | >10.0000 | |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 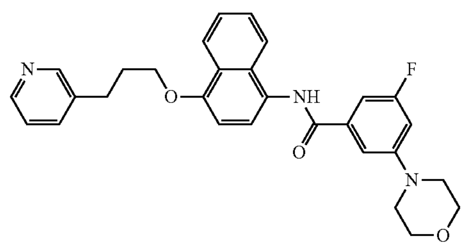 | B222 | | 0.8195 | 9.3818 |
| 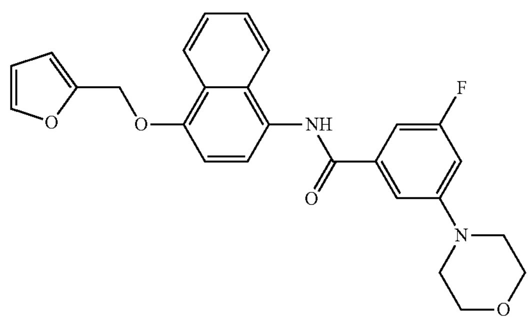 | B223 | | 12.8479 | |
| 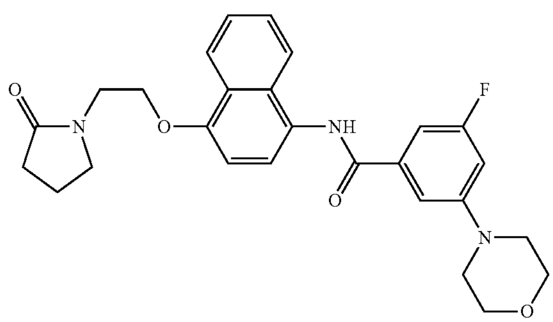 | B224 | | 6.5497 | |
| 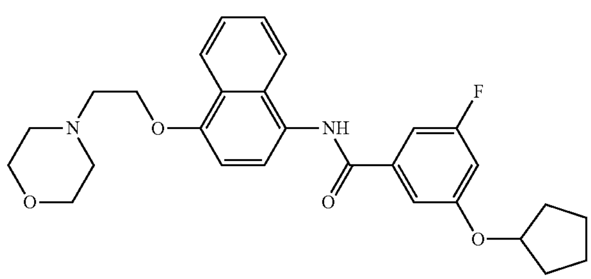 | B225 | | 0.4393 | 4.0949 |
| 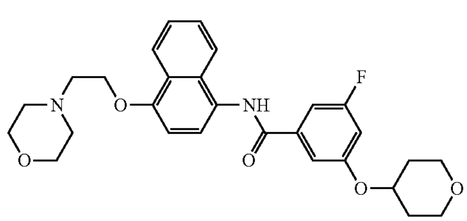 | B226 | | 5.3907 | |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 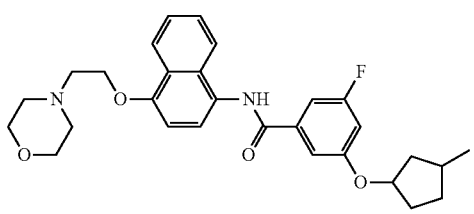 | B227 | | 0.8077 | 4.1231 |
| 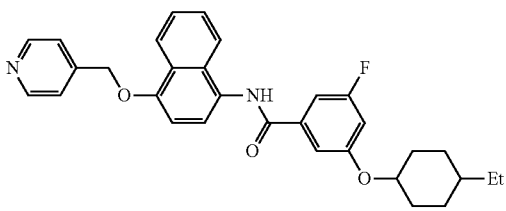 | B228 | | >10.0000 | |
| 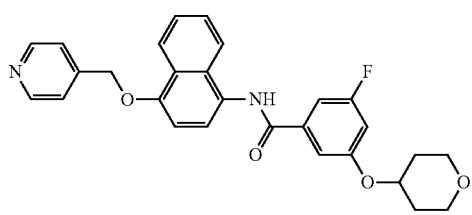 | B229 | | 0.8207 | 5.6623 |
| 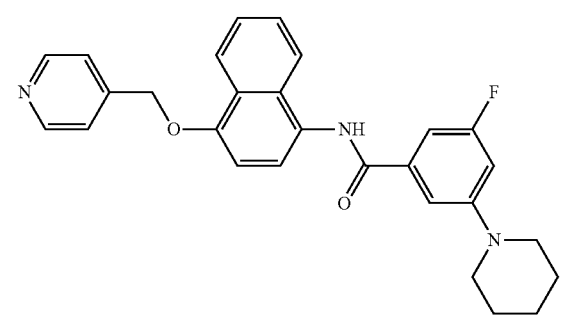 | B230 | | 0.0257 | 0.6297 |
| 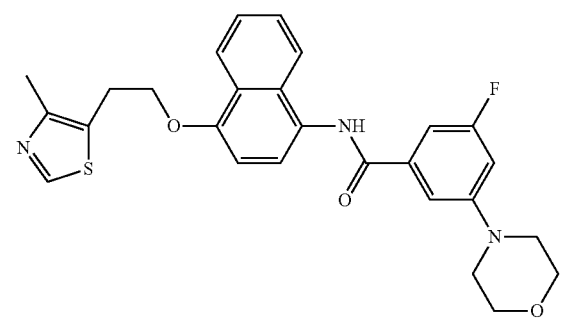 | B231 | | 0.0277 | 0.193 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 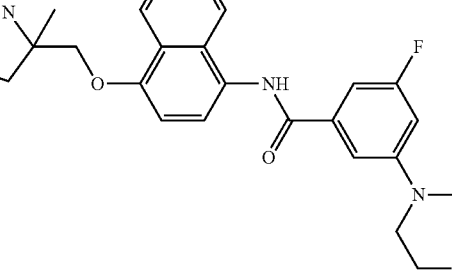 | B232 | | 7.8598 | 4.2766 |
| 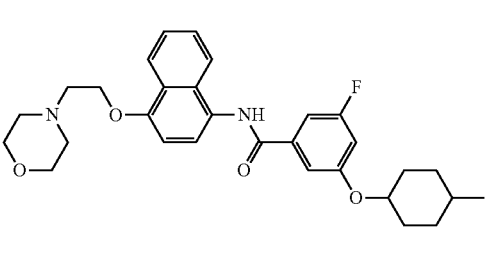 | B234 | | 1.0499 | 3.1927 |
| 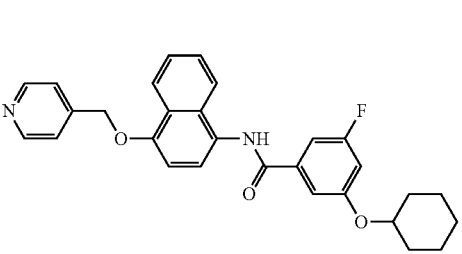 | B235 | | 0.125 | 0.557 |
| 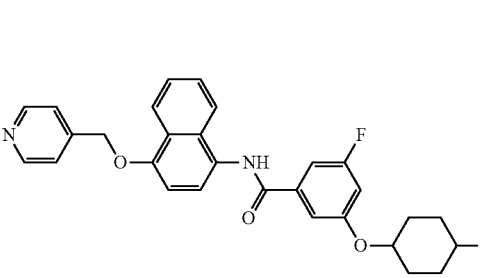 | B236 | | >10.0000 | >10.0000 |
| 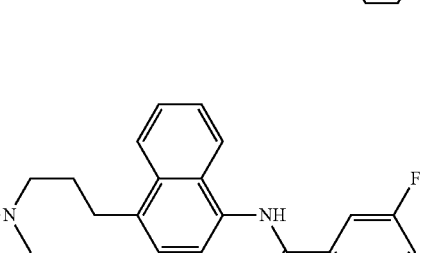 | B240 | | 1.0088 | 1.0102 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 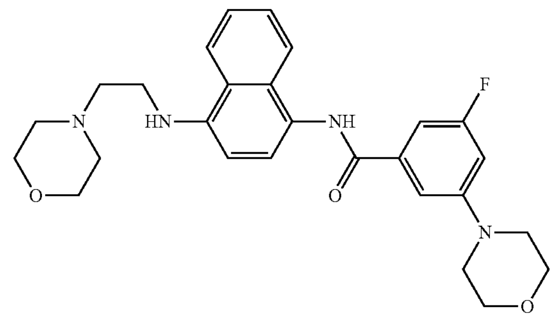 | B241 | | 8.2491 | 9.4176 |
| 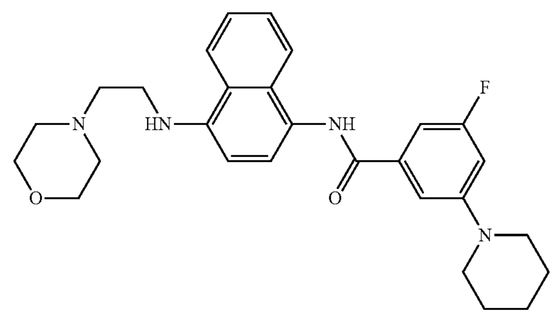 | B242 | | 2.0262 | 10.6145 |
| 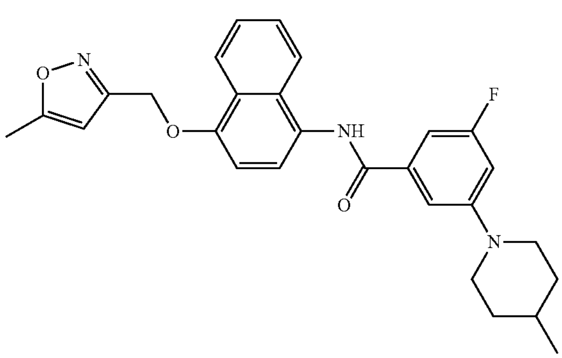 | B243 | | >10.0000 | >10.0000 |
| 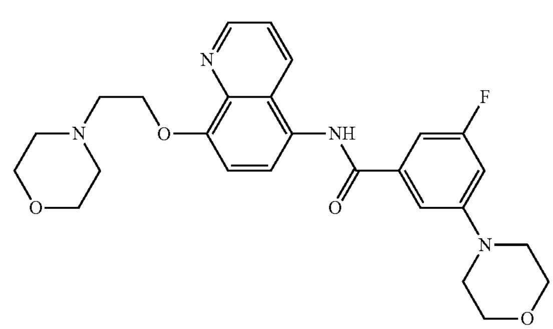 | B244 | | >10.0000 | >10.0000 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 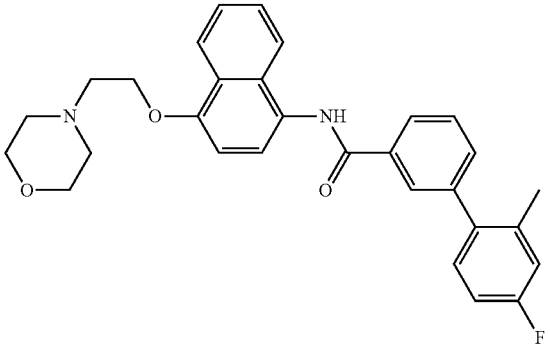 | B245 | | 0.6307 | 1.1397 |
| 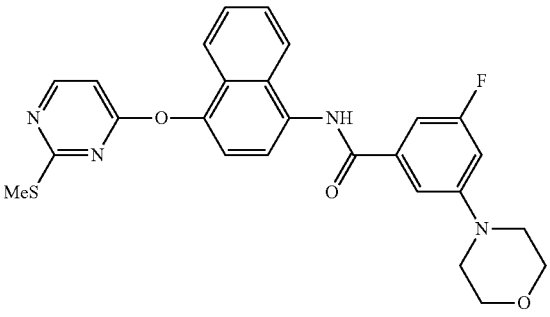 | B246 | | 0.0402 | 0.0694 |
| 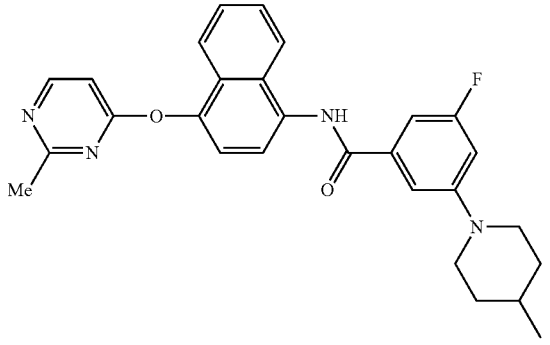 | B247 | | 0.5872 | 0.7797 |
| 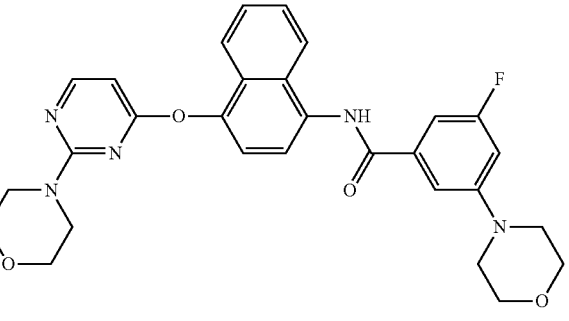 | B248 | | 0.0466 | 0.1567 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 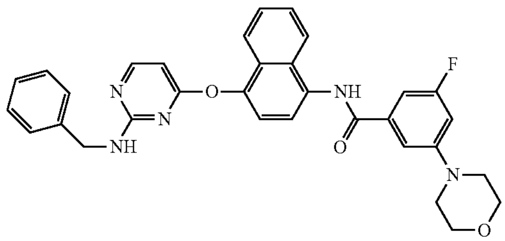 | B249 | | 0.0139 | 0.0124 |
| 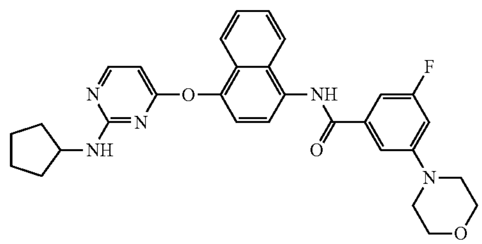 | B250 | | 0.0305 | 0.042 |
| 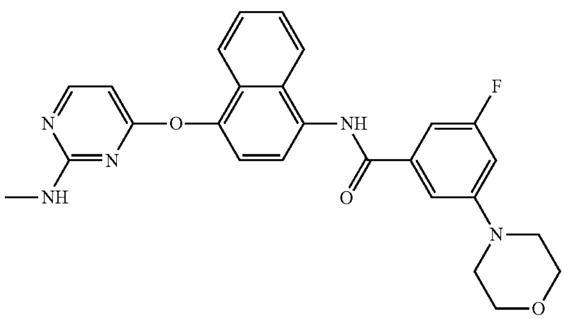 | B251 | | 0.1345 | 0.7645 |
| 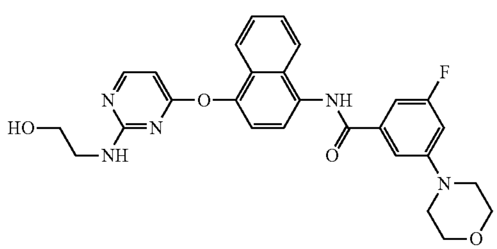 | B252 | | 0.0319 | 0.0308 |
| 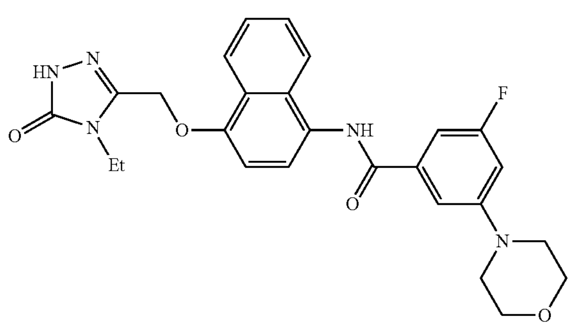 | B255 | | 0.5783 | 1.9431 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 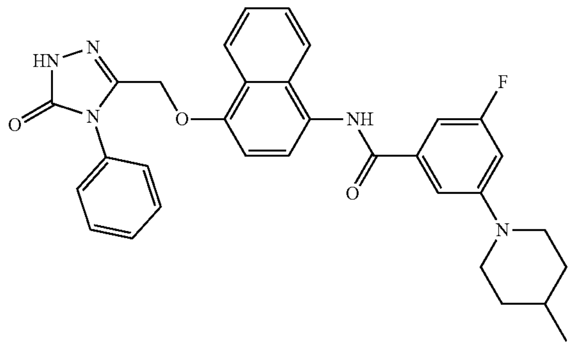 | B263 | | 5.0762 | 4.2586 |
| 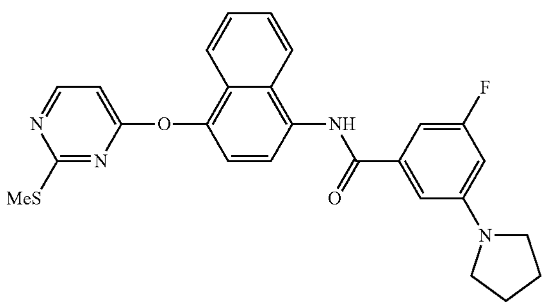 | B264 | | 0.1888 | 0.1773 |
| 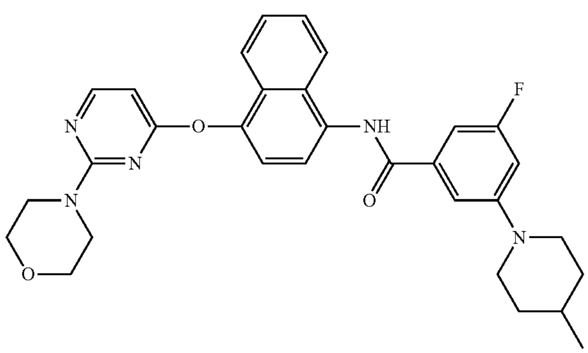 | B265 | | 5.0621 | 0.765 |
| 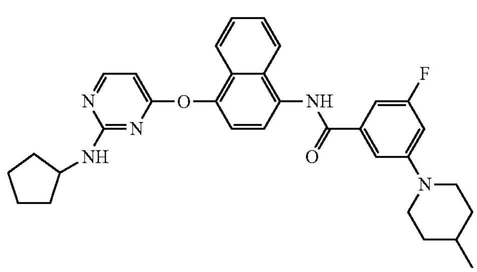 | B266 | | 0.363 | 0.2555 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 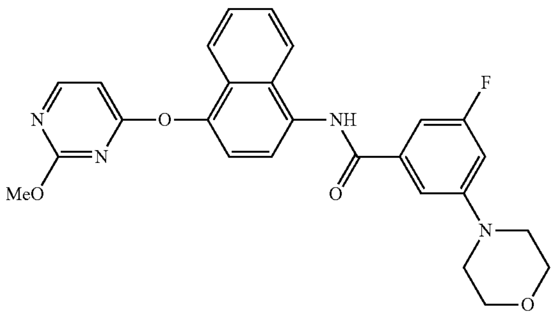 | B267 | | 0.0569 | 0.0292 |
| 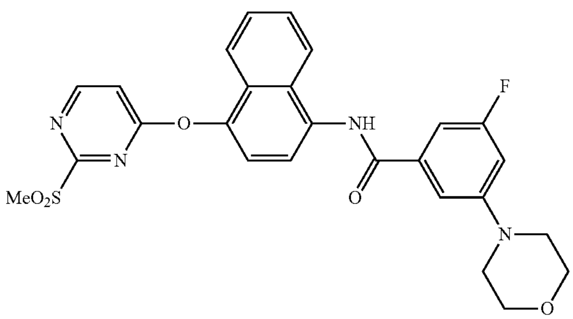 | B268 | | 0.5194 | 1.367 |
| 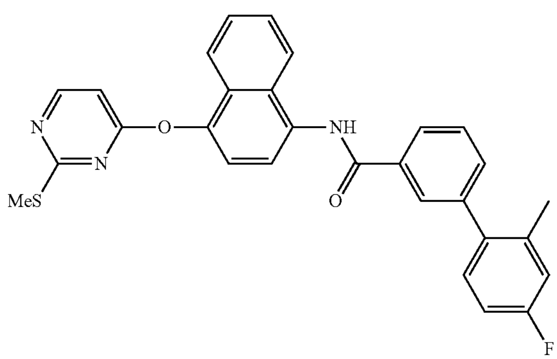 | B269 | | 0.1623 | 0.1522 |
| 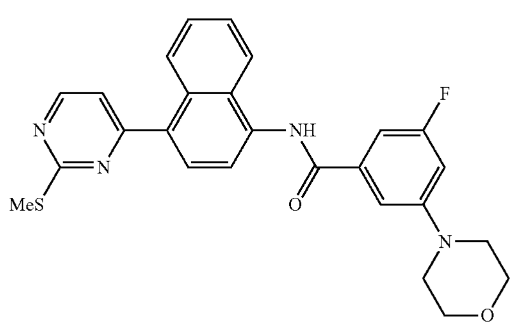 | B270 | | 1.6529 | 6.416 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 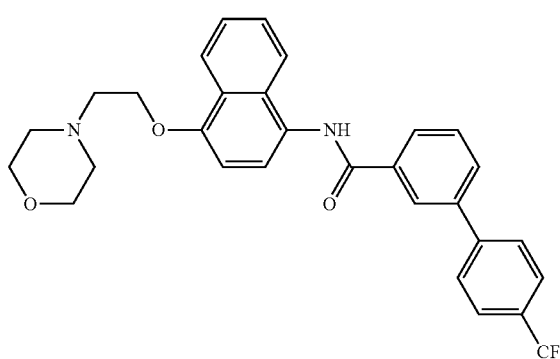 | B271 | | >10.0000 | 4.0329 |
| 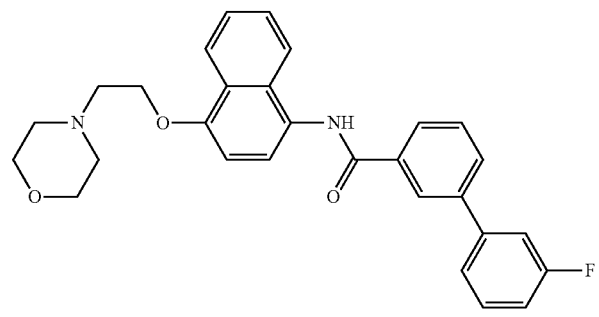 | B272 | | 1 | 3.3999 |
| 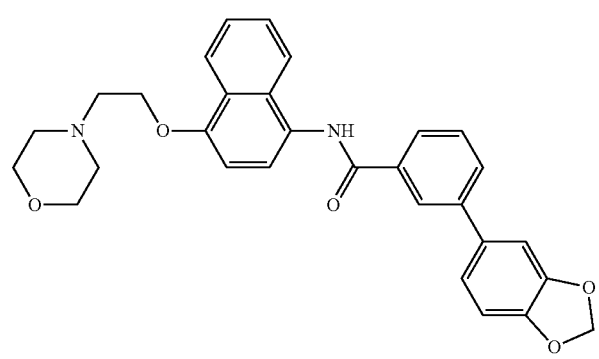 | B273 | | >10.0000 | >10.0000 |
| 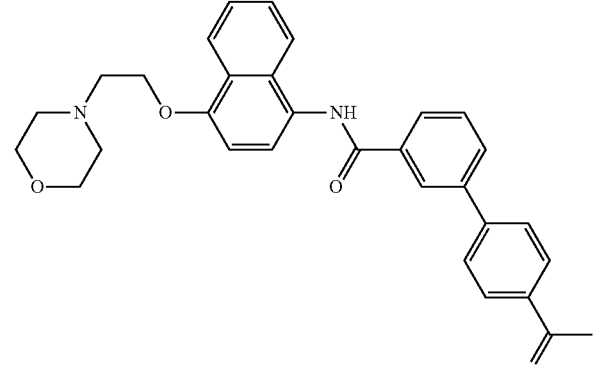 | B274 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 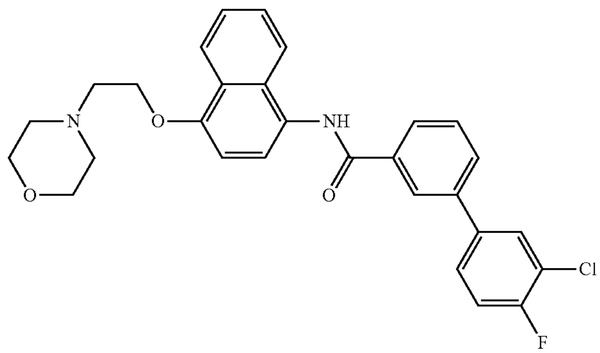 | B275 | | 3.976 | 3.5748 |
| 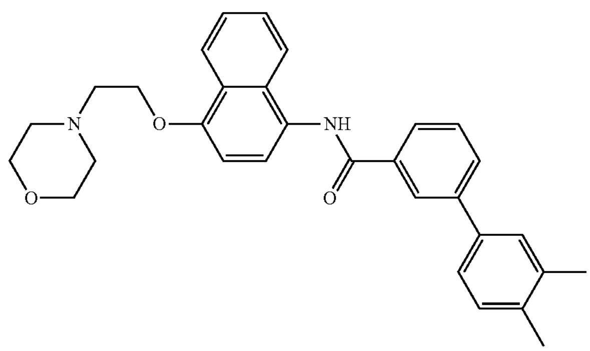 | B276 | | >10.0000 | >10.0000 |
| 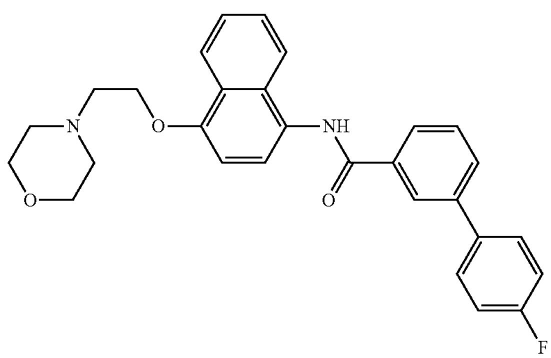 | B277 | | 0.777 | 1.8426 |
| 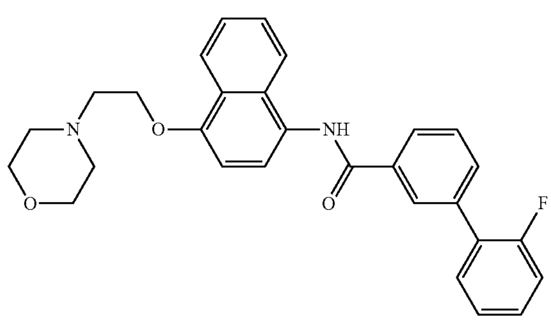 | B278 | | 0.9348 | 3.6905 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 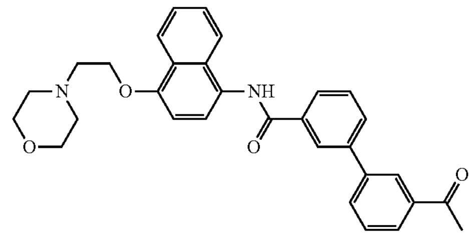 | B279 | | >10.0000 | >10.0000 |
| 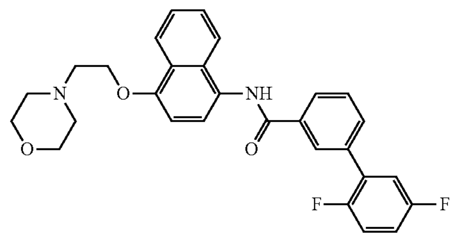 | B280 | | 5.5967 | 3.5234 |
| 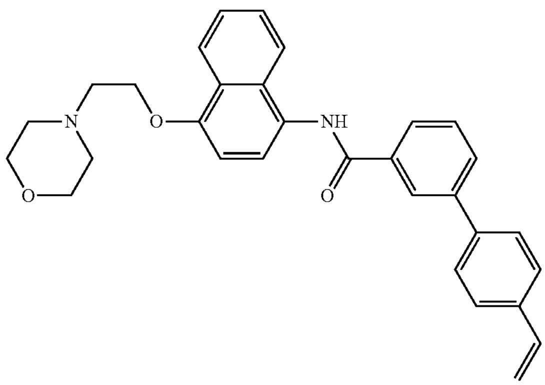 | B281 | | >10.0000 | >10.0000 |
| 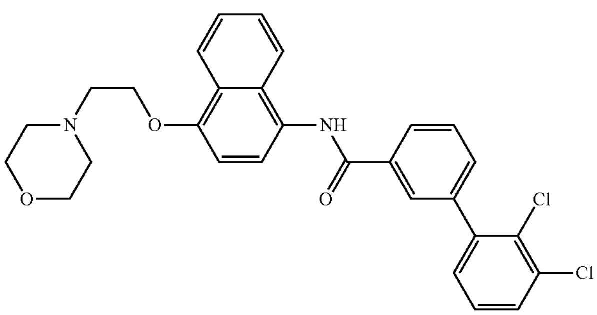 | B282 | | 3.6741 | 4.7719 |
| 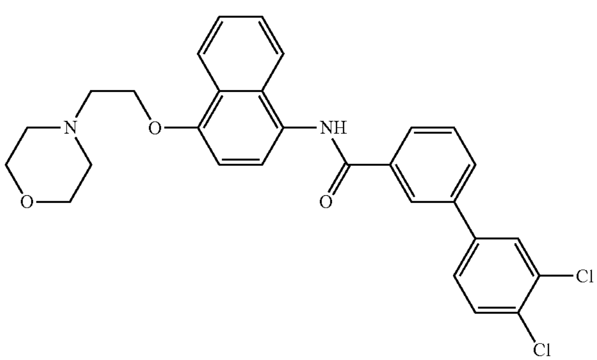 | B283 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 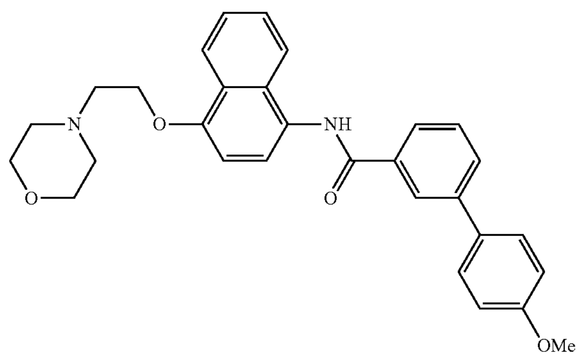 | B284 | | >10.0000 | >10.0000 |
| 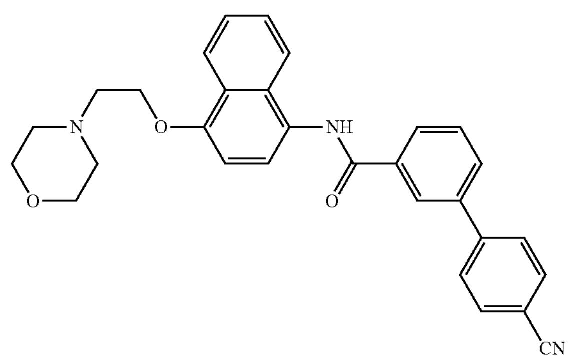 | B285 | | >10.0000 | 9.7884 |
| 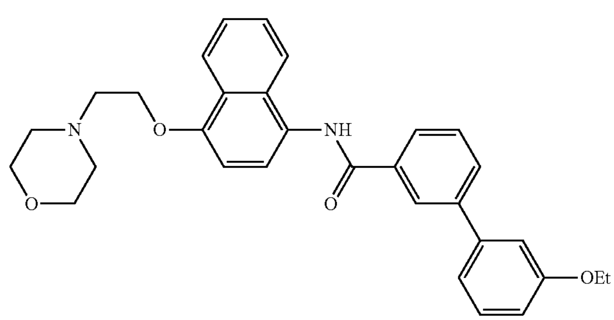 | B286 | | >10.0000 | >10.0000 |
| 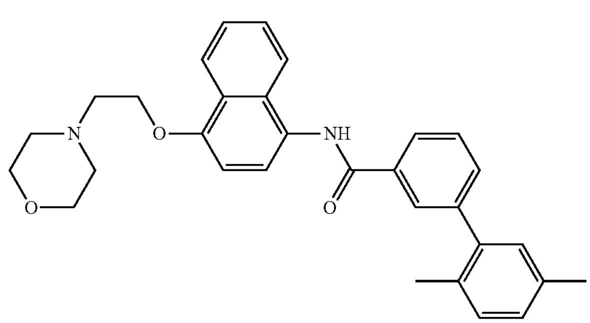 | B287 | | 0.9343 | 4.9998 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 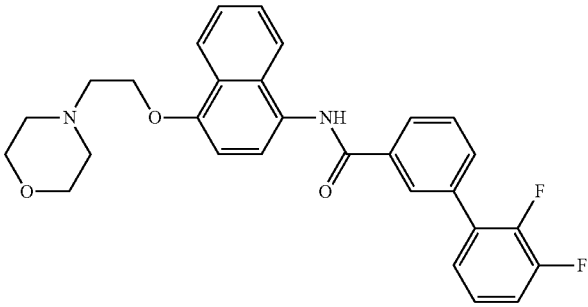 | B288 | | 2.7228 | 10.0959 |
| 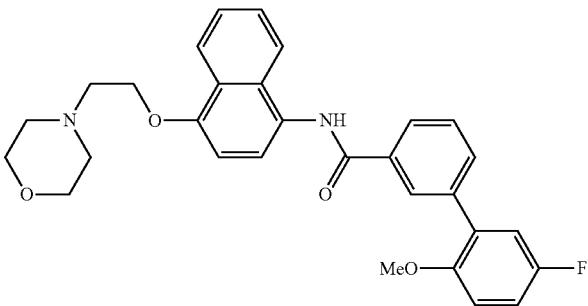 | B289 | | 1.4693 | 3.0871 |
| 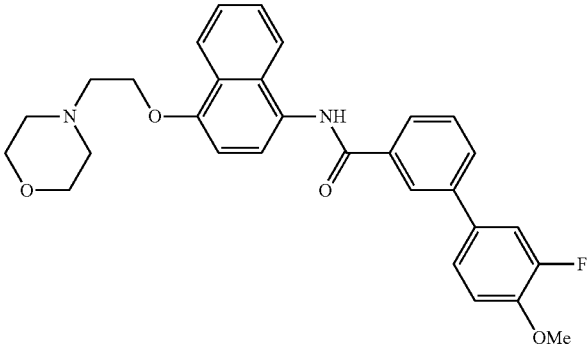 | B290 | | >10.0000 | >10.0000 |
| 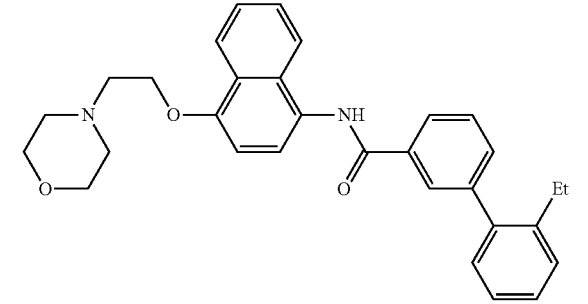 | B291 | | 9.1947 | 6.1398 |
| 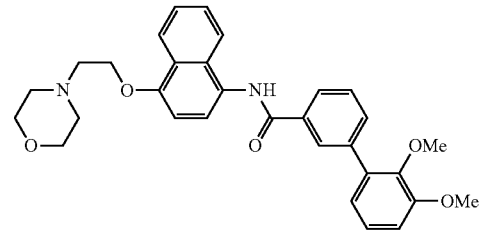 | B292 | | >10.0000 | >10.0000 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 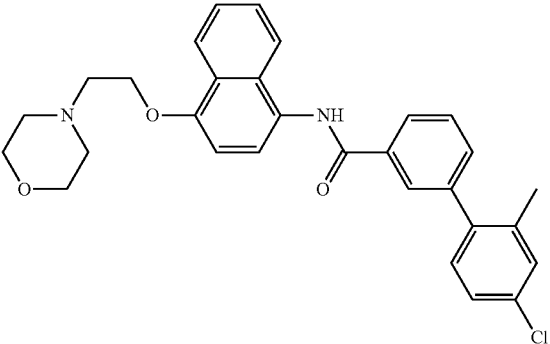 | B293 | | 10.3179 | >10.0000 |
| 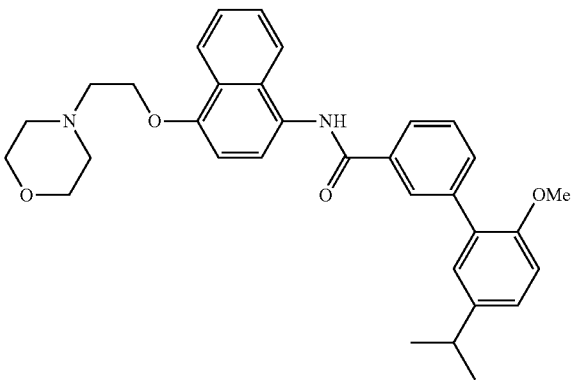 | B294 | | >10.0000 | >10.0000 |
| 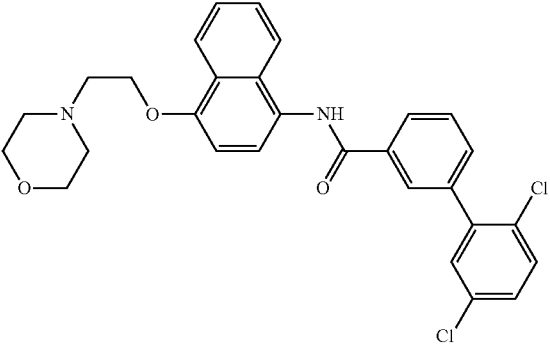 | B295 | | 5.0269 | 2.8344 |
| 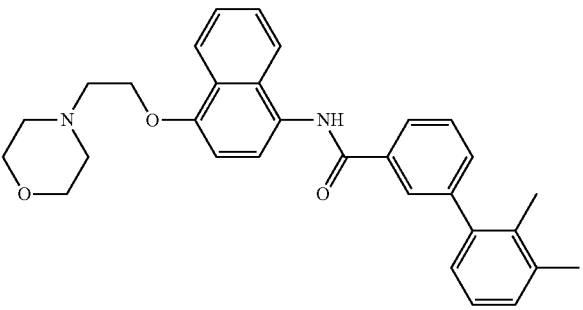 | B296 | | 1.8815 | 8.7132 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 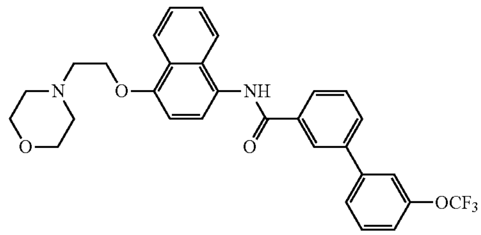 | B297 | | >10.0000 | >10.0000 |
| 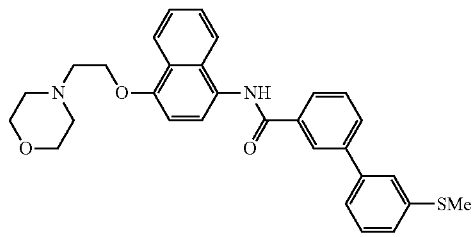 | B298 | | 7.3749 | >10.0000 |
| 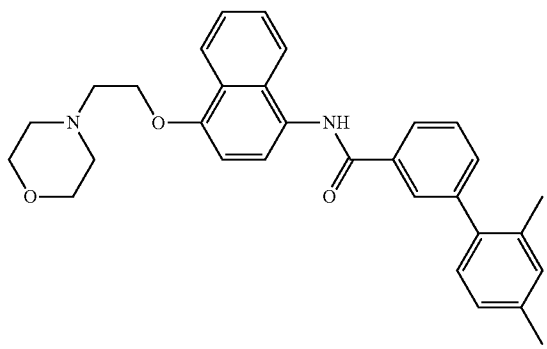 | B299 | | >10.0000 | >10.0000 |
| 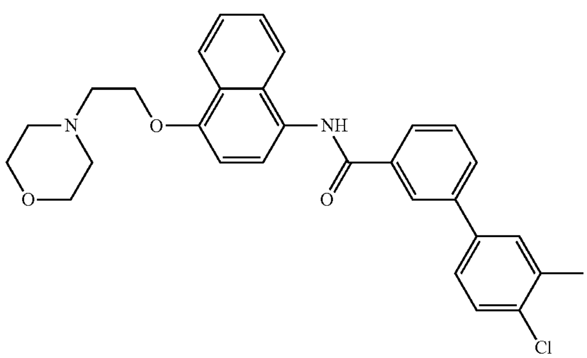 | B300 | | 9.0772 | 9.0621 |
| 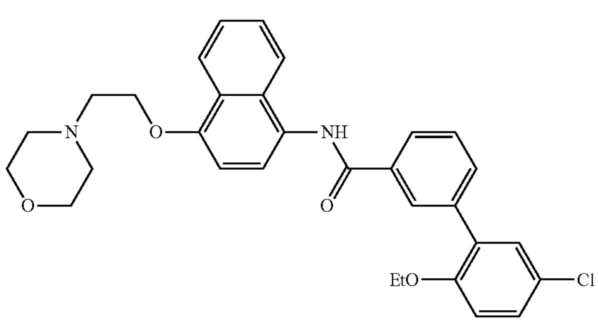 | B301 | | >10.0000 | >10.0000 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 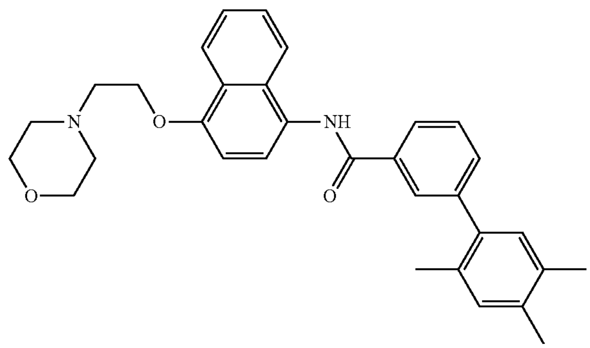 | B302 | | >10.0000 | >10.0000 |
| 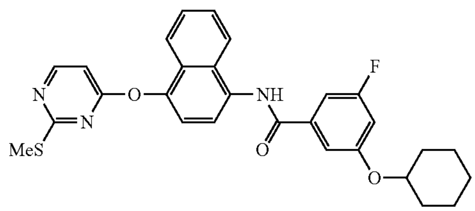 | B303 | | 0.2752 | 0.2319 |
| 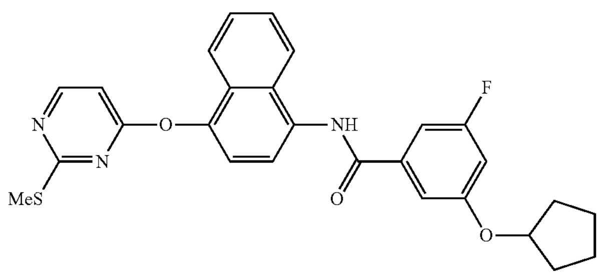 | B304 | | 0.2246 | 0.2391 |
| 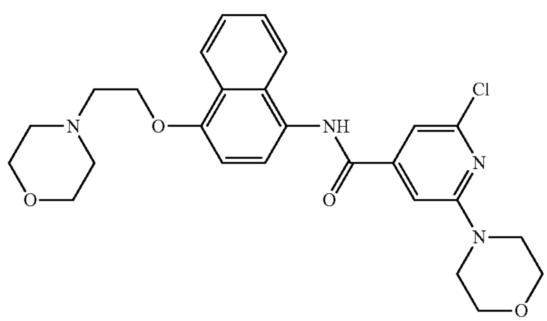 | B305 | | 1.4067 | 2.4815 |
| 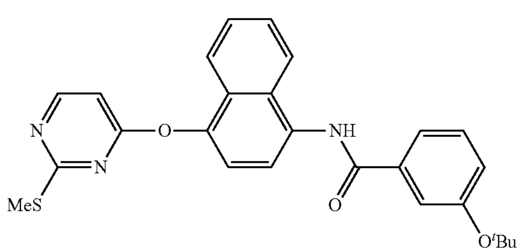 | B306 | | 0.0745 | 0.152 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 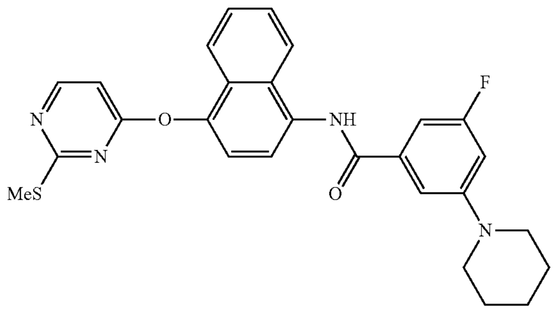 | B311 | | 0.056 | 0.1787 |
| 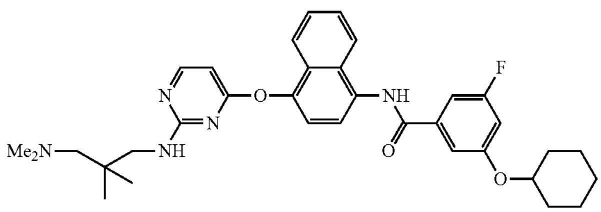 | B313 | | 0.0020, 0.0022 | 0.0483 |
| 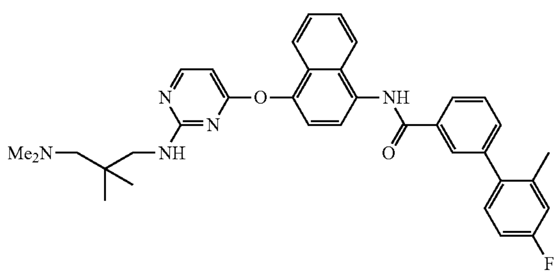 | B314 | | 0.001 | 0.0412 |
| 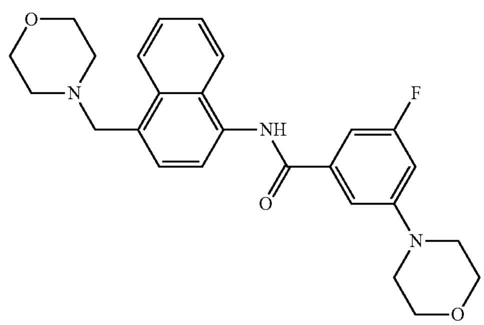 | B316 | | 1.1978 | 0.8792 |
| 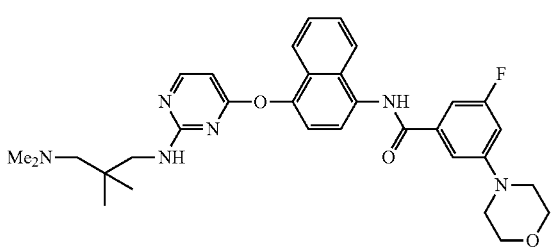 | B317 | | 0.0099 | 0.0238 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
| --- | --- | --- | --- | --- |
| 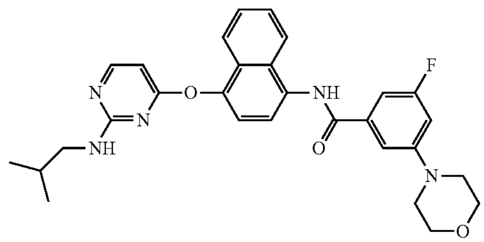 | B318 | | 0.0072 | 0.0383 |
| 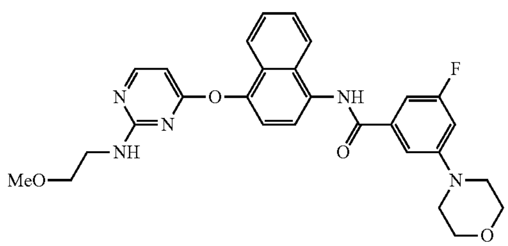 | B319 | | 0.001 | 0.0593 |
| 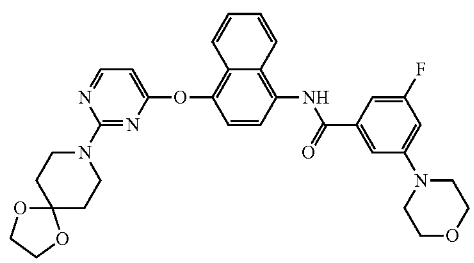 | B320 | | 0.0071 | 0.1901 |
| 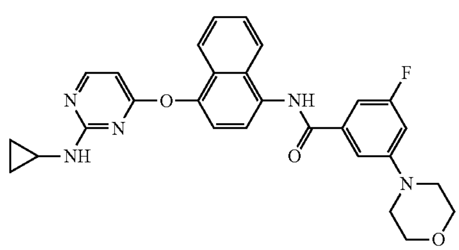 | B321 | | 0.0031 | 0.0761 |
| 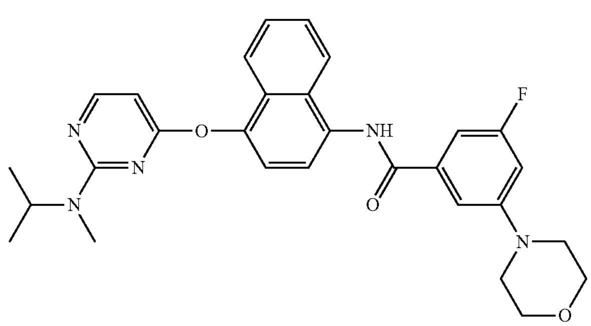 | B322 | | 0.0446 | 0.6073 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 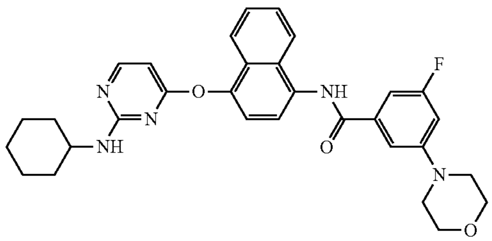 | B323 | | 0.0119 | 0.0361 |
| 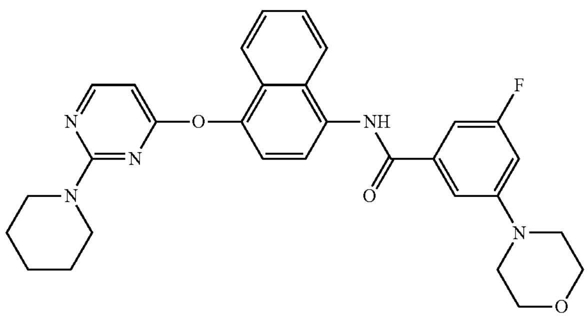 | B324 | | 0.019 | >1.0000 |
| 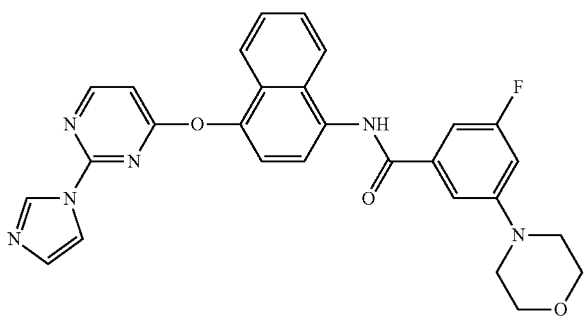 | B325 | | 0.0344 | 0.247 |
| 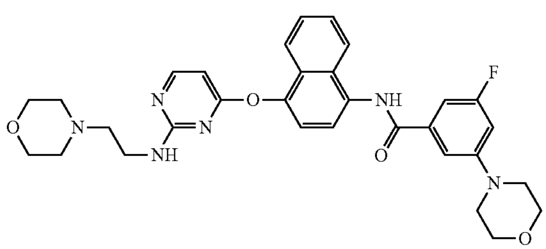 | B326 | | 0.0031 | 0.0768 |
| 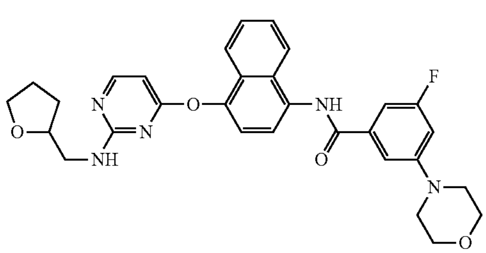 | B327 | | 0.0021 | 0.0248 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 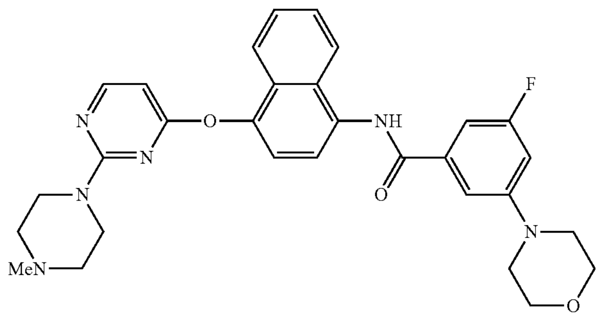 | B328 | | 0.0044 | 0.1488 |
| 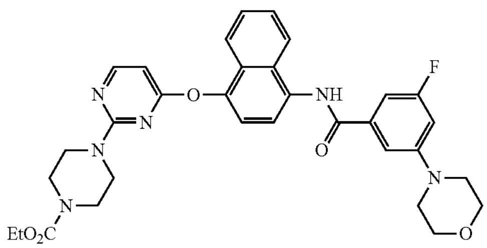 | B329 | | 0.0105 | >1.0000 |
| 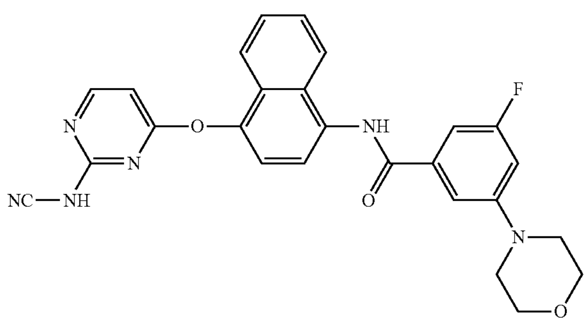 | B330 | | 0.0515 | >1.0000 |
| 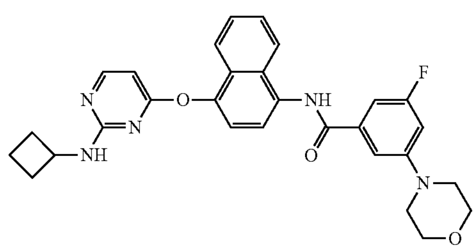 | B331 | | 0.0037 | 0.237 |
| 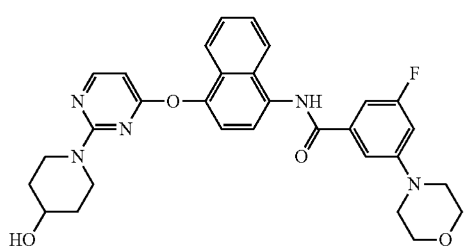 | B332 | | 0.005 | 0.2519 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 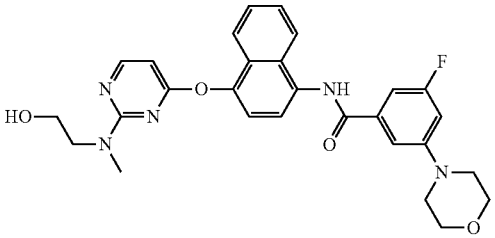 | B333 | | 0.0187 | >1.5000 |
| 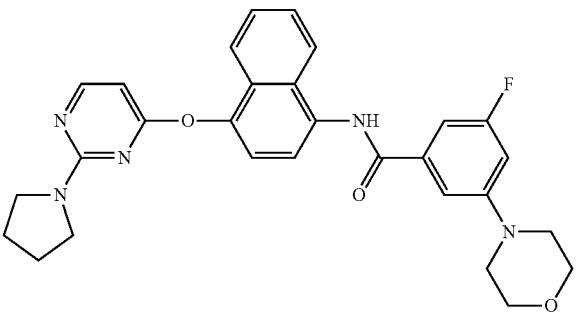 | B334 | | 0.0082 | 0.2765 |
| 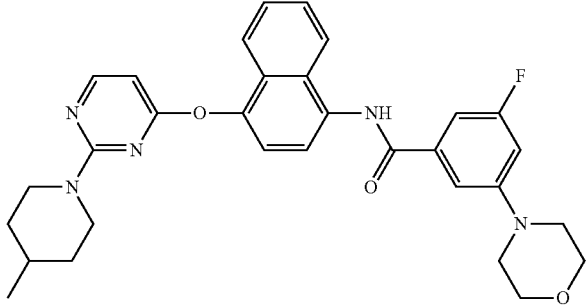 | B335 | | 0.0222 | >1.0000 |
| 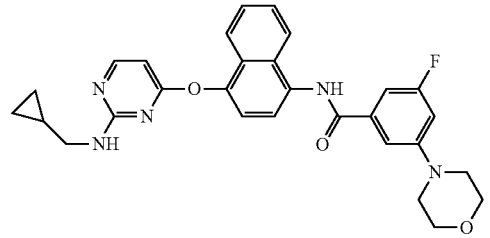 | B336 | | 0.0025 | 0.0058 |
| 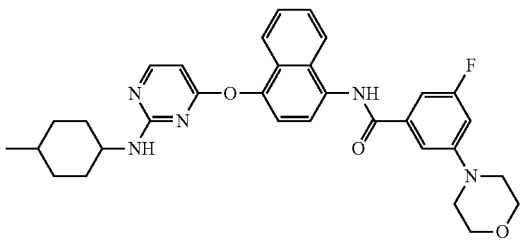 | B337 | | 0.0333 | 0.0656 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 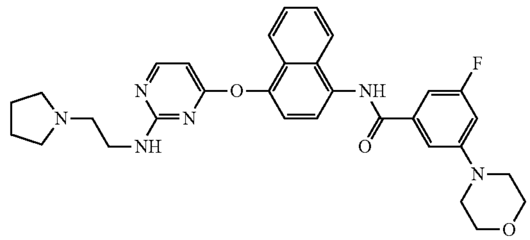 | B338 | | 0.0171 | 0.0609 |
| 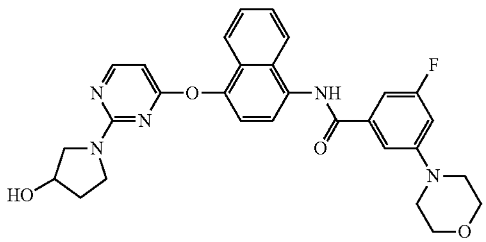 | B339 | | 0.0391 | 0.3467 |
| 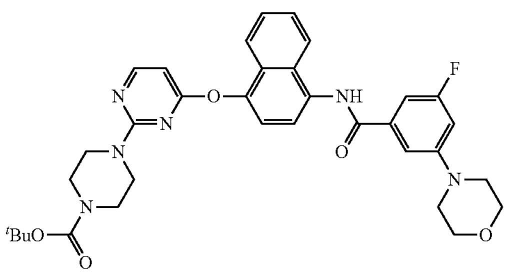 | B340 | | 0.0559 | >1.0000 |
| 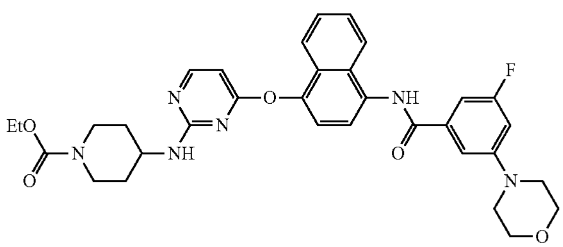 | B341 | | 0.0105 | 0.5898 |
| 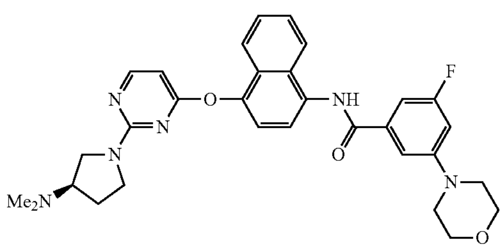 | B342 | | 0.0223 | 0.0615 |
| 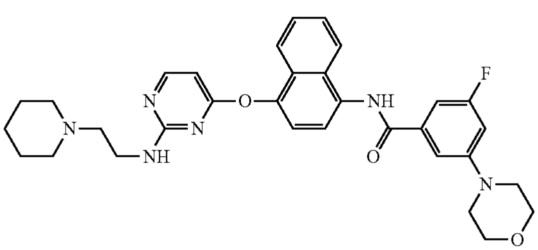 | B343 | | 0.0152 | 0.1355 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 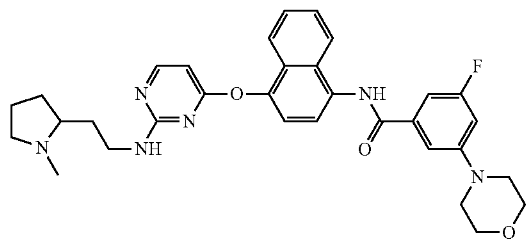 | B344 | | 0.0011 | 0.0061 |
| 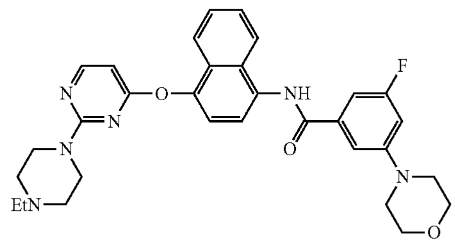 | B345 | | 0.0133 | 0.0796 |
| 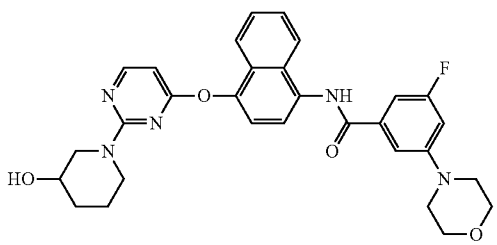 | B346 | | 0.0052 | 0.4311 |
| 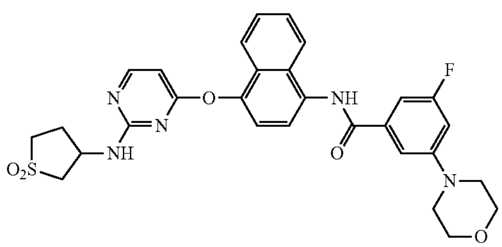 | B347 | | 0.0139 | 0.0422 |
| 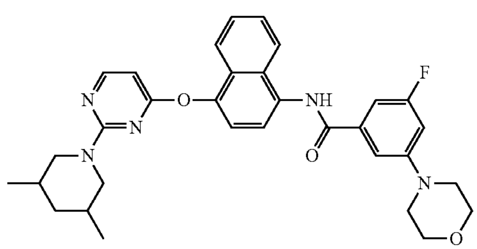 | B348 | | 0.1655 | >1.0000 |
| 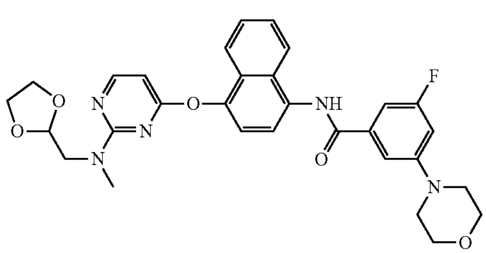 | B349 | | 0.0187 | 0.0747 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 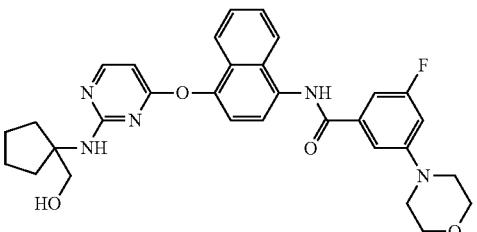 | B350 | | 0.0095 | 0.0681 |
| 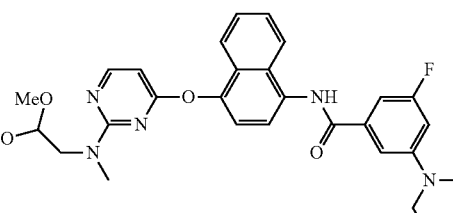 | B351 | | 0.0271 | 0.2745 |
| 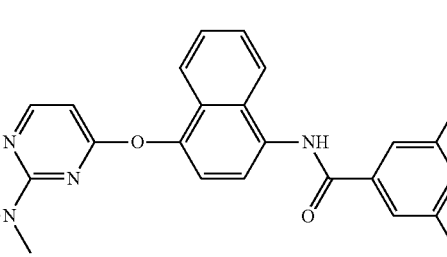 | B352 | | 0.0325 | 0.5185 |
| 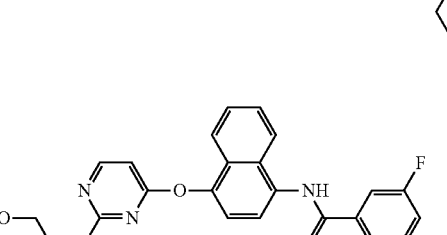 | B353 | | 0.0039 | 0.0926 |
| 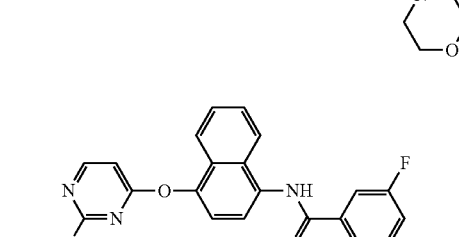 | B354 | | 0.0094 | 0.2171 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 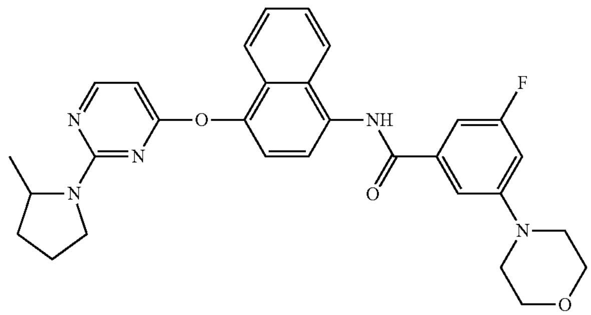 | B355 | | 0.0687 | 0.8781 |
| 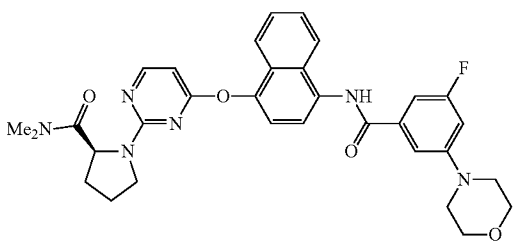 | B356 | | 0.2642 | >1.0000 |
| 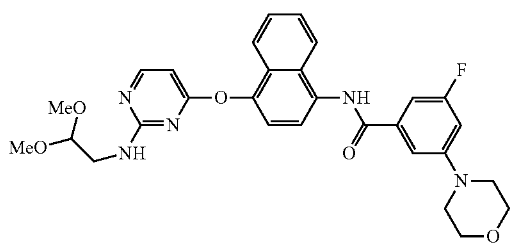 | B357 | | 0.003 | 0.0301 |
| 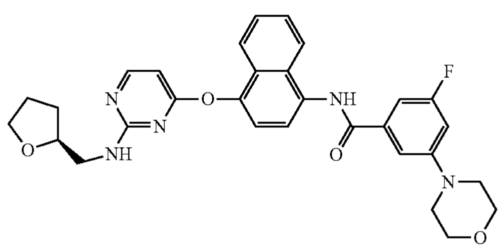 | B358 | | 0.0032 | 0.0095 |
| 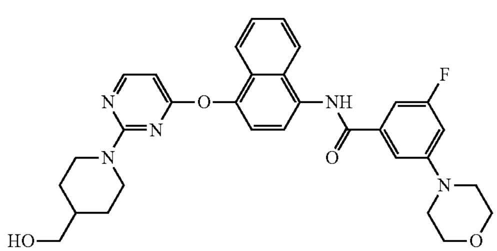 | B359 | | 0.0042 | 0.1041 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 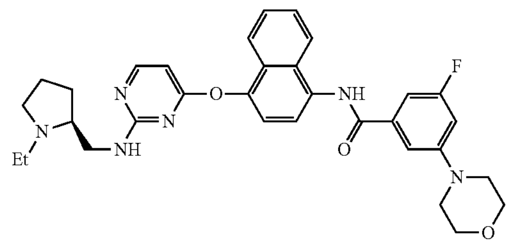 | B360 | | 0.0225 | 0.063 |
| 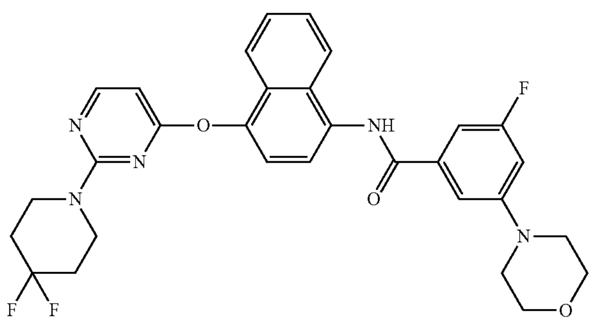 | B361 | | 0.0555 | 0.4747 |
| 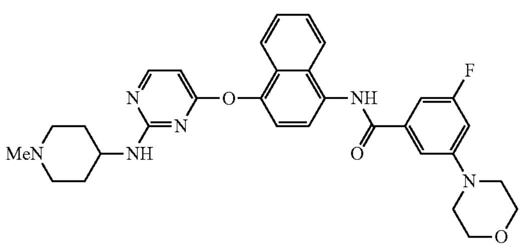 | B362 | | 0.0078 | 0.0487 |
| 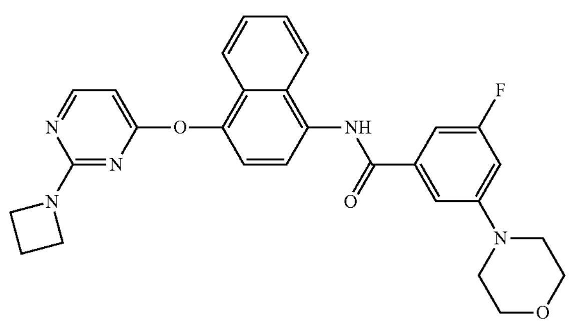 | B363 | | 0.0058 | 0.078 |
| 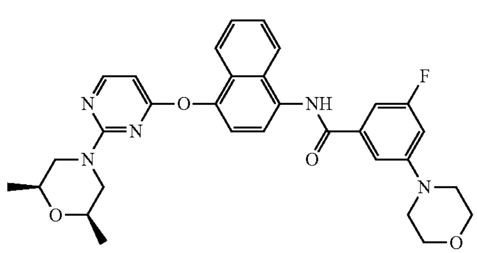 | B364 | | 0.0273 | 0.4122 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
| --- | --- | --- | --- | --- |
| 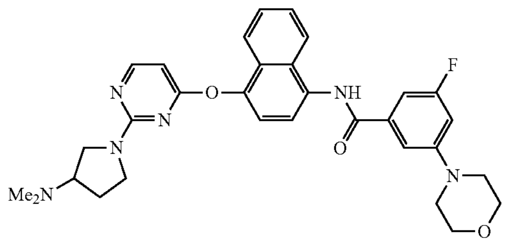 | B365 | | 0.028 | 0.0567 |
| 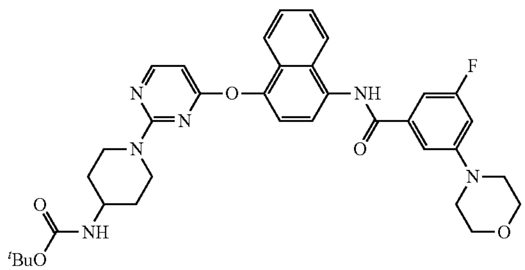 | B366 | | 0.0283 | 0.3863 |
| 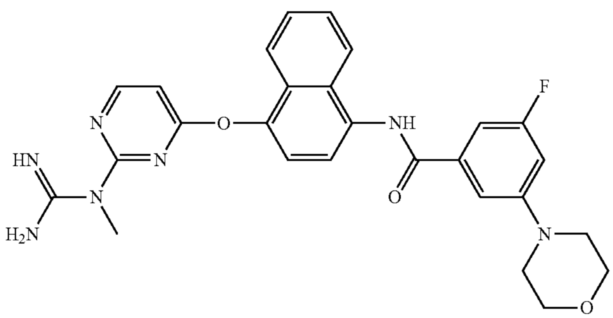 | B367 | | 0.0182 | 0.6494 |
| 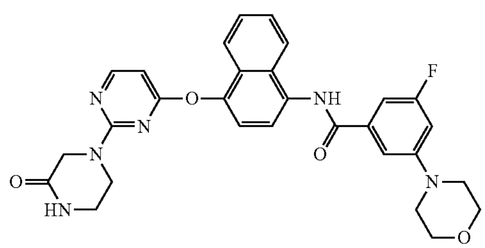 | B368 | | 0.0197 | 0.1409 |
| 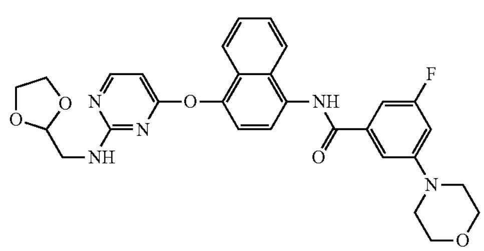 | B369 | | 0.0029 | 0.0333 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 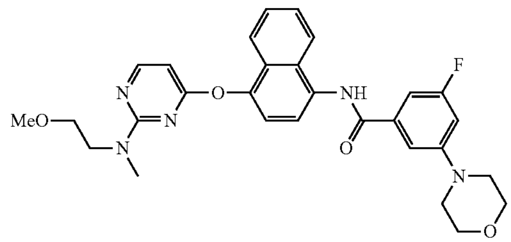 | B370 | | 0.0211 | 0.3295 |
| 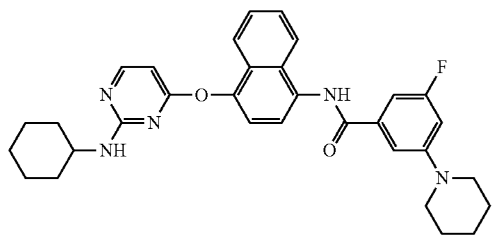 | B371 | | 0.0264 | 0.0371 |
| 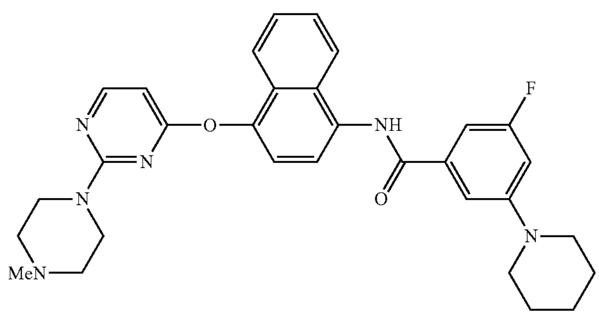 | B372 | | 0.0084 | 0.2173 |
| 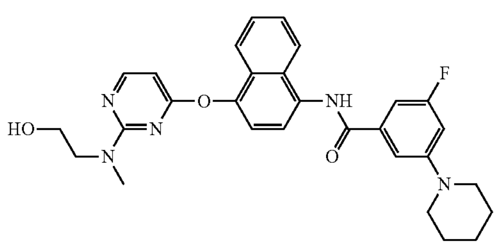 | B373 | | 0.0209 | 0.6739 |
| 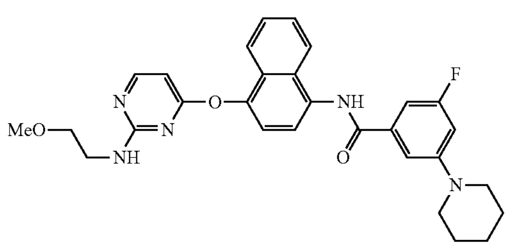 | B374 | | 0.0043 | 0.147 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 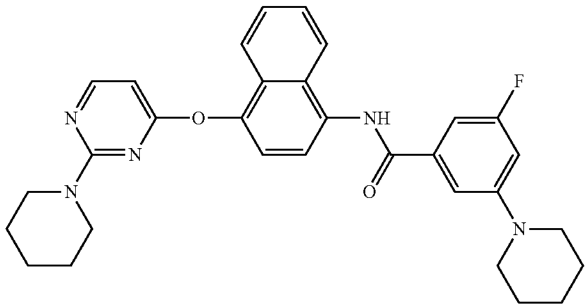 | B375 | | 0.1066 | >1.0000 |
| 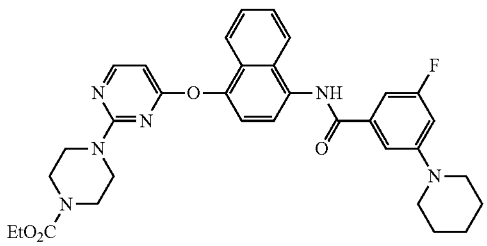 | B376 | | 0.0377 | >1.0000 |
| 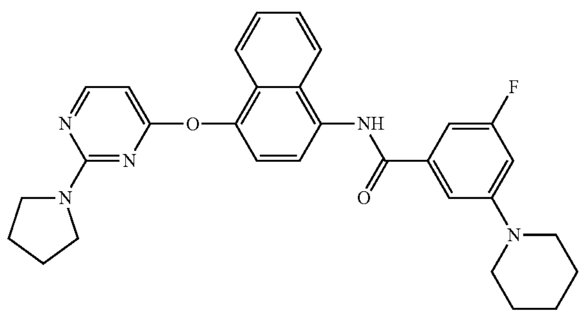 | B377 | | 0.0419 | 0.5151 |
| 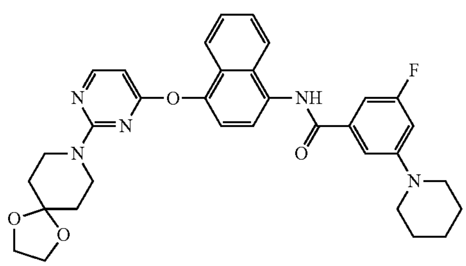 | B378 | | 0.0171 | 0.2248 |
| 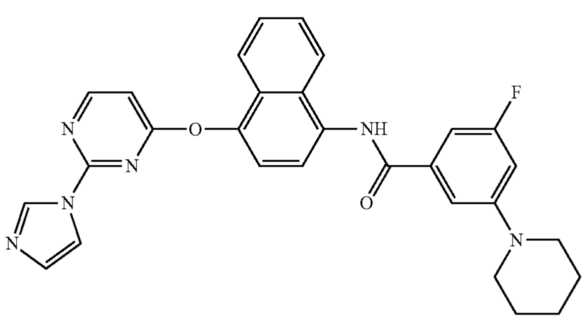 | B379 | | 0.0151 | 0.5301 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 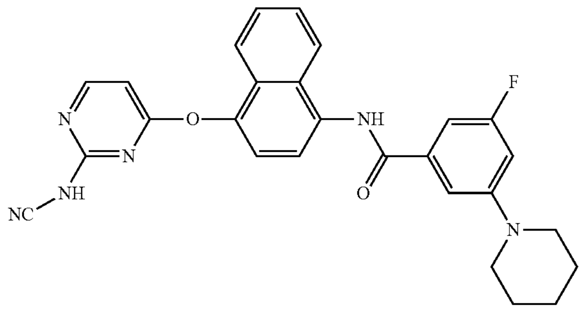 | B380 | | 0.0066 | >1.0000 |
| 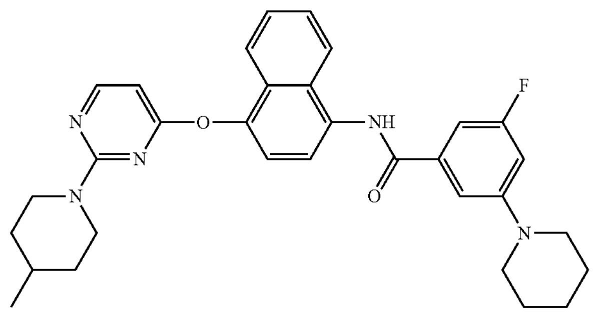 | B381 | | 0.0878 | 0.5902 |
| 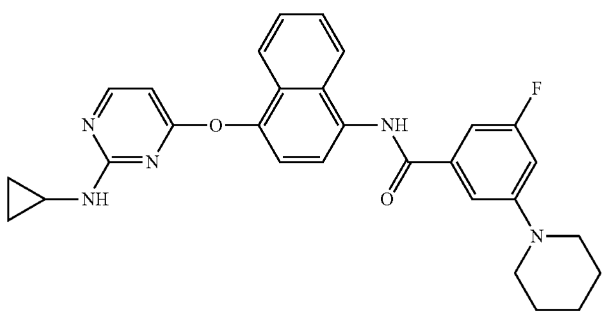 | B382 | | 0.0069 | 0.1849 |
| 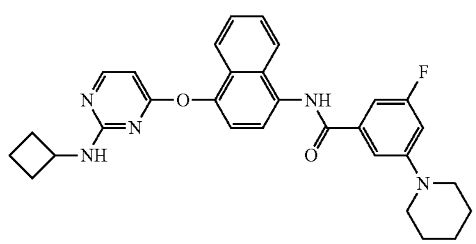 | B383 | | 0.0114 | 0.3108 |
| 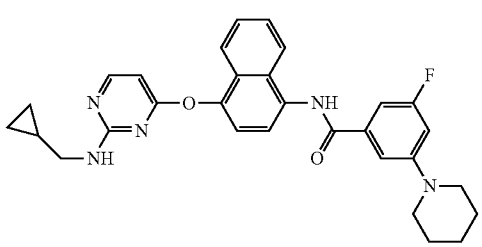 | B384 | | 0.0063 | 0.0903 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 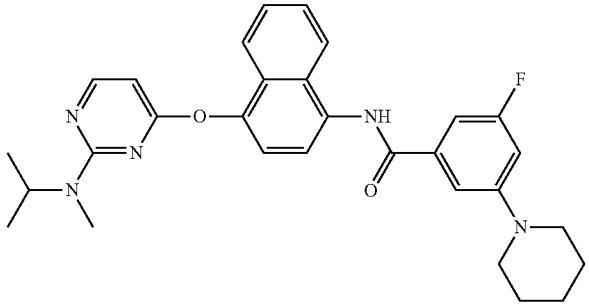 | B385 | | 0.0956 | >1.0000 |
| 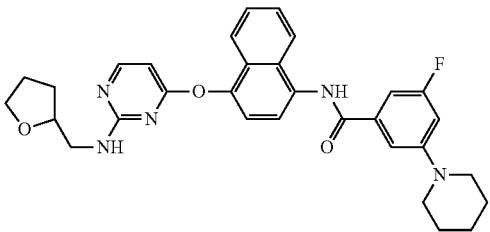 | B386 | | 0.0018 | 0.0262 |
| 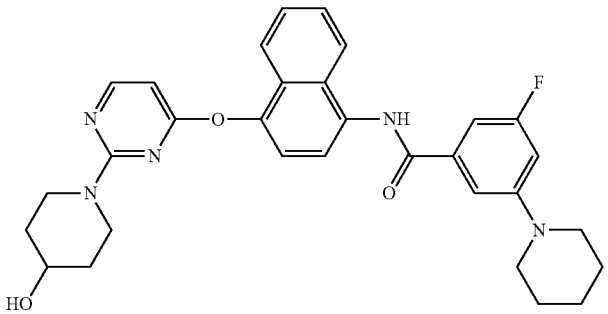 | B387 | | 0.0057 | 0.3089 |
| 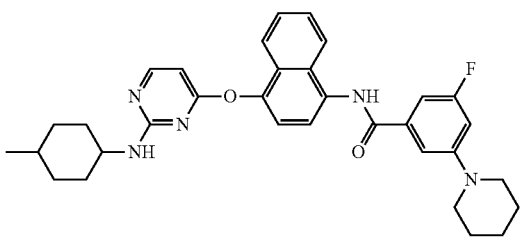 | B388 | | 0.0427 | 0.1025 |
| 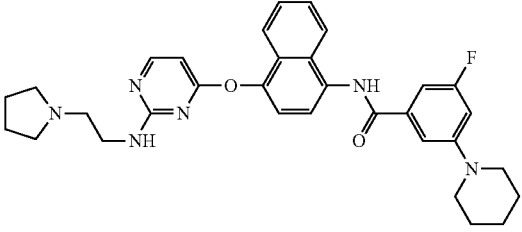 | B389 | | 0.0021 | 0.089 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 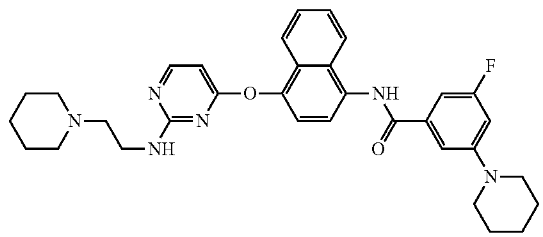 | B390 | | 0.003 | 0.1148 |
| 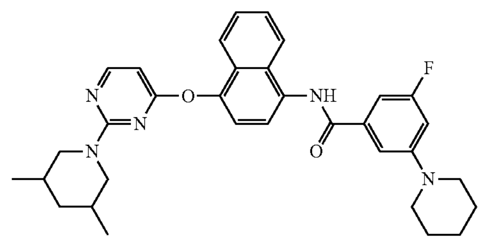 | B391 | | 0.2072 | >1.0000 |
| 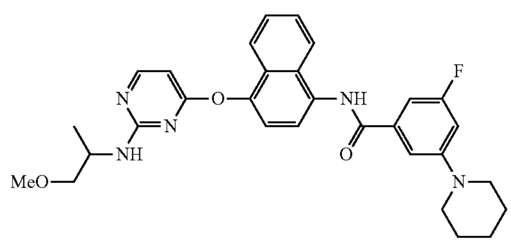 | B392 | | 0.0071 | 0.1222 |
| 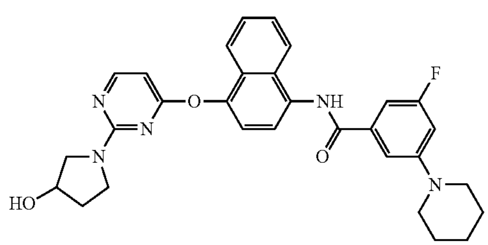 | B393 | | 0.0168 | 0.7146 |
| 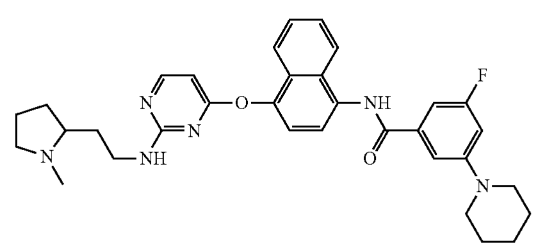 | B394 | | 0.0007 | 0.0108 |
| 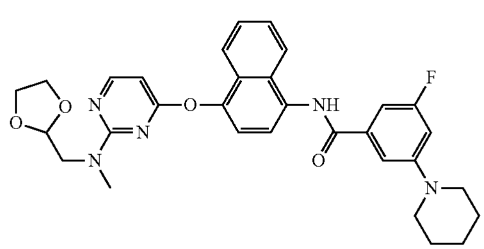 | B395 | | 0.0313 | 0.2119 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
| --- | --- | --- | --- | --- |
| 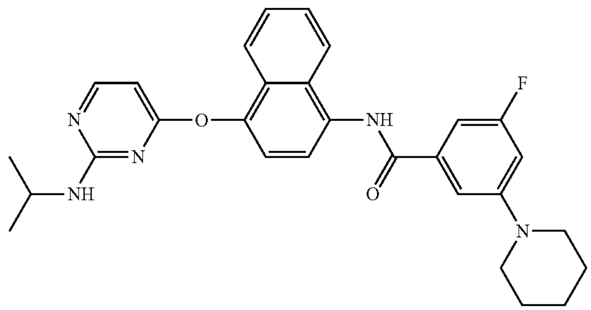 | B396 | | 0.006 | 0.201 |
| 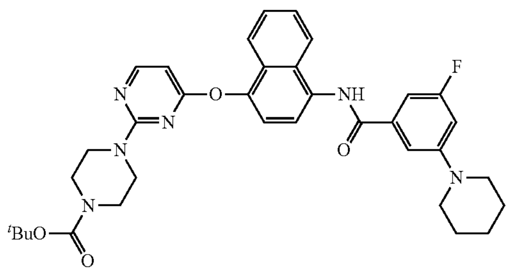 | B397 | | 0.1088 | >1.0000 |
| 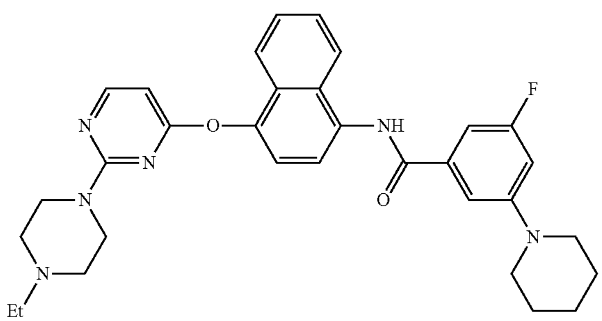 | B398 | | 0.0079 | 0.2409 |
| 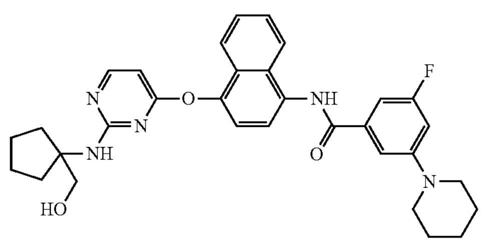 | B399 | | 0.0127 | 0.1361 |
| 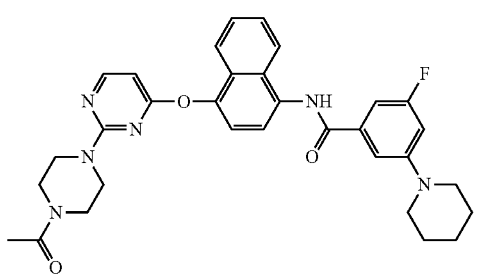 | B400 | | 0.0074 | 0.5646 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 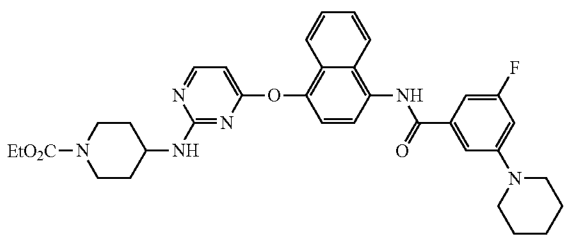 | B401 | | 0.0256 | 1.1 |
| 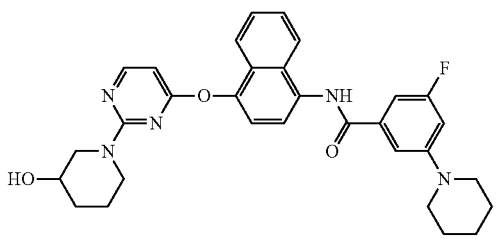 | B402 | | 0.0146 | 0.6552 |
| 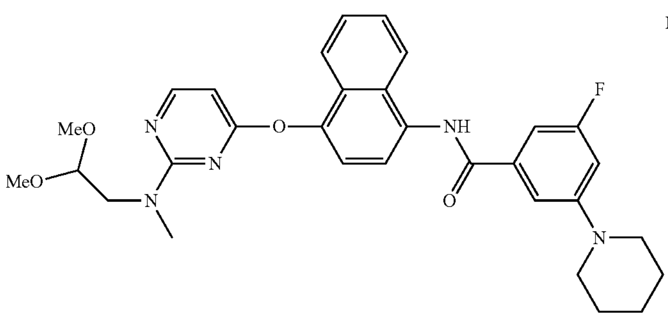 | B403 | | 0.0483 | 0.2538 |
| 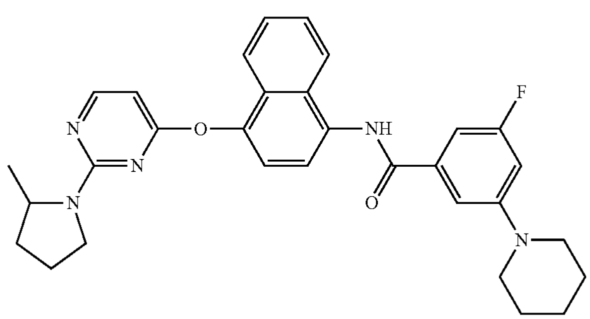 | B404 | | 0.1506 | 1.1164 |
| 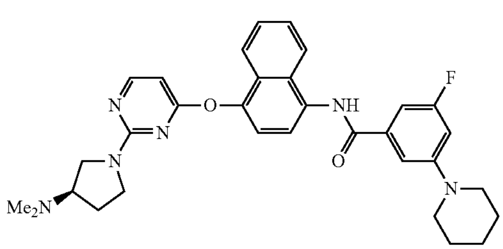 | B405 | | 0.0304 | 0.2017 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 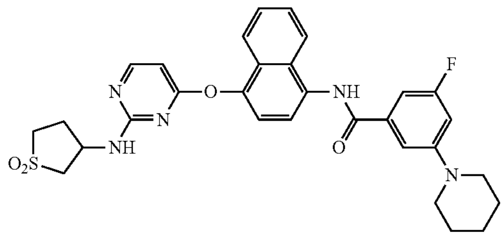 | B406 | | 0.0196 | 0.1168 |
| 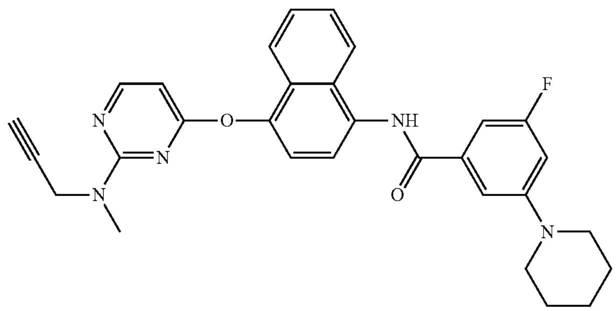 | B407 | | 0.0561 | 0.7001 |
| 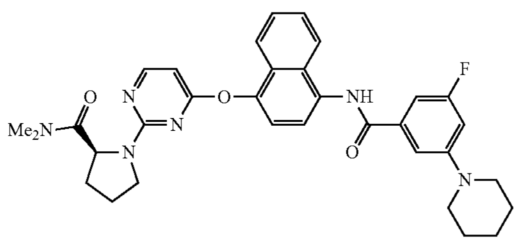 | B408 | | 0.1265 | >1.0000 |
| 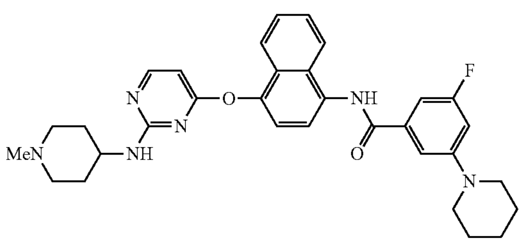 | B409 | | 0.0018 | 0.0687 |
| 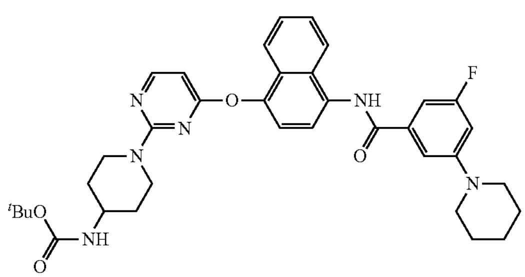 | B410 | | 0.0909 | >1.0000 |
| 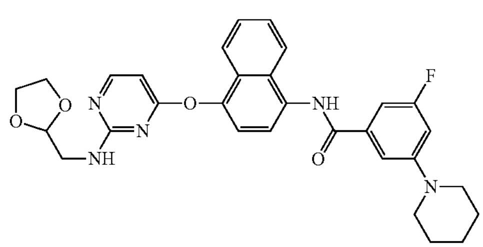 | B411 | | 0.0017 | 0.0235 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 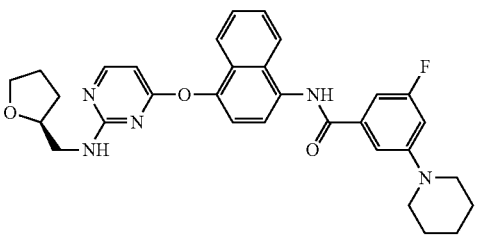 | B412 | | 0.0023 | 0.011 |
| 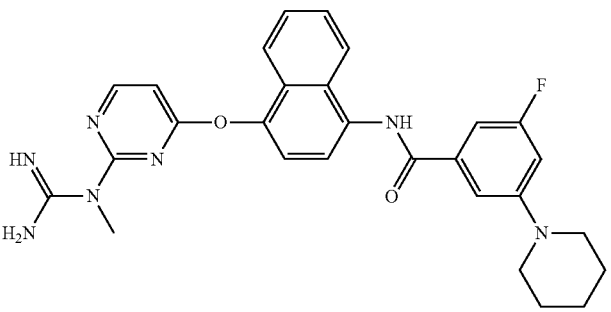 | B413 | | 0.0363 | >1.0000 |
| 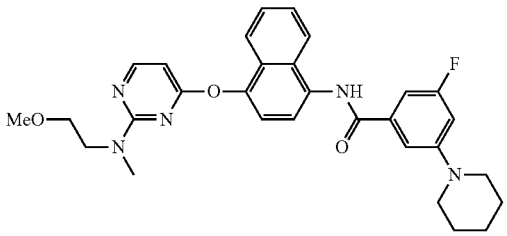 | B414 | | 0.0289 | 0.5805 |
| 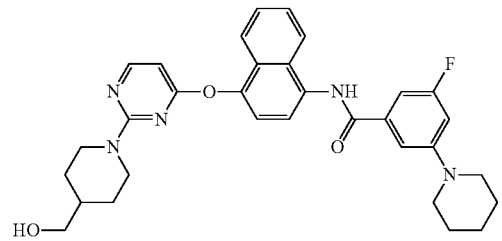 | B415 | | 0.0061 | 0.1621 |
| 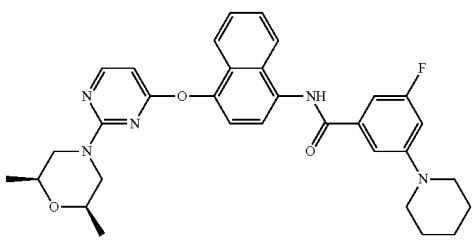 | B416 | | 0.0502 | 0.4718 |

TABLE 1-continued
| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 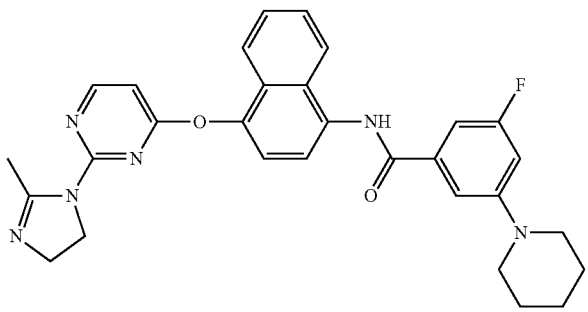 | B417 | | 0.0127 | 0.3363 |
| 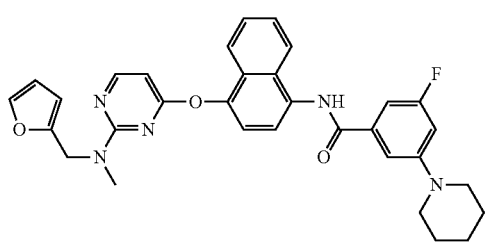 | B418 | | 0.1023 | 0.5382 |
| 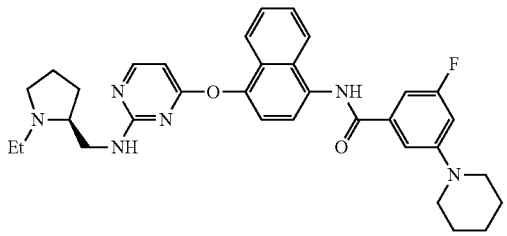 | B419 | | 0.003 | 0.0554 |
| 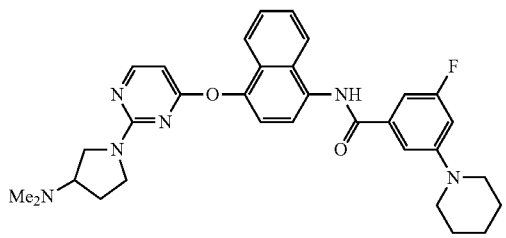 | B420 | | 0.0152 | 0.2253 |
| 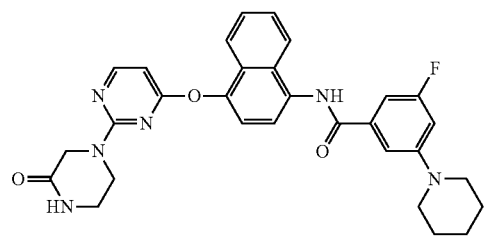 | B421 | | 0.0178 | 0.6892 |
| 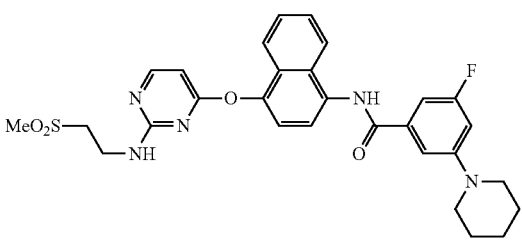 | B422 | | 0.0016 | 0.0632 |

TABLE 1-continued

| Structure | Compound | [ENZ] P38 ALPHA, PCT INH, ELISA (10 uM; ATF2) (Percent) | [ENZ] P38 ALPHA, IC50, ELISA (uM) | [CELL] THP-1, IC50, TNF ALPHA, ELISA (uM) |
|---|---|---|---|---|
| 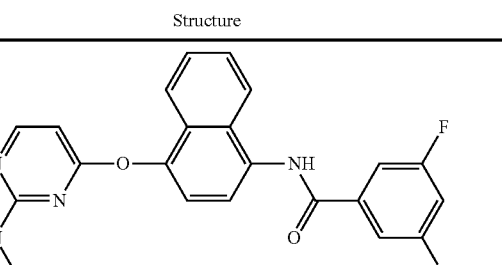 | B423 | | 0.1111 | 0.7728 |
| 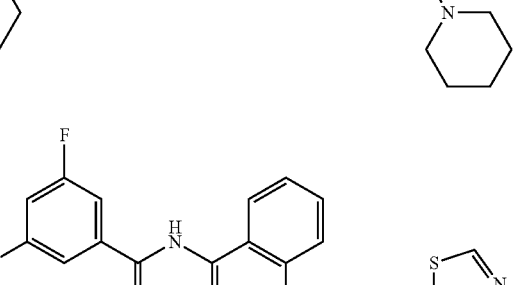 | B424 | | 0.0399 | 2.21 |

What is claimed is:

1. A compound of Formula I:

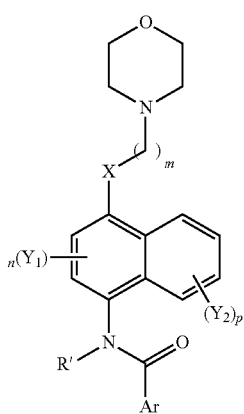

wherein:
X is O, NR, CH$_2$, or a bond;
R is H or alkyl;
R' is H or alkyl;
m is 0, 1 or 2;
n is 0, 1 or 2;
p is 0, 1, 2, 3, or 4;
Ar is an aryl group;
Y$_1$ is independently selected from the group consisting of halogen, alkyl, nitro, hydroxyl, and alkyloxy; and
Y$_2$ is independently selected from the group consisting of halogen, alkyl, nitro, hydroxyl, and alkyloxy.

2. The compound according to claim 1, wherein X is oxygen.

3. The compound according to claim 1, wherein Ar is a phenyl group.

4. The compound according to claim 1, wherein said aryl group is optionally substituted with one or more substituents selected from the group consisting of hydroxyl group, halogen, cyano, nitro, amino, —NR$_{12}$R$_{13}$, C$_1$-C$_6$ alkylthio, arylthio, C$_1$-C$_6$ alkyl, C$_1$-C$_6$ alkoxy, aryloxy, alkylcarbonyloxy, arylcarbonyloxy, C$_3$-C$_6$ cycloalkyl, C$_3$-C$_6$ cycloalkyloxy, C$_2$-C$_6$ alkenyl, C$_2$-C$_6$ alkynyl, aryl, aminocarbonyl, C$_1$-C$_6$ alkylcarbonyl, C$_3$-C$_6$ cycloalkylcarbonyl, heterocyclylcarbonyl, arylcarbonyl, aryloxycarbonyl, C$_1$-C$_6$ alkoxycarbonyl, C$_3$-C$_6$ cycloalkyloxycarbonyl, heterocyclyloxycarbonyl, C$_1$-C$_6$ alkylsulfonyl, arylsulfonyl, and a heterocyclyl group.

5. The compound according to claim 1, wherein said compound is represented by Formula Ia:

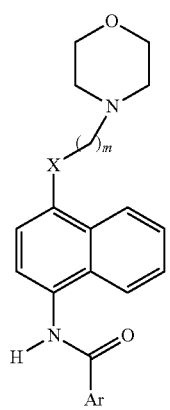

wherein:
X is O, NR, CH$_2$, or a bond;
R is H or alkyl;
m is 0, 1 or 2; and
Ar is an aryl group.

6. The compound according to claim 1, wherein said compound is a pharmaceutically acceptable salt.

7. The compound according to claim 5, wherein said compound is a pharmaceutically acceptable salt.

8. A pharmaceutical composition comprising one or more compounds represented by Formula I according to claim 1 and a pharmaceutically acceptable carrier.

9. The compound of Formula I according to claim 1, wherein Ar is a phenyl group substituted with a fluorine group, and wherein the phenyl group is further substituted with a group selected from the group consisting of

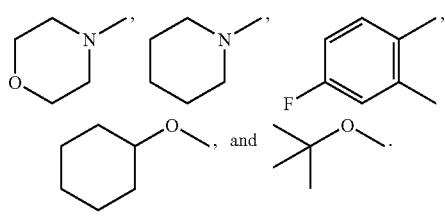

* * * * *